United States Patent
Ring et al.

(10) Patent No.: US 11,850,276 B2
(45) Date of Patent: Dec. 26, 2023

(54) INTERLEUKIN-18 VARIANTS AND METHODS OF USE

(71) Applicants: Simcha IL-18, Inc., New Haven, CT (US); Yale University, New Haven, CT (US)

(72) Inventors: Aaron Ring, Milford, CT (US); Tom Boone, New Haven, CT (US)

(73) Assignees: Simcha IL-18, Inc., New Haven, CT (US); Yale University, New Haven, CT (US)

( * ) Notice: Subject to any disclaimer, the term of this patent is extended or adjusted under 35 U.S.C. 154(b) by 0 days.

(21) Appl. No.: 18/060,816

(22) Filed: Dec. 1, 2022

(65) Prior Publication Data

US 2023/0277625 A1 Sep. 7, 2023

Related U.S. Application Data

(63) Continuation of application No. PCT/US2021/057741, filed on Nov. 2, 2021.

(60) Provisional application No. 63/108,794, filed on Nov. 2, 2020.

(51) Int. Cl.
*A61K 38/20* (2006.01)
(52) U.S. Cl.
CPC .................................. *A61K 38/20* (2013.01)
(58) Field of Classification Search
CPC ........................................................ A61K 38/20
See application file for complete search history.

(56) References Cited

U.S. PATENT DOCUMENTS

| 6,156,501 | A | 12/2000 | McGall et al. |
|---|---|---|---|
| 2003/0095946 | A1 | 5/2003 | Gillspie et al. |
| 2008/0206189 | A1 | 8/2008 | Bam et al. |
| 2019/0070262 | A1 | 3/2019 | Ring et al. |
| 2021/0015891 | A1 | 1/2021 | Ring |

FOREIGN PATENT DOCUMENTS

| EP | 0861663 | A2 | 9/1998 |
|---|---|---|---|
| EP | 1669454 | A2 | 6/2006 |
| WO | WO-9959565 | A1 | 11/1999 |
| WO | WO-0193898 | A1 | 12/2001 |
| WO | WO-02101049 | A2 | 12/2002 |
| WO | WO-2017103088 | A1 | 6/2017 |

OTHER PUBLICATIONS

Cho, I-K. et al., "Oncolytic adenovirus co-expressing IL-12 and IL-18 improves tumor-specific immunity via differentiation of T cells expressing IL-1 2Rbeta2 or IL-18Ralpha," Gene Therapy, 2011;1: 898-909.
Garrido, F. et al., "The urgent need to recover MHC class I in cancers for effective immunotherapy," Current Opinion in Immunology, 2016;39:44-51.
Kim, S.H. et al., "Structural requirements of six naturally occurring isoforms of the IL-18 binding protein to inhibit IL-18," PNAS, 2000;97(3):1190-1195.
Ma, Z. et al., "Augmentation of Immune Checkpoint Cancer Immunotherapy with IL18," Clin Cancer Res., 2016;22(12).
Bird, R.E. et al., "Single-Chain Antigen-Binding Proteins," Science, 1988;242:423-426.
Hanes, J. et al., "New advances in microsphere-based single-dose vaccines," Advanced Drug Delivery Reviews, 1997;28:97-119.
Harlow, E. et al., "Antibodies: A Laboratory Manual, " Cold Spring Harbor, New York, 1989.
Huston, J.S. et al., "Protein engineering of antibody binding sites: recovery of specific activity in an anti-digoxin single-chain Fv analogue produced in *Escherichia coli*," Proceedings of the National Academy of Sciences, 1988;85(16):5879-5883.
International Preliminary Report on Patentability issued in PCT/US2021/057741, dated May 2, 2023.
International Search Report and Written Opinion issued in PCT/US2021/057741, dated Mar. 8, 2022.
Kim, S.H. et al., "Site-specific mutations in the mature form of human IL-18 with enhanced biological activity and decreased neutralization by IL-18 binding protein," PNAS, 2001;98(6):3304-3309.
Kwon E.D. et al., "Elimination of residual metastatic prostate cancer after surgery and adjunctive cytotoxic T lymphocyte-associated antigen 4 (CTLA-4) blockade immunotherapy," PNAS, 1999;96(26):15074-15079.
Langer, R., "New methods of drug delivery," Science, 1990;249:1527-1533.
Singer M. et al., "A Distinct Gene Module for Dysfunction Uncoupled from Activation in Tumor-Infiltrating T Cells," Cell, 2016; 166(6):1500-1511.e9.
Wang J. et al., "UV-induced somatic mutations elicit a functional T cell response in the YUMMER1.7 mouse melanoma model," Pigment Cell Melanoma Res., 2017;30(4):428-435.

*Primary Examiner* — Prema M Mertz
(74) *Attorney, Agent, or Firm* — Wilson Sonsini Goodrich & Rosati

(57) ABSTRACT

The present disclosure provides compositions and methods comprising stabilized IL-18 polypeptides for use in therapeutic and non-therapeutic applications. In some cases, the stabilized IL-18 proteins provide IL-18 signaling activity even in the presence of an inhibitory molecule such as IL-18BP. Also provide are methods of administration and methods for making active polypeptides.

31 Claims, 56 Drawing Sheets

Specification includes a Sequence Listing.

FIG. 4

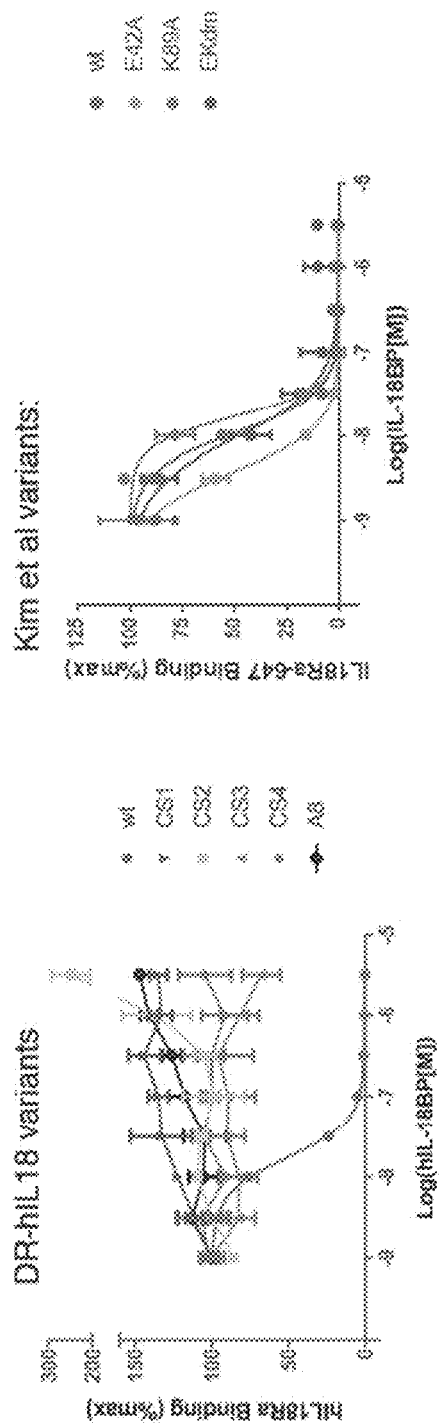
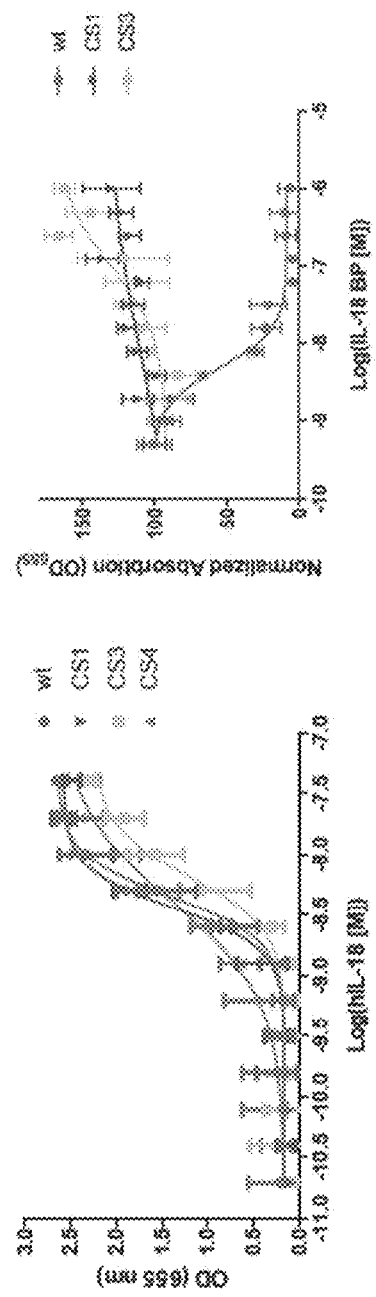
FIG. 6A
FIG. 6B

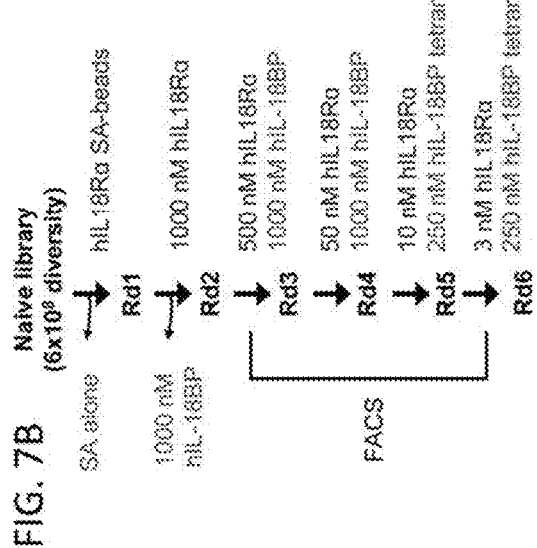
FIG. 7A
FIG. 7B
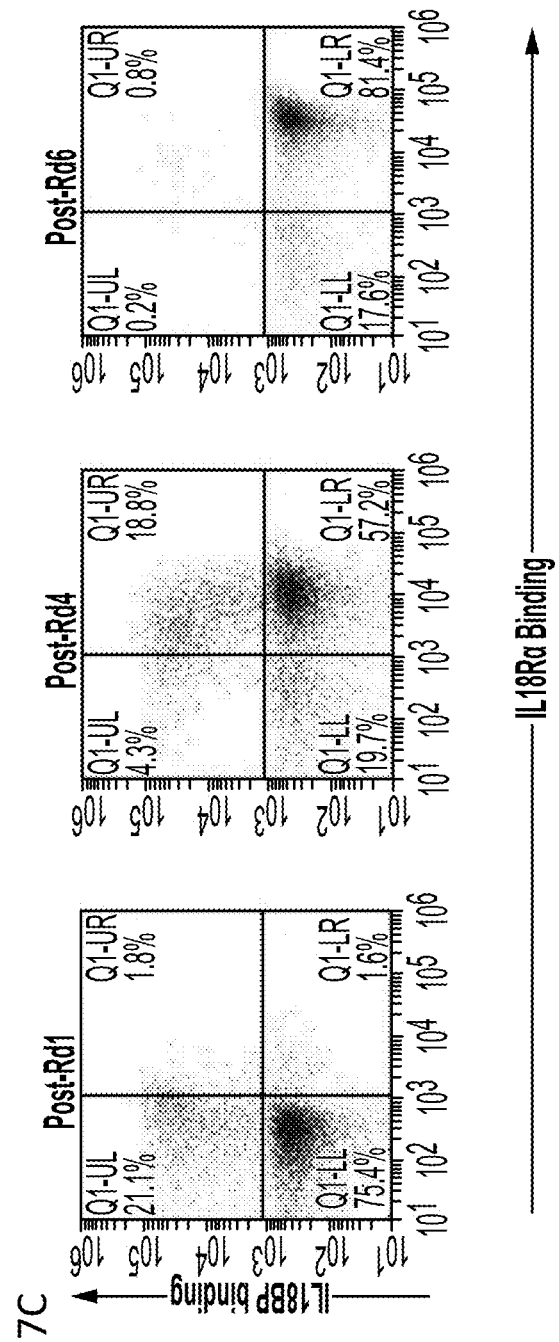
FIG. 7C

| | 51 | 53 | 56 | 57 | 60 | 103 | 105 | 110 | 111 | 113 | SEQ ID NO: |
|---|---|---|---|---|---|---|---|---|---|---|---|
| WT hIL-18 | M | | E | | M | Q | S | D | N | M | |
| 5-18 | K | | A | L | L | P | A | N | R | V | 73 |
| 5-29 | K | G | A | G | L | E | D | S | S | R | 74 |
| 5-8 | K | G | A | A | L | | | K | R | | 75 |
| 5-6 | K | G | R | G | L | E | D | N | S | R | 76 |
| 5-26 | K | S | V | | L | A | A | S | R | T | 77 |
| 5-20 | K | S | G | A | L | A | A | G | R | T | 78 |
| 5-2 | K | S | K | A | L | | D | S | S | R | 79 |
| 5-9 | K | S | L | A | L | A | N | G | R | | 80 |
| 5-42 | K | S | R | A | L | A | | G | R | T | 81 |
| 5-17 | K | S | R | A | L | A | | G | R | T | 192 |
| 5-41 | K | T | R | A | L | A | D | S | S | R | 193 |
| 5-1 | K | T | R | A | L | E | D | S | D | K | 84 |
| 5-33 | K | | R | | L | E | D | N | R | R | 85 |
| 5-21 | R | | G | K | L | R | | S | R | V | 86 |
| 6-31 | K | G | G | A | L | E | D | S | G | V | 87 |
| 6-20 | K | G | R | | L | | A | N | R | | 88 |
| 6-12 | K | S | L | A | L | A | D | S | R | | 89 |
| 6-27 | K | S | R | A | L | A | | G | R | T | 90 |
| 6-29 | K | S | R | A | L | | N | G | R | | 91 |

Round 5 variants (5-18 through 5-21)
Round 6 variants (6-31 through 6-29)

FIG. 8

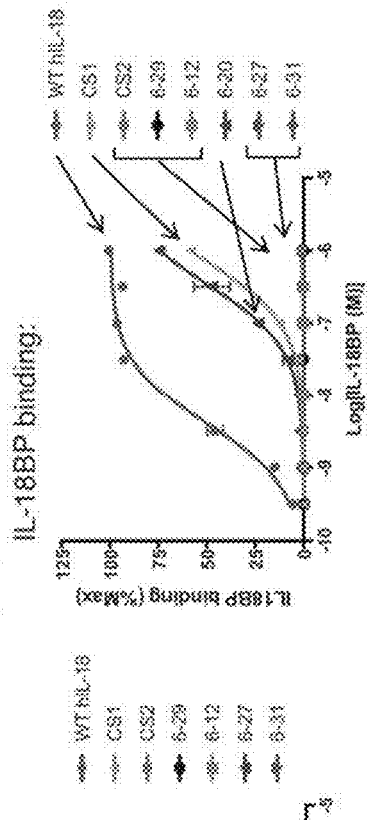
IL-18Ra binding:
FIG. 9B
IL-18BP binding:
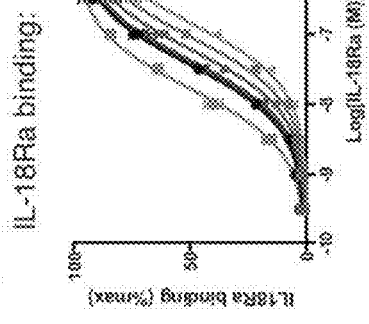
Thermal stability:
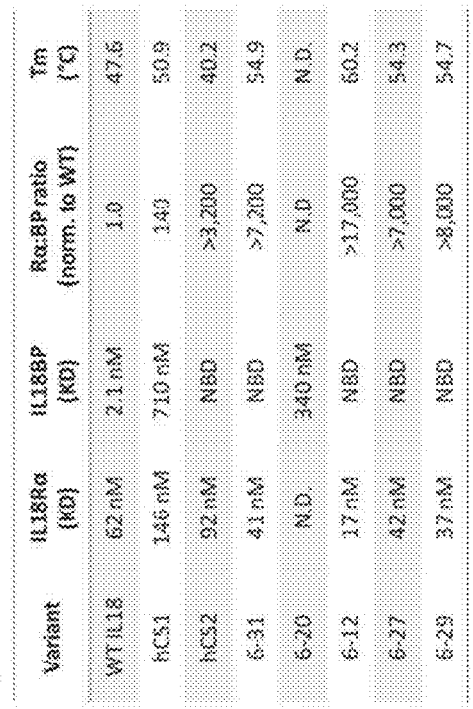
FIG. 9D
| Variant | IL18Rα (KD) | IL18BP (KD) | Rα:BP ratio (norm. to WT) | Tm (°C) |
|---|---|---|---|---|
| WT IL18 | 62 nM | 2.1 nM | 1.0 | 47.6 |
| hCS1 | 146 nM | 710 nM | 140 | 50.9 |
| hCS2 | 92 nM | NBD | >3,200 | 40.2 |
| 6-31 | 41 nM | NBD | >7,200 | 54.9 |
| 6-20 | N.D. | 340 nM | N.D | N.D. |
| 6-12 | 17 nM | NBD | >17,000 | 60.2 |
| 6-27 | 42 nM | NBD | >7,000 | 54.3 |
| 6-29 | 37 nM | NBD | >8,000 | 54.7 |

FIG. 10C

Murine DR-IL-18 variants sequence summary

| mIL-18 | 1 | 50 | 51 | 52 | 54 | 55 | 56 | 57 | 58 | 59 | 104 | 109 | 151 | SEQ ID NO: |
|---|---|---|---|---|---|---|---|---|---|---|---|---|---|---|
|  | N | M | Y | K | S | E | V | R | G | L | R | N | L |  |
| mC1 | H | A |  | V |  | R | L |  |  | K | K |  |  | 62 |
| mA12 | H | S |  | S |  |  |  |  |  |  | L |  |  | 63 |
| mE8 | H | V |  | T | K | H | M |  |  | K | K | D |  | 64 |
| mC10 | H | A |  | G | G | R | R |  |  | K | Q |  |  | 65 |
| mB7 | Y | A |  | G |  | H | M | G |  | R | K |  | V | 66 |
| mB1 | H | G |  | A |  | N | A |  | A | K | S |  |  | 67 |
| mD1 |  | G |  | S | R | D | A | K |  | K | Q | D | V | 68 |
| mH7 | Y | A |  | A | R | G | S |  |  | K | K |  |  | 69 |
| mA7 | Y | G |  | G | N | R | A |  |  | K | K | D |  | 70 |
| mE1 | Y | G |  | G |  | R | R | G |  | R | R | D |  | 71 |
| mH3 | Y | T | R | T | G | G | Q | K |  | V | V | D |  | 72 |
| mCS1 | H | G |  | A |  | R | R |  |  | K | K |  |  | 60 |
| mCS2 |  | A |  | G |  | R | A |  |  | K | K |  |  | 61 |

Selected Variants: mC1–mH3
Consensus Variants: mCS1, mCS2

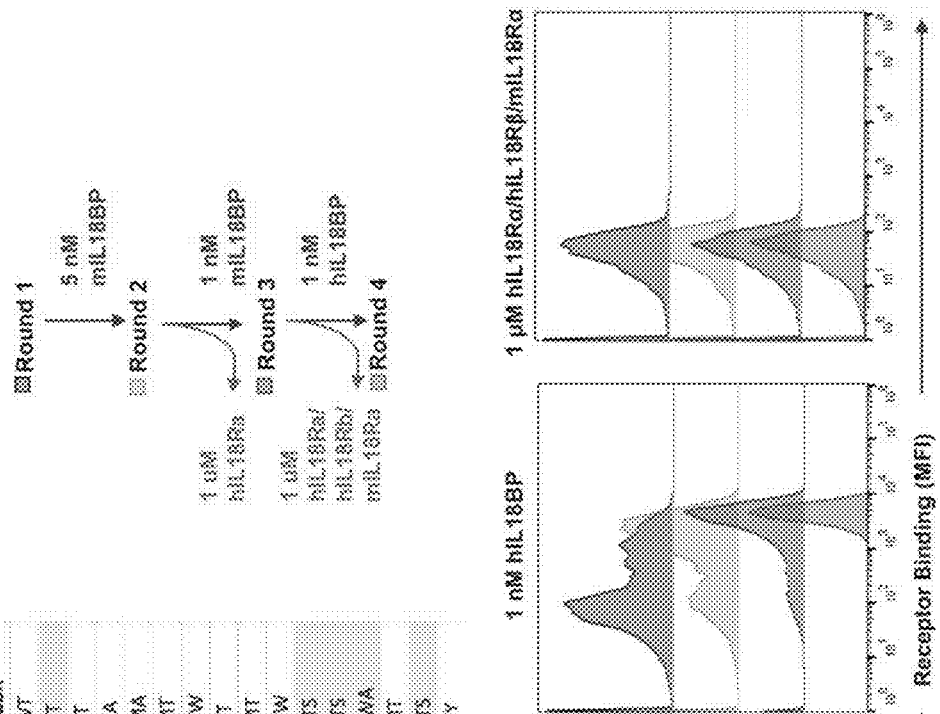
FIG. 20A
FIG. 20B
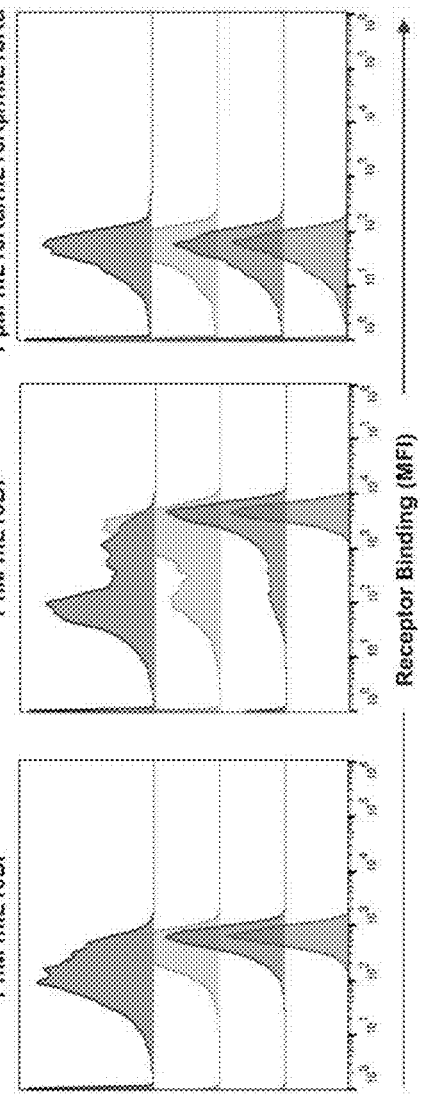
FIG. 20C

FIG. 21

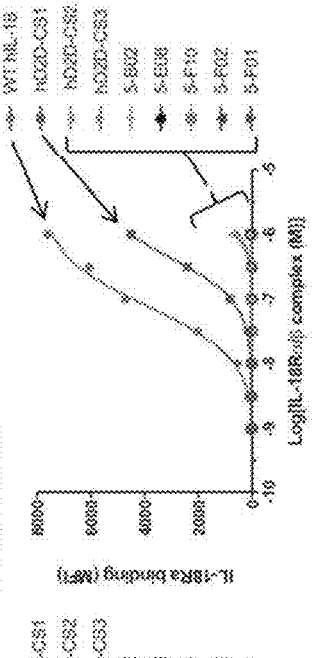
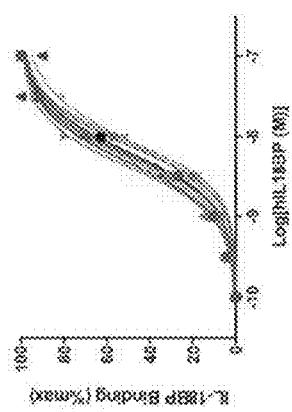
FIG. 22A
FIG. 22B
FIG. 22C

| WT mIL-18 | 1 N | 5 L | 17 D | 30 E | 33 T | 34 D | 35 I | 36 D | 50 M | 102 Q | 104 R | 108 H | 109 N | 111 M | 129 D | 130 D | SEQ ID NO: |
|---|---|---|---|---|---|---|---|---|---|---|---|---|---|---|---|---|---|
| mD2D-A5 | Y | Y | Q | A | G | Y | T | V |   | L | E |   | R | L |   | E | 126 |
| mD2D-A6 | D |   |   | A | G | S |   | A | F | L | A | D |   | I | A | T | 127 |
| mD2D-A7 | Y |   | G | R | A |   | T | V | F | I | P | A | S |   | A | G | 128 |
| mD2D-A8 | H |   |   | K | E | Y | T | V |   | I | A | D | R | I |   | N | 129 |
| mD2D-A9 | Y |   | A | A | A |   | K | G |   | L | P | D | T |   | F | G | 130 |
| mD2D-A11 | Y |   | E |   | A | G |   | R | H | I | P | A | S | L |   |   | 131 |
| mD2D-A12 | H |   |   | R | G | A |   | G | F | I | P | D | S | L | V |   | 132 |
| mD2D-B4 | H |   | S | T | G | S |   | V |   | I | G | D |   | I |   | R | 133 |
| mD2D-B7 | Y |   | S | R | E |   | T | P | F | I |   | D | S | L | F | E | 134 |
| mD2D-B11 | H |   | A | G |   | A | T | V | F | I | P | D | S | L |   | N | 135 |
| mD2D-B12 |   |   | N | K | E | Y | T | L | F | I | P | D |   | L | Y | E | 136 |
| mD2D-C1 | Y |   | G | A | E | A | T | R | F | I | G | A |   |   |   | G | 137 |
| mD2D-C3 |   |   | G | A | R | A |   | L | F | L | G | D |   | L |   | R | 138 |
| mD2D-C5 | Y |   | A | A | E | A | T | A | F | I | G | A | S |   |   | G | 139 |
| mD2D-C6 | L |   | G | A | G | A | T | L |   | L | P | D | T |   | A | S | 140 |
| mD2D-C9 |   |   | G |   | A | Y | T | V | F | I | G | D | S |   | Y |   | 141 |
| mD2D-C10 | D |   |   | K | E | S | K | P | F | L | A | A | S | L | A | N | 142 |
| mD2D-C11 | L |   | G | A | G |   | K | V |   | I | P | D |   | L |   | E | 143 |
| mD2D-D1 | Y | H | Q | R | A | A | T | R |   | L | G | D |   |   |   |   | 144 |
| mD2D-D9 |   |   | Q | T | E | S |   | G | F | L | A | A |   | L |   | S | 145 |
| mD2D-D12 | F | H | G | G | G |   | R | V |   | I | A | D | S | I |   | G | 146 |
| mD2D-E3 | V | H | G | K |   | Y |   |   |   | L | A | D | T |   | A | Q | 147 |
| mD2D-E4 |   |   | G | A |   | A | T | R |   | I | Q | A |   | I | F | R | 148 |
| mD2D-E5 | D |   | G | G | A | Y |   | G | F | I | A |   | S | I | S | G | 149 |
| mD2D-E7 | Y |   |   | R | G | S |   | A |   | I | P | A | T | L |   | G | 150 |
| mD2D-E8 | Y |   | E | T | E | A |   | G | F | I | G | D | R |   |   | G | 151 |
| mD2D-E9 | F |   | N |   | E | Y | R | L |   | L | P | A | S | L | S |   | 152 |
| mD2D-E10 |   |   | N | A | E |   | R | L |   | L | G | D |   |   |   | H | 153 |
| mD2D-E11 | Y |   | A | R | G | Y |   | L | L | L | P | D | T | I |   | N | 154 |
| mD2D-E12 | Y |   |   | G | A |   | T | A | F | I | P | D | S |   | A |   | 155 |
| mD2D-F3 | D |   | G |   | A | Y |   | A | F | I | P | D | S | I | A |   | 156 |
| mD2D-F4 |   |   | E | R | K | Y |   | L | F | L | G | D |   |   | Y | G | 157 |
| mD2D-F5 | D |   | E | T | A | Y |   | L | F | I | A | D | S | L |   | T | 158 |
| mD2D-F7 | D |   | N | K | E | S | T | A |   | L | G | A | S | L | A | G | 159 |
| mD2D-F8 | H |   | E | A | E | A |   | G | F | I | G | D | T | L |   | G | 160 |
| mD2D-F9 | I |   | E | K | R | Y |   | V | F | I | E | A | S | L |   | E | 161 |
| mD2D-G1 | Y |   | A | T | G | Y | T | L | L | I | P |   |   | I |   | R | 162 |
| mD2D-G7 |   |   | N | R | A | S | T | A |   | I | G |   |   | I |   |   | 163 |
| mD2D-G9 | D |   | G |   | K |   | R | A | F | L | A |   | S |   |   | E | 164 |
| mD2D-H7 | I |   | E | A |   |   |   | A |   | L | P | D | I |   | Y | G | 165 |
| mD2D-E1 | Y |   | E | A |   | T | L | F | L | G | D |   |   |   |   | T | 166 |
| mD2D-A10 | H |   | G | K | K | Y |   | V |   | L | A |   |   | S | I | S | 169 |
| mD2D-F12 | Y |   | G |   | K | A | K | A | F | I | P | A | S |   |   | G | 171 |
| mD2D-E2 | L |   | G | G | G | S |   | P | F | I | H | A | T |   |   | N | 174 |
| mD2D-C4 | Y |   | S | T | A | Y | T | V | F | I | A | D | S | L |   | N | 176 |
| mD2D-C2 | Y |   | G | T | G | A | R | V | F | L | P | D |   | L | S | G | 178 |
| mD2D-A2 | D |   | G | G | K | A | T | G | F | I | A | A |   | L | A | G | 180 |
| mD2D-A1 | D |   | S | R | G | S |   | H | F | L | A | A |   | L |   | G | 182 |
| mD2D-D4 | Y |   | E | K | K |   | K | L | F | L | G | D |   | L | F | G | 184 |
| mD2D-A3 | Y |   | G | A | A | S | T | H | F | L | G | A |   | I |   |   | 186 |
| mD2D-B9 | Y |   | S | G | K | Y |   | V | F | L | G | D | T |   | S | G | 190 |

FIG. 23

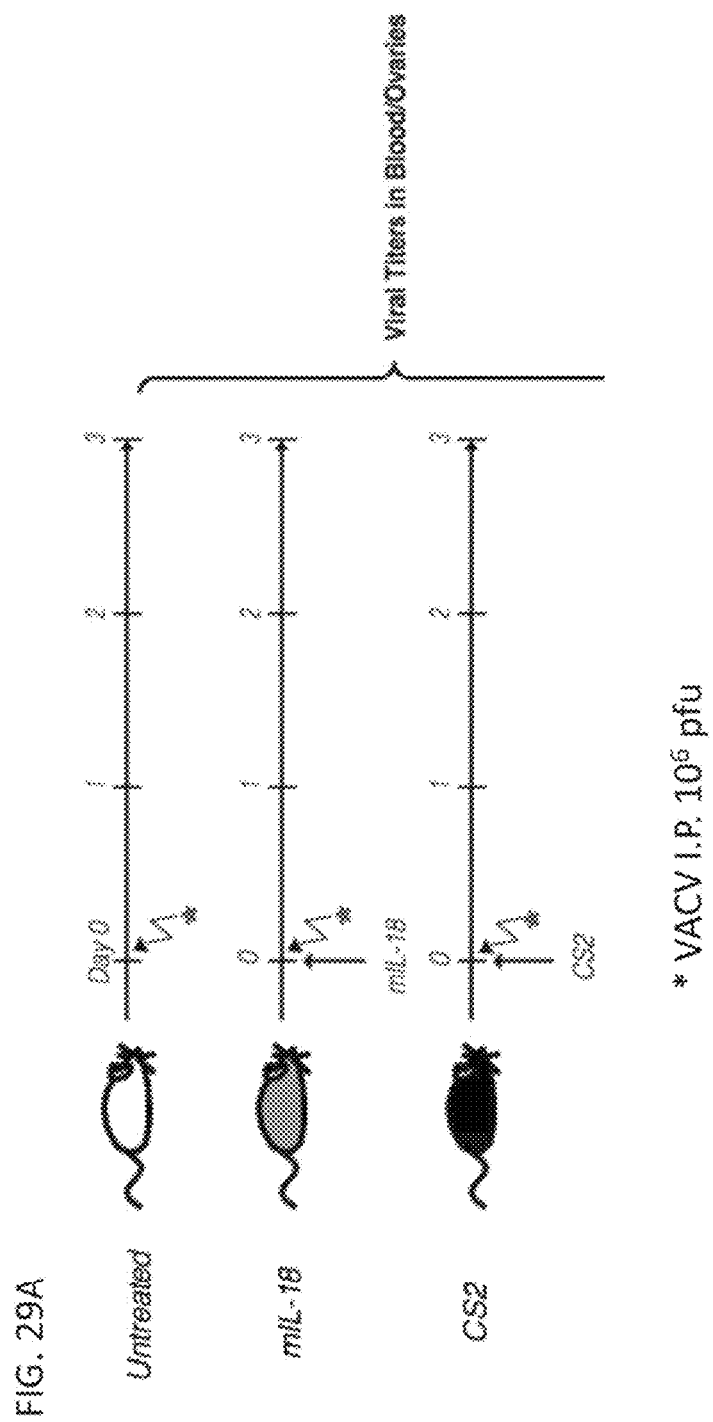

FIG. 34
Preparation #1
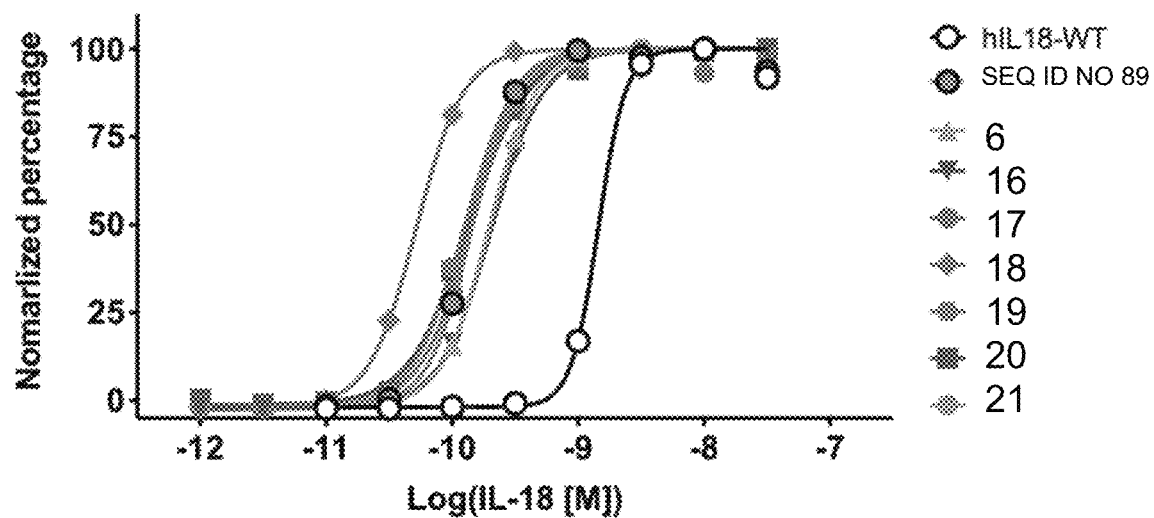
Preparation #2
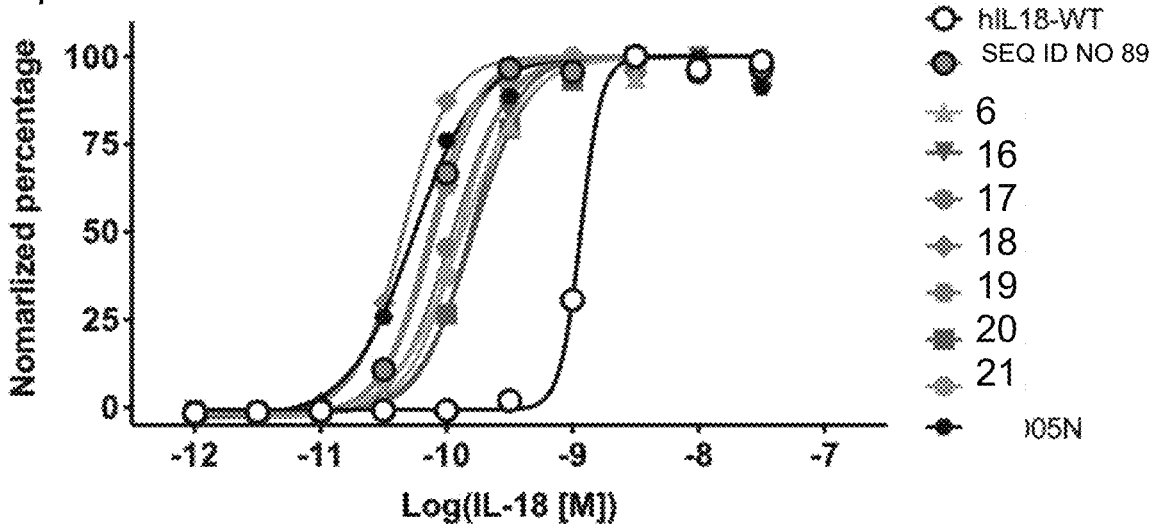

FIG. 40
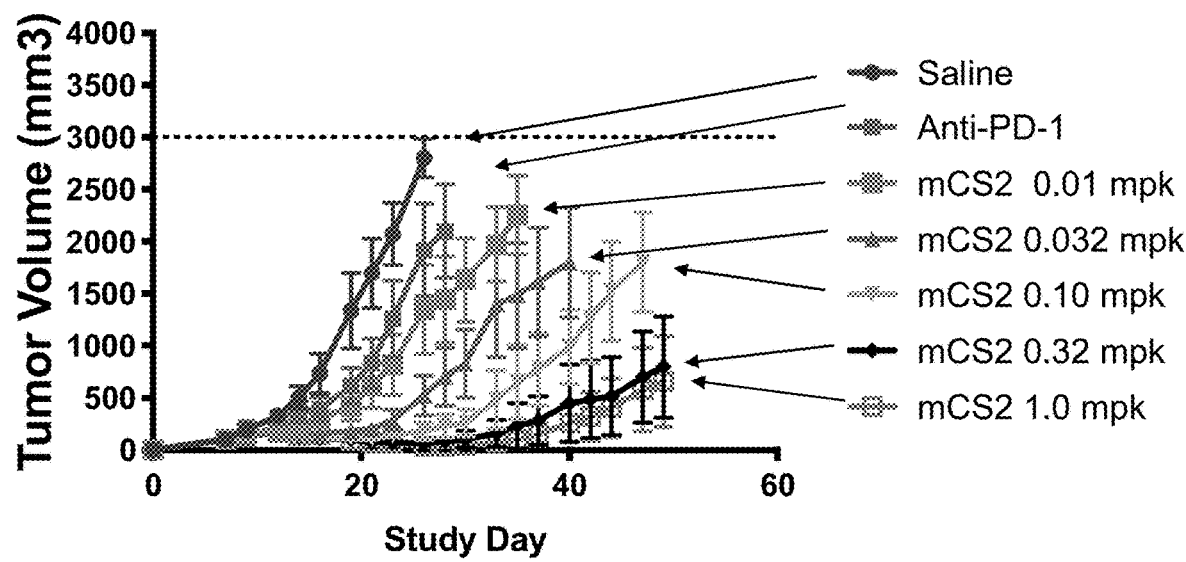
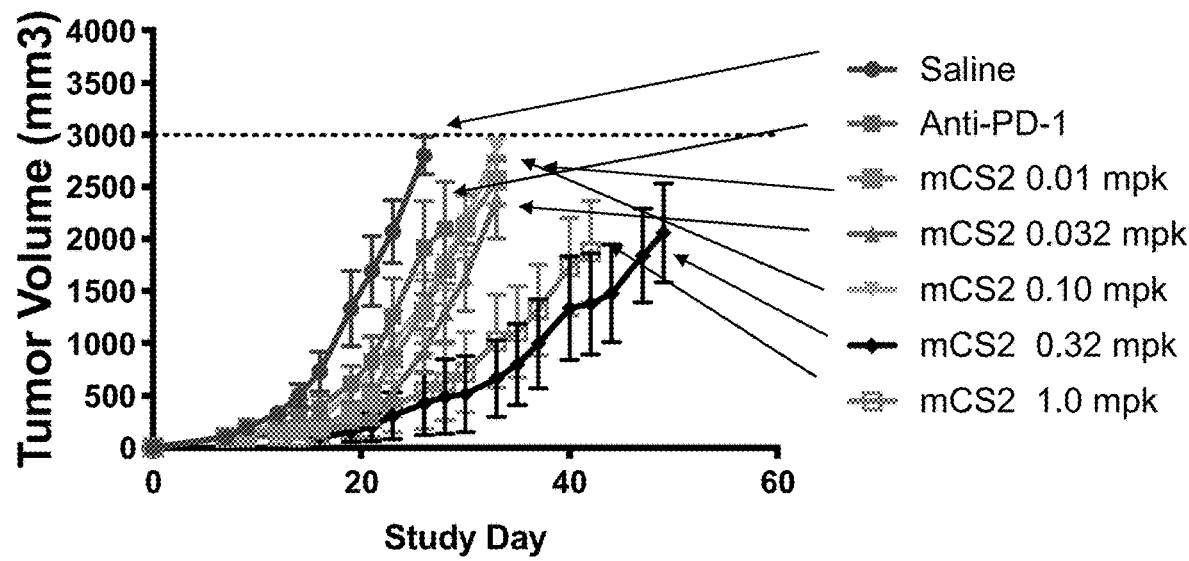

SEC of final SEQ ID NO 89 material:

```
                        SEQUENCE LISTING

Sequence total quantity: 222
SEQ ID NO: 1           moltype = AA  length = 157
FEATURE                Location/Qualifiers
source                 1..157
                       mol_type = protein
                       organism = synthetic construct
SEQUENCE: 1
YFGKLESKLS VIRNLNDQVL FIDQGNRPLF EDMTDSDSRD NAPRTIFIIS KYSDSLARGL   60
AVTISVKSEK ISTLSSENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 2           moltype = AA  length = 157
FEATURE                Location/Qualifiers
source                 1..157
                       mol_type = protein
                       organism = synthetic construct
SEQUENCE: 2
YFGKLESKLS VIRNLNDQVL FIDQGNRPLF EDMTDSDCRD NAPRTIFIIS KYSDSLARGL   60
AVTISVKSEK ISTLSSENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 3           moltype = AA  length = 157
FEATURE                Location/Qualifiers
source                 1..157
                       mol_type = protein
                       organism = synthetic construct
SEQUENCE: 3
YFGKLESKLS VIRNLNDQVL FIDQGNRPLF EDMTDSDSRD NAPRTIFIIS KYSDSLARGL   60
AVTISVKCEK ISTLSSENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 4           moltype = AA  length = 157
FEATURE                Location/Qualifiers
source                 1..157
                       mol_type = protein
                       organism = synthetic construct
SEQUENCE: 4
```

-continued

```
YFGKLESKLS VIRNLNDQVL FIDQGNRPLF EDMTDSDSRD NAPRTIFIIS KYSDSLARGL  60
AVTISVKSEK ISTLSCENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 5           moltype = AA  length = 157
FEATURE                Location/Qualifiers
source                 1..157
                       mol_type = protein
                       organism = synthetic construct
SEQUENCE: 5
YFGKLESKLS VIRNLNDQVL FIDQGNRPLF EDMTDSDSRD NAPRTIFIIS KYSDSLARGL  60
AVTISVKSEK ISTLSSENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 6           moltype = AA  length = 157
FEATURE                Location/Qualifiers
source                 1..157
                       mol_type = protein
                       organism = synthetic construct
SEQUENCE: 6
YFGKLESKLS VIRNLNDQVL FIDQGNRPLF EDMTDSDSRD NAPRTIFIIS KYSDSLARGL  60
AVTISVKSEK ISTLSCENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 7           moltype = AA  length = 157
FEATURE                Location/Qualifiers
source                 1..157
                       mol_type = protein
                       organism = synthetic construct
SEQUENCE: 7
YFGKLESKLS VIRNLNDQVL FIDQGNRPLF EDMTDSDSRD NAPRTIFIIS KYSDSLARGL  60
AVTISVKCEK ISTLSSENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 8           moltype = AA  length = 157
FEATURE                Location/Qualifiers
source                 1..157
                       mol_type = protein
                       organism = synthetic construct
SEQUENCE: 8
YFGKLESKLS VIRNLNDQVL FIDQGNRPLF EDMTDSDSRD NAPRTIFIIS KYSDSLARGL  60
AVTISVKCEK ISTLSCENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 9           moltype = AA  length = 157
FEATURE                Location/Qualifiers
source                 1..157
                       mol_type = protein
                       organism = synthetic construct
SEQUENCE: 9
YFGKLESKLS VIRNLNDQVL FIDQGNRPLF EDMTDSDCRD NAPRTIFIIS KYSDSLARGL  60
AVTISVKSEK ISTLSSENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 10          moltype = AA  length = 157
FEATURE                Location/Qualifiers
source                 1..157
                       mol_type = protein
                       organism = synthetic construct
SEQUENCE: 10
YFGKLESKLS VIRNLNDQVL FIDQGNRPLF EDMTDSDCRD NAPRTIFIIS KYSDSLARGL  60
AVTISVKSEK ISTLSCENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 11          moltype = AA  length = 157
FEATURE                Location/Qualifiers
source                 1..157
                       mol_type = protein
                       organism = synthetic construct
SEQUENCE: 11
YFGKLESKLS VIRNLNDQVL FIDQGNRPLF EDMTDSDCRD NAPRTIFIIS KYSDSLARGL  60
AVTISVKCEK ISTLSSENKI ISFKEMNPPD NIKDTKSDII FFQRDVPGHS RKMQFESSSY  120
EGYFLASEKE RDLFKLILKK EDELGDRSIM FTVQNED                          157

SEQ ID NO: 12          moltype = AA  length = 157
FEATURE                Location/Qualifiers
source                 1..157
                       mol_type = protein
                       organism = synthetic construct
```

```
SEQUENCE: 12
YFGKLESKLS VIRNLNDQVL FIDQGNRPLF EDMTDSDSRD NAPRTIFIIS KYSDSLARGL    60
AVTISVKCEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 13           moltype = AA   length = 157
FEATURE                 Location/Qualifiers
source                  1..157
                        mol_type = protein
                        organism = synthetic construct
SEQUENCE: 13
YFGKLESKLS VIRNLNDQVL FIDQGNRPLF EDMTDSDCRD NAPRTIFIIS KYSDSLARGL    60
AVTISVKSEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 14           moltype = AA   length = 157
FEATURE                 Location/Qualifiers
source                  1..157
                        mol_type = protein
                        organism = synthetic construct
SEQUENCE: 14
YFGKLESKLS VIRNLNDQVL FIDQGNRPLF EDMTDSDCRD NAPRTIFIIS KYSDSLARGL    60
AVTISVKCEK ISTLSSENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 15           moltype = AA   length = 157
FEATURE                 Location/Qualifiers
source                  1..157
                        mol_type = protein
                        organism = synthetic construct
SEQUENCE: 15
YFGKLESKLS VIRNLNDQVL FIDQGNRPLF EDMTDSDCRD NAPRTIFIIS KYSDSLARGL    60
AVTISVKCEK ISTLSCENKI ISFKEMNPPD NIKDTKSDII FFQRDVPGHS RKMQFESSSY   120
EGYFLASEKE RDLFKLILKK EDELGDRSIM FTVQNED                            157

SEQ ID NO: 16           moltype = AA   length = 157
FEATURE                 Location/Qualifiers
source                  1..157
                        mol_type = protein
                        organism = synthetic construct
SEQUENCE: 16
YFGKLESKLS VIRNLNDQVL FIDQGNRPLF EDMTDSDSRD NAPRTIFIIS KYSDSLARGL    60
AVTISVKGEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 17           moltype = AA   length = 157
FEATURE                 Location/Qualifiers
source                  1..157
                        mol_type = protein
                        organism = synthetic construct
SEQUENCE: 17
YFGKLESKLS VIRNLNDQVL FIDQGNRPLF EDMTDSDSRD NAPRTIFIIS KYSDSLARGL    60
AVTISVKAEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 18           moltype = AA   length = 157
FEATURE                 Location/Qualifiers
source                  1..157
                        mol_type = protein
                        organism = synthetic construct
SEQUENCE: 18
YFGKLESKLS VIRNLNDQVL FIDQGNRPLF EDMTDSDSRD NAPRTIFIIS KYSDSLARGL    60
AVTISVKVEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 19           moltype = AA   length = 157
FEATURE                 Location/Qualifiers
source                  1..157
                        mol_type = protein
                        organism = synthetic construct
SEQUENCE: 19
YFGKLESKLS VIRNLNDQVL FIDQGNRPLF EDMTDSDSRD NAPRTIFIIS KYSDSLARGL    60
AVTISVKDEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 20           moltype = AA   length = 157
FEATURE                 Location/Qualifiers
source                  1..157
                        mol_type = protein
```

```
                        organism = synthetic construct
SEQUENCE: 20
YFGKLESKLS VIRNLNDQVL FIDQGNRPLF EDMTDSDSRD NAPRTIFIIS KYSDSLARGL   60
AVTISVKEEK ISTLSCENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 21           moltype = AA   length = 157
FEATURE                 Location/Qualifiers
source                  1..157
                        mol_type = protein
                        organism = synthetic construct
SEQUENCE: 21
YFGKLESKLS VIRNLNDQVL FIDQGNRPLF EDMTDSDSRD NAPRTIFIIS KYSDSLARGL   60
AVTISVKNEK ISTLSCENKI ISFKEMNPPD NIKDTKSDII FFQRDVPGHS RKMQFESSSY  120
EGYFLACEKE RDLFKLILKK EDELGDRSIM FTVQNED                          157

SEQ ID NO: 22           moltype =    length =
SEQUENCE: 22
000

SEQ ID NO: 23           moltype =    length =
SEQUENCE: 23
000

SEQ ID NO: 24           moltype = AA   length = 4
FEATURE                 Location/Qualifiers
source                  1..4
                        mol_type = protein
                        organism = synthetic construct
SEQUENCE: 24
AAAA                                                                4

SEQ ID NO: 25           moltype =    length =
SEQUENCE: 25
000

SEQ ID NO: 26           moltype = AA   length = 96
FEATURE                 Location/Qualifiers
source                  1..96
                        mol_type = protein
                        organism = synthetic construct
SEQUENCE: 26
DSEVNQEAKP EVKPEVKPET HINLKVSDGS SEIFFKIKKT TPLRRLMEAF AKRQGKEMDS   60
LRFLYDGIRI QADQAPEDLD MEDNDIIEAH REQIGG                            96

SEQ ID NO: 27           moltype = AA   length = 108
FEATURE                 Location/Qualifiers
source                  1..108
                        mol_type = protein
                        organism = synthetic construct
SEQUENCE: 27
MGHHHHHHGS LQDSEVNQEA KPEVKPEVKP ETHINLKVSD GSSEIFFKIK KTTPLRRLME   60
AFAKRQGKEM DSLRFLYDGI RIQADQAPED LDMEDNDIIE AHREQIGG              108

SEQ ID NO: 28           moltype = AA   length = 219
FEATURE                 Location/Qualifiers
source                  1..219
                        mol_type = protein
                        organism = synthetic construct
SEQUENCE: 28
LVPELNEKDD DQVQKALASR ENTQLMNRDN IEITVRDFKT LAPRRWLNDT IIEFFMKYIE   60
KSTPNTVAFN SFFYTNLSER GYQGVRRWMK RKKTQIDKLD KIFTPINLNQ SHWALGIIDL  120
KKKTIGYVDS LSNGPNAMSF AILTDLQKYV MEESKHTIGE DFDLIHLDCP QQPNGYDCGI  180
YVCMNTLYGS ADAPLDFDYK DAIRMRRFIA HLILTDALK                        219

SEQ ID NO: 29           moltype = AA   length = 233
FEATURE                 Location/Qualifiers
source                  1..233
                        mol_type = protein
                        organism = synthetic construct
SEQUENCE: 29
MGSSHHHHHH SSGSLVPELN EKDDDQVQKA LASRENTQLM NRDNIEITVR DFKTLAPRRW   60
LNDTIIEFFM KYIEKSTPNT VAFNSFFYTN LSERGYQGVR RWMKRKKTQI DKLDKIFTPI  120
NLNQSHWALG IIDLKKKTIG YVDSLSNGPN AMSFAILTDL QKYVMEESKH TIGEDFDLIH  180
LDCPQQPNGY DCGIYVCMNT LYGSADAPLD FDYKDAIRMR RFIAHLILTD ALK        233

SEQ ID NO: 30           moltype = AA   length = 157
FEATURE                 Location/Qualifiers
source                  1..157
```

```
                            mol_type = protein
                            organism = Homo sapiens
SEQUENCE: 30
YFGKLESKLS VIRNLNDQVL FIDQGNRPLF EDMTDSDCRD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 31               moltype = AA  length = 157
FEATURE                     Location/Qualifiers
source                      1..157
                            mol_type = protein
                            organism = Mus musculus
SEQUENCE: 31
NFGRLHCTTA VIRNINDQVL FVDKRQPVFE DMTDIDQSAS EPQTRLIIYM YKDSEVRGLA   60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                           157

SEQ ID NO: 32               moltype = AA  length = 193
FEATURE                     Location/Qualifiers
source                      1..193
                            mol_type = protein
                            organism = synthetic construct
SEQUENCE: 32
MAAEPVEDNC INFVAMKFID NTLYFIAEDD ENLESDYFGK LESKLSVIRN LNDQVLFIDQ   60
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NED                                                    193

SEQ ID NO: 33               moltype = AA  length = 192
FEATURE                     Location/Qualifiers
source                      1..192
                            mol_type = protein
                            organism = synthetic construct
SEQUENCE: 33
MAAMSEDSCV NFKEMMFIDN TLYFIPEENG DLESDNFGRL HCTTAVIRNI NDQVLFVDKR   60
QPVFEDMTDI DQSASEPQTR LIIYMYKDSE VRGLAVTLSV KDSKMSTLSC KNKIISFEEM  120
DPPENIDDIQ SDLIFFQKRV PGHNKMEFES SLYEGHFLAC QKEDDAFKLI LKKKDENGDK  180
SVMFTLTNLH QS                                                     192

SEQ ID NO: 34               moltype = AA  length = 157
FEATURE                     Location/Qualifiers
source                      1..157
                            mol_type = protein
                            organism = synthetic construct
SEQUENCE: 34
YFGKLESKLS VIRNLNDQVL FIDQGNRPLF EDMTDSDCRD NAPRTIFIIS TYKDSQPRGK   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTVQNED                           157

SEQ ID NO: 35               moltype = AA  length = 157
FEATURE                     Location/Qualifiers
source                      1..157
                            mol_type = protein
                            organism = synthetic construct
SEQUENCE: 35
YFGKLESKLS VIRNLNDQVL FIDQGNRPLF EDMTDSDCRD NAPRTIFIIS TYKDKQPRAK   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                           157

SEQ ID NO: 36               moltype = AA  length = 157
FEATURE                     Location/Qualifiers
source                      1..157
                            mol_type = protein
                            organism = synthetic construct
SEQUENCE: 36
RFGKLESKLS VIRNLNDQVL FIDQGNRPLF EDMTDSDCRD NAPRTIFIIS TYKDSQPRGK   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTVQNED                           157

SEQ ID NO: 37               moltype = AA  length = 157
FEATURE                     Location/Qualifiers
source                      1..157
                            mol_type = protein
                            organism = synthetic construct
SEQUENCE: 37
RFGKLESKLS VIRNLNDQVL FIDQGNRPLF EDMTDSDCRD NAPRTIFIIS TYRDSQPRGK   60
AVTISVKCEK ISTLSCENKI ISFKEMNPPD NIKDTKSDII FFQRNVPGHK YKMQFESSSY  120
EGYFLACEKE RDLFKLILKK EDELGDRSIM FTVQNED                           157
```

```
SEQ ID NO: 38              moltype = AA  length = 157
FEATURE                    Location/Qualifiers
source                     1..157
                           mol_type = protein
                           organism = synthetic construct
SEQUENCE: 38
YFGKLESQLS VIRNLNDQVL FIDQGNRPLF EDMTDSDCRD NAPRTIFIIS TYKDKQPRTK   60
AVTISVKCEK ISTLSCENKI ISFKEMNPPD NIKDTKSDII FFQRRVPGHH NKMQFESSSY  120
EGYFLACEKE RDLFKLILKK EDELGDRSIM FTVQKED                          157

SEQ ID NO: 39              moltype = AA  length = 157
FEATURE                    Location/Qualifiers
source                     1..157
                           mol_type = protein
                           organism = synthetic construct
SEQUENCE: 39
YFGKLESRLS VIRNLNDQVL FIDQGNRPLF EDMTDSDCRD NAPRTIFIIS KYKDKQPRAQ   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                          157

SEQ ID NO: 40              moltype = AA  length = 157
FEATURE                    Location/Qualifiers
VARIANT                    60
                           note = Any amino acid
source                     1..157
                           mol_type = protein
                           organism = synthetic construct
SEQUENCE: 40
YFGKLESRLS VIRNLNDQVL FIDQGNRPLF EDMTDSDCRD NAPRTIFIIS DYKDKQPRAX   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTIQNED                          157

SEQ ID NO: 41              moltype = AA  length = 157
FEATURE                    Location/Qualifiers
source                     1..157
                           mol_type = protein
                           organism = synthetic construct
SEQUENCE: 41
YFGKHESKLS VIRNLNDQVL FIDQGNRPLF EDMTDSDCRD NAPRTIFIIS TYRDSQPRGK   60
AVTISVKCEK ISTLSCENKI ISFKEMNPPD NIKDTKSDII FFQRDVPGHN NKMQFESSSY  120
EGYFLACEKE RDLFKLILKK EDELGDRSIM FTTQNED                          157

SEQ ID NO: 42              moltype = AA  length = 157
FEATURE                    Location/Qualifiers
source                     1..157
                           mol_type = protein
                           organism = synthetic construct
SEQUENCE: 42
YFGKIESKLS VIRNLNDQVL FIDQGNRPLF EDMTDSDCRD NAPRTIFIIS KYKDKQPRAQ   60
AVTISVKCEK ISTLSCENKI ISFKEMNPPD NIKDTKSDII FFQRKVPGHQ HKMQFESSSY  120
EGYFLACEKE RDLFKLILKK EDELGDRSIM FTVQKED                          157

SEQ ID NO: 43              moltype = AA  length = 157
FEATURE                    Location/Qualifiers
source                     1..157
                           mol_type = protein
                           organism = synthetic construct
SEQUENCE: 43
YFGKIESKLS VIRNLNDQVL FIDQGNRPLF EDMTDSDCRD NAPRTIFIIS TYKDRQPRGK   60
AVTISVKCEK ISTLSCENKI ISFKEMNPPD NIKDTKSDII FFERDVPGHH HKMQFESSSY  120
EGYFLACEKE RDLFKLILKK EDELGDRSIM FTIQNED                          157

SEQ ID NO: 44              moltype = AA  length = 157
FEATURE                    Location/Qualifiers
source                     1..157
                           mol_type = protein
                           organism = synthetic construct
SEQUENCE: 44
YFGKIESKLS VIRNLNDQVL FIDQGNRPLF EDMTDSDCRD NAPRTIFIIS TYKDKQPRGK   60
AVTISVKCEK ISTLSCENKI ISFKEMNPPD NIKDTKSDII FFQRDVPGHK HKMQFESSSY  120
EGYFLACEKE RDLFKLILKK EDELGDRSIM FTTQHED                          157

SEQ ID NO: 45              moltype = AA  length = 157
FEATURE                    Location/Qualifiers
source                     1..157
                           mol_type = protein
                           organism = synthetic construct
SEQUENCE: 45
YFGKIESKLS VIRNLNDQVL FIDQGNRPLF EDMTDSDCRD NAPRTIFIIS TYKDKQPRAK   60
```

```
AVTISVKCEK ISTLSCENKI ISFKEMNPPD NIKDTKSDII FFQRRVPGHH HKMQFESSSY    120
EGYFLACEKE RDLFKLILKK EDELGDRSIM FTIQKED                             157

SEQ ID NO: 46          moltype = AA  length = 157
FEATURE                Location/Qualifiers
source                 1..157
                       mol_type = protein
                       organism = synthetic construct
SEQUENCE: 46
YFGKIESRLS VIRNLNDQVL FIDQGNRPLF EDMTDSDCRD NAPRTIFIIS TYKDKQPRGK    60
AVTISVKCEK ISTLSCENKI ISFKEMNPPD NIKDTKSDII FFQRDVPGHD YKMQFESSSY    120
EGYFLACEKE RDLFKLILKK EDELGDRSIM FTIQKED                             157

SEQ ID NO: 47          moltype = AA  length = 157
FEATURE                Location/Qualifiers
source                 1..157
                       mol_type = protein
                       organism = synthetic construct
SEQUENCE: 47
YFGKYESRLS VIRNLNDQVL FIDQGNRPLF EDMTDSDCRD NAPRTIFIIS TYRDSQPRGK    60
AVTISVKCEK ISTLSCENKI ISFKEMNPPD NIKDTKSDII FFQRDVPGHE HKMQFESSSY    120
EGYFLACEKE RDLFKLILKK EDELGDRSIM FTVQKED                             157

SEQ ID NO: 48          moltype = AA  length = 157
FEATURE                Location/Qualifiers
source                 1..157
                       mol_type = protein
                       organism = synthetic construct
SEQUENCE: 48
HFGKYESKLS VIRNLNDQVL FIDQGNRPLF EDMTDSDCRD NAPRTIFIIS TYRDSQPRGK    60
AVTISVKCEK ISTLSCENKI ISFKEMNPPD NIKDTKSDII FFQRDVPGHH NKMQFESSSY    120
EGYFLACEKE RDLFKLILKK EDELGDRSIM FTVQKED                             157

SEQ ID NO: 49          moltype = AA  length = 157
FEATURE                Location/Qualifiers
source                 1..157
                       mol_type = protein
                       organism = synthetic construct
SEQUENCE: 49
RFGKLESKLS VIRNLNDQVL FIDQGNRPLF EDMTDSDCRD NAPRTIFIIS TYRDSQPRAK    60
AVTISVKCEK ISTLSCENKI ISFKEMNPPD NIKDTKSDII FFQRDVPGHQ HKMQFESSSY    120
EGYFLACEKE RDLFKLILKK EDELGDRSIM FTAQKED                             157

SEQ ID NO: 50          moltype = AA  length = 157
FEATURE                Location/Qualifiers
source                 1..157
                       mol_type = protein
                       organism = synthetic construct
SEQUENCE: 50
RFGKLESRLS VIRNLNDQVL FIDQGNRPLF EDMTDSDCRD NAPRTIFIIS DYRDSQPRGR    60
AVTISVKCEK ISTLSCENKI ISFKEMNPPD NIKDTKSDII FFKRNVPGHK YKMQFESSSY    120
EGYFLACEKE RDLFKLILKK EDELGDRSIM FTVQHED                             157

SEQ ID NO: 51          moltype = AA  length = 157
FEATURE                Location/Qualifiers
source                 1..157
                       mol_type = protein
                       organism = synthetic construct
SEQUENCE: 51
RFGKLESRLS VIRNLNDQVL FIDQGNRPLF EDMTDSDCRD NAPRTIFIIS NYRDSQPRGQ    60
AVTISVKCEK ISTLSCENKI ISFKEMNPPD NIKDTKSDII FFKRRVPGHN HKMQFESSSY    120
EGYFLACEKE RDLFKLILKK EDELGDRSIM FTVQKED                             157

SEQ ID NO: 52          moltype = AA  length = 157
FEATURE                Location/Qualifiers
source                 1..157
                       mol_type = protein
                       organism = synthetic construct
SEQUENCE: 52
RFGKLESRLS VIRNLNDQVL FIDQGNRPLF EDMTDSDCRD NAPRTIFIIS TYKDSQPRGK    60
AVTISVKCEK ISTLSCENKI ISFKEMNPPD NIKDTKSDII FFQRDVPGHK HKMQFESSSY    120
EGYFLACEKE RDLFKLILKK EDELGDRSIM FTVQNED                             157

SEQ ID NO: 53          moltype = AA  length = 157
FEATURE                Location/Qualifiers
source                 1..157
                       mol_type = protein
                       organism = synthetic construct
SEQUENCE: 53
```

```
RFGKHESKLS VIRNLNDQVL FIDQGNRPLF EDMTDSDCRD NAPRTIFIIS TYRDSQPRGK   60
AVTISVKCEK ISTLSCENKI ISFKEMNPPD NIKDTKSDII FFERNVPGHK YKMQFESSSY  120
EGYFLACEKE RDLFKLILKK EDELGDRSIM FTVQNED                          157

SEQ ID NO: 54            moltype = AA   length = 157
FEATURE                  Location/Qualifiers
VARIANT                  155
                         note = Xaa can be any naturally occurring amino acid
source                   1..157
                         mol_type = protein
                         organism = synthetic construct
SEQUENCE: 54
RFGKLESRLS VIRNLNDQVL FIDQGNRPLF EDMTDSDCRD NAPRTIFIIS TYRDSQPRAK   60
AVTISVKCEK ISTLSCENKI ISFKEMNPPD NIKDTKSDII FFERDVPGHQ HKMQFESSSY  120
EGYFLACEKE RDLFKLILKK EDELGDRSIM FTIQXED                          157

SEQ ID NO: 55            moltype = AA   length = 157
FEATURE                  Location/Qualifiers
source                   1..157
                         mol_type = protein
                         organism = synthetic construct
SEQUENCE: 55
RFGKLESRLS VIRNLNDQVL FIDQGNRPLF EDMTDSDCRD NAPRTIFIIS TYRDSQPRTK   60
AVTISVKCEK ISTLSCENKI ISFKEMNPPD NIKDTKSDII FFQRNVPGHH DKMQFESSSY  120
EGYFLACEKE RDLFKLILKK EDELGDRSIM FTVQHED                          157

SEQ ID NO: 56            moltype = AA   length = 157
FEATURE                  Location/Qualifiers
source                   1..157
                         mol_type = protein
                         organism = synthetic construct
SEQUENCE: 56
RFGKLESRLS VIRNLNDQVL FIDQGNRPLF EDMTDSDCRD NAPRTIFIIS TYKDSQPRAK   60
AVTISVKCEK ISTLSCENKI ISFKEMNPPD NIKDTKSDII FFERDVPGHQ HKMQFESSSY  120
EGYFLACEKE RDLFKLILKK EDELGDRSIM FTIQKED                          157

SEQ ID NO: 57            moltype = AA   length = 157
FEATURE                  Location/Qualifiers
source                   1..157
                         mol_type = protein
                         organism = synthetic construct
SEQUENCE: 57
RFGKHESKLS VIRNLNDQVL FIDQGNRPLF EDMTDSDCRD NAPRTIFIIS TYRDSQPRGK   60
AVTISVKCEK ISTLSCENKI ISFKEMNPPD NIKDTKSDII FFERNVPGHK YKMQFESSSY  120
EGYFLACEKE RDLFKLILKK EDELGDRSIM FTVQNED                          157

SEQ ID NO: 58            moltype = AA   length = 157
FEATURE                  Location/Qualifiers
source                   1..157
                         mol_type = protein
                         organism = synthetic construct
SEQUENCE: 58
RFGKYESKLS VIRNLNDQVL FIDQGNRPLF EDMTDSDCRD NAPRTIFIIS TYKDSQPRTK   60
AVTISVKCEK ISTLSCDNKI ISFKEMNPPD NIKDTKSDII FFQRDVPGHK HKMQFESSSY  120
EGYFLACEKE RDLFKLILKK EDELGDRSIM FTVQNED                          157

SEQ ID NO: 59            moltype = AA   length = 157
FEATURE                  Location/Qualifiers
source                   1..157
                         mol_type = protein
                         organism = synthetic construct
SEQUENCE: 59
RFGKLESRLS VIRNLNDQVL FIDQGNRPLF EDMTDSDCRD NAPRTIFIIS TYRDSQPRTK   60
AVTISVKCEK ISTLSCENKI ISFKEMNPPD NIKDTKSDII FFQRKVPGHN HKMQFESSSY  120
EGYFLACEKE RDLFKLILKK EDELGDRSIM FTVQKED                          157

SEQ ID NO: 60            moltype = AA   length = 157
FEATURE                  Location/Qualifiers
source                   1..157
                         mol_type = protein
                         organism = synthetic construct
SEQUENCE: 60
NFGRLHCTTA VIRNINDQVL FVDKRQPVFE DMTDIDQSAS EPQTRLIIYG YADSRVRGKA   60
VTLSVKSKM STLSCKNKII SFEEMDPPEN IDDIQSDLIF FQKRVPGHNK MEFESSLYEG  120
HFLACQKEDD AFKLILKKKD ENGDKSVMFT LTNLHQS                          157

SEQ ID NO: 61            moltype = AA   length = 157
FEATURE                  Location/Qualifiers
source                   1..157
```

```
                            mol_type = protein
                            organism = synthetic construct
SEQUENCE: 61
HFGRLHCTTA VIRNINDQVL FVDKRQPVFE DMTDIDQSAS EPQTRLIIYA YGDSRARGKA    60
VTLSVKDSKM STLSCKNKII SFEEMDPPEN IDDIQSDLIF FQKRVPGHNK MEFESSLYEG   120
HFLACQKEDD AFKLILKKKD ENGDKSVMFT LTNLHQS                            157

SEQ ID NO: 62           moltype = AA  length = 157
FEATURE                 Location/Qualifiers
source                  1..157
                        mol_type = protein
                        organism = synthetic construct
SEQUENCE: 62
NFGRLHCTTA VIRNINDQVL FVDKRQPVFE DMTDIDQSAS EPQTRLIIYA YVDRRLRGKA    60
VTLSVKDSKM STLSCKNKII SFEEMDPPEN IDDIQSDLIF FQKKVPGHNK MEFESSLYEG   120
HFLACQKEDD AFKLILKKKD ENGDKSVMFT LTNLHQS                            157

SEQ ID NO: 63           moltype = AA  length = 157
FEATURE                 Location/Qualifiers
source                  1..157
                        mol_type = protein
                        organism = synthetic construct
SEQUENCE: 63
NFGRLHCTTA VIRNINDQVL FVDKRQPVFE DMTDIDQSAS EPQTRLIIYS YSDKHMRGKA    60
VTLSVKDSKM STLSCKNKII SFEEMDPPEN IDDIQSDLIF FQKLVPGHNK MEFESSLYEG   120
HFLACQKEDD AFKLILKKKD ENGDKSVMFT LTNLHQS                            157

SEQ ID NO: 64           moltype = AA  length = 157
FEATURE                 Location/Qualifiers
source                  1..157
                        mol_type = protein
                        organism = synthetic construct
SEQUENCE: 64
NFGRLHCTTA VIRNINDQVL FVDKRQPVFE DMTDIDQSAS EPQTRLIIYV YTDGRRRGKA    60
VTLSVKDSKM STLSCKNKII SFEEMDPPEN IDDIQSDLIF FQKKVPGHDK MEFESSLYEG   120
HFLACQKEDD AFKLILKKKD ENGDKSVMFT LTNLHQS                            157

SEQ ID NO: 65           moltype = AA  length = 157
FEATURE                 Location/Qualifiers
source                  1..157
                        mol_type = protein
                        organism = synthetic construct
SEQUENCE: 65
HFGRLHCTTA VIRNINDQVL FVDKRQPVFE DMTDIDQSAS EPQTRLIIYA YGDSHMRGKA    60
VTLSVKDSKM STLSCKNKII SFEEMDPPEN IDDIQSDLIF FQKQVPGHNK MEFESSLYEG   120
HFLACQKEDD AFKLILKKKD ENGDKSVMFT VTNLHQS                            157

SEQ ID NO: 66           moltype = AA  length = 157
FEATURE                 Location/Qualifiers
source                  1..157
                        mol_type = protein
                        organism = synthetic construct
SEQUENCE: 66
HFGRLHCTTA VIRNINDQVL FVDKRQPVFE DMTDIDQSAS EPQTRLIIYA YGDSNAGGRA    60
VTLSVKDSKM STLSCKNKII SFEEMDPPEN IDDIQSDLIF FQKKVPGHNK MEFESSLYEG   120
HFLACQKEDD AFKLILKKKD ENGDKSVMFT LTNLHQS                            157

SEQ ID NO: 67           moltype = AA  length = 157
FEATURE                 Location/Qualifiers
source                  1..157
                        mol_type = protein
                        organism = synthetic construct
SEQUENCE: 67
HFGRLHCTTA VIRNINDQVL FVDKRQPVFE DMTDIDQSAS EPQTRLIIYG YADSDARAKA    60
VTLSVKDSKM STLSCKNKII SFEEMDPPEN IDDIQSDLIF FQKSVPGHNK MEFESSLYEG   120
HFLACQKEDD AFKLILKKKD ENGDKSVMFT VTNLHQS                            157

SEQ ID NO: 68           moltype = AA  length = 157
FEATURE                 Location/Qualifiers
source                  1..157
                        mol_type = protein
                        organism = synthetic construct
SEQUENCE: 68
HFGRLHCTTA VIRNINDQVL FVDKRQPVFE DMTDIDQSAS EPQTRLIIYG YSDRGSKGKA    60
VTLSVKDSKM STLSCKNKII SFEEMDPPEN IDDIQSDLIF FQKQVPGHNK MEFESSLYEG   120
HFLACQKEDD AFKLILKKKD ENGDKSVMFT LTNLHQS                            157

SEQ ID NO: 69           moltype = AA  length = 157
FEATURE                 Location/Qualifiers
```

```
source                  1..157
                        mol_type = protein
                        organism = synthetic construct
SEQUENCE: 69
YFGRLHCTTA VIRNINDQVL FVDKRQPVFE DMTDIDQSAS EPQTRLIIYM YADRRARGKA   60
VTLSVKDSKM STLSCKNKII SFEEMDPPEN IDDIQSDLIF FQKKVPGHDK MEFESSLYEG  120
HFLACQKEDD AFKLILKKKD ENGDKSVMFT VTNLHQS                           157

SEQ ID NO: 70           moltype = AA   length = 157
FEATURE                 Location/Qualifiers
source                  1..157
                        mol_type = protein
                        organism = synthetic construct
SEQUENCE: 70
YFGRLHCTTA VIRNINDQVL FVDKRQPVFE DMTDIDQSAS EPQTRLIIYA YGDNRVRGKA   60
VTLSVKDSKM STLSCKNKII SFEEMDPPEN IDDIQSDLIF FQKRVPGHNK MEFESSLYEG  120
HFLACQKEDD AFKLILKKKD ENGDKSVMFT LTNLHQS                           157

SEQ ID NO: 71           moltype = AA   length = 157
FEATURE                 Location/Qualifiers
source                  1..157
                        mol_type = protein
                        organism = synthetic construct
SEQUENCE: 71
YFGRLHCTTA VIRNINDQVL FVDKRQPVFE DMTDIDQSAS EPQTRLIIYG YGDSERGGRA   60
VTLSVKDSKM STLSCKNKII SFEEMDPPEN IDDIQSDLIF FQKRVPGHDK MEFESSLYEG  120
HFLACQKEDD AFKLILKKKD ENGDKSVMFT LTNLHQS                           157

SEQ ID NO: 72           moltype = AA   length = 157
FEATURE                 Location/Qualifiers
source                  1..157
                        mol_type = protein
                        organism = synthetic construct
SEQUENCE: 72
YFGRLHCTTA VIRNINDQVL FVDKRQPVFE DMTDIDQSAS EPQTRLIIYT RTDGGQKGVA   60
VTLSVKDSKM STLSCKNKII SFEEMDPPEN IDDIQSDLIF FQKRVPGHDK MEFESSLYEG  120
HFLACQKEDD AFKLILKKKD ENGDKSVMFT LTNLHQS                           157

SEQ ID NO: 73           moltype = AA   length = 157
FEATURE                 Location/Qualifiers
source                  1..157
                        mol_type = protein
                        organism = synthetic construct
SEQUENCE: 73
YFGKLESKLS VIRNLNDQVL FIDQGNRPLF EDMTDSDCRD NAPRTIFIIS EYKDSELRGR   60
AVTISVKCEK ISTLSCENKI ISFKEMNPPD NIKDTKSDII FFPRAVPGHN RKVQFESSSY  120
EGYFLACEKE RDLFKLILKK EDELGDRSIM FTVQNED                           157

SEQ ID NO: 74           moltype = AA   length = 157
FEATURE                 Location/Qualifiers
source                  1..157
                        mol_type = protein
                        organism = synthetic construct
SEQUENCE: 74
YFGKLESKLS VIRNLNDQVL FIDQGNRPLF EDMTDSDCRD NAPRTIFIIS KYKDSAGRGL   60
AVTISVKCEK ISTLSCENKI ISFKEMNPPD NIKDTKSDII FFERDVPGHS NKVQFESSSY  120
EGYFLACEKE RDLFKLILKK EDELGDRSIM FTVQNED                           157

SEQ ID NO: 75           moltype = AA   length = 157
FEATURE                 Location/Qualifiers
source                  1..157
                        mol_type = protein
                        organism = synthetic construct
SEQUENCE: 75
YFGKLESKLS VIRNLNDQVL FIDQGNRPLF EDMTDSDCRD NAPRTIFIIS KYGDSAARGL   60
AVTISVKCEK ISTLSCENKI ISFKEMNPPD NIKDTKSDII FFQRSVPGHK RKMQFESSSY  120
EGYFLACEKE RDLFKLILKK EDELGDRSIM FTVQNED                           157

SEQ ID NO: 76           moltype = AA   length = 157
FEATURE                 Location/Qualifiers
source                  1..157
                        mol_type = protein
                        organism = synthetic construct
SEQUENCE: 76
YFGKLESKLS VIRNLNDQVL FIDQGNRPLF EDMTDSDCRD NAPRTIFIIS KYGDSRGRGL   60
AVTISVKCEK ISTLSCENKI ISFKEMNPPD NIKDTKSDII FFERDVPGHN SKRQFESSSY  120
EGYFLACEKE RDLFKLILKK EDELGDRSIM FTVQNED                           157

SEQ ID NO: 77           moltype = AA   length = 157
```

```
FEATURE                 Location/Qualifiers
source                  1..157
                        mol_type = protein
                        organism = synthetic construct
SEQUENCE: 77
YFGKLESKLS VIRNLNDQVL FIDQGNRPLF EDMTDSDCRD NAPRTIFIIS KYGDSVPRGL   60
AVTISVKCEK ISTLSCENKI ISFKEMNPPD NIKDTKSDII FFARAVPGHS RKTQFESSSY  120
EGYFLACEKE RDLFKLILKK EDELGDRSIM FTVQNED                           157

SEQ ID NO: 78           moltype = AA  length = 157
FEATURE                 Location/Qualifiers
source                  1..157
                        mol_type = protein
                        organism = synthetic construct
SEQUENCE: 78
YFGKLESKLS VIRNLNDQVL FIDQGNRPLF EDMTDSDCRD NAPRTIFIIS KYSDSGARGL   60
AVTISVKCEK ISTLSCENKI ISFKEMNPPD NIKDTKSDII FFARAVPGHG RKTQFESSSY  120
EGYFLACEKE RDLFKLILKK EDELGDRSIM FTVQNED                           157

SEQ ID NO: 79           moltype = AA  length = 157
FEATURE                 Location/Qualifiers
source                  1..157
                        mol_type = protein
                        organism = synthetic construct
SEQUENCE: 79
YFGKLESKLS VIRNLNDQVL FIDQGNRPLF EDMTDSDCRD NAPRTIFIIS KYSDSKARGM   60
AVTISVKCEK ISTLSCENKI ISFKEMNPPD NIKDTKSDII FFARDVPGHS SKRQFESSSY  120
EGYFLACEKE RDLFKLILKK EDELGDRSIM FTVQNED                           157

SEQ ID NO: 80           moltype = AA  length = 157
FEATURE                 Location/Qualifiers
source                  1..157
                        mol_type = protein
                        organism = synthetic construct
SEQUENCE: 80
YFGKLESKLS VIRNLNDQVL FIDQGNRPLF EDMTDSDCRD NAPRTIFIIS KYSDSLARGL   60
AVTISVKCEK ISTLSCENKI ISFKEMNPPD NIKDTKSDII FFQRDVPGHS RKMQFESSSY  120
EGYFLACEKE RDLFKLILKK EDELGDRSIM FTVQNED                           157

SEQ ID NO: 81           moltype = AA  length = 157
FEATURE                 Location/Qualifiers
source                  1..157
                        mol_type = protein
                        organism = synthetic construct
SEQUENCE: 81
YFGKLESKLS VIRNLNDQVL FIDQGNRPLF EDMTDSDCRD NAPRTIFIIS KYSDSRARGL   60
AVTISVKCEK ISTLSCENKI ISFKEMNPPD NIKDTKSDII FFQRNVPGHG RKMQFESSSY  120
EGYFLACEKE RDLFKLILKK EDELGDRSIM FTVQNED                           157

SEQ ID NO: 82           moltype = AA  length = 157
FEATURE                 Location/Qualifiers
source                  1..157
                        mol_type = protein
                        organism = synthetic construct
SEQUENCE: 82
YFGKLESKLS VIRNLNDQVL FIDQGNRPLF EDMTDSDCRD NAPRTIFIIS KYSDSRARGL   60
AVTISVKCEK ISTLSCENKI ISFKEMNPPD NIKDTKSDII FFARSVPGHG RKTQFESSSY  120
EGYFLACEKE RDLFKLILKK EDELGDRSIM FTVQNED                           157

SEQ ID NO: 83           moltype = AA  length = 157
FEATURE                 Location/Qualifiers
source                  1..157
                        mol_type = protein
                        organism = synthetic construct
SEQUENCE: 83
YFGKLESKLS VIRNLNDQVL FIDQGNRPLF EDMTDSDCRD NAPRTIFIIS KYSDSRARGL   60
AVTISVKCEK ISTLSCENKI ISFKEMNPPD NIKDTKSDII FFARDVPGHS GKRQFESSSY  120
EGYFLACEKE RDLFKLILKK EDELGDRSIM FTVQNED                           157

SEQ ID NO: 84           moltype = AA  length = 157
FEATURE                 Location/Qualifiers
source                  1..157
                        mol_type = protein
                        organism = synthetic construct
SEQUENCE: 84
YFGKLESKLS VIRNLNDQVL FIDQGNRPLF EDMTDSDCRD NAPRTIFIIS KYTDSRPRGL   60
AVTISVKCEK ISTLSCENKI ISFKEMNPPD NIKDTKSDII FFERDVPGHS SKKQFESSSY  120
EGYFLACEKE RDLFKLILKK EDELGDRSIM FTVQNED                           157
```

```
SEQ ID NO: 85            moltype = AA  length = 157
FEATURE                  Location/Qualifiers
source                   1..157
                         mol_type = protein
                         organism = synthetic construct
SEQUENCE: 85
YFGKLESKLS VIRNLNDQVL FIDQGNRPLF EDMTDSDCRD NAPRTIFIIS KYTDSRARGM    60
AVTISVKCEK ISTLSCENKI ISFKEMNPPD NIKDTKSDII FFERDVPGHN DKRQFESSSY   120
EGYFLACEKE RDLFKLILKK EDELGDRSIM FTVQNED                            157

SEQ ID NO: 86            moltype = AA  length = 157
FEATURE                  Location/Qualifiers
source                   1..157
                         mol_type = protein
                         organism = synthetic construct
SEQUENCE: 86
YFGKLESKLS VIRNLNDQVL FIDQGNRPLF EDMTDSDCRD NAPRTIFIIS RYKDSGKRGL    60
AVTISVKCEK ISTLSCENKI ISFKEMNPPD NIKDTKSDII FFRRSVPGHS RKVQFESSSY   120
EGYFLACEKE RDLFKLILKK EDELGDRSIM FTVQNED                            157

SEQ ID NO: 87            moltype = AA  length = 157
FEATURE                  Location/Qualifiers
source                   1..157
                         mol_type = protein
                         organism = synthetic construct
SEQUENCE: 87
YFGKLESKLS VIRNLNDQVL FIDQGNRPLF EDMTDSDCRD NAPRTIFIIS KYGDSGARGL    60
AVTISVKCEK ISTLSCENKI ISFKEMNPPD NIKDTKSDII FFERDVPGHS GKVQFESSSY   120
EGYFLACEKE RDLFKLILKK EDELGDRSIM FTVQNED                            157

SEQ ID NO: 88            moltype = AA  length = 157
FEATURE                  Location/Qualifiers
source                   1..157
                         mol_type = protein
                         organism = synthetic construct
SEQUENCE: 88
YFGKLESKLS VIRNLNDQVL FIDQGNRPLF EDMTDSDCRD NAPRTIFIIS KYGDSRPRGM    60
AVTISVKCEK ISTLSCENKI ISFKEMNPPD NIKDTKSDII FFQRAVPGHN RKMQFESSSY   120
EGYFLACEKE RDLFKLILKK EDELGDRSIM FTVQNED                            157

SEQ ID NO: 89            moltype = AA  length = 157
FEATURE                  Location/Qualifiers
source                   1..157
                         mol_type = protein
                         organism = synthetic construct
SEQUENCE: 89
YFGKLESKLS VIRNLNDQVL FIDQGNRPLF EDMTDSDCRD NAPRTIFIIS KYSDSLARGL    60
AVTISVKCEK ISTLSCENKI ISFKEMNPPD NIKDTKSDII FFQRDVPGHS RKMQFESSSY   120
EGYFLACEKE RDLFKLILKK EDELGDRSIM FTVQNED                            157

SEQ ID NO: 90            moltype = AA  length = 157
FEATURE                  Location/Qualifiers
source                   1..157
                         mol_type = protein
                         organism = synthetic construct
SEQUENCE: 90
YFGKLESKLS VIRNLNDQVL FIDQGNRPLF EDMTDSDCRD NAPRTIFIIS KYSDSRARGL    60
AVTISVKCEK ISTLSCENKI ISFKEMNPPD NIKDTKSDII FFARSVPGHG RKTQFESSSY   120
EGYFLACEKE RDLFKLILKK EDELGDRSIM FTVQNED                            157

SEQ ID NO: 91            moltype = AA  length = 157
FEATURE                  Location/Qualifiers
source                   1..157
                         mol_type = protein
                         organism = synthetic construct
SEQUENCE: 91
YFGKLESKLS VIRNLNDQVL FIDQGNRPLF EDMTDSDCRD NAPRTIFIIS KYSDSRARGL    60
AVTISVKCEK ISTLSCENKI ISFKEMNPPD NIKDTKSDII FFQRNVPGHG RKMQFESSSY   120
EGYFLACEKE RDLFKLILKK EDELGDRSIM FTVQNED                            157

SEQ ID NO: 92            moltype = AA  length = 157
FEATURE                  Location/Qualifiers
source                   1..157
                         mol_type = protein
                         organism = synthetic construct
SEQUENCE: 92
HFGKLESKLS VIRNLNGQVL FIDQGNRPLF KDMTASDCRA NAPRTIFIIS FYKDSQPRGM    60
AVTISVKCEK ISTLSCENKI ISFKEMNPPD NIKDTKSDII FFIRSVPGAD NKFQFESSSY   120
EGYFLACEKE RDLFKLILKK EDELGDRSIM FTVQNED                            157
```

```
SEQ ID NO: 93          moltype = AA   length = 157
FEATURE                Location/Qualifiers
source                 1..157
                       mol_type = protein
                       organism = synthetic construct
SEQUENCE: 93
DFGKLESKLS VIRNLNDQVL FIDQGNRPLF ADMTDNPCRS NAPRTIFIIS FYKDSQPRGI  60
AVTISVKCEK ISTLSCENKI ISFKEMNPPD NIKDTKSDII FFLRSVPGPD NKMQFESSSY 120
EGYFLACEKE RDLFKLILKK EDELGDRSIM FTVQNED                          157

SEQ ID NO: 94          moltype = AA   length = 157
FEATURE                Location/Qualifiers
source                 1..157
                       mol_type = protein
                       organism = synthetic construct
SEQUENCE: 94
HFGKLESKLS VIRNLNGQVL FIDQGNRPLF ADMEASPCRD NAPRTIFIIS FYKDSQPRGL  60
AVTISVKCEK ISTLSCENKI ISFKEMNPPD NIKDTKSDII FFLRSVPGHD NKMQFESSSY 120
EGYFLACEKE RDLFKLILKK EDELGDRSIM FTVQNED                          157

SEQ ID NO: 95          moltype = AA   length = 157
FEATURE                Location/Qualifiers
source                 1..157
                       mol_type = protein
                       organism = synthetic construct
SEQUENCE: 95
LFGKLESKLS VIRNLNGQVL FIDQGNRPLF ADMTSSPCRS RAPRTIFIIS FYKDSQPRGF  60
AVTISVKCEK ISTLSCENKI ISFKEMNPPD NIKDTKSDII FFIRSVPGHD NKIQFESSSY 120
EGYFLACEKE RDLFKLILKK EDELGDRSIM FTVQNED                          157

SEQ ID NO: 96          moltype = AA   length = 157
FEATURE                Location/Qualifiers
source                 1..157
                       mol_type = protein
                       organism = synthetic construct
SEQUENCE: 96
HFGKLESKLS VIRNLNDQVL FIDQGNRPLF TDMESKPCRD SAPRTIFIIS MYKDSQPRGI  60
AVTISVKCEK ISTLSCENKI ISFKEMNPPD NIKDTKSDII FFIRSVPGHD NKFQFESSSY 120
EGYFLACEKE RDLFKLILKK EDELGDRSIM FTVQNED                          157

SEQ ID NO: 97          moltype = AA   length = 157
FEATURE                Location/Qualifiers
source                 1..157
                       mol_type = protein
                       organism = synthetic construct
SEQUENCE: 97
YFGKLESKLS VIRNLNRQVL FIDQGNRPLF TDMTYKDCRD NAPRTIFIIS FYKDSQPRGF  60
AVTISVKCEK ISTLSCENKI ISFKEMNPPD NIKDTKSDII FFIRSVPGAD NKIQFESSSY 120
EGYFLACEKE RDLFKLILKK EDELGDRSIM FTVQNED                          157

SEQ ID NO: 98          moltype = AA   length = 157
FEATURE                Location/Qualifiers
source                 1..157
                       mol_type = protein
                       organism = synthetic construct
SEQUENCE: 98
HFGKLESKLS VIRNLNGQVL FIDQGNRPLF GDMEASPCRD NAPRTIFIIS FYKDSQPRGM  60
AVTISVKCEK ISTLSCENKI ISFKEMNPPD NIKDTKSDII FFIRSVPGAD NKLQFESSSY 120
EGYFLACEKE RDLFKLILKK EDELGDRSIM FTVQNED                          157

SEQ ID NO: 99          moltype = AA   length = 157
FEATURE                Location/Qualifiers
source                 1..157
                       mol_type = protein
                       organism = synthetic construct
SEQUENCE: 99
HFGKLESKLS VIRNLNGQVL FIDQGNRPLF TDMTSSDCRD KAPRTIFIIS FYKDSQPRGL  60
AVTISVKCEK ISTLSCENKI ISFKEMNPPD NIKDTKSDII FFLRSVPGPD NKFQFESSSY 120
EGYFLACEKE RDLFKLILKK EDELGDRSIM FTVQNED                          157

SEQ ID NO: 100         moltype = AA   length = 157
FEATURE                Location/Qualifiers
source                 1..157
                       mol_type = protein
                       organism = synthetic construct
SEQUENCE: 100
HFGKLESKLS VIRNLNGQVL FIDQGNRPLF ADMESNRCRD SAPRTIFIIS MYKDSQPRGF  60
AVTISVKCEK ISTLSCENKI ISFKEMNPPD NIKDTKSDII FFLRSVPGHD NKIQFESSSY 120
```

```
EGYFLACEKE RDLFKLILKK EDELGDRSIM FTVQNED                             157

SEQ ID NO: 101          moltype = AA   length = 157
FEATURE                 Location/Qualifiers
source                  1..157
                        mol_type = protein
                        organism = synthetic construct
SEQUENCE: 101
YFGKLESKLS VIRNLNGQVL FIDQGNRPLF TDMTASPCRD NAPRTIFIIS FYKDSQPRGL     60
AVTISVKCEK ISTLSCENKI ISFKEMNPPD NIKDTKSDII FFLRSVPGHD NKIQFESSSY    120
EGYFLACEKE RSLFKLILKK EDELGDRSIM FTVQNED                             157

SEQ ID NO: 102          moltype = AA   length = 157
FEATURE                 Location/Qualifiers
source                  1..157
                        mol_type = protein
                        organism = synthetic construct
SEQUENCE: 102
DFGKLESKLS VIRNLNDQVL FIDQGNRPLF ADMKSNVCRA NAPRTIFIIS MYKDSQPRGM     60
AVTISVKCEK ISTLSCENKI ISFKEMNPPD NIKDTKSDII FFIRSVPGPD NKLQFESSSY    120
EGYFLACEKE RDLFKLILKK EDELGDRSIM FTVQNED                             157

SEQ ID NO: 103          moltype = AA   length = 157
FEATURE                 Location/Qualifiers
source                  1..157
                        mol_type = protein
                        organism = synthetic construct
SEQUENCE: 103
HFGKLESKLS VIRNLNGQVL FIDQGNRPLF GDMEASPCRA KAPRTIFIIS IYKDSQPRGF     60
AVTISVKCEK ISTLSCENKI ISFKEMNPPD NIKDTKSDII FFLRSVPGHD NKFQFESSSY    120
EGYFLACEKE RSLFKLILKK EDELGDRSIM FTVQNED                             157

SEQ ID NO: 104          moltype = AA   length = 157
FEATURE                 Location/Qualifiers
source                  1..157
                        mol_type = protein
                        organism = synthetic construct
SEQUENCE: 104
HFGKLESKLS VIRNLNGQVL FIDQGNRPLF ADMASNRCRA NAPRTIFIIS MYKDSQPRGF     60
AVTISVKCEK ISTLSCENKI ISFKEMNPPD NIKDTKSDII FFIRSVPGPD NKFQFESSSY    120
EGYFLACEKE RDLFKLILKK EDELGDRSIM FTVQNED                             157

SEQ ID NO: 105          moltype = AA   length = 157
FEATURE                 Location/Qualifiers
source                  1..157
                        mol_type = protein
                        organism = synthetic construct
SEQUENCE: 105
YFGKLESKLS VIRNLNDQVL FIDQGNRPLF ADMKAKACRS NAPRTIFIIS FYKDSQPRGF     60
AVTISVKCEK ISTLSCENKI ISFKEMNPPD NIKDTKSDII FFLRSVPGAD NKIQFESSSY    120
EGYFLACEKE RDLFKLILKK EDELGDRSIM FTVQNED                             157

SEQ ID NO: 106          moltype = AA   length = 157
FEATURE                 Location/Qualifiers
source                  1..157
                        mol_type = protein
                        organism = synthetic construct
SEQUENCE: 106
HFGKLESKLS VIRNLNHQVL FIDQGNRPLF TDMADNACRD NAPRTIFIIS FYKDSQPRGL     60
AVTISVKCEK ISTLSCENKI ISFKEMNPPD NIKDTKSDII FFIRSVPGDD NKMQFESSSY    120
EGYFLACEKE RDLFKLILKK EDELGDRSIM FTVQNED                             157

SEQ ID NO: 107          moltype = AA   length = 157
FEATURE                 Location/Qualifiers
source                  1..157
                        mol_type = protein
                        organism = synthetic construct
SEQUENCE: 107
YFGKLESKLS VIRNLNGQVL FIDQGNRPLF TDMKSNLCRS NAPRTIFIIS FYKDSQPRGI     60
AVTISVKCEK ISTLSCENKI ISFKEMNPPD NIKDTKSDII FFIRSVPGDD NKIQFESSSY    120
EGYFLACEKE RDLFKLILKK EDELGDRSIM FTVQNED                             157

SEQ ID NO: 108          moltype = AA   length = 157
FEATURE                 Location/Qualifiers
source                  1..157
                        mol_type = protein
                        organism = synthetic construct
SEQUENCE: 108
HFGKLESKLS VIRNLNGQVL FIDQGNRPLF RDMAASHCRD SAPRTIFIIS IYKDSQPRGF     60
```

```
AVTISVKCEK ISTLSCENKI ISFKEMNPPD NIKDTKSDII FFLRSVPGHD NKIQFESSSY    120
EGYFLACEKE RDLFKLILKK EDELGDRSIM FTVQNED                             157

SEQ ID NO: 109          moltype = AA  length = 157
FEATURE                 Location/Qualifiers
source                  1..157
                        mol_type = protein
                        organism = synthetic construct
SEQUENCE: 109
YFGKLESKLS VIRNLNDQVL FIDQGNRPLF ADMASNPCRY KAPRTIFIIS MYKDSQPRGL    60
AVTISVKCEK ISTLSCENKI ISFKEMNPPD NIKDTKSDII FFLRSVPGAD NKLQFESSSY    120
EGYFLACEKE RDLFKLILKK EDELGDRSIM FTVQNED                             157

SEQ ID NO: 110          moltype = AA  length = 157
FEATURE                 Location/Qualifiers
source                  1..157
                        mol_type = protein
                        organism = synthetic construct
SEQUENCE: 110
HFGKLESKLS VIRNLNGQVL FIDQGNRPLF TDMASNHCRY NAPRTIFIIS MYKDSQPRGL    60
AVTISVKCEK ISTLSCENKI ISFKEMNPPD NIKDTKSDII FFLRSVPGAD NKIQFESSSY    120
EGYFLACEKE RDLFKLILKK EDELGDRSIM FTVQNED                             157

SEQ ID NO: 111          moltype = AA  length = 157
FEATURE                 Location/Qualifiers
source                  1..157
                        mol_type = protein
                        organism = synthetic construct
SEQUENCE: 111
HFGKLESKLS VIRNLNGQVL FIDQGNRPLF ADMTDNPCRS RAPRTIFIIS FYKDSQPRGM    60
AVTISVKCEK ISTLSCENKI ISFKEMNPPD NIKDTKSDII FFIRSVPGHD NKFQFESSSY    120
EGYFLACEKE RDLFKLILKK EDELGDRSIM FTVQNED                             157

SEQ ID NO: 112          moltype = AA  length = 157
FEATURE                 Location/Qualifiers
source                  1..157
                        mol_type = protein
                        organism = synthetic construct
SEQUENCE: 112
YFGKLESKLS VIRNLNGQVL FIDQGNRPLF TDMTASHCRS SAPRTIFIIS LYKDSQPRGM    60
AVTISVKCEK ISTLSCENKI ISFKEMNPPD NIKDTKSDII FFLRSVPGHD NKFQFESSSY    120
EGYFLACEKE RDLFKLILKK EDELGDRSIM FTVQNED                             157

SEQ ID NO: 113          moltype = AA  length = 157
FEATURE                 Location/Qualifiers
source                  1..157
                        mol_type = protein
                        organism = synthetic construct
SEQUENCE: 113
YFGKLESKLS VIRNLNGQVL FIDQGNRPLF TDMEYRLCRA NAPRTIFIIS FYKDSHPRGL    60
AVTISVKCEK ISTLSCENKI ISFKEMNPPD NIKDTKSDII FFLRSVPGDD NKLQFESSSY    120
EGYFLACEKE RDLFKLILKK EDELGDRSIM FTVQNED                             157

SEQ ID NO: 114          moltype = AA  length = 157
FEATURE                 Location/Qualifiers
source                  1..157
                        mol_type = protein
                        organism = synthetic construct
SEQUENCE: 114
YFGKLESKLS VIRNLNGQVL FIDQGNRPLF TDMESSLCRD NAPRTIFIIS LYKDSQPRGM    60
AVTISVKCEK ISTLSCENKI ISFKEMNPPD NIKDTKSDII FFLRSVPGAD NKFQFESSSY    120
EGYFLACEKE RSLFKLILKK EDELGDRSIM FTVQNED                             157

SEQ ID NO: 115          moltype = AA  length = 157
FEATURE                 Location/Qualifiers
source                  1..157
                        mol_type = protein
                        organism = synthetic construct
SEQUENCE: 115
YFGKLESKLS VIRNLNGQVL FIDQGNRPLF KDMEANDCRS SAPRTIFIIS IYKDSQPRGL    60
AVTISVKCEK ISTLSCENKI ISFKEMNPPD NIKDTKSDII FFIRSVPGAD NKMQFESSSY    120
EGYFLACEKE RDLFKLILKK EDELGDRSIM FTVQNED                             157

SEQ ID NO: 116          moltype = AA  length = 157
FEATURE                 Location/Qualifiers
source                  1..157
                        mol_type = protein
                        organism = synthetic construct
SEQUENCE: 116
```

```
DFGKLESKLS VIRNLNDQVL FIDQGNRPLF ADMKASACRA NAPRTIFIIS MYKDSQPRGL    60
AVTISVKCEK ISTLSCENKI ISFKEMNPPD NIKDTKSDII FFLRSVPGHD NKFQFESSSY   120
EGYFLACEKE RDLFKLILKK EDELGDRSIM FTVQNED                           157

SEQ ID NO: 117          moltype = AA   length = 157
FEATURE                 Location/Qualifiers
source                  1..157
                        mol_type = protein
                        organism = synthetic construct
SEQUENCE: 117
YFGKLESKLS VIRNLNGQVL FIDQGNRPLF GDMTAKHCRA RAPRTIFIIS FYKDSQPRGM    60
AVTISVKCEK ISTLSCENKI ISFKEMNPPD NIKDTKSDII FFIRSVPGAD NKFQFESSSY   120
EGYFLACEKE RDLFKLILKK EDELGDRSIM FTVQNED                           157

SEQ ID NO: 118          moltype = AA   length = 157
FEATURE                 Location/Qualifiers
source                  1..157
                        mol_type = protein
                        organism = synthetic construct
SEQUENCE: 118
FFGKFESKLS VIRNLNGQVL FIDQGNRPLF TDMESKDCRD RAPRTIFIIS FYKDSQPRGL    60
AVTISVKCEK ISTLSCENKI ISFKEMNPPD NIKDTKSDII FFLRSVPGHD NKLQFESSSY   120
EGYFLACEKE RDLFKLILKK EDELGDRSIM FTVQNED                           157

SEQ ID NO: 119          moltype = AA   length = 157
FEATURE                 Location/Qualifiers
source                  1..157
                        mol_type = protein
                        organism = synthetic construct
SEQUENCE: 119
FFGKLESKLS VIRNLNGQVL FIDQGNRPLF ADMASNHCRA NAPRTIFIIS LYKDSQPRGL    60
AVTISVKCEK ISTLSCENKI ISFKEMNPPD NIKDTKSDII FFIRSVPGHD NKMQFESSSY   120
EGYFLACEKE RDLFKLILKK EDELGDRSIM FTVQNED                           157

SEQ ID NO: 120          moltype = AA   length = 157
FEATURE                 Location/Qualifiers
source                  1..157
                        mol_type = protein
                        organism = synthetic construct
SEQUENCE: 120
YFGKLESKLS VIRNLNGQVL FIDQGNRPLF ADMTSKRCRD NAPRTIFIIS LYKDSQPRGF    60
AVTISVKCEK ISTLSCENKI ISFKEMNPPD NIKDTKSDII FFIRSVPGHD NKIQFESSSY   120
EGYFLACEKE RDLFKLILKK EDELGDRSIM FTVQNED                           157

SEQ ID NO: 121          moltype = AA   length = 157
FEATURE                 Location/Qualifiers
source                  1..157
                        mol_type = protein
                        organism = synthetic construct
SEQUENCE: 121
LFGKHESKLS VIRNLNGQVL FIDQGNRPLF GDMESSPCRY NAPRTIFIIS FYKDSQPRGL    60
AVTISVKCEK ISTLSCENKI ISFKEMNPPD NIKDTKSDII FFIRSVPGHD NKMQFESSSY   120
EGYFLACEKE RDLFKLILKK EDELGDRSIM FTVQNED                           157

SEQ ID NO: 122          moltype = AA   length = 157
FEATURE                 Location/Qualifiers
source                  1..157
                        mol_type = protein
                        organism = synthetic construct
SEQUENCE: 122
YFGKLESKLS VIRNLNAQVL FIDQGNRPLF TDMTASPCRS SAPRTIFIIS LYKDSQPRGL    60
AVTISVKCEK ISFKEMNPPD NIKDTKSDII FFLRSVPGPD NKIQFESSSY   120
EGYFLACEKE RDLFKLILKK EDELGDRSIM FTVQNED                           157

SEQ ID NO: 123          moltype = AA   length = 157
FEATURE                 Location/Qualifiers
source                  1..157
                        mol_type = protein
                        organism = synthetic construct
SEQUENCE: 123
YFGKLESKLS VIRNLNGQVL FIDQGNRPLF ADMTDSDCRD NAPRTIFIIS MYKDSQPRGM    60
AVTISVKCEK ISTLSCENKI ISFKEMNPPD NIKDTKSDII FFLRSVPGHD NKMQFESSSY   120
EGYFLACEKE RDLFKLILKK EDELGDRSIM FTVQNED                           157

SEQ ID NO: 124          moltype = AA   length = 157
FEATURE                 Location/Qualifiers
source                  1..157
                        mol_type = protein
                        organism = synthetic construct
```

```
SEQUENCE: 124
YFGKLESKLS VIRNLNGQVL FIDQGNRPLF ADMTSSDCRD NAPRTIFIIS FYKDSQPRGM    60
AVTISVKCEK ISTLSCENKI ISFKEMNPPD NIKDTKSDII FFLRSVPGHD NKMQFESSSY   120
EGYFLACEKE RDLFKLILKK EDELGDRSIM FTVQNED                            157

SEQ ID NO: 125           moltype = AA  length = 157
FEATURE                  Location/Qualifiers
source                   1..157
                         mol_type = protein
                         organism = synthetic construct
SEQUENCE: 125
YFGKLESKLS VIRNLNGQVL FIDQGNRPLF ADMESSDCRD NAPRTIFIIS FYKDSQPRGL    60
AVTISVKCEK ISTLSCENKI ISFKEMNPPD NIKDTKSDII FFLRSVPGHD NKMQFESSSY   120
EGYFLACEKE RDLFKLILKK EDELGDRSIM FTVQNED                            157

SEQ ID NO: 126           moltype = AA  length = 157
FEATURE                  Location/Qualifiers
source                   1..157
                         mol_type = protein
                         organism = synthetic construct
SEQUENCE: 126
YFGRYHCTTA VIRNINQQVL FVDKRQPVFA DMGYTVQSAS EPQTRLIIYM YKDSEVRGLA    60
VTLSVKDSKM STLSCKNKII SFEEMDPPEN IDDIQSDLIF FLKEVPGHRK LEFESSLYEG   120
HFLACQKEDE AFKLILKKKD ENGDKSVMFT LTNLHQS                            157

SEQ ID NO: 127           moltype = AA  length = 157
FEATURE                  Location/Qualifiers
source                   1..157
                         mol_type = protein
                         organism = synthetic construct
SEQUENCE: 127
DPFGRLHCTTA VIRNINDQVL FVDKRQPVFA DMGSIAQSAS EPQTRLIIYF YKDSEVRGLA   60
VTLSVKDSKM YTLSCKNKII SFEEMDPPEN IDDIQSDLIF FLKAVPGDNK IEFESSLYEG  120
HFLACQKEAT AFKLILKKKD ENGDKSVMFT LTNLHQS                           157

SEQ ID NO: 128           moltype = AA  length = 157
FEATURE                  Location/Qualifiers
source                   1..157
                         mol_type = protein
                         organism = synthetic construct
SEQUENCE: 128
YFGRLHCTTA VIRNINGQVL FVDKRQPVFR DMADTVQSAS EPQTRLIIYF YKDSEVRGLA    60
VTLSVKDSKM STLSCKNKII SFEEMDPPEN IDDIQSDLIF FIKPVPGASK MEFESSLYEG  120
HFLACQKEAG AFKLILKKKD ENGDKSVMFT LTNLHQS                           157

SEQ ID NO: 129           moltype = AA  length = 157
FEATURE                  Location/Qualifiers
source                   1..157
                         mol_type = protein
                         organism = synthetic construct
SEQUENCE: 129
HFGRLHCTTA VIRNINDQVL FVDKRQPVFK DMEYTVQSAS EPQTRLIIYM YKDSEVRGLA    60
VTLSVKDSKM STLSCKNKII SFEEMDPPEN IDDIQSDLIF FIKAVPGDRK IEFESSLYEG  120
HFLACQKEDN AFKLILKKKD ENGDKSVMFT LTNLHQS                           157

SEQ ID NO: 130           moltype = AA  length = 157
FEATURE                  Location/Qualifiers
source                   1..157
                         mol_type = protein
                         organism = synthetic construct
SEQUENCE: 130
YFGRLHCTTA VIRNINAQVL FVDKRQPVFA DMADKGQSAS EPQTRLIIYM YKDSEVRGLA    60
VTLSVKDSKM STLSCKNKII SFEEMDPPEN IDDIQSDLIF FLKPVPGDTK MEFESSLYEG  120
HFLACQKEFG AFKLILKKKD ENGDKSVMFT LTNLHQS                           157

SEQ ID NO: 131           moltype = AA  length = 157
FEATURE                  Location/Qualifiers
source                   1..157
                         mol_type = protein
                         organism = synthetic construct
SEQUENCE: 131
YFGRLHCTTA VIRNINEQVL FVDKRQPVFA DMGDRHQSAS EPQTRLIIYM YKDSEVRGLA    60
VTLSVKDSKM STLSCKNKII SFEEMDPPEN IDDIQSDLIF FIKPVPGASK LEFESSLYEG  120
HFLACQKEDD AFKLILKKKD ENGDKSVMFT LTNLHQS                           157

SEQ ID NO: 132           moltype = AA  length = 157
FEATURE                  Location/Qualifiers
source                   1..157
                         mol_type = protein
```

```
                        organism = synthetic construct
SEQUENCE: 132
HFGRLHCTTA VIRNINDQVL FVDKRQPVFR DMGAIGQSAS EPQTRLIIYF YKDSEVRGLA    60
VTLSVKDSKM STLSCKNKII SFEEMDPPEN IDDIQSDLIF FIKPVPGDSK LEFESSLYEG   120
HFLACQKEVD AFKLILKKKD ENGDKSVMFT LTNLHQS                            157

SEQ ID NO: 133          moltype = AA  length = 157
FEATURE                 Location/Qualifiers
source                  1..157
                        mol_type = protein
                        organism = synthetic construct
SEQUENCE: 133
HFGRLHCTTA VIRNINSQVL FVDKRQPVFT DMGSIVQSAS EPQTRLIIYM YKDSEVRGLA    60
VTLSVKDSKM STLSCKNKII SFEEMDPPEN IDDIQSDLIF FIKGVPGDNK IEFESSLYEG   120
HFLACQKEDR AFKLILKKKD ENGDKSVMFT LTNLHQS                            157

SEQ ID NO: 134          moltype = AA  length = 157
FEATURE                 Location/Qualifiers
source                  1..157
                        mol_type = protein
                        organism = synthetic construct
SEQUENCE: 134
YFGRLHCTTA VIRNINSQVL FVDKRQPVFR DMEDTPQSAS EPQTRLIIYF YKDSEVRGLA    60
VTLSVKDSKM STLSCKNKII SFEEMDPPEN IDDIQSDLIF FIKRVPGDSK LEFESSLYEG   120
HFLACQKEFE AFKLILKKKD ENGDKSVMFT LTNLHQS                            157

SEQ ID NO: 135          moltype = AA  length = 157
FEATURE                 Location/Qualifiers
source                  1..157
                        mol_type = protein
                        organism = synthetic construct
SEQUENCE: 135
HFGRLHCTTA VIRNINAQVL FVDKRQPVFG DMTATVQSAS EPQTRLIIYF YKDSEVRGLA    60
VTLSVKDSKM STLSCKNKII SFEEMDPPEN IDDIQSDLIF FIKPVPGDSK LEFESSLYEG   120
HFLACQKEDN AFKLILKKKD ENGDKSVMFT LTNLHQS                            157

SEQ ID NO: 136          moltype = AA  length = 157
FEATURE                 Location/Qualifiers
source                  1..157
                        mol_type = protein
                        organism = synthetic construct
SEQUENCE: 136
NFGRLHCTTA VIRNINNQVL FVDKRQPVFK DMEYTLQSAS EPQTRLIIYF YKDSEVRGLA    60
VTLSVKDSKM STLSCKNKII SFEEMDPPEN IDDIQSDLIF FIKPVPGDNK LEFESSLYEG   120
HFLACQKEYE AFKLILKKKD ENGDKSVMFT LTNLHQS                            157

SEQ ID NO: 137          moltype = AA  length = 157
FEATURE                 Location/Qualifiers
source                  1..157
                        mol_type = protein
                        organism = synthetic construct
SEQUENCE: 137
YFGRLHCTTA VIRNINGQVL FVDKRQPVFA DMEATRQSAS EPQTRLIIYF YKDSEVRGLA    60
VTLSVKDSKM STLSCKNKII SFEEMDPPEN IDDIQSDLIF FIKGVPGANK MEFESSLYEG   120
HFLACQKEDG AFKLILKKKD ENGDNSVMFT LTNLHQS                            157

SEQ ID NO: 138          moltype = AA  length = 157
FEATURE                 Location/Qualifiers
source                  1..157
                        mol_type = protein
                        organism = synthetic construct
SEQUENCE: 138
NFGRLHCTTA VIRNINGQVL FVDKRQPVFA DMRAILQSAS EPQTRLIIYF YKDSEVRGLA    60
VTLSVKDSKM STLSCKNKII SFEEMDPPEN IDDIQSDLIF FLKGVPGDNK LEFESSLYEG   120
HFLACQKEDR AFKLILKKKD ENGDKSVMFT LTNLHQS                            157

SEQ ID NO: 139          moltype = AA  length = 157
FEATURE                 Location/Qualifiers
source                  1..157
                        mol_type = protein
                        organism = synthetic construct
SEQUENCE: 139
YFGRLHCTTA VIRNINAQVL FVDKRQPVFA DMEATAQSAS EPQTRLIIYF YKDSEVRGLA    60
VTLSVKDSKM STLSCKNKII SFEEMDPPEN IDDIQSDLIF FIKGVPGASK MEFESSLYEG   120
HFLACQKEDG AFKLILKKKD ENGDKSVMFT LTNLHQS                            157

SEQ ID NO: 140          moltype = AA  length = 157
FEATURE                 Location/Qualifiers
source                  1..157
```

```
                        mol_type = protein
                        organism = synthetic construct
SEQUENCE: 140
LFGRLHCTTA VIRNINGQVL FVDKRQPVFA DMGATLQSAS EPQTRLIIYM YKDSEVRGLA    60
VTLSVKDSKM STLSCKNKII SFEEMDPPEN IDDIQSDLIF FLKPVPGDTK MEFESSLYEG   120
HFLACQKEAS AFKLILKKKD ENGDKSVMFT LTNLHQS                            157

SEQ ID NO: 141          moltype = AA  length = 157
FEATURE                 Location/Qualifiers
source                  1..157
                        mol_type = protein
                        organism = synthetic construct
SEQUENCE: 141
NFGRLHCTTA VIRNINGQVL FVDKRQPVFE DMAYTVQSAS EPQTRLIIYF YKDSEVRGLA    60
VTLSVKDSKM STLSCKNKII SFEEMDPPEN IDDIQSDLIF FIKGVPGDSK MEFESSLYEG   120
HFLACQKEYD AFKLILKKKD ENGDKSVMFT LTNLHQS                            157

SEQ ID NO: 142          moltype = AA  length = 157
FEATURE                 Location/Qualifiers
source                  1..157
                        mol_type = protein
                        organism = synthetic construct
SEQUENCE: 142
DFGRLHCTTA VIRNINDQVL FVDKRQPVFK DMESKPQSAS EPQTRLIIYF YKDSEVRGLA    60
VTLSVKDSKM STLSCKNKII SFEEMDPPEN IDDIQSDLIF FLKAVPGASK LEFESSLYEG   120
HFLACQKEAN AFKLILKKKD ENGDKSVMFT LTNLHQS                            157

SEQ ID NO: 143          moltype = AA  length = 157
FEATURE                 Location/Qualifiers
source                  1..157
                        mol_type = protein
                        organism = synthetic construct
SEQUENCE: 143
LFGRLHCTTA VIRNINGQVL FVDKRQPVFA DMGDKVQSAS EPQTRLIIYM YKDSEVRGLA    60
VTLSVKDSKM STLSCKNKII SFEEMDPPEN IDDIQSDLIF FIKPVPGDNK LEFESSLYEG   120
HFLACQKEDE AFKLILKTKD ENGDKSVMFT LTNLHQS                            157

SEQ ID NO: 144          moltype = AA  length = 157
FEATURE                 Location/Qualifiers
source                  1..157
                        mol_type = protein
                        organism = synthetic construct
SEQUENCE: 144
YFGRHHCTTA VIRNINQQVL FVDKRQPVFR DMAATRQSAS EPQTRLIIYM YKDSEVRGLA    60
VTLSVKDSKM STLSCKNKII SFEEMDPPEN IDDIQSDLIF FLKGVPGDNK MEFESSLYEG   120
HFLACQKEDD AFKLILKKKD ENGDKSVMFT LTNLHQS                            157

SEQ ID NO: 145          moltype = AA  length = 157
FEATURE                 Location/Qualifiers
source                  1..157
                        mol_type = protein
                        organism = synthetic construct
SEQUENCE: 145
NFGRLHCTTA VIRNINQQVL FVDKRQPVFT DMESIGQSAS EPQTRLIIYF YKDSEVRGLA    60
VTLSVKDSKM STLSCKNKII SFEEMDPPEN IDDIQSDLIF FLKAVPGANK LEFESSLYEG   120
HFLACQKEDS AFKLILKKKD ENGDKSVMFT LTNLHQS                            157

SEQ ID NO: 146          moltype = AA  length = 157
FEATURE                 Location/Qualifiers
source                  1..157
                        mol_type = protein
                        organism = synthetic construct
SEQUENCE: 146
FFGRHHCTTA VIRNINGQVL FVDKRQPVFG DMGDRVQSAS EPQTRLIIYM YKDSEVRGLA    60
VTLSVKDSKM STLSCKNKII SFEEMDPPEN IDDIQSDLIF FIKAVPGDSK IEFESSLYEG   120
HFLACQKEDG AFKLILKKKD ENGDKSVMFT LTNLHQS                            157

SEQ ID NO: 147          moltype = AA  length = 157
FEATURE                 Location/Qualifiers
source                  1..157
                        mol_type = protein
                        organism = synthetic construct
SEQUENCE: 147
VFGRHHCTTA VIRNINGQVL FVDKRQPVFK DMTYIDQSAS EPQTRLIIYM YKDSEVRGLA    60
VTLSVKDSKM STLSCKNKII SFEEMDPPEN IDDIQSDLIF FLKAVPGDTK MEFESSLYEG   120
HFLACQKEAQ AFKLILKKKD EIGDKSVMFT LTNLHQS                            157

SEQ ID NO: 148          moltype = AA  length = 157
FEATURE                 Location/Qualifiers
```

```
source                       1..157
                             mol_type = protein
                             organism = synthetic construct
SEQUENCE: 148
NFGRLHCTTA VIRNINGQVL FVDKRQPVFA DMTATRQSAS EPQTRLIIYM YKDSEVRGLA    60
VTLSVKDSKM STLSCKNKII SFEEMDPPEN IDDIQSDLIF FIKQVPGANK IEFESSLYEG   120
HFLACQKEFR AFKLILKKKD ENGDKSVMFT LTNLHQS                            157

SEQ ID NO: 149               moltype = AA  length = 157
FEATURE                      Location/Qualifiers
source                       1..157
                             mol_type = protein
                             organism = synthetic construct
SEQUENCE: 149
DFGRLHCTTA VIRNINGQVL FVDKRQPVFG DMAYIGQSAS EPQTRLIIYF YKDSEVRGLA    60
VTLSVKDSKM STLSCKNKII SFEEMDPPEN IDDIQSDLIF FIKAVPGHSK IEFESSLYEG   120
HFLACQKESG AFKLILKKKD ENGDKSVMFT LTNLHQS                            157

SEQ ID NO: 150               moltype = AA  length = 157
FEATURE                      Location/Qualifiers
source                       1..157
                             mol_type = protein
                             organism = synthetic construct
SEQUENCE: 150
YFGRLHCTTA VIRNINDQVL FVDKRQPVFR DMGSIAQSAS EPQTRLIIYM YKDSEVRGLA    60
VTLSVKDSKM STLSCKNKII SFEEMDPPEN IDDIQSDLIF FIKPVPGATK LEFESSLYEG   120
HFLACQKEDG AFKLILKKKD ENGDNSVMFT LTNLHQS                            157

SEQ ID NO: 151               moltype = AA  length = 157
FEATURE                      Location/Qualifiers
source                       1..157
                             mol_type = protein
                             organism = synthetic construct
SEQUENCE: 151
YFGRLHCTTA VIRNINEQVL FVDKRQPVFT DMEAIGQSAS EPQTRLIIYF YKDSEVRGLA    60
VTLSVKDSKM STLSCKNKII SFEEMDPPEN IDDIQSDLIF FIKGVPGDRK MEFESSLYEG   120
HFLACQKEDG AFKLILKKKD ENGDKSVMFT LTNLHQS                            157

SEQ ID NO: 152               moltype = AA  length = 157
FEATURE                      Location/Qualifiers
source                       1..157
                             mol_type = protein
                             organism = synthetic construct
SEQUENCE: 152
FFGRLHCTTA VIRNINNQVL FVDKRQPVFE DMEYRLQSAS EPQTRLIIYM YKDSEVRGLA    60
VTLSVKDSKM STLSCKNKII SFEEMDPPEN IDDIQSDLIF FLKPVPGASK LEFESSLYEG   120
HFLACQKESD AFKLILKKKD ENGDKSVMFT LTNLHQS                            157

SEQ ID NO: 153               moltype = AA  length = 157
FEATURE                      Location/Qualifiers
source                       1..157
                             mol_type = protein
                             organism = synthetic construct
SEQUENCE: 153
NFGRLHCTTA VIRNINNQVL FVDKRQPVFA DMEDRLQSAS EPQTRLIIYM YKDSEVRGLA    60
VTLSVKDSKM STLSCKNKII SFEEMDPPEN IDDIQSDLIF FLKGVPGDNK MEFESSLYEG   120
HFLACQKEDH AFKLILKKKD ENGDKSVMFT LTNLHQS                            157

SEQ ID NO: 154               moltype = AA  length = 157
FEATURE                      Location/Qualifiers
source                       1..157
                             mol_type = protein
                             organism = synthetic construct
SEQUENCE: 154
YFGRLHCTTA VIRNINAQVL FVDKRQPVFR DMGYILQSAS EPQTRLIIYL YKDSEVRGLA    60
VTLSVKESKM STLSCKNKII SFEEMDPPEN IDDIQSDLIF FLKPVPGDTK IEFESSLYEG   120
HFLACQKEDN AFKLILKKKD ENGDKSVMFT LTNLHQS                            157

SEQ ID NO: 155               moltype = AA  length = 157
FEATURE                      Location/Qualifiers
source                       1..157
                             mol_type = protein
                             organism = synthetic construct
SEQUENCE: 155
YFGRLHCTTA VIRNINDQVL FVDKRQPVFG DMADTAQSAS EPQTRLIIYF YKDSEVRGLA    60
VTLSVKDSKM STLSCKNKII SFEEMDPPEN IDDIQSDLIF FIKPVPGDSK MEFESSLYEG   120
HFLACQKEAD AFKLILKKKD ENGDKSVMFT LTNLHQS                            157

SEQ ID NO: 156               moltype = AA  length = 157
```

```
FEATURE                 Location/Qualifiers
source                  1..157
                        mol_type = protein
                        organism = synthetic construct
SEQUENCE: 156
DFGRLHCTTA VIRNINGQVL FVDKRQPVFE DMAYIAQSAS EPQTRLIIYF YKDSEVRGLA    60
VTLSVKDSKM STLSCKNKII SFEEMDPPEN IDDIQSDLIF FIKPVPGDSK IEFESSLYEG   120
HFLACQKEAD AFKLILKKKD ENGDKSVMFT LTNLHQS                            157

SEQ ID NO: 157          moltype = AA  length = 157
FEATURE                 Location/Qualifiers
source                  1..157
                        mol_type = protein
                        organism = synthetic construct
SEQUENCE: 157
NFGRLHCTTA VIRNINEQVL SVDKRQPVFR DMKYILQSAS EPQTRLIIYF YKDSEVRGLA    60
VTLSVKDSKM STLSCKNKII SFEEMDPPEN IDDIQSDLIF FLKGVPGDNK MEFESSLYEG   120
HFLACQKEYG AFKLILKKKD ENGDKSVMFT LTNLHQS                            157

SEQ ID NO: 158          moltype = AA  length = 157
FEATURE                 Location/Qualifiers
source                  1..157
                        mol_type = protein
                        organism = synthetic construct
SEQUENCE: 158
DFGRLHCTTA VIRNINEQVL FVDKRQPVFT DMAYILQSAS EPQTRLIIYF YKDSEVRGLA    60
VTLSVKESKM STLSCKNKII SFEEMDPPEN IDDIQSDLIF FIKAVPGDSK LEFESSLYEG   120
HFLACQKEDT AFKLILKKKD ENGDKSVMFT LTNLHQS                            157

SEQ ID NO: 159          moltype = AA  length = 157
FEATURE                 Location/Qualifiers
source                  1..157
                        mol_type = protein
                        organism = synthetic construct
SEQUENCE: 159
DFGRLHCTTA VIRNINNQVL FVDKRQPVFK DMESTAQSAS EPQTRLIIYM YKDSEVRGLA    60
VTLSVKDSKM STLSCKNKII SFEEMDPPEN IDDIQSDLIF FLKGVPGASK LEFESSLYEG   120
HFLACQKEAG AFKLILKKKD ENGDKSVMFT LTNLHQS                            157

SEQ ID NO: 160          moltype = AA  length = 157
FEATURE                 Location/Qualifiers
source                  1..157
                        mol_type = protein
                        organism = synthetic construct
SEQUENCE: 160
HFGRLHCTTA VIRNINEQVL FVDKRQPVFA DMEAIGQSAS EPQTRLIIYF YKDSEVRGLA    60
VTLSVKESKM STLSCKNKII SFEEMDPPEN IDDIQSDLIF FIKGVPGDTK LEFESSLYAG   120
HFLACQKEDG AFKLILKKKD ENGDKSVMFT LTNLHQS                            157

SEQ ID NO: 161          moltype = AA  length = 157
FEATURE                 Location/Qualifiers
source                  1..157
                        mol_type = protein
                        organism = synthetic construct
SEQUENCE: 161
IFGRLHCTTA VIRNINEQVL FVDKRQPVFK DMRYIVQSAS EPQTRLIIYF YKDSEVRGLA    60
VTLSVKDSKM STLSCKNKII SFEEMDPPEN IDDIQSDLIF FIKEVPGASK LEFESSLYEG   120
HFLACQKEDE AFKLILKKKD ENGDKSVMFT LTNLHQS                            157

SEQ ID NO: 162          moltype = AA  length = 157
FEATURE                 Location/Qualifiers
source                  1..157
                        mol_type = protein
                        organism = synthetic construct
SEQUENCE: 162
YFGRLHCTTA VIRNINAQVL FVDKRQPVFT DMGYTLQSAS EPQTRLIIYL YKDSEVRGLA    60
VTLSVKDSKM STLSCKNKII SFEEMDPPEN IDDIQSDLIF FIKPVPGHNK IEFESSLYEG   120
HFLACQKEDR AFKLILKKKD ENGDKSVMFT LTNLHQS                            157

SEQ ID NO: 163          moltype = AA  length = 157
FEATURE                 Location/Qualifiers
source                  1..157
                        mol_type = protein
                        organism = synthetic construct
SEQUENCE: 163
NFGRLHCTTA VIRNINNQVL FVDKRQPVFR DMASTAQSAS EPQTRLIIYM YKDSEVRGLA    60
VTLSVKDSKM STLSCKNKII SFEEMDPPEN IDDIQSDLIF FIKGVPGANK IEFESSLYEG   120
HFLACQKEDD AFKLILKKKD ENGDKSVMFT LTNLHQS                            157
```

```
SEQ ID NO: 164           moltype = AA  length = 157
FEATURE                  Location/Qualifiers
source                   1..157
                         mol_type = protein
                         organism = synthetic construct
SEQUENCE: 164
DFGRLHCTTA VIRNINGQVL FVDKRQPVFE DMKDRAQSAS EPQTRLIIYF YKDSEVRGLA    60
VTLSVKDSKM STLSCKNKII SFEEMDPPEN IDDIQSDLIF FLKAVPGHSK MEFESSLYEG   120
HFLACQKEDE AFKLILKKKD ENGDKSVMFT LTNLHQS                            157

SEQ ID NO: 165           moltype = AA  length = 157
FEATURE                  Location/Qualifiers
source                   1..157
                         mol_type = protein
                         organism = synthetic construct
SEQUENCE: 165
NFGRLHCTTA VIRNINEQVL FVDKRQPVFA DMTDIAQSAS EPQTRLIIYM YKDSEVRGLA    60
VTLSVKESKM STLSCKNKII SFEEMDPPEN IDDIQSDLIF FLKPVPGDIK MEFESSLYEG   120
HFLACQKEYG AFKLILKKKD ENGDNSVMFT LTNLHQS                            157

SEQ ID NO: 166           moltype = AA  length = 157
FEATURE                  Location/Qualifiers
source                   1..157
                         mol_type = protein
                         organism = synthetic construct
SEQUENCE: 166
YFGRLHCTTA VIRNINEQVL FVDKRQPVFA DMTDTLQSAS EPQTRLIIYF YKDSEVRGLA    60
VTLSVKDSKM STLSCKNKII SFEEMDPPEN IDDIQSDLIF FLKGVPGDNK MEFESSLYEG   120
HFLACQKEDT AFKLILKKKD ENGDKSVMFT LTNLHQS                            157

SEQ ID NO: 167           moltype = AA  length = 157
FEATURE                  Location/Qualifiers
source                   1..157
                         mol_type = protein
                         organism = synthetic construct
SEQUENCE: 167
YFGRLHCTTA VIRNINEQVL FVDKRQPVFA DMTDTLQSAS EPQTRLIIYF YKDSEVRGLA    60
VTLSVKDSKM STLSCKNKII SFEEMDPPEN IDDIQSDLIF FLKGVPGDNK MEFESSLYEG   120
HFLACQKEDT AFKLILKKKD ENGDKSVMFT LTNLHQS                            157

SEQ ID NO: 168           moltype = AA  length = 157
FEATURE                  Location/Qualifiers
source                   1..157
                         mol_type = protein
                         organism = synthetic construct
SEQUENCE: 168
YFGRLHCTTA VIRNINEQVL FVDKRQPVFA DMTDTLQSAS EPQTRLIIYF YKDSEVRGLA    60
VTLSVKDSKM STLSCKNKII SFEEMDPPEN IDDIQSDLIF FLKGVPGDNK MEFESSLYEG   120
HFLACQKEDT AFKLILKKKD ENGDKSVMFT LTNLHQS                            157

SEQ ID NO: 169           moltype = AA  length = 157
FEATURE                  Location/Qualifiers
source                   1..157
                         mol_type = protein
                         organism = synthetic construct
SEQUENCE: 169
HFGRLHCTTA VIRNINGQVL FVDKRQPVFK DMKYIVQSAS EPQTRLIIYM YKDSEVRGLA    60
VTLSVKDSKM STLSCKNKII SFEEMDPPEN IDDIQSDLIF FLKAVPGHSK IEFESSLYEG   120
HFLACQKEDS AFKLILKKKD ENGDKSVMFT LTNLHQS                            157

SEQ ID NO: 170           moltype = AA  length = 157
FEATURE                  Location/Qualifiers
source                   1..157
                         mol_type = protein
                         organism = synthetic construct
SEQUENCE: 170
HFGRLHCTTA VIRNINGQVL FVDKRQPVFK DMKYIVQSAS EPQTRLIIYM YKDSEVRGLA    60
VTLSVKDSKM STLSCKNKII SFEEMDPPEN IDDIQSDLIF FLKAVPGHSK IEFESSLYEG   120
HFLACQKEDS AFKLILKKKD ENGDKSVMFT LTNLHQS                            157

SEQ ID NO: 171           moltype = AA  length = 157
FEATURE                  Location/Qualifiers
source                   1..157
                         mol_type = protein
                         organism = synthetic construct
SEQUENCE: 171
YFGRLHCTTA VIRNINGQVL FVDKRQPVFE DMKAKAQSAS EPQTRLIIYF YKDSEVRGLA    60
VTLSVKDSKM STLSCKNKII SFEEMDPPEN IDDIQSDLIF FIKPVPGASK MEFESSLYEG   120
HFLACQKEDG AFKLILKKKD ENGDKSVMFT LTNLHQS                            157
```

```
SEQ ID NO: 172          moltype = AA   length = 157
FEATURE                 Location/Qualifiers
source                  1..157
                        mol_type = protein
                        organism = synthetic construct
SEQUENCE: 172
YFGRLHCTTA VIRNINGQVL FVDKRQPVFE DMKAKAQSAS EPQTRLIIYF YKDSEVRGLA    60
VTLSVKDSKM STLSCKNKII SFEEMDPPEN IDDIQSDLIF FIKPVPGASK MEFESSLYEG   120
HFLACQKEDG AFKLILKKKD ENGDKSVMFT LTNLHQS                            157

SEQ ID NO: 173          moltype = AA   length = 157
FEATURE                 Location/Qualifiers
source                  1..157
                        mol_type = protein
                        organism = synthetic construct
SEQUENCE: 173
YFGRLHCTTA VIRNINGQVL FVDKRQPVFE DMKAKAQSAS EPQTRLIIYF YKDSEVRGLA    60
VTLSVKDSKM STLSCKNKII SFEEMDPPEN IDDIQSDLIF FIKPVPGASK MEFESSLYEG   120
HFLACQKEDG AFKLILKKKD ENGDKSVMFT LTNLHQS                            157

SEQ ID NO: 174          moltype = AA   length = 157
FEATURE                 Location/Qualifiers
source                  1..157
                        mol_type = protein
                        organism = synthetic construct
SEQUENCE: 174
LFGRLHCTTA VIRNINGQVL FVDKRQPVFG DMGSIPQSAS EPQTRLIIYF YKDSEVRGLA    60
VTLSVKDSKM STLSCKNKII SFEEMDPPEN IDDIQSDLIF FIKHVPGATK MEFESSLYEG   120
HFLACQKEDN AFKLILKKKD ENGDKSVMFT LTNLHQS                            157

SEQ ID NO: 175          moltype = AA   length = 157
FEATURE                 Location/Qualifiers
source                  1..157
                        mol_type = protein
                        organism = synthetic construct
SEQUENCE: 175
LFGRLHCTTA VIRNINGQVL FVDKRQPVFG DMGSIPQSAS EPQTRLIIYF YKDSEVRGLA    60
VTLSVKDSKM STLSCKNKII SFEEMDPPEN IDDIQSDLIF FIKHVPGATK MEFESSLYEG   120
HFLACQKEDN AFKLILKKKD ENGDKSVMFT LTNLHQS                            157

SEQ ID NO: 176          moltype = AA   length = 157
FEATURE                 Location/Qualifiers
source                  1..157
                        mol_type = protein
                        organism = synthetic construct
SEQUENCE: 176
YFGRLHCTTA VIRNINSQVL FVDKRQPVFT DMAYTVQSAS EPQTRLIIYF YKDSEVRGLA    60
VTLSVKDSKM STLSCKNKII SFEEMDPPEN IDDIQSDLIF FIKAVPGDSK LEFESSLYEG   120
HFLACQKEDN AFKLILKKKD ENGDKSVMFT LTNLHQS                            157

SEQ ID NO: 177          moltype = AA   length = 157
FEATURE                 Location/Qualifiers
source                  1..157
                        mol_type = protein
                        organism = synthetic construct
SEQUENCE: 177
YFGRLHCTTA VIRNINSQVL FVDKRQPVFT DMAYTVQSAS EPQTRLIIYF YKDSEVRGLA    60
VTLSVKDSKM STLSCKNKII SFEEMDPPEN IDDIQSDLIF FIKAVPGDSK LEFESSLYEG   120
HFLACQKEDN AFKLILKKKD ENGDKSVMFT LTNLHQS                            157

SEQ ID NO: 178          moltype = AA   length = 157
FEATURE                 Location/Qualifiers
source                  1..157
                        mol_type = protein
                        organism = synthetic construct
SEQUENCE: 178
YFGRLHCTTA VIRNINGQVL FVDKRQPVFT DMGARVQSAS EPQTRLIIYF YKDSEVRGLA    60
VTLSVKDSKM YTLSCKNKII SFEEMDPPEN IDDIQSDLIF FLKPVPGDNK LEFESSLYEG   120
HFLACQKESG AFKLILKKKD ENGDKSVMFT LTNLHQS                            157

SEQ ID NO: 179          moltype = AA   length = 157
FEATURE                 Location/Qualifiers
source                  1..157
                        mol_type = protein
                        organism = synthetic construct
SEQUENCE: 179
YFGRLHCTTA VIRNINGQVL FVDKRQPVFT DMGARVQSAS EPQTRLIIYF YKDSEVRGLA    60
VTLSVKDSKM YTLSCKNKII SFEEMDPPEN IDDIQSDLIF FLKPVPGDNK LEFESSLYEG   120
```

```
HFLACQKESG AFKLILKKKD ENGDKSVMFT LTNLHQS                              157

SEQ ID NO: 180          moltype = AA  length = 157
FEATURE                 Location/Qualifiers
source                  1..157
                        mol_type = protein
                        organism = synthetic construct
SEQUENCE: 180
DFGRLHCTTA VIRNINGQVL FVDKRQPVFG DMKATGQSAS EPQTRLIIYF YKDSEVRGLA     60
VTLSVKDSKM STLSCKNKII SFEEMDPPEN IDDIQSDLIF FIKAVPGANK LEFESSLYEG    120
HFLACQKEAG AFKLILKKKD ENGDKSVMFT LTNLHQS                              157

SEQ ID NO: 181          moltype = AA  length = 157
FEATURE                 Location/Qualifiers
source                  1..157
                        mol_type = protein
                        organism = synthetic construct
SEQUENCE: 181
DFGRLHCTTA VIRNINGQVL FVDKRQPVFG DMKATGQSAS EPQTRLIIYF YKDSEVRGLA     60
VTLSVKDSKM STLSCKNKII SFEEMDPPEN IDDIQSDLIF FIKAVPGANK LEFESSLYEG    120
HFLACQKEAG AFKLILKKKD ENGDKSVMFT LTNLHQS                              157

SEQ ID NO: 182          moltype = AA  length = 157
FEATURE                 Location/Qualifiers
source                  1..157
                        mol_type = protein
                        organism = synthetic construct
SEQUENCE: 182
DFGRLHCTTA VIRNINSQVL FVDKRQPVFR DMGSIHQSAS EPQTRLIIYF YKDSEVRGLA     60
VTLSVKDSKM STLSCKNKII SFEEMDPPEN IDDIQSDLIF FLKAVPGANK LEFESSLYEG    120
HFLACQKEDG AFKLILKKKD ENGDKSVMFT LTNLHQS                              157

SEQ ID NO: 183          moltype = AA  length = 157
FEATURE                 Location/Qualifiers
source                  1..157
                        mol_type = protein
                        organism = synthetic construct
SEQUENCE: 183
DFGRLHCTTA VIRNINSQVL FVDKRQPVFR DMGSIHQSAS EPQTRLIIYF YKDSEVRGLA     60
VTLSVKDSKM STLSCKNKII SFEEMDPPEN IDDIQSDLIF FLKAVPGANK LEFESSLYEG    120
HFLACQKEDG AFKLILKKKD ENGDKSVMFT LTNLHQS                              157

SEQ ID NO: 184          moltype = AA  length = 157
FEATURE                 Location/Qualifiers
source                  1..157
                        mol_type = protein
                        organism = synthetic construct
SEQUENCE: 184
YFGRLHCTTA VIRNINEQVL FVDKRQPVFK DMKDKLQSAS EPQTRLIIYF YKDSEVRGLA     60
VTLSVKDSKM STLSCKNKII SFEEMDPPEN IDDIQSDLIF FLKGVPGDNK LEFESSLYEG    120
HFLACQKEFG AFKLILKKKD ENGDKSVMFT LTNLHQS                              157

SEQ ID NO: 185          moltype = AA  length = 157
FEATURE                 Location/Qualifiers
source                  1..157
                        mol_type = protein
                        organism = synthetic construct
SEQUENCE: 185
YFGRLHCTTA VIRNINEQVL FVDKRQPVFK DMKDKLQSAS EPQTRLIIYF YKDSEVRGLA     60
VTLSVKDSKM STLSCKNKII SFEEMDPPEN IDDIQSDLIF FLKGVPGDNK LEFESSLYEG    120
HFLACQKEFG AFKLILKKKD ENGDKSVMFT LTNLHQS                              157

SEQ ID NO: 186          moltype = AA  length = 157
FEATURE                 Location/Qualifiers
source                  1..157
                        mol_type = protein
                        organism = synthetic construct
SEQUENCE: 186
YFGRLHCTTA VIRNINGQVL FVDKRQPVFA DMASTHQSAS EPQTRLIIYF YKDSEVRGLA     60
VTLSVKDSKM STLSCKNKII SFEEMDPPEN IDDIQSDLIF FLKGVPGANK IEFESSLYEG    120
HFLACQKEDD AFKLILKKKD ENGDKSVMFT LTNLHQS                              157

SEQ ID NO: 187          moltype = AA  length = 157
FEATURE                 Location/Qualifiers
source                  1..157
                        mol_type = protein
                        organism = synthetic construct
SEQUENCE: 187
YFGRLHCTTA VIRNINGQVL FVDKRQPVFA DMASTHQSAS EPQTRLIIYF YKDSEVRGLA     60
```

```
VTLSVKDSKM STLSCKNKII SFEEMDPPEN IDDIQSDLIF FLKGVPGANK IEFESSLYEG    120
HFLACQKEDD AFKLILKKKD ENGDKSVMFT LTNLHQS                             157

SEQ ID NO: 188          moltype = AA  length = 157
FEATURE                 Location/Qualifiers
source                  1..157
                        mol_type = protein
                        organism = synthetic construct
SEQUENCE: 188
YFGRLHCTTA VIRNINGQVL FVDKRQPVFA DMASTHQSAS EPQTRLIIYF YKDSEVRGLA     60
VTLSVKDSKM STLSCKNKII SFEEMDPPEN IDDIQSDLIF FLKGVPGANK IEFESSLYEG    120
HFLACQKEDD AFKLILKKKD ENGDKSVMFT LTNLHQS                             157

SEQ ID NO: 189          moltype = AA  length = 157
FEATURE                 Location/Qualifiers
source                  1..157
                        mol_type = protein
                        organism = synthetic construct
SEQUENCE: 189
YFGRLHCTTA VIRNINSQVL FVDKRQPVFG DMKYIVQSAS EPQTRLIIYF YKDSEVRGLA     60
VTLSVKDSKM STLSCKNKII SFEEMDPPEN IDDIQSDLIF FLKGVPGDTK MEFESSLYEG    120
HFLACQKESG AFKLILKKKD ENGDKSVMFT LTNLHQS                             157

SEQ ID NO: 190          moltype = AA  length = 157
FEATURE                 Location/Qualifiers
source                  1..157
                        mol_type = protein
                        organism = synthetic construct
SEQUENCE: 190
YFGRLHCTTA VIRNINSQVL FVDKRQPVFG DMKYIVQSAS EPQTRLIIYF YKDSEVRGLA     60
VTLSVKDSKM STLSCKNKII SFEEMDPPEN IDDIQSDLIF FLKGVPGDTK MEFESSLYEG    120
HFLACQKESG AFKLILKKKD ENGDKSVMFT LTNLHQS                             157

SEQ ID NO: 191          moltype = AA  length = 157
FEATURE                 Location/Qualifiers
source                  1..157
                        mol_type = protein
                        organism = synthetic construct
SEQUENCE: 191
YFGKLESKLS VIRNLNDQVL FIDQGNRPLF EDMTDSDCRD NAPRTIFIIS KYGDSVPRGL     60
AVTISVKCEK ISTLSCENKI ISFKEMNPPD NIKDTKSDII FFARAVPGHS RKTQFESSSY    120
EGYFLACEKE RDLFKLILKK EDELGDRSIM FTVQNED                             157

SEQ ID NO: 192          moltype = AA  length = 157
FEATURE                 Location/Qualifiers
source                  1..157
                        mol_type = protein
                        organism = synthetic construct
SEQUENCE: 192
YFGKLESKLS VIRNLNDQVL FIDQGNRPLF EDMTDSDCRD NAPRTIFIIS KYSDSRARGL     60
AVTISVKCEK ISTLSCENKI ISFKEMNPPD NIKDTKSDII FFARSVPGHG RKTQFESSSY    120
EGYFLACEKE RDLFKLILKK EDELGDRSIM FTVQNED                             157

SEQ ID NO: 193          moltype = AA  length = 157
FEATURE                 Location/Qualifiers
source                  1..157
                        mol_type = protein
                        organism = synthetic construct
SEQUENCE: 193
YFGKLESKLS VIRNLNDQVL FIDQGNRPLF EDMTDSDCRD NAPRTIFIIS KYSDSRARGL     60
AVTISVKCEK ISTLSCENKI ISFKEMNPPD NIKDTKSDII FFARDVPGHS GKRQFESSSY    120
EGYFLACEKE RDLFKLILKK EDELGDRSIM FTVQNED                             157

SEQ ID NO: 194          moltype = DNA  length = 58
FEATURE                 Location/Qualifiers
source                  1..58
                        mol_type = other DNA
                        organism = synthetic construct
SEQUENCE: 194
cattttcatt aagatgcagt tacttcgctg tttttcaata ttttctgtta ttgctagc      58

SEQ ID NO: 195          moltype = DNA  length = 80
FEATURE                 Location/Qualifiers
misc_difference         31
                        note = a, c, g, t/u, unknown, or other
misc_difference         42
                        note = a, c, g, t/u, unknown, or other
source                  1..80
                        mol_type = other DNA
```

```
                              organism = synthetic construct
SEQUENCE: 195
aattacggat gaccgaaagt ykggattcaw ncttgccgaa anrtgctaaa acgctagcaa    60
taacagaaaa tattgaaaaa                                                80

SEQ ID NO: 196          moltype = DNA   length = 51
FEATURE                 Location/Qualifiers
source                  1..51
                        mol_type = other DNA
                        organism = synthetic construct
SEQUENCE: 196
actttcggtc atccgtaatt tgaacgacca agtccttttt attgaccagg g             51

SEQ ID NO: 197          moltype = DNA   length = 55
FEATURE                 Location/Qualifiers
source                  1..55
                        mol_type = other DNA
                        organism = synthetic construct
SEQUENCE: 197
actatccgtc atatcctcga ataagggacg attgccctgg tcaataaaaa ggact         55

SEQ ID NO: 198          moltype = DNA   length = 44
FEATURE                 Location/Qualifiers
source                  1..44
                        mol_type = other DNA
                        organism = synthetic construct
SEQUENCE: 198
cttattcgag gatatgacgg atagtgattg ccgtgacaac gccc                     44

SEQ ID NO: 199          moltype = DNA   length = 84
FEATURE                 Location/Qualifiers
misc_difference         22
                        note = a, c, g, t/u, unknown, or other
misc_difference         46
                        note = a, c, g, t/u, unknown, or other
source                  1..84
                        mol_type = other DNA
                        organism = synthetic construct
SEQUENCE: 199
actgagattg ttaccgcchb tnyacggggt tgwyyatcty tatasnyaga gatgatgaaa    60
attgtacgag gggcgttgtc acgg                                           84

SEQ ID NO: 200          moltype = DNA   length = 52
FEATURE                 Location/Qualifiers
source                  1..52
                        mol_type = other DNA
                        organism = synthetic construct
SEQUENCE: 200
ggcggtaaca atctcagtta agtgcgaaaa aatctcgaca ctttcttgtg aa            52

SEQ ID NO: 201          moltype = DNA   length = 53
FEATURE                 Location/Qualifiers
source                  1..53
                        mol_type = other DNA
                        organism = synthetic construct
SEQUENCE: 201
ggttcatttc cttgaacgaa atgatcttgt tttcacaaga aagtgtcgag att           53

SEQ ID NO: 202          moltype = DNA   length = 62
FEATURE                 Location/Qualifiers
source                  1..62
                        mol_type = other DNA
                        organism = synthetic construct
SEQUENCE: 202
catttcgttc aaggaaatga acccgccgga taatatcaag gatacaaaat cagatattat    60
tt                                                                   62

SEQ ID NO: 203          moltype = DNA   length = 88
FEATURE                 Location/Qualifiers
misc_difference         27
                        note = a, c, g, t/u, unknown, or other
source                  1..88
                        mol_type = other DNA
                        organism = synthetic construct
SEQUENCE: 203
tgatgagctc tcgaattgca tcttatnwtb gtgtccaggc acwyyacgwt bgaagaaaat    60
aatatctgat tttgtatcct tgatatta                                       88

SEQ ID NO: 204          moltype = DNA   length = 51
```

```
FEATURE              Location/Qualifiers
source               1..51
                     mol_type = other DNA
                     organism = synthetic construct
SEQUENCE: 204
ataagatgca attcgagagc tcatcatacg aaggttactt tttagcctgc g          51

SEQ ID NO: 205       moltype = DNA   length = 50
FEATURE              Location/Qualifiers
source               1..50
                     mol_type = other DNA
                     organism = synthetic construct
SEQUENCE: 205
aattaactta aacaggtcgc gctccttctc gcaggctaaa aagtaacctt            50

SEQ ID NO: 206       moltype = DNA   length = 49
FEATURE              Location/Qualifiers
source               1..49
                     mol_type = other DNA
                     organism = synthetic construct
SEQUENCE: 206
gcgacctgtt taagttaatt cttaagaaag aagatgagtt gggggatcg             49

SEQ ID NO: 207       moltype = DNA   length = 61
FEATURE              Location/Qualifiers
source               1..61
                     mol_type = other DNA
                     organism = synthetic construct
SEQUENCE: 207
ccagaaccac cgtcctcwtb ctgadyggta aacatgatgc tacgatcccc caactcatct 60
t                                                                 61

SEQ ID NO: 208       moltype = DNA   length = 52
FEATURE              Location/Qualifiers
source               1..52
                     mol_type = other DNA
                     organism = synthetic construct
SEQUENCE: 208
gaggacggtg gttctggatc cgaacaaaag cttatctccg aagaagactt gg         52

SEQ ID NO: 209       moltype = DNA   length = 41
FEATURE              Location/Qualifiers
source               1..41
                     mol_type = other DNA
                     organism = synthetic construct
SEQUENCE: 209
ccaccagatc caccaccacc caagtcttct tcggagataa g                     41

SEQ ID NO: 210       moltype = DNA   length = 62
FEATURE              Location/Qualifiers
source               1..62
                     mol_type = other DNA
                     organism = synthetic construct
SEQUENCE: 210
cattttcatt aagatgcagt tacttcgctg tttttcaata ttttctgtta ttgctagcgt 60
tt                                                                62

SEQ ID NO: 211       moltype = DNA   length = 55
FEATURE              Location/Qualifiers
misc_difference      25
                     note = a, c, g, t/u, unknown, or other
source               1..55
                     mol_type = other DNA
                     organism = synthetic construct
SEQUENCE: 211
ttgtacagtg aagtcggcca aaawntgcta aaacgctagc aataacagaa aatat      55

SEQ ID NO: 212       moltype = DNA   length = 59
FEATURE              Location/Qualifiers
source               1..59
                     mol_type = other DNA
                     organism = synthetic construct
SEQUENCE: 212
gccgacttca ctgtacaacc gcagtaatac ggaatataaa tgaccaagtt ctcttcgtt  59

SEQ ID NO: 213       moltype = DNA   length = 67
FEATURE              Location/Qualifiers
source               1..67
                     mol_type = other DNA
```

```
                            organism = synthetic construct
SEQUENCE: 213
ttgatcaata tcagtcatat cctcgaacac aggctgtctt ttgtcaacga agagaacttg    60
gtcattt                                                              67

SEQ ID NO: 214          moltype = DNA  length = 54
FEATURE                 Location/Qualifiers
source                  1..54
                        mol_type = other DNA
                        organism = synthetic construct
SEQUENCE: 214
gtgttcgagg atatgactga tattgatcaa agtgccagtg aacccagac caga           54

SEQ ID NO: 215          moltype = DNA  length = 78
FEATURE                 Location/Qualifiers
misc_difference         24
                        note = a, c, g, t/u, unknown, or other
misc_difference         30
                        note = a, c, g, t/u, unknown, or other
misc_difference         32
                        note = a, c, g, t/u, unknown, or other
misc_difference         42
                        note = a, c, g, t/u, unknown, or other
misc_difference         44
                        note = a, c, g, t/u, unknown, or other
misc_difference         46
                        note = a, c, g, t/u, unknown, or other
misc_difference         48
                        note = a, c, g, t/u, unknown, or other
source                  1..78
                        mol_type = other DNA
                        organism = synthetic construct
SEQUENCE: 215
tcacagagag ggtcacagcy hbtnywbybn bnybwyygtc snbnynsnyg tatattatca    60
gtctggtctg gggttcac                                                  78

SEQ ID NO: 216          moltype = DNA  length = 58
FEATURE                 Location/Qualifiers
source                  1..58
                        mol_type = other DNA
                        organism = synthetic construct
SEQUENCE: 216
gctgtgaccc tctctgtgaa ggatagtaaa atgtctaccc tctcctgtaa gaacaaga     58

SEQ ID NO: 217          moltype = DNA  length = 69
FEATURE                 Location/Qualifiers
source                  1..69
                        mol_type = other DNA
                        organism = synthetic construct
SEQUENCE: 217
gtatatcatc aatattttca ggtggatcca tttcctcaaa ggaaatgatc ttgttcttac    60
aggagaggg                                                            69

SEQ ID NO: 218          moltype = DNA  length = 99
FEATURE                 Location/Qualifiers
misc_difference         59
                        note = a, c, g, t/u, unknown, or other
misc_difference         74
                        note = a, c, g, t/u, unknown, or other
source                  1..99
                        mol_type = other DNA
                        organism = synthetic construct
SEQUENCE: 218
aatggatcca cctgaaaata ttgatgatat acaaagtgat ctcatattct ttcagaaand    60
hgttccagga cacnataaga tggagtttga atcttcact                           99

SEQ ID NO: 219          moltype = DNA  length = 57
FEATURE                 Location/Qualifiers
source                  1..57
                        mol_type = other DNA
                        organism = synthetic construct
SEQUENCE: 219
ccttttggca agcaagaaag tgtccttcat acagtgaaga ttcaaactcc atcttat       57

SEQ ID NO: 220          moltype = DNA  length = 60
FEATURE                 Location/Qualifiers
source                  1..60
                        mol_type = other DNA
                        organism = synthetic construct
```

```
SEQUENCE: 220
ctttcttgct tgccaaaagg aagatgatgc tttcaaactc attctgaaaa aaaaggatga    60

SEQ ID NO: 221          moltype = DNA  length = 77
FEATURE                 Location/Qualifiers
source                  1..77
                        mol_type = other DNA
                        organism = synthetic construct
SEQUENCE: 221
ccaccacttt gatgtaagtt agtrdbagtg aacattacag atttatcccc attttcatcc    60
ttttttttca gaatgag                                                   77

SEQ ID NO: 222          moltype = DNA  length = 59
FEATURE                 Location/Qualifiers
source                  1..59
                        mol_type = other DNA
                        organism = synthetic construct
SEQUENCE: 222
actaacttac atcaaagtgg tggttctgga tccgaacaaa agcttatctc cgaagaaga     59
```

INTERLEUKIN-18 VARIANTS AND METHODS OF USE

CROSS-REFERENCE

This application is a continuation of International Application No. PCT/US2021/057741, filed on Nov. 2, 2021, which claims benefit of U.S. Provisional Application No. 63/108,794, filed on Nov. 2, 2020, each of which is incorporated herein by reference in its entirety.

SEQUENCE LISTING

The instant application contains a Sequence Listing which has been submitted electronically in XML format and is hereby incorporated by reference in its entirety. Said XML copy, created on Nov. 14, 2022, is named 62106-703_301_SL.xml and is 228,044 bytes in size.

BACKGROUND

Interleukin 18 (IL-18) is a pro-inflammatory cytokine that can stimulate T cells, NK cells, and myeloid cells. IL-18 has been proposed as an immunotherapeutic agent for the treatment of cancer, given its ability to stimulate anti-tumor immune cells. However, the clinical efficacy of IL-18 has been limited.

Thus, there is a need for compositions and methods that provide effective IL-18 signaling activity to treat and prevent cancer and other diseases and disorders. The present disclosure addresses these needs.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In one aspect, the present disclosure provides a method of promoting interleukin-18 (IL-18) signaling activity, the method comprising administering a modified IL-18 polypeptide to a subject in need thereof, the modified IL-18 polypeptide comprising: (i) an amino acid sequence having 85% or more sequence identity with the IL-18 variant amino acid sequence set forth in any one of SEQ ID NO: 89-91; and (ii) mutations at amino acid positions Cysteine-38 and Cysteine-68 relative to wild-type (WT) IL-18 as set forth in SEQ ID NO: 30, thereby promoting IL-18 signaling activity.

In some embodiments, the subject is a human. In some embodiments, the mutation at position Cysteine-68 is a substitution of Cysteine-68 to serine. In some embodiments, the mutation at position Cysteine-68 is a substitution of Cysteine-68 to glycine. In some embodiments, the mutation at position Cysteine-68 is a substitution of Cysteine-68 to alanine. In some embodiments, the mutation at position Cysteine-68 is a substitution of Cysteine-68 to aspartic acid. In some embodiments, the mutation at position Cysteine-68 is a substitution of Cysteine-68 to asparagine.

In some embodiments, the IL-18 polypeptide has one or more substitutions selected from the group consisting of: (1) Tyrosine-1 to histidine, or Tyrosine-1 to arginine, (2) Leucine-5 to histidine, Leucine-5 to isoleucine, or Leucine-5 to tyrosine, (3) Lysine-8 to glutamine, or Lysine-8 to arginine, (4) Methionine-51 to threonine, Methionine-51 to lysine, Methionine-51 to aspartic acid, Methionine-51 to asparagine, Methionine-51 to glutamic acid, or Methionine-51 to arginine, (5) Lysine-53 to arginine, Lysine 53-glycine, Lysine-53 to serine, or Lysine-53 to threonine, (6) Serine-55 to lysine, or Serine-55 to arginine, (7) Glutamine-56 to glutamic acid, Glutamine-56 to alanine, Glutamine-56 to arginine, Glutamine-56 to valine, Glutamine-56 to glutamic acid, Glutamine-56 to glycine, Glutamine-56 to lysine, or Glutamine-56 to leucine, (8) Proline-57 to leucine, Proline-57 to glycine, Proline-57 to alanine, or Proline-57 to lysine, (9) Glycine-59 to threonine, or Glycine-59 to alanine, (10) Methionine-60 to lysine, Methionine-60 to glutamine, Methionine-60 to arginine, or Methionine-60 to leucine, (11) Glutamic acid-77 to aspartic Acid, (12) Glycine-103 to glutamic acid, Glycine-103 to lysine, Glycine-103 to proline, Glycine-103 to alanine, or Glycine-103 to arginine, (13) Serine-105 to arginine, Serine-105 to aspartic acid, Serine-105 to asparagine, or Serine-105 to alanine, (14) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, or Aspartic acid-110 to glycine, (15) Asparagine-111 to histidine, Asparagine-111 to tyrosine, Asparagine-111 to aspartic acid, Asparagine-111 to arginine, Asparagine-111 to serine, or Asparagine-111 to glycine, (16) Methionine-113 to valine, Methionine-113 to arginine, Methionine-113 to threonine, or Methionine-113 to lysine, (17) Valine-153 to isoleucine, Valine-153 to threonine, or Valine-153 to alanine, and (18) Asparagine-155 to lysine, or Asparagine-155 to histidine, relative to SEQ ID NO: 30.

In some embodiments, the IL-18 polypeptide is a decoy resistant (DR) IL-18 variant or a decoy-to-the-decoy (D2D) IL-18 variant.

In some embodiments, the DR IL-18 variant comprises mutations in at least two of the following positions: Tyrosine-1, Leucine-5, Lysine-8, Methionine-51, Lysine-53, Serine-55, Glutamine-56, Proline-57, Glycine-59, Methionine-60, Glutamic acid-77, Glutamine-103, Serine-105, Aspartic acid-110, Asparagine-111, Methionine-113, Valine-153, and Asparagine-155, relative to SEQ ID NO: 30.

In some embodiments, the DR IL-18 variant comprises mutations in at least two of the following positions: Methionine-51, Lysine-53, Serine-55, Glutamine-56, Proline-57, Methionine-60, Glutamine-103, Serine-105, Aspartic acid-110, Asparagine-111, and Methionine-113, relative WT IL-18 as set forth in SEQ ID NO: 30.

In some embodiments, the DR IL-18 variant comprises mutations at positions Methionine-51, Lysine-53, Glutamine-56, Aspartic acid-110, and Asparagine-111, relative to WT IL-18 as set forth in SEQ ID NO: 30. In some embodiments, the DR IL-18 variant further comprises mutations at positions Proline-57 and Methionine-60, relative to WT IL-18 as set forth in SEQ ID NO: 30. In some embodiments, the DR IL-18 variant further comprises a mutation at position Serine-105, relative to WT IL-18 as set forth in SEQ ID NO: 30.

In some embodiments, the DR IL-18 variant has at least five substitutions selected from the group consisting of: (1) Methionine-51 to threonine, Methionine-51 to lysine, Methionine-51 to aspartic acid, Methionine-51 to asparagine, Methionine-51 to glutamic acid, or Methionine-51 to arginine, (2) Lysine-53 to arginine, Lysine-53 to glycine, Lysine-53 to serine, or Lysine-53 to threonine, (3) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (4) Proline-57 to leucine, Proline-57 to glycine, Proline-P57 to alanine, or Proline-57 to lysine, (5) Methionine-60 to lysine, Methionine-60 glutamine, Methionine-60 to arginine, or Methionine-60 to leucine, (6) Glutamine-103 to glutamic acid, Glutamine-103 to lysine, Glutamine-103 to proline, Glutamine-103 to alanine, or Glutamine-103 to arginine, (7) Serine-105 to arginine, Serine-105 to aspartic acid, Serine-105 to lysine, Serine-105 to histidine, or Serine-105 to alanine, (8) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, Aspartic acid-110 to glycine, (9) Asparagine-111 to histidine, Asparagine-111 to tyrosine Asparagine-111 to aspartic acid, Asparagine-111 to arginine, Asparagine-111 to serine, or Asparagine-111 to glycine, and (10) Methionine-113 to valine, Methionine-113 to arginine, Methionine-113 to threonine, or Methionine-113 to lysine, relative to SEQ ID NO: 30.

In some embodiments, the DR IL-18 variant has at least five substitutions selected from the group consisting of: (1) Methionine-51 to glutamic acid, Methionine-51 to arginine, Methionine-51 to lysine, Methionine-51 to threonine, Methionine-51 to aspartic acid, or Methionine-51 to asparagine; (2) Lysine-53 to glycine, Lysine-53 to serine, Lysine-53 to threonine, or Lysine-53 to arginine; (3) Glutamine-56 to glycine, Glutamine-56 to arginine, Glutamine-56 to leucine, Glutamine-56 to glutamic acid, Glutamine-56 to alanine, Q56V, or Glutamine-56 to lysine; (4) Aspartic acid-110 to serine, Aspartic acid-110 to asparagine, Aspartic acid-110 to glycine, Aspartic acid-110 to lysine, Aspartic acid-110 to histidine, Aspartic acid-110 to glutamine, or Aspartic acid-110 to glutamic acid; (5) Asparagine-111 to glycine, Asparagine-111 to arginine, Asparagine-111 to serine, Asparagine-111 to aspartic acid, Asparagine-111 to histidine, or Asparagine-111 to tyrosine; (6) Proline-57 to alanine, Proline-57 to leucine, Proline-57 to glycine, or Proline-57 lysine; and (7) Methionine-60 to leucine, Methionine-60 to arginine, Methionine-60 to lysine, or Methionine-60 to glutamine, relative to SEQ ID NO: 30. In some embodiments, the DR IL-18 variant further comprises the substitution Serine-105 to aspartic acid, Serine-105 to alanine, Serine-105 to asparagine, Serine-105 to arginine, Serine-105 to aspartic acid, or Serine-105 to lysine relative to SEQ ID NO: 30.

In some embodiments, the DR IL-18 variant specifically binds to IL-18 receptor (IL-18R) but exhibits reduced binding to IL-18 binding protein (IL-18BP) compared to the WT IL-18. In some embodiments, the DR IL-18 variant comprises substitutions of Methionine-50 to lysine, Lysine-53 to serine, Glutamine-56 to leucine, Aspartic acid-110 to serine, and Asparagine-111 to arginine, relative to SEQ ID NO: 30. In some embodiments, the DR IL-18 variant further comprises substitutions of Proline-57 to alanine, Methionine-60 to leucine, and Serine-105 to aspartic acid.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A provides a chart showing that the IL-18 pathway (including IL-18 and its receptor subunits) is upregulated in both activated and dysfunctional tumor T cell programs, as seen in RNAseq expression analysis for cytokines and receptors in CD8+ TILs. Genes are assigned "activation" and "dysfunction" scores in comparison to naïve T cells, as seen in the chart. Data points marked with a diamond-shape and black text indicate IL-18 cytokine, IL-18R1 (Ra), and IL-18RAP (Rβ). Data are adapted from Singer et al. (Singer, M. et al., 2016, Cell, 166:1500-1511, e1509). FIG. 1B provides the results of infection with LCMV (left; CD4) or VSV-OVA (right; CD8). The IL-18 receptor subunits IL-18Rα and IL-18Rβ are part of a gene expression program associated with chronic antigen exposure, as seen after infection with LCMV (left; CD4) or VSV-OVA (right; CD8). Data are from the ImmGen database.

FIG. 2A shows how the IL-18BP mediates Interferon-γ (IFN-γ) driven negative feedback of IL-18, reminiscent of the immune checkpoint PD-L1. A schematic of the IL-18/IFN-γ/IL-18BP feedback loop is depicted. Black arrows indicate stimulation, dark gray circuits indicate inhibition. FIG. 2B shows that IL-18BP is upregulated in gastric and breast cancer using data from the TCGA and Oncomine databases. FIG. 2C demonstrates that PD-1 and IL-18BP expression is strongly correlated in bulk breast and gastric cancer samples (from TCGA database). R=0.78 and 0.65, respectively.

FIG. 3A provides a structure-guided library, which was designed to randomize residues on the IL-18:IL-18BP interface and introduced into a yeast-display system. Yeast clones were selected using magnetic and fluorescence cell sorting for binding to IL-18Rα and counter-selected against IL-18BP. FIG. 3B provides a summary of directed evolution to generate IL-18BP resistant IL-18 variants. Positive selection conditions are: hIL18Rα SA-beads and hIL18Ra. Counter-selection conditions are: SA-alone, hIL-18BP, and nIL-18BP tetramer. FIG. 3C provides flow cytometric analysis of yeast-displayed WT IL-18 (left) or variants after directed evolution (right). Y-axes show IL-18BP binding, x-axes show IL-18Rα binding. After 5 rounds of directed evolution, the remaining clones greatly preferred IL-18Rα to IL-18BP.

FIG. 4 depicts results from example experiments, demonstrating a summary of the sequences of decoy-resistant human IL-18 ("DR-IL-18", also called "DR-18") variants. The position of each mutated position and the corresponding residue in the mature form of wild-type human IL-18 is indicated at the top of the table. SEQ ID NO: 38 through SEQ ID NO: 58 represent sequences obtained after selection with directed evolution. SEQ ID NO: 34-SEQ ID NO: 37 are consensus sequences derived from the selected sequences. Shaded residues represent the five most conserved mutations observed. The sequence for the top row ("WT hIL-18") is set forth as SEQ ID NO: 30.

FIG. 5A provides binding isotherms on yeast-displayed DR-hIL-18 variants. As shown, yeast-displayed DR-IL-18 variants SEQ ID NO: 34-37 and SEQ ID NO: 39 are capable of binding hIL-18Rα with comparable binding isotherms as WT human IL-18 (left). By contrast, very little binding is observed with the same variants and hIL-18BP (right). FIG. 5B shows representative surface plasmon resonance sensor grams between immobilized biotinylated hIL-18BP and the DR-IL-18 variants. Recombinant hIL-18 (left) binds IL-18BP with exquisitely high affinity, KD=2.0 pM, whereas SEQ ID NO: 34 (right) shows greatly attenuated binding, with a much faster off-rate and KD=15.2 nM. This data is summarized in Table 6 and Table 7.

FIG. 6A and FIG. 6B depict results from example experiments, demonstrating human DR-IL-18 variants are not inhibited by IL-18BP. FIG. 6A provides a chart showing that recombinant IL-18BP inhibits biotinylated IL-18Rα from binding yeast-displayed WT IL-18, but does not affect the DR-IL-18 variants SEQ ID NO: 34-37 and SEQ ID NO: 39 (shown in chart on left). By contrast, IL-18BP effectively neutralizes the IL-18 E42A, K89A and E42A/K89A previously described (Kim et al., 2001, Proc. Natl. Acad. Sci., 98(6):3304-3309) (shown in chart on right) [E42 and K89 of Kim et al. are E6 and K53 of SEQ ID NO: 30, respectively]. Biotinylated IL-18Rα was kept at a fixed concentration of 100 nM for all samples. FIG. 6B provides results of HEK Blue IL-18 signaling assay, showing that WT IL-18 and SEQ ID NO: 34, SEQ ID NO: 36, and SEQ ID NO: 37 stimulate IL-18 HEK-Blue reporter cells with comparable potency and efficacy (left). Wild-type IL-18 is highly sensitive to application of recombinant IL-18BP in this assay (IC50=3 nM), whereas SEQ ID NO: 34 and SEQ ID NO: 36 are not inhibited by recombinant IL-18BP, even at IL-18BP concentrations of 1 µM (Right). hIL-18 was kept at a fixed concentration of 5 nM and SEQ ID NO: 34 and SEQ ID NO: 36 at 2.5 nM.

FIG. 7A through FIG. 7C depict results from example experiments demonstrating engineering additional human IL-18 variants for independence to IL-18BP (version 2 variants) using yeast display. FIG. 7A provides a summary of the positions in human IL-18 randomized in the version 2.0 library. Degenerate codons and the set of encoded amino acids are given for each position. FIG. 7B provides a summary of directed evolution to generate version 2.0 IL-18BP resistant IL-18 variants. Positive selection conditions are: hIL18Rα SA-beads and hIL18Rα Counterselection conditions are: SA alone, hIL-18BP, and hIL-18BP tetramer. FIG. 7C provides a flow cytometric analysis of progress in creating version 2.0 DR-IL-18 variants. Yeast obtained after rounds 1, 4, and 6 were stained simultaneously with 250 nM IL-18BP streptavidin-PE tetramers or 100 nM IL-18Rα directly labeled with AlexaFluor647. Y-axes show IL-18BP binding, x-axes show IL-18Rα binding. After 6 rounds of directed evolution, the remaining clones greatly preferred IL-18Rα to IL-18BP.

FIG. 8 depicts results from example experiments, demonstrating a summary of the sequences of version 2.0 decoy-resistant human IL-18 (DR-IL-18) variants. The position of each mutated position and the corresponding residue in the mature form of wild-type human IL-18 is indicated at the top of the table. Shaded rows indicate recurrent sequence variants obtained in both round 5 and round 6. The sequence for the top row ("WT hIL-18") is set forth as SEQ ID NO: 30.

FIGS. 9A-9D depict results from example experiments, demonstrating biophysical characterization of version 2.0 human DR-IL-18 variants. FIG. 9A shows that yeast-displayed version 2.0 DR-IL-18 variants are capable of binding hIL-18Rα with comparable binding isotherms as WT human IL-18. FIG. 9B shows, by contrast, that very little binding is observed with the same variants and hIL-18BP. FIG. 9C provides thermal stability of the version 2.0 DR-IL-18 variants, as was assessed by heating the yeast-displayed variants across a range of temperatures for 15 minutes, followed by staining with hIL-18Ra. The version 2.0 DR-IL-18 variants were more thermostable than WT IL-18 (Tm=47.6 C) and the first-generation consensus sequences (Tm=50.9 and 40.2 for SEQ ID NO: 24 and SEQ ID NO: 35, respectively). FIG. 9D provides a summary of the receptor binding properties and thermal stability of the second-generation DR-IL-18 variants. NBD=no binding detected. N.D.=value not determined.

FIG. 10A through FIG. 10C depict results from example experiments, demonstrating engineering murine IL-18 variants for independence to IL-18BP using yeast display. FIG. 10A provides a summary of directed evolution to generate IL-18BP resistant murine IL-18 variants. Positive selection conditions are: mIL18Ra SA-beads and mIL18Ra. Counterselection conditions are: mIL-18BP and mIL-18BP tetramer. FIG. 10B shows results of flow cytometric analysis of yeast-displayed murine IL-18 variants after 5 rounds of directed evolution. Y-axes show IL-18BP binding, x-axes show IL-18Rα binding. FIG. 10C provides a summary of the sequences of decoy-resistant murine IL-18 (DR-IL-18) variants. The sequence for the top row ("mIL-18") is set forth as SEQ ID NO: 31. The position of each mutated position and the corresponding residue in the mature form of wild-type murine IL-18 is indicated at the top of the table. SEQ ID NO: 62 through SEQ ID NO: 72 represent sequences obtained after selection with directed evolution. SEQ ID NO: 60 and SEQ ID NO: 61 are consensus sequences derived from the selected sequences. Shaded residues represent the five most conserved mutations observed.

FIG. 11A shows that yeast-displayed DR-IL-18 variants SEQ ID NO: 70, SEQ ID NO: 67, SEQ ID NO: 62, SEQ ID NO: 64, SEQ ID NO: 60, and SEQ ID NO: 61 are capable of binding mIL-18Rα with comparable binding isotherms as WT murine IL-18 (left). By contrast, very little binding is observed with the same variants and mIL-18BP (right). FIG. 11B provides measurement of IL-18BP binding using representative surface plasmon resonance sensor grams between immobilized biotinylated mIL-18BP and the murine DR-IL-18 variants. Recombinant mIL-18 (left) binds mIL-18BP with high affinity, KD=0.8 pM, whereas SEQ ID NO: 61 (right) shows greatly decreased binding with a KD value greater than 10 NM. This data is summarized in Tables 8 and 9.

FIG. 12A is a schematic of study design. Mice were administered vehicle (PBS), mIL-18 (1 mg/kg), or the DR-IL-18 variant SEQ ID NO: 61 (1 mg/kg) once daily for seven total doses (depicted as syringes). Blood samples were taken five hours post-injection two days prior to the experiment, and on days 0, 3, and 6. FIG. 12B shows peripheral blood cell counts for CD4, CD8, NK cells, and monocytes at day 0, day 3, and day 6. Both IL-18 and SEQ ID NO: 61 expanded NK cells and monocytes to a similar degree by day 3. For each time point (day), left bar is PBS, middle bar is IL-18, and right bar is SEQ ID NO: 61. FIG. 12C shows the CD69 expression on peripheral CD4, CD8, and NK cells. SEQ ID NO: 61, but not IL-18 stimulated CD69 expression on CD4 and CD8 cells. Both IL-18 and SEQ ID NO: 61 increased CD69 on NK cells, but SEQ ID NO: 61 treatment caused sustained CD69 expression evident at day 6, in comparison to IL-18, which reverted to baseline CD69 levels. For each time point (day), left bar is PBS, middle bar is IL-18, and right bar is SEQ ID NI: 61. FIG. 12D provides Serum cytokine levels for interferon-g (IFN-g), MIP-1b, and G-CSF. SEQ ID NO: 61 treatment yielded higher levels of IFN-g, MIP-1b, and G-CSF than mIL-18 treatment.

FIG. 14A provides tumor growth spider plots for mice bearing Yummer1.7 melanoma tumors treated with saline (control), WT IL-18 (0.32 mg/kg), the DR-IL-18 variant SEQ ID NO: 61 (0.32 mg/kg), anti-PD1 (8 mg/kg), IL-18+anti-PD1, or SEQ ID NO: 61+anti-PD-1 twice per week. FIG. 14B provides survival curves from the same groups as in FIG. 14A. As shown in FIG. 14B, SEQ ID NO: 61 was effective as a monotherapy and synergized in combination with anti-PD1 in this model.

FIG. 15A provides tumor growth spider plots for mice bearing Yummer1.7 melanoma tumors treated with saline (control), or the DR-IL-18 variant SEQ ID NO: 61 (0.32 mg/kg) alone, or in combination with depleting antibodies against CD8, CD4, interferon gamma, or NK1.1. FIG. 15B provides survival curves from the same groups as in FIG. 15A.

FIG. 18A provides results of tumor immunophenotyping experiments from mice treated twice weekly for four doses with saline, WT IL-18, or the DR-IL-18 variant SEQ ID NO: 61. DR-IL-18 treatment resulted in increased numbers of CD8 and NK cells per mg of tumor (upper left two panels) and increased expression of activation markers granzyme B and KLRG1 on CD8 and NK cells (upper right two panels). DR-IL-18 treatment did not improve the CD8:Treg ratio compared to saline treatment, whereas WT IL-18 made the ratio less favorable. However, DR-IL-18 treatment increased the ratio of CD8 cells to inhibitory myeloid populations including tumor associated macrophages (TAM), and monocytic and granulocytic myeloid derived suppressor cells (mMDSCs and gMDSCs). FIG. 18B provides Serum Luminex cytokine measurements from the same mice as FIG. 18A, taken 24 hours after the 4th treatment dose. DR-IL-18 shows a dramatically altered secondary cytokine release profile from treatment with WT IL-18, notably increasing Interferon-gamma, IL-7, and IL-15 levels by more than 100-fold.

FIG. 19A shows tumor growth spider plots from mice bearing B2m-deficient Yummer1.7 tumors treated with saline, anti-PD1+anti-CTLA4, or the DR-IL-18 variant SEQ ID NO: 61. FIG. 19B contains a chart showing percent survival versus days post engraftment. DR-IL-18 demonstrated strong efficacy in terms of tumor growth and survival, curing 60% of treated mice in this model that is completely resistant to even combination treatment with anti-CTLA4+anti-PD1. This efficacy is NK cell dependent since administration of DR-IL-18 with anti-NK1.1 (which depletes NK cells) abrogates the SEQ ID NO: 61 treatment effect. FIG. 19C provides plots comparing Interferon-gamma production and Ki67 levels in tumors. NK cells isolated from B2m-deficient Yummer1.7 are dysfunctional and show diminished proliferation (Ki67 staining) and function (Interferon-gamma secretion). However, treatment with DR-IL-18 reverses this phenotype to enable robust proliferation and cytokine secretion.

FIG. 20A through FIG. 20C depicts example experiments demonstrating engineering of human IL-18 variants as IL-18BP antagonists (or "decoys-to-the-decoy", D2D) using yeast display. These variants bind IL-18BP but do not signal, thereby antagonizing the effect of IL-18BP on endogenous IL-18. FIG. 20A is a summary of the positions in human IL-18 randomized in the D2D library. Degenerate codons and the set of encoded amino acids are given for each position. FIG. 20B provides a summary of directed evolution to generate D2D IL-18 variants that bind and neutralize IL-18BP, but do not signal through the IL-18R. The positive selection condition is mIL18BP. Counter-selection conditions are: nIL18Rα, hIL18Rb, and mIL18Rα. (FIG. 20C) Flow cytometric analysis of progress in creating D2D hIL-18 variants. Yeast obtained after rounds 1~4 were stained with 1 nM of mouse IL-18BP (left panel), 1 nM human IL-18BP (middle panel), or 1 μM IL18Ra plus 1 μM IL18Rβ. Selected variants show enhanced IL-18BP binding across rounds of selection without increases in IL18Rα or IL18Rβ binding.

FIG. 21 depicts results from example experiments demonstrating a summary of the sequences of D2D human IL-18 variants. The position of each mutated position and the corresponding residue in the mature form of wild-type human IL-18 is indicated at the top of the table. The sequence for the top row ("WT hIL-18") is set forth as SEQ ID NO: 30.

FIG. 22A through FIG. 22C depict results from example experiments demonstrating biophysical characterization of the human decoy-to-the-decoy (D2D) IL-28 variants. FIG. 22A shows that yeast-displayed D2D IL-8 variants SEQ ID NO: 120, SEQ ID NO: 101, SEQ ID NO: 94, SEQ ID NO: 98, SEQ ID NO: 99, SEQ ID NO: 123, SEQ ID NO: 124, and SEQ ID NO: 125 are capable of binding hIL-18RBP with comparable binding isotherms as WT human IL-18. FIG. 22B shows that, by contrast, very little binding is observed with the same variants and hIL-18Ra. FIG. 22C provides a summary of the receptor binding properties of the D2D IL-18 variants. NBD=no binding detected.

FIG. 23 depicts results from example experiments demonstrating a summary of the sequences of D2D murine IL-18 variants. The position of each mutated position and the corresponding residue in the mature form of wild-type murine IL-18 is indicated at the top of the table. The sequence for the top row ("WT mIL-18") is set forth as SEQ ID NO: 31.

FIG. 25A is an overlay of spider plots showing tumor growth of saline (PBS) treated animals in black lines (circles), WT IL-18 in dark gray (squares), and DR-IL-18 (SEQ ID NO: 61) in gray (triangles). Only treatment with DR-IL-18, but not WT IL-18, resulted in tumor growth inhibition and tumor clearance in a subset of animals. FIG. 25B comprises survival curves for mice treated with anti-PD-1, WT IL-18, and DR-IL-18 (SEQ ID NO: 61). Numbers of complete responses are indicated in parentheses. DR-IL-18, but not WT IL-18 resulted in prolonged survival and tumor clearance in 40% of mice, an improvement over the checkpoint inhibitor anti-PD-1.

FIG. 26A shows tumor growth curves of 4T1 tumors engrafted into BALB/C mice after treatment with saline (PBS; black), WT IL-18 (dark gray), or the DR-IL-18 variant SEQ ID NO: 61 (gray). FIG. 26B shows tumor growth curves of B16-F10 tumors engrafted into C57BL/6 mice after treatment with saline (PBS; black), WT IL-18/TA99 (dark gray), or the DR-IL-18 variant SEQ ID NO: 61 (gray). In both models, only DR-IL-18, but not WT IL-18 resulted in tumor growth inhibition. Treatments were administered after tumors exceeded an average volume 50 mm$^3$ as indicated by the boxes marked with "t".

FIG. 27A provides a chart of tumor volume versus days post implantation for mice implanted with B2m deficient MC38 cells, which were prepared using CRISPR/Cas9 mediated deletion as described for B2m deficient YUMMER cells. B2m−/− MC38 cells were implanted subcutaneously and treatment initiated at day 7 once tumors were ~65 mm$^3$ on average. SEQ ID NO: 61 was dosed at 0.32 mg/kg twice weekly for 5 doses. Anti-PD1 and anti-CTLA4 were given at 8 mg/kg at the same schedule. FIG. 27B shows a chart of tumor volume versus days post implantation for mice implanted with RMA/S cells. RMA/S is a variant of the RMA lymphoma line that contains a spontaneous mutation in Tapasin. The result is a defect in antigen loading and therefore decreased MHC class I surface expression. It is congenic to C57BL/6 and refractory to immune checkpoint inhibitors. Mice were implanted with 1,000,000 RMA/S cells subcutaneously and treatment initiated at day 7. SEQ ID NO: 61 was dosed at 0.32 mg/kg twice weekly. Anti-PD1 was given at 8 mg/kg at the same schedule. In both studies, only treatment with the DR-18 variant SEQ ID NO: 61 exhibited anti-tumor efficacy in the form of tumor growth inhibition (B2m$^{-/-}$ MC38) or tumor clearance (RMA/S).

FIG. 29A and FIG. 29B depict data demonstrating antiviral efficacy of DR-18 variant SEQ ID NO: 61 for the treatment viral infections (e.g., in this case in the treatment of systemic vaccinia virus infection). FIG. 29A shows the experimental design scheme. C57BL/6 mice were infected with 106 PFU of Vaccinia virus (VACV) intraperitoneally (IP) and administered 1 mg/kg WT mIL-18 or SEQ ID NO: 61 IP. Mice were sacrificed and viral titers were measured in the blood and ovaries by RT-PCR on day 3 post-infection. FIG. 29B. demonstrates the quantification of VACV viral copies in ovaries and blood of treated mice at day 3 post infection. Treatment with SEQ ID NO: 61 showed a significant reduction of viral titers, whereas WT IL-18 was not effective. * p<0.05,  p<0.01, * p<0.001.

(FIG. 30) WT IL-18 and human SEQ ID NO: 89, SEQ ID NO: 90, SEQ ID NO: 91, and SEQ ID NO: 87 stimulate IL-18 HEK-Blue reporter cells. Human SEQ ID NO: 89, SEQ ID NO: 90, and SEQ ID NO: 91 show enhanced potency compared to WT hIL-18, whereas SEQ ID NO: 87 has equivalent potency as WT hIL-18. The data demonstrate, therefore, that all tested second generation human DR-IL-18 variants actively signal through IL-18R.

FIG. 34 depicts dose-response data using an HEK-Blue reporter cell line. All variants showed increased potency compared to WT IL-18 and similar potency to the parent variant SEQ ID NO: 89.

FIG. 40 depicts tumor growth data in mice from additional dosing experiments (using the mouse DR IL-18 variant SEQ ID NO: 61).

DETAILED DESCRIPTION OF THE INVENTION

Figure 1A:
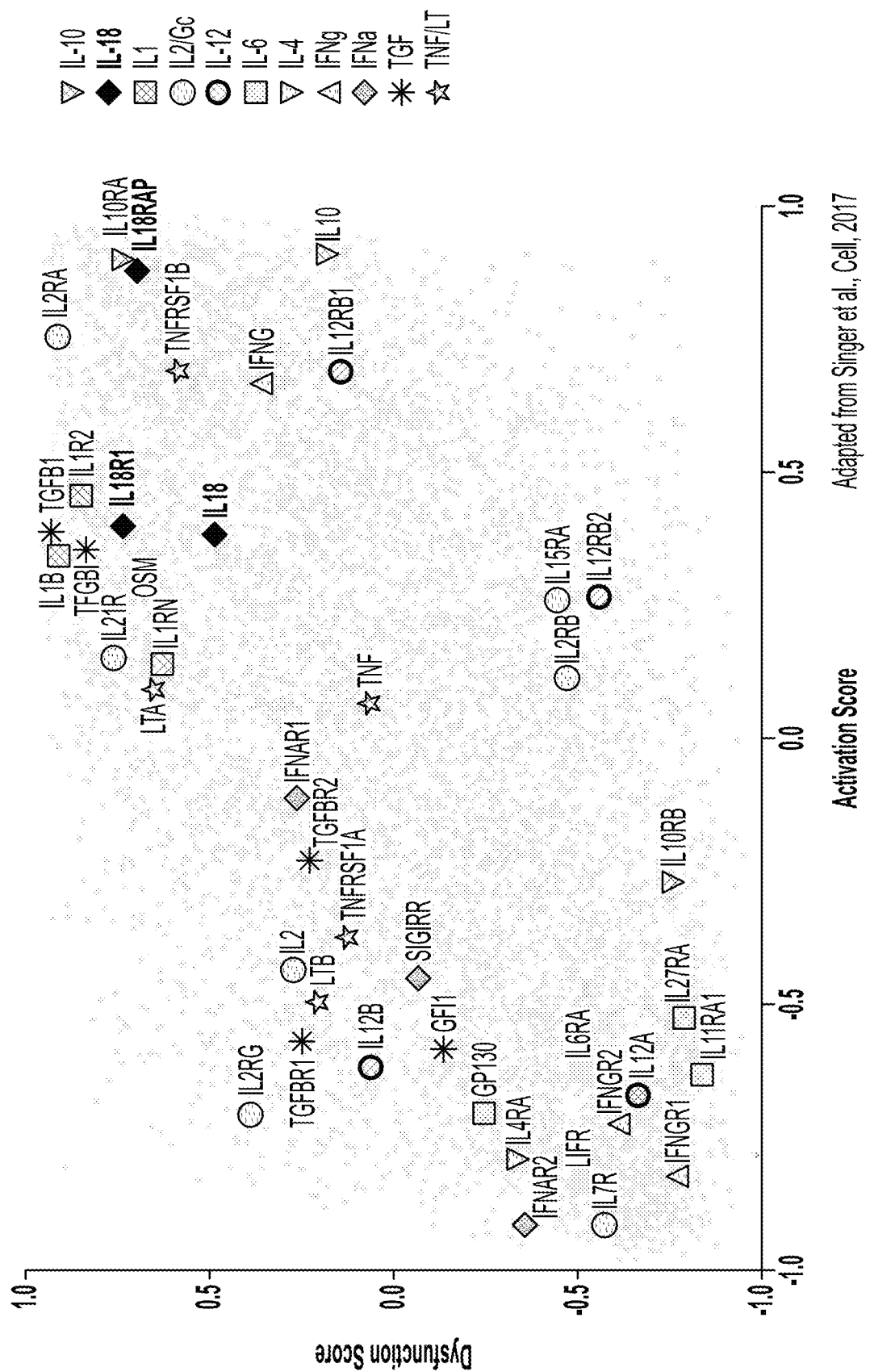
FIG. 1A and FIG. 1B depict results from example experiments, demonstrating the IL-18 pathway is a target for tumor immunotherapy.

Provided are variant (e.g., stabilized) IL-18 polypeptides and methods of use (e.g., to treat a disease or disorder). A subject stabilized IL-18 polypeptide includes mutations of two cysteine residues (C38 and C68) relative to the human wild type IL-18 (SEQ ID NO: 30). In some cases, the mutation is a C to S substitution and as such the stabilized IL-18 polypeptide can in some cases comprise the mutations C38S and C68S. In some cases a subject stabilized IL-18 polypeptide comprises the mutation pair C38S/C68S, C38S/C68G, C38S/C68A, C38S/C68V, C38S/C68D, C38S/C68E, or C38S/C68N (e.g., in some cases C38S/C68G, C38S/C68A, C38S/C68V, C38S/C68D, C38S/C68E, or C38S/C68N; in some cases C38S/C68S, C38S/C68G, C38S/C68A, C38S/C68D, or C38S/C68N; and in some cases C38S/C68G, C38S/C68A, C38S/C68D, or C38S/C68N).

In some cases, a subject stabilized IL-18 polypeptide is a stabilized IL-18 variant polypeptide (e.g., a stabilized "decoy resistant" (DR) IL-18 variant or a stabilized "decoy-to-the-decoy" (D2D) IL-18 variant), i.e., an IL-18 variant that additionally includes mutations at positions C38 and C68 relative to human wild type IL-18.

Provided are methods of administering an IL-18 polypeptide (e.g., a wild type IL-18 or a variant such as a stabilized, DR, D2D, stabilized DR, or stabilized D2D IL-18 variant) to an individual (e.g., subcutaneously) where the frequency of administration is not more than once per week. Also provided are methods of producing/making a polypeptide. Some such methods include contacting an exogenously provided fusion protein inside of a cell (e.g., a bacterial cell) with a SUMO protease—where the fusion protein includes a protein of interest fused at the N-terminus to a SUMO tag, whereby the SUMO protease cleaves the fusion protein to remove the SUMO tag from the protein of interest.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112

Definitions

Unless defined otherwise, all technical and scientific terms used herein have the same meaning as commonly understood by one of ordinary skill in the art to which the invention pertains. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)2, as well as single chain antibodies (scFv), heavy chain antibodies, such as camelid antibodies, synthetic antibodies, chimeric antibodies, and a humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, NY; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an "immunoassay" refers to any binding assay that uses an antibody capable of binding specifically to a target molecule to detect and quantify the target molecule.

By the term "specifically binds," as used herein, e.g., with respect to an IL-18 variant polypeptide, is meant an IL-18 variant polypeptide that recognizes and binds to a specific molecule, such as IL-18R, or to IL-18BP. As an example, wild type IL-18 can be said to specifically bind to both IL-18R and to IL-18BP. In some instances, the IL-18 variant polypeptide substantially reduced binding to IL-18BP. For example, an IL-18 variant polypeptide that specifically binds to a receptor from one species may also bind to that receptor from one or more species. But, such cross-species reactivity does not itself alter the classification of an IL-18 variant polypeptide as specific. In another example, an IL-18 variant polypeptide that specifically binds to a receptor may also bind to different allelic forms of the receptor. However, such cross reactivity does not itself alter the classification of an IL-18 variant polypeptide as specific. In some instances, the terms "specific binding" or "specifically binding," can be used in reference to the interaction of an antibody, a protein, or a peptide with a chemical species, to mean that the interaction is dependent upon the presence of a particular structure (e.g., an antigenic determinant or epitope) on the chemical species; for example, an IL-18 variant polypeptide recognizes and binds to a specific protein structure rather than to proteins generally. Similarly, the term "targets", e.g., in the context of antibodies that "target" a particular antigen, is used to refer to the specific binding partner of a given molecule. For example, an agent (e.g., an antibody) that "targets" a particular protein/antigen specifically binds that protein/antigen in the sense that it preferentially binds to that particular protein/antigen over other proteins/antigens.

By the term "applicator," as the term is used herein, is meant any device including, but not limited to, a hypodermic syringe, a pipette, an iontophoresis device, a patch, and the like, for administering the compositions of the invention to a subject.

The term "coding sequence," as used herein, means a sequence of a nucleic acid or its complement, or a part thereof, that can be transcribed and/or translated to produce the mRNA and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the coding sequence can be deduced therefrom. In contrast, the term "non-coding sequence," as used herein, means a sequence of a nucleic acid or its complement, or a part thereof, that is not translated into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, and the like.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would been the absence of the disorder. Left untreated, a disorder does not necessarily cause a further decrease in the animal's state of health.

An "effective amount" as used herein, means an amount which provides a therapeutic, prophylactic, or other desired benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., guide RNA, rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between). As used herein, the term "fragment," as applied to a protein, polypeptide or peptide, refers to a subsequence of a larger protein, polypeptide or peptide. A "fragment" of a protein, polypeptide, or peptide can be at least about 5 amino acids in length; for example, at least about 10 amino acids in length; at least about 20 amino acids in length; at least about 50 amino acids in length; at least about 100 amino acids in length; at least about 200 amino acids in length; or at least about 300 amino acids in length (and any integer value in between).

The term "gene" refers to a nucleic acid (e.g., DNA) sequence that includes coding sequences necessary for the production of a polypeptide, precursor, or RNA (e.g., mRNA). The polypeptide may be encoded by a full-length coding sequence or by any portion of the coding sequence so long as the desired activity or functional property (e.g., enzymatic activity, receptor binding, signal transduction, immunogenicity, etc.) of the full-length or fragment is retained. The term also encompasses the coding region of a structural gene and the sequences located adjacent to the coding region on both the 5' and 3' ends for a distance of about 2 kb or more on either end such that the gene corresponds to the length of the full-length mRNA and 5' regulatory sequences which influence the transcriptional properties of the gene. Sequences located 5' of the coding region and present on the mRNA are referred to as 5'-untranslated sequences. The 5'-untranslated sequences usually contain the regulatory sequences. Sequences located 3' or downstream of the coding region and present on the mRNA are referred to as 3'-untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

"Homologous", "identical," or "identity" as used herein in the context of two or more nucleic acids or polypeptide sequences means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

"Instructional material," as that term is used herein, includes a publication, a recording, a diagram, or any other medium of expression which can be used to communicate the usefulness of the nucleic acid, peptide, polypeptide, and/or compound of the invention in the kit for identifying or alleviating or treating the various diseases or disorders recited herein. Optionally, or alternately, the instructional material may describe one or more methods of identifying or alleviating the diseases or disorders in a cell or a tissue of a subject. The instructional material of the kit may, for example, be affixed to a container that contains the nucleic acid, polypeptide, and/or compound of the invention or be shipped together with a container that contains the nucleic acid, polypeptide, and/or compound. Alternatively, the instructional material may be shipped separately from the container with the intention that the recipient uses the instructional material and the compound cooperatively.

"Isolated" means altered or removed from the natural state. For example, a nucleic acid or a polypeptide naturally present in a living animal is not "isolated," but the same nucleic acid or polypeptide partially or completely separated from the coexisting materials of its natural state is isolated." An isolated nucleic acid or protein can exist in substantially purified form, or can exist in a non-native environment such as, for example, a host cell.

As used herein, the terms "purify" and "purified" in the context of a protein refers to level of purity that allows for the effective use of the protein, e.g., in vitro, ex vivo, or in vivo. For a protein to be useful for a given application, it should be substantially free of contaminants, other proteins, and/or chemicals that could interfere with the use of that protein in such application, or that at least would be undesirable for inclusion with the protein of interest. Such applications include that preparation of therapeutic compositions, the administration of the protein in a therapeutic composition, and other methods disclosed herein. Preferably, a "purified" protein, as referenced herein, is a protein that can be produced by any method (i.e., by direct purification from a natural source, recombinantly, or synthetically), and that has been purified from other protein components such that the protein comprises at least about 75% weight/weight of the total protein in a given composition, 80% weight/weight of the total protein in a given composition, and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99% weight/weight of the total protein in a given composition. As an example, a purified polypeptide is a polypeptide which has been separated from other components with which it might normally be associated in its naturally occurring state (e.g., if the protein is a naturally existing protein) and from components with which it may be associated while inside of a cell or in extracellular milieu. For example, in some cases a protein can be purified from a cellular lysate (e.g., from a lysate of bacterial cells in which the protein was exogenously expressed). As another example a protein can, be purified from an extracellular medium, e.g., from culture medium into which cells (e.g., yeast cells) have secreted the protein.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

By the term "modulating," as used herein, is meant mediating a detectable increase or decrease in the activity and/or level of a mRNA, polypeptide, or a response in a subject compared with the activity and/or level of the mRNA, polypeptide or response in the subject in the absence of a treatment or compound, and/or compared with the activity and/or level of the mRNA, polypeptide, or response in an otherwise identical but untreated subject. The term encompasses activating, inhibiting and/or otherwise affecting a native signal or response thereby mediating a beneficial therapeutic, prophylactic, or other desired response in a subject, for example, a human. A "mutation," "mutant," or "variant," as used herein, refers to a change in nucleic acid or amino acid sequence relative to a reference sequence (which may be a naturally-occurring normal/"wild-type" sequence), and includes translocations, deletions, insertions, and substitutions/point mutations. A "mutant" or "variant" as used herein, refers to either a nucleic acid or protein comprising a mutation.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this disclosure. It will be understood that when a nucleotide sequence is represented herein by a DNA sequence (e.g., A, T, G, and C), this also includes the corresponding RNA sequence (e.g., A, U, G, C) in which "U" replaces "T".

The terms "individual," "subject," "host," and "patient," are used interchangeably herein and refer to any mammalian subject for whom diagnosis, treatment, or therapy is desired, particularly humans.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, mutant polypeptides, variant polypeptides, or a combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to exhibit non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, the terms "therapy" or "therapeutic regimen" refer to those activities taken to prevent, treat or alter a disease or disorder, e.g., a course of treatment intended to reduce or eliminate at least one sign or symptom of a disease or disorder using pharmacological, surgical, dietary and/or other techniques. A therapeutic regimen may include a prescribed dosage of one or more compounds or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound or composition that will elicit the intended biological, physiologic, clinical or medical response of a cell, tissue, organ, system, or subject that is being sought by the researcher, veterinarian, medical doctor or other clinician. The term "therapeutically effective amount" includes that amount of a compound or composition that, when administered, is sufficient to treat one or more of the signs or symptoms of the disorder or disease being treated. The therapeutically effective amount will vary depending on the compound or composition, the disease and its severity and the age, weight, etc., of the subject to be treated.

To "treat" a disease or disorder as the term is used herein, means to reduce the frequency or severity of at least one sign or symptom of a disease or disorder experienced by a subject. The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), e.g., slowing or arresting their development (e.g., halting the growth of tumors, slowing the rate of tumor growth, halting the rate of cancer cell proliferation, and the like); or (c) relieving the disease symptom(s), i.e., causing regression of the disease and/or symptom(s) (e.g., causing decrease in tumor size, reducing the number of cancer cells present, and the like). Those in need of treatment include those already inflicted (e.g., those with cancer, those with an infection, those with a metabolic disorder, those with macular degeneration, etc.) as well as those in which prevention is desired (e.g., those with increased susceptibility to cancer, those with an increased likelihood of infection, those suspected of having cancer, those suspected of harboring an infection, those with increased susceptibility for metabolic disease, those with increased susceptibility for macular degeneration, etc.).

As used herein, the term "wild-type" refers to a gene or gene product isolated from a naturally occurring source or having a naturally occurring sequence (e.g., a wild type protein with a naturally occurring amino acid sequence can be isolated from a natural source or from a synthetic source, but would still be considered a wild type protein). In contrast, the term "modified," "variant," or "mutant" refers to a gene or gene product that possesses modifications in sequence and/or functional properties (i.e., altered characteristics) when compared to the wild type gene or gene product.

Ranges: throughout this disclosure, various aspects can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 2, 1 to 3, 1 to 4, 1 to 5, 2 to 3, 2 to 4, 2 to 5, 2 to 6, etc., as well as individual numbers within that range, for example, 1, 2, 2.7. 3, 4, 5, 5.3, and 6. This applies regardless of the breadth of the range.

Compositions and Methods

As summarized above, in some embodiments, the compositions and methods of the disclosure comprise an IL-18 polypeptide having mutations at amino acid positions C38 and C68 relative to wild type IL-18 (SEQ ID NO: 30). Such variants are referred to herein as "stabilized" IL-18 variants.

In some embodiments, the compositions and methods of the disclosure comprise an IL-18 variant polypeptide that is mutated relative to wild type IL-18 such that it can bind to one of IL-18's natural binding partners, but not to the other (or has reduced binding to the other). For example, wild type IL-18 binds to both IL-18R (to signal through the receptor) and IL-18BP (which inhibits IL-18 by preventing it from binding to IL-18R). In some case an IL-18 variant polypeptide discussed herein is a "decoy resistant IL-18" ("DR IL-18") variant; such variants bind to IL-18R but have reduced binding to (and in some cases do not bind to) IL-18BP. In other cases an IL-18 variant polypeptide discussed herein is a "decoy-to-the-decoy IL-18" ("D2D IL-18") variant; such variants bind to IL-18BP but have reduced binding to (and in some cases do not bind to) IL-18R. As shown in this disclosure, an IL-18 variant polypeptide may show comparable binding affinity to IL-18Rα as wild type IL-18, while also exhibiting decreased binding affinity to IL-18BP compared to wild type IL-18.

In some cases, there is overlap between the terms to describe the various variants. For example, a DR IL-18 variant or D2D IL-18 variant can include mutations at C38 and C68 and in such cases the IL-18 variants would be "stabilized" variants. As such, the term "stabilized" encompasses stabilized wild type IL-18 (WT IL-18 with C38 and C68 mutations) as well as stabilized variant proteins such as DR IL-18 and D2D IL-18 variants that have C38 and C68 mutations. Likewise, the term "DR IL-18" variant encompasses such variants with and without C38/C68 mutations and the term "D2D IL-18" variant encompasses such variants with and without C38/C68 mutations. As such, the term "stabilized DR IL-18" variant can be used when discussing DR IL-18 variants that have C38/C68 mutations and the term stabilized D2D IL-18" variant can be used when discussing D2D IL-18 variants that have C38/C68 mutations.

As such, the following will discuss various embodiments of "stabilized" IL-18 proteins (various C38/C68 mutants). This description equally applies to any type of IL-18 protein (e.g., wild type, DR IL-18 variant, D2D IL-18 variant, etc.). Mutations in C38/C68 are first discussed, followed by a discussion of DR IL-18 variants and D2D IL-18 variants. All of the discussed variants can be used in any of the methods described herein.

A stabilized IL-18 polypeptide is an IL-18 polypeptide that includes 'stabilizing mutations' which are mutations of two cysteine residues (C38 and C68) relative to the human wild type IL-18 (SEQ ID NO: 30). Surprisingly, mutation of these two amino acids was found to stabilize IL-18 better than all other possible combinations of Cysteine mutations, see, e.g., the working examples below. In some cases, the mutation is a C to S substitution and as such the stabilized IL-18 polypeptide can in some cases comprise the mutations C38S and C68S (also referred to herein as "mutation pair C38S/C68S") relative to the human wild type IL-18 (SEQ ID NO: 30). In some cases, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes mutations at amino acid positions C38 and C68 relative to SEQ ID NO: 30. In some cases, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes mutations at amino acid positions C38 and C68 relative to SEQ ID NO: 30. Examples of such variant proteins include those set forth as SEQ ID NOs: 6 and 16-21, although these sequences also include additional mutations that render them DR IL-18 variants (See below)—and such SEQ ID NOs: 6 and 16-21 are examples of stabilized DR IL-18 variants.

In some cases the mutation is a C to S substitution and as such the stabilized IL-18 polypeptide can in some cases comprise the mutations C38S and C68S (also referred to herein as "C38S/C68S") relative to the human wild type IL-18 (SEQ ID NO: 30). Mutation of C68 can in some cases result in an immunogenic epitope. Thus, in some embodiments the mutation at C68 is a non-immunogenic substitution. In some such cases the mutation is a C68 to G, A, V, D, E, or N mutation (in some cases C68 to G, A, D, or N). Thus, in some such cases a subject stabilized IL-18 polypeptide comprises the mutations C38S/C68S, C38S/C68G, C38S/C68A, C38S/C68V, C38S/C68D, C38S/C68E, or C38S/C68N. In some cases, a subject stabilized IL-18 polypeptide comprises the mutations C38S/C68G, C38S/C68A, C38S/C68V, C38S/C68D, C38S/C68E, or C38S/C68N. In some cases, a subject stabilized IL-18 polypeptide comprises the mutations C38S/C68S, C38S/C68G, C38S/C68A, C38S/C68D, or C38S/C68N. In some cases, a subject stabilized IL-18 polypeptide comprises the mutations C38S/C68G, C38S/C68A, C38S/C68D, or C38S/C68N. In some cases, a subject stabilized IL-18 polypeptide comprises the mutations C38S/C68D. In some cases, a subject stabilized IL-18 polypeptide comprises the mutations C38S/C68G. In some cases, a subject stabilized IL-18 polypeptide comprises the mutations C38S/C68A. In some cases, a subject stabilized IL-18 polypeptide comprises the mutations C38S/C68A. In some cases, a subject stabilized IL-18 polypeptide comprises the mutations C38S/C68N.

Thus, in some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68S, C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68S, C38S/C68G, C38S/C68A, C38S/C68D, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68G, C38S/C68A, C38S/C68D, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68D relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68G relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68A relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) and includes the mutations C38S/C68N relative to SEQ ID NO: 30.

In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68S, C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68S, C38S/C68G, C38S/C68A, C38S/C68D, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68G, C38S/C68A, C38S/C68D, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68D relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68G relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68A relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) and includes the mutations C38S/C68N relative to SEQ ID NO: 30.

Stabilized DR IL-18 or D2D IL-18 Variants

In some cases, a subject stabilized IL-18 polypeptide is a stabilized IL-18 variant polypeptide, i.e., an IL-18 variant polypeptide that includes the stabilizing mutations (i.e., mutations at positions C38 and C68 relative to human wild type IL-18). In some such cases the stabilized IL-18 variant polypeptide is a stabilized "decoy resistant" (DR) IL-18 variant, and in other such cases the stabilized IL-18 variant polypeptide is a stabilized "decoy-to-the-decoy" (D2D) IL-18 variant. Examples of human DR IL-18 variants include but are not limited to those set forth in SEQ ID NOs: 34-59, 73-91, and 191-193, while examples of human D2D IL-18 variants include but are not limited to those set forth in SEQ ID NOs: 92-125; also see the working examples below. DR-IL18 variants are described in detail below and any of such variant can include a C38/C68 mutation as described herein in order to be a stabilized DR-IL18.

In some cases, a subject stabilized DR IL-18 variant comprises the amino acid sequence set forth in SEQ ID NO: 89, except the C38 and C68 are mutated (e.g., C38S/C68S, C38S/C68G, C38S/C68A, C38S/C68V, C38S/C68D, C38S/C68E, or C38S/C68N—in some cases C38S/C68G, C38S/C68A, C38S/C68V, C38S/C68D, C38S/C68E, or C38S/C68N—in some cases C38S/C68S, C38S/C68G, C38S/C68A, C38S/C68D, or C38S/C68N—in some cases C38S/C68G, C38S/C68A, C38S/C68D, or C38S/C68N—in some cases C38S/C68D—in some cases C38S/C68G—in some cases C38S/C68A—in some cases C38S/C68N). Examples of stabilized DR IL-18 variants include those set forth as SEQ ID NOs: 6 and 16-21 (these are C38/C68 mutated versions of the DR-18 variant set forth as SEQ ID NO: 89). One of ordinary skill in the art would readily recognize that equivalent stabilized variants can easily be produced for any desired IL-18 variant (see, e.g., the working examples below) (e.g., any of the human DR-IL variants set forth as SEQ ID NOs: 34-59, 73-91, and 191-193, e.g., SEQ ID NOs 87-91, or for any of the human D2D IL-18 variants set forth as SEQ ID NOs: 92-125).

Thus, in some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68S, C38S/C68G, C38S/C68A, C38S/C68V, C38S/C68D, C38S/C68E, or C38S/

C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68S, C38S/C68G, C38S/C68A, C38S/C68D, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68G, C38S/C68A, C38S/C68D, or C38S/C68N relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68D relative to SEQ ID NO: 30.

In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68G relative to SEQ ID NO: 30. In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68A relative to SEQ ID NO: 30.

In some embodiments, a subject IL-18 polypeptide includes an amino acid sequence having 80% or more sequence identity (e.g., 85% or more, 90% or more, 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68S, C38S/C68G, C38S/C68A, C38S/C68V, C38S/C68D, C38S/C68E, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68G, C38S/C68A, C38S/C68V, C38S/C68D, C38S/C68E, or C38S/C68N relative to SEQ ID NO: 30.

In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68S, C38S/C68G, C38S/C68A, C38S/C68D, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68G, C38S/C68A, C38S/C68D, or C38S/C68N relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68D relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of EQ ID NOs: 34-59, 73-91, and 191-193 or any one of SEQ ID NOs:87-91 or SEQ ID NO: 89] and includes the mutations C38S/C68G relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68A relative to SEQ ID NO: 30. In some embodiments, a subject IL-18 polypeptide includes an amino acid sequence having 90% or more sequence identity (e.g., 92% or more, 95% or more, 97% or more, 98% or more, or 98.5% or more sequence identity) with human wild type IL-18 (SEQ ID NO: 30) [or any one of SEQ ID NOs: 6 and 16-21 or any one of SEQ ID NOs: 34-59, 73-91, and 191-193 or any one of SEQ ID NOs:87-91 or SEQ ID NO: 89] and includes the mutations C38S/C68N relative to SEQ ID NO: 30.

In some embodiments, the IL-18 variant polypeptide is a DR IL-18 variant (i.e., it binds to IL-18R and exhibits reduced binding to IL-18BP). In some embodiments, the DR IL-18 variant binds to IL-18BP with a binding affinity that is 95% or less of the binding affinity of wild-type IL-18 to IL-18BP (e.g., 90% or less, 80% or less, 70% or less, 60% or less, 50% or less, 40% or less, 30% or less, 20% or less, 10% or less, 5% or less, 2% or less, 1% or less, 0.05% or less, or 0.001% or less). In some embodiments, the DR IL-18 variant binds to IL-18BP with a binding affinity that is 10% or less (e.g., 5% or less, 2% or less, 1% or less, 0.05% or less, or 0.001% or less) of the binding affinity of wild-type IL-18 to IL-18BP.

In some embodiments, a subject DR IL-18 variant has a $K_D$ for IL-18BP that is 10 nM or greater (higher $K_D$ means lower binding affinity). In some embodiments, a subject DR-IL-18 variant polypeptide has a $K_D$ for IL-18BP that is 20 nM or greater (e.g., 50 nM or greater, 100 nM or greater, 500 nM or greater, or 1 μM or greater).

An IL-18 polypeptide (e.g., DR IL-18 polypeptide comprising mutations at positions C38 and C68 relative to human wild type IL-18) can exhibit enhanced stability compared to an IL-18 polypeptide with a different sequence (e.g., a wild type IL-18 sequence, or an IL-18 sequence that lacks the C38 and C68 mutations but otherwise contains the same sequence as the subject IL-18 polypeptide).

In some embodiments, stability of an IL-18 polypeptide (e.g., DR IL-18) disclosed herein can be evaluated by subjecting the polypeptide or a formulation disclosed herein that contains the polypeptide to freeze thaw cycles, for example, 1, 2, 3, 4, 5, 6, 7, 8, 9, 10, 15, 20, 1, at least 2, at least 3, at least 4, at least 5, at least 6, at least 7, at least 8, at least 9, at least 10, at least 15, or at least 20 freeze that cycles. A freeze thaw cycle can comprise freezing the polypeptide or a formulation comprising the polypeptide (e.g., to about −20° C. or −80° C.) and thawing the polypeptide or a formulation (e.g., to about 20° C., 23° C., 25° C., or 37° C.).

In some embodiments, stability of an IL-18 polypeptide (e.g., DR IL-18) disclosed herein can be evaluated by subjecting the polypeptide or a formulation disclosed herein that contains the polypeptide to agitation. Agitation can comprise, for example, incubating the polypeptide or formulation (e.g., at about 20° C., about 23° C., about 25° C., about 30° C., about 37° C., or about 40° C.) with agitation at about 100 rpm, about 150 rpm, about 200 rpm, or about 250 rpm. Samples can be tested after, for example, about 1 day, about 2 days, about 3 days, about 4 days, about 5 days, about a week, or about 2 weeks of incubation at the temperature and agitation rate.

Stability of an IL-18 polypeptide (e.g., DR IL-18) can be evaluated by comparing the size of the main IL-18 peak measured by size exclusion chromatography before and after a stability assay disclosed herein (e.g., before and after freeze thaw cycles and/or agitation). In some embodiments, after exposure to the stability assay conditions, the main peak remains at least about 80%, at least about 85%, at least about 90%, at least about 91%, at least about 92%, at least about 93%, at least about 94%, at least about 95%, at least about 95.5%, at least about 96%, at least about 96.5%, at least about 97%, at least about 97.5%, at least about 98%, at least about 98.5%, at least about 99%, at least about 99.1%, at least about 99.1%, at least about 99.3%, at least about 99.4%, at least about 99.5%, at least about 99.6%, at least about 99.7%, at least about 99.8%, at least about 99.9%, at least about 99.95%, at least about 99.99%, or about 100% of the size of the main peak before exposure to the assay conditions.

In some embodiments, after exposure to the stability assay conditions, retention of the main peak at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, or at least about 50% greater than an IL-18 polypeptide with a different sequence (e.g., a wild type IL-18 sequence, or an IL-18 sequence that lacks the C38 and C68 mutations but otherwise contains the same sequence as the subject IL-18 polypeptide).

Stability of an IL-18 polypeptide (e.g., DR IL-18) can be evaluated by determining presence and size of one or more peaks measured by size exclusion chromatography that are indicative of formation of a dimer, multimer, aggregate, or degradation product, before and after a stability assay disclosed herein (e.g., before and after freeze thaw cycles and/or agitation). In some embodiments, after exposure of an IL-18 polypeptide (e.g., DR IL-18 in a formulation disclosed herein) to stability assay conditions, no or substantially no peak is detected that is indicative of formation of dimers. In some embodiments, after exposure of an IL-18 polypeptide (e.g., DR IL-18 in a formulation disclosed herein) to stability assay conditions, no or substantially no peak is detected that is indicative of formation of multimers. In some embodiments, after exposure of an IL-18 polypeptide (e.g., DR IL-18 in a formulation disclosed herein) to stability assay conditions, no or substantially no peak is detected that is indicative of formation of aggregates. In some embodiments, after exposure of an IL-18 polypeptide (e.g., DR IL-18 in a formulation disclosed herein) to stability assay conditions, no or substantially no peak is detected that is indicative of formation of degradation products.

In some embodiments, after exposure of an IL-18 polypeptide (e.g., DR IL-18 in a formulation disclosed herein) to stability assay conditions, the IL-18 polypeptide exhibits at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30%, at least about 40%, at least about 50%, at least about 60%, at least about 70%, at least about 80%, at least about 90%, or at least about 95% less dimer, multimer, aggregate, and/or degradation product formation compared to an IL-18 polypeptide with a different sequence (e.g., a wild type IL-18 sequence, or an IL-18 sequence that lacks the C38 and C68 mutations but otherwise contains the same sequence as the subject IL-18 polypeptide), e.g., as determined by size exclusion chromatography.

In some embodiments, a DR IL-18 variant disclosed has a $K_D$ for IL-18BP that is at least about 100 μM, at least about 10 μM, at least about 1 μM, at least about 900 nM, at least about 800 nM, at least about 700 nM, at least about 600 nM, at least about 500 nM, at least about 400 nM, at least about 300 nM, at least about 200 nM, at least about 150 nM, at least about 100 nM, at least about 90 nM, at least about 80 nM, at least about 70 nM, at least about 60 nM, at least about 50 nM, at least about 40 nM, at least about 30 nM, at least about 20 nM, or at least about 10 nM. In some embodiments, a DR IL-18 variant disclosed does not bind IL-18BP, substantially does not bind IL-18BP, or binds IL-18BP below a limit of detection in an assay disclosed herein.

A DR IL-18 variant disclosed herein can exhibit binding to human IL-18R, for example, with can bind to human IL-18R at a comparable affinity to wild type human IL-18, or can bind to human IL-18R with a higher affinity than wild type human IL-18. In some embodiments, a DR IL-18 variant disclosed herein binds to human IL-18R with at least comparable affinity as wild type human IL-18 exhibits for human IL-18R.

In some embodiments, a DR IL-18 variant disclosed herein binds to human IL-18Rα or human IL-18R with a $K_D$ of, for example, less than about 100 μM, less than about 10 μM, less than about 1 μM, less than about 900 nM, less than about 800 nM, less than about 700 nM, less than about 600 nM, less than about 500 nM, less than about 400 nM, less than about 300 nM, less than about 200 nM, less than about 150 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, or less than about 1 nM.

In some embodiments, a DR IL-18 variant disclosed herein binds to human IL-18Rα or human IL-18R with a $K_D$ of, for example, about 1 pM to about 1 μM, about 1 pM to about 500 nM, about 1 pM to about 400 nM, about 1 pM to about 300 nM, about 1 pM to about 200 nM, about 1 pM to about 100 nM, about 1 pM to about 50 nM, about 100 pM to about 1 μM, about 100 pM to about 500 nM, about 100 pM to about 400 nM, about 100 pM to about 300 nM, about 100 pM to about 200 nM, about 100 pM to about 100 nM, about 100 pM to about 50 nM, about 1 nM to about 1 μM, about 1 nM to about 500 nM, about 1 nM to about 400 nM, about 1 nM to about 300 nM, about 1 nM to about 200 nM, about 1 nM to about 100 nM, about 1 nM to about 75 nM, about 1 nM to about 50 nM, about 1 nM to about 40 nM, about 1 nM to about 30 nM, or about 1 nM to about 10 nM.

In some embodiments, a DR IL-18 variant has an IL-18BP/IL-18R dissociation constant ratio that is about at least 2-fold higher than the IL-18BP/IL-18R dissociation constant ratio of wild-type IL-18 (note that an increased dissociation constant ratio implies a relative decrease in IL-18BP binding relative to IL-18R binding). In some embodiments, DR IL-18 variant has an IL-18BP/IL-18R dissociation constant ratio that is about at least 20-fold higher than the IL-18BP/IL-18R dissociation constant ratio of wild-type IL-18. In some embodiments, the DR IL-18 variant has an IL-18BP/IL-18R dissociation constant ratio that is about at least 200-fold higher than the IL-18BP/IL-18R dissociation constant ratio of wild-type IL-18. In some embodiments, the DR IL-18 variant has an IL-18BP/IL-18R dissociation constant ratio that is about at least 2,000-fold higher than the IL-18BP/IL-18R dissociation constant ratio of wild-type IL-18. In some embodiments, the DR IL-18 variant has an IL-18BP/IL-18R dissociation constant ratio that is about at least 20,000-fold higher than the IL-18BP/IL-18R dissociation constant ratio of wild-type IL-18. In some embodiments, the DR IL-18 variant has an IL-18BP/IL-18R dissociation constant ratio that is about at least 200,000-fold higher than the IL-18BP/IL-18R dissociation constant ratio of wild-type IL-18. In some embodiments, the DR IL-18 variant has an IL-18BP/IL-18R dissociation constant ratio that is about at least 2,000,000-fold higher than the IL-18BP/IL-18R dissociation constant ratio of wild-type IL-18. In some embodiments, the DR IL-18 variant has an IL-18BP/IL-18R dissociation constant ratio that is about at least 20,000,000-fold higher than the IL-18BP/IL-18R dissociation constant ratio of wild-type IL-18.

In some embodiments, the DR IL-18 variant has an IL-18BP/IL-18R dissociation constant ratio that is about at least 3-fold higher than the IL-18BP/IL-18R dissociation constant ratio of wild-type IL-18. In some embodiments, the DR IL-18 variant has an IL-18BP/IL-18R dissociation constant ratio that is about at least 30-fold higher than the IL-18BP/IL-18R dissociation constant ratio of wild-type IL-18. In some embodiments, the DR IL-18 variant has an IL-18BP/IL-18R dissociation constant ratio that is about at least 300-fold higher than the IL-18BP/IL-18R dissociation constant ratio of wild-type IL-18. In some embodiments, the DR IL-18 variant has an IL-18BP/IL-18R dissociation constant ratio that is about at least 3,000-fold higher than the IL-18BP/IL-18R dissociation constant ratio of wild-type IL-18. In some embodiments, the DR IL-18 variant has an IL-18BP/IL-18R dissociation constant ratio that is about at least 30,000-fold higher than the IL-18BP/IL-18R dissociation constant ratio of wild-type IL-18. In some embodiments, the DR IL-18 variant has an IL-18BP/IL-18R dissociation constant ratio that is about at least 300,000-fold higher than the IL-18BP/IL-18R dissociation constant ratio of wild-type IL-18. In some embodiments, the DR IL-18 variant has an IL-18BP/IL-18R dissociation constant ratio that is about at least 3,000,000-fold higher than the IL-18BP/IL-18R dissociation constant ratio of wild-type IL-18. In some embodiments, the DR IL-18 variant has an IL-18BP/IL-18R dissociation constant ratio that is about at least 30,000,000-fold higher than the IL-18BP/IL-18R dissociation constant ratio of wild-type IL-18.

In some embodiments, the DR IL-18 variant has an IL-18BP/IL-18R dissociation constant ratio that is about at least 10-fold higher than the IL-18BP/IL-18R dissociation constant ratio of wild-type IL-18. In some embodiments, the DR IL-18 variant has an IL-18BP/IL-18R dissociation constant ratio that is about at least 100-fold higher than the IL-18BP/IL-18R dissociation constant ratio of wild-type IL-18. In some embodiments, the DR IL-18 variant has an IL-18BP/IL-18R dissociation constant ratio that is about at least 1000-fold higher than the IL-18BP/IL-18R dissociation constant ratio of wild-type IL-18. In some embodiments, the DR IL-18 variant has an IL-18BP/IL-18R dissociation constant ratio that is about at least 10,000-fold higher than the IL-18BP/IL-18R dissociation constant ratio of wild-type IL-18. In some embodiments, the DR IL-18 variant has an IL-18BP/IL-18R dissociation constant ratio that is about at least 100,000-fold higher than the IL-18BP/IL-18R dissociation constant ratio of wild-type IL-18. In some embodiments, the DR IL-18 variant has an IL-18BP/IL-18R dissociation constant ratio that is about at least 1,000,000-fold higher than the IL-18BP/IL-18R dissociation constant ratio of wild-type IL-18. In some embodiments, the DR IL-18 variant has an IL-18BP/IL-18R dissociation constant ratio that is about at least 10,000,000-fold higher than the IL-18BP/IL-18R dissociation constant ratio of wild-type IL-18. In some embodiments, the DR IL-18 variant has an IL-18BP/IL-18R dissociation constant ratio that is about at least 100,000,000-fold higher than the IL-18BP/IL-18R dissociation constant ratio of wild-type IL-18.

In some embodiments, a subject DR IL-18 variant has an inhibitor constant (Ki) for IL-18BP that is greater than 3 nM (e.g., 5 nM or more, 10 nM or more, 50 nM or more, 100 nM or more, 500 nM or more, 750 nM or more, or 1 μM or more). In some embodiments, a subject DR-IL-18 variant polypeptide has a Ki for IL-18BP that is 500 nM or more. In some embodiments, a subject DR-IL-18 variant polypeptide has a Ki for IL-18BP that is 1 µM or more.

In some embodiments, a subject IL-18 variant polypeptide (a DR-IL-18) that binds to IL-1518R and exhibits reduced binding to IL-18BP has a Ki for IL-18BP that is greater than 200 nM (e.g., 500 nM or more, 750 nM or more, or 1 µM or more). In some embodiments, a subject DR-IL-18 variant polypeptide has a Ki for IL-18BP that is 1 µM or more.

In some embodiments, a subject IL-18 variant polypeptide (a DR-IL-18) that binds to IL-18R and exhibits substantially reduced binding to IL-18BP has an inhibitor constant (Ki) for IL-18BP that is at least 2-fold higher than the Ki of wild type IL-18 for IL-18BP (i.e., the Ki of the subject IL-18 variant polypeptide for IL-18BP is at least 2-fold relative to the Ki of WT IL-18 for IL-18BP). For example, in some cases a subject DR-IL-18 variant polypeptide has a Ki for IL-18BP that is at least 5-fold higher (e.g., at least 10-fold, at least 50-fold, at least 100-fold, at least 200-fold, at least 500-fold, or at least 1000-folder higher) than the Ki of wild type IL-18 for IL-18BP.

In some embodiments, a subject IL-18 variant polypeptide (a DR-IL-18) that binds to IL-18R and exhibits substantially reduced binding to IL-18BP has an EC50 for IL-18BP that is at least 2-fold higher than the EC50 of wild type IL-18 for IL-18BP (i.e., the EC50 of the subject IL-18 variant polypeptide for IL-18BP is at least 2-fold relative to the EC50 of WT IL-18 for IL-18BP). For example, in some cases a subject DR-IL-18 variant polypeptide has a EC50 for IL-18BP that is at least 5-fold higher (e.g., at least 10-fold, at least 50-fold, at least 100-fold, at least 200-fold, at least 500-fold, or at least 1000-folder higher) than the EC50 of wild type IL-18 for IL-18BP.

In any of the above cases, the DR IL-18 variant can include C38/C68 mutations in any of the combinations presented above (e.g. in some cases C38S/C68S, C38S/C68G, C38S/C68A, C38S/C68A, C38S/C68V, C38S/C68D, C38S/C68E, or C38S/C68N; in some cases C38S/C68S, C38S/C68G, C38S/C68A, C38S/C68D, or C38S/C68N; in some cases C38S/C68G, C38S/C68A, C38S/C68D, or C38S/C68N; C38S/C68D; in some cases C38S/C68G; in some cases C38S/C68A; in some cases C38S/C68N; in some cases C38S/C68S).

Likewise, for any of the below, the DR IL-18 variant can include C38/C68 mutations in any of the combinations presented above (e.g. in some cases C38S/C68S, C38S/C68G, C38S/C68A, C38S/C68V, C38S/C68D, C38S/C68E, or C38S/C68N; in some cases C38S/C68G, C38S/C68A, C38S/C68V, C38S/C68D, C38S/C68E, or C38S/C68N; in some cases C38S/C68S, C38S/C68G, C38S/C68A, C38S/C68D, or C38S/C68N; in some cases C38S/C68G, C38S/C68A, C38S/C68D, or C38S/C68N; C38S/C68D; in some cases C38S/C68G; in some cases C38S/C68A; in some cases C38S/C68N; in some cases C38S/C68S).

In some embodiments a DR-IL-18 variant comprises at least one mutation (e.g., at least 2, at least 3, at least 4, at least 5, or at least 6 mutations) at an amino acid position selected from the group consisting of Y1, L5, K8, M51, K53, S55, Q56, P57, G59, M60, E77, Q103, S105, D110, N111, M113, V153, and N155. In various embodiments, the human IL-18 variant polypeptide comprises at least 4 mutations at amino acid positions selected from the group consisting of Y1, L5, K8, M51, K53, S55, Q56, P57, G59, M60, E77, Q103, S105, D110, N111, M113, V153, and N155. In various embodiments, the human IL-18 variant polypeptide comprises at least 6 mutations at amino acid positions selected from the group consisting of Y1, L5, K8, M51, K53, S55, Q56, P57, G59, M60, E77, Q103, S105, D110, N111, M113, V153, and N155. In various embodiments, the human IL-18 variant polypeptide comprises at least one mutation (e.g., at least 2, at least 3, at least 4, at least 5, or at least 6 mutations) at an amino acid position selected from the group consisting of Y1, L5, K8, S55, Q56, P57, G59, E77, Q103, S105, D110, N111, M113, V153, and N155. In some embodiments, a human IL-18 variant polypeptide comprises at least one mutation (e.g., at least 2, at least 3, at least 4, at least 5, or at least 6 mutations) at an amino acid position selected from the group consisting of Y1H, Y1R, L5H, L5I, L5Y, K8Q, K8R, M51T, M51K, M51D, M51N, M51E, M51R, K53R, K53G, K53S, K53T, S55K, S55R, Q56E, Q56A, Q56R, Q56V, Q56G, Q56K, Q56L, P57L, P57G, P57A, P57K, G59T, G59A, M60K, M60Q, M60R, M60L, E77D, Q103E, Q103K, Q103P, Q103A, Q103R, S105R, S105D, S105K, S105N, S105A, D110H, D110K, D110N, D110Q, D110E, D110S, D110G, N111H, N111Y, N111D, N111R, N111S, N111G, M113V, M113R, M113T, M113K, V153I, V153T, V153A, N155K, and N155H.

In some embodiments, a DR IL-18 variant polypeptide comprises the amino acid sequence set forth in any one of SEQ ID NOs: 34-59, 73-91, and 191-193. In some embodiments, a DR IL-18 variant polypeptide comprises an amino acid sequence having 80% or more sequence identity (e.g., 85% or more, 90% or more, 95% or more, 98% or more, 99% or more, or 100%) with the amino acid sequence set forth in any one of SEQ ID NOs: 34-59, 73-91, and 191-193. In some embodiments, a DR IL-18 variant polypeptide comprises an amino acid sequence having 85% or more sequence identity (e.g., 90% or more, 95% or more, 98% or more, 99% or more, or 100%) with the amino acid sequence set forth in any one of SEQ ID NOs: 34-59, 73-91, and 191-193. In some embodiments, a DR IL-18 variant polypeptide comprises an amino acid sequence having 90% or more sequence identity (e.g., 95% or more, 98% or more, 99% or more, or 100%) with the amino acid sequence set forth in any one of SEQ ID NOs: 34-59, 73-91, and 191-193.

In some cases a subject DR-IL-18 variant includes at least one mutation (e.g., at least 2, at least 3, or at least 4 mutations) at an amino acid position selected from the group consisting of M51, M60, S105, D110, and N111, relative to SEQ ID NO: 30. In some cases a subject DR-IL-18 variant includes at least 3 mutations at amino acid positions selected from the group consisting of M51, M60, S105, D110, and N111, relative to SEQ ID NO: 30. In some cases a subject DR-IL-18 variant includes at least one mutation (e.g., at least 2, at least 3, or at least 4 mutations) at an amino acid position selected from the group consisting of M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G. In some cases a subject DR-IL-18 variant includes at least 3 mutations (e.g., at least 2, at least 3, or at least 4 mutations) at amino acid positions selected from the group consisting of M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G. In some cases, a subject DR-IL-18 variant includes at least one mutation (e.g., at least 2, at least 3, or at least 4 mutations) at an amino acid position selected from the group consisting of M51, M60, S105, D110, and N111, relative to SEQ ID NO: 30, where M51 is T or K; M60 is K or L; S105 is D, N, or A; D110 is K, N, S, or G; and N111 is H, Y, G, or R.

In some cases a subject DR-IL-18 variant includes the mutations at amino acid positions M51, M60, S105, D110, and N111, relative to SEQ ID NO: 30. For example, in some cases a subject DR-IL-18 variant includes the mutations M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G. In some cases, a subject DR-IL-18 variant includes the mutations M51, M60, S105, D110, and N111, relative to SEQ ID NO: 30, where M51 is T or K; M60 is K or L; S105 is D, N, or A; D110 is K, N, S, or G; and N111 is H, Y, G, or R. In other words, in some cases a subject DR-IL-18 variant includes the mutations {M51T or M51K}; {M60K or M60L}; {S105D, S105N, S105A}; {D110K, D110N, D110S, or D110G}; and {N111H, N111Y, N111R, or N111G}, relative to SEQ ID NO: 30.

In some cases a subject DR-IL-18 variant includes at least one mutation (e.g., at least 2, at least 3, or at least 4 mutations) at an amino acid position selected from the group consisting of M51, K53, Q56, S105, and N111, relative to SEQ ID NO: 30. In some cases a subject DR-IL-18 variant includes at least 3 mutations at amino acid positions selected from the group consisting of M51, K53, Q56, S105, and N111, relative to SEQ ID NO: 30. In some cases a subject DR-IL-18 variant includes at least one mutation (e.g., at least 2, at least 3, or at least 4 mutations) selected from the group consisting of M51, K53, Q56, S105, and N111, relative to SEQ ID NO: 30, where M51 is E, R, or K; K53 is G, S, or T; Q56 is E, A, R, V, G, K, or L; S105 is N, S, K, or G; and N111 is R, S, G, or D. In some cases, a subject DR-IL-18 variant includes at least 3 mutations selected from the group consisting of M51, K53, Q56, S105, and N111, relative to SEQ ID NO: 30, where M51 is E, R, or K; K53 is G, S, or T; Q56 is E, A, R, V, G, K, or L; S105 is N, S, K, or G; and N111 is R, S, G, or D. In some cases, a subject DR-IL-18 variant includes at least one mutation (e.g., at least 2, at least 3, or at least 4 mutations) selected from the group consisting of M51, K53, Q56, S105, and N111, relative to SEQ ID NO: 30, where M51 is K; K53 is G or S; Q56 is G, R, or L; S105 is S, N, or G; and N111 is G or R.

In some cases a subject DR-IL-18 variant includes mutations at amino acid positions M51, K53, Q56, D110, and N111, relative to SEQ ID NO: 30. For example, in some cases a subject DR-IL-18 variant includes the mutations M51, K53, Q56, D110, and N111, relative to SEQ ID NO: 30, where M51 is E, R, or K; K53 is G, S, or T; Q56 is E, A, R, V, G, K, or L; D110 is S, N, G, or K; and N111 is R, S, G, or D. In some cases, a subject DR-IL-18 variant includes the mutations M51, K53, Q56, D110, and N111, relative to SEQ ID NO: 30, where M51 is K; K53 is G or S; Q56 is G, R, or L; D110 is S, N, or G; and N111 is G or R. In other words, in some cases a subject DR-IL-18 variant includes the mutations {M51K}; {K53G or K53S}; {Q56G, Q56R, or Q56L}; {D110S, D110N, or D110G}; and {N111R, or N111G}, relative to SEQ ID NO: 30.

In some cases, in addition to the mutations of the previous paragraph the DR IL-18 variant also includes mutations at positions P57 and M60, and in some cases S105 as well. For example, in some cases P57 is A, K, G or L; M60 is L or R—and in some such case S105 is A, N, or D. In some cases, P57 is A (i.e., P57A) and M60 is L (i.e., M60L)—and in some such case S105 is A, N, or D (in some cases S105D).

In some cases a subject DR-IL-18 variant comprises an amino acid sequence having 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30. As such in some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) relative to wild type IL-18 (e.g., human IL-18) (e.g., see all of the mutation combinations above).

In some cases, a subject DR-IL-18 variant comprises an amino acid sequence having 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193. As such in some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the amino acid sequence set forth in any one of SEQ ID NOs: 34-59, 73-91, and 191-193; and (ii) includes at least one mutation (e.g., at least 2, at least 3, at least 4, at least 5, or at least 6 mutations) relative to wild type IL-18 (e.g., human IL-18).

In some cases, a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) at amino acid positions selected from the group consisting of Y1, L5, K8, M51, K53, S55, Q56, P57, G59, M60, E77, Q103, S105, D110, N111, M113, V153, and N155, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 4 mutations at amino acid positions selected from the group consisting of Y1, L5, K8, M51, K53, S55, Q56, P57, G59, M60, E77, Q103, S105, D110, N111, M113, V153, and N155, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 6 mutations at amino acid positions selected from the group consisting of Y1, L5, K8, M51, K53, S55, Q56, P57, G59, M60, E77, Q103, S105, D110, N111, M113, V153, and N155, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, at least 4, at least 5, or at least 6 mutations) at an amino acid position selected from the group consisting of Y1, L5, K8, S55, Q56, P57, G59, E77, Q103, S105, D110, N111, M113, V153, and N155, relative to SEQ ID NO: 30.

In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) at an amino acid position selected from the group consisting of M51, M60, S105, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations at amino acid positions selected from the group consisting of M51, M60, S105, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations at amino acid positions selected from the group consisting of M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) at an amino acid position selected from the group consisting of M51, M60, S105, D110, and N111, relative to SEQ ID NO: 30, where M51 is T or K; M60 is K or L; S105 is D, N, or A; D110 is K, N, S, or G; and N111 is H, Y, G, or R.

In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations at positions M51, M60, S105, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51, M60, S105, D110, and N111, relative to SEQ ID NO: 30, where M51 is T, K, D, E, R, or N; M60 is K, Q, L, or R; S105 is R, D, K, A, or N; D110 is H, K, N, Q, E, N, S, or G; and N111 is H, D, Y, R, S, or G.

In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51, M60, S105, D110, and N111, relative to SEQ ID NO: 30, where M51 is T or K; M60 is K or L; S105 is D, N, or A; D110 is K, N, S, or G; and N111 is H, Y, G, or R.

In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) at positions selected from the group consisting of M51, K53, Q56, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations at positions selected from the group consisting of M51, K53, Q56, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51, K53, Q56, D110, and N111, relative to SEQ ID NO: 30, where M51 is E, R, or K; K53 is G, S, or T; Q56 is E, A, R, V, G, K, or L; D110 is N, S, K, or G; and N111 is R, S, G, or D. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least 3 mutations selected from the group consisting of M51, K53, Q56, D110, and N111, relative to SEQ ID NO: 30, where M51 is E, R, or K; K53 is G, S, or T; Q56 is E, A, R, V, G, K, or L; D110 is N, S, K, or G; and N111 is R, S, G, or D. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes at least one mutation (e.g., at least 2, at least 3, or at least 4 mutations) selected from the group consisting of M51, K53, Q56, D110, and N111, relative to SEQ ID NO: 30, where M51 is K; K53 is G or S; Q56 is G, R, or L; D110 is S, N, or G; and N111 is G or R.

In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes mutations at positions M51, K53, Q56, D110, and N111, relative to SEQ ID NO: 30. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51, K53, Q56, D110, and N111, relative to SEQ ID NO: 30, where M51 is E, R, or K; K53 is G, S, or T; Q56 is E, A, R, V, G, K, or L; D110 is N, S, K, or G; and N111 is R, S, G, or D. In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (ii) includes the mutations M51, K53, Q56, D110, and N111, relative to SEQ ID NO: 30, where M51 is K; K53 is G or S; Q56 is G, R, or L; D110 is S, N, or G; and N111 is G or R.

In some cases, in addition to the mutations of the previous paragraph the DR IL-18 variant also includes mutations at positions P57 and M60, and in some cases S105 as well. For example, in some cases P57 is A, K, G or L; M60 is L or R—and in some such case S105 is A, N, or D. In some cases, P57 is A (i.e., P57A) and M60 is L (i.e., M60L)—and in some such case S105 is A, N, or D (in some cases S105D).

Examples of murine IL-18 variant polypeptides (in this case DR IL-18 variants) include, but are not limited to mCS1 (SEQ ID NO: 60), mCS2 (SEQ ID NO: 61), mC1 (SEQ ID NO: 62), mA12 (SEQ ID NO: 63), mE8 (SEQ ID NO: 64), mC10 (SEQ ID NO: 65), mB7 (SEQ ID NO: 66), mB1 (SEQ ID NO: 67), mD1 (SEQ ID NO: 68), mH7 (SEQ ID NO: 69), mA7 (SEQ ID NO: 70), mE1 (SEQ ID NO: 71), and mH3 (SEQ ID NO: 72).

As noted above, any of the IL-18 variants herein can be 'stabilized' by further mutating C38 and C68 relative to SEQ ID NO: 30. As an illustrative example, in some cases, a subject stabilized DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30; (ii) includes mutations at positions M51, K53, Q56, D110, and N111, relative to SEQ ID NO: 30 [or any one of SEQ ID NOs: 6 and 16-21 or any one of SEQ ID NOs: 34-59, 73-91, and 191-193 or any one of SEQ ID NOs: 87-91 or SEQ ID NO: 89]; and (iii) includes mutations at C38 and C68 (e.g., C38S/C68S, C38S/C68G, C38S/C68A, C38S/C68V, C38S/C68D, C38S/C68E, or C38S/C68N—in some cases C38S/C68G, C38S/C68A, C38S/C68V, C38S/C68D, C38S/C68E, or C38S/C68N—in some cases C38S/C68S, C38S/C68G, C38S/C68A, C38S/C68D, or C38S/C68N—in some cases C38S/C68G, C38S/C68A, C38S/C68D, or C38S/C68N—in some cases C38S/C68D—in some cases C38S/C68G—in some cases C38S/C68A—in some cases C38S/C68N). In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30 [or any one of SEQ ID NOs: 6 and 16-21 or any one of SEQ ID NOs: 34-59, 73-91, and 191-193 or any one of SEQ ID NOs:87-91 or SEQ ID NO: 89]; (ii) includes the mutations M51, K53, Q56, D110, and N111, relative to SEQ ID NO: 30, where M51 is E, R, or K; K53 is G, S, or T; Q56 is E, A, R, V, G, K, or L; D110 is N, S, K, or G; and N111 is R, S, G, or D; and (iii) includes mutations at C38 and C68 (e.g., C38S/C68S, C38S/C68G, C38S/C68A, C38S/C68V, C38S/C68D, C38S/C68E, or C38S/C68N—in some cases C38S/C68G, C38S/C68A, C38S/C68V, C38S/C68D, C38S/C68E, or C38S/C68N—in some cases C38S/C68S, C38S/C68G, C38S/C68A, C38S/C68D, or C38S/C68N—in some cases C38S/C68G, C38S/C68A, C38S/C68D, or C38S/C68N—in some cases C38S/C68D—in some cases C38S/C68G—in some cases C38S/C68A—in some cases C38S/C68N). In some cases a subject DR-IL-18 variant comprises an amino acid sequence that (i) has 85% or more sequence identity (e.g., 90% or more, 92% or more, 93% or more, 94% or more, 95% or more, 96% or more, 97% or more, 98% or more, or 99% or more sequence identity) with the wild type human IL-18 amino acid sequence set forth as SEQ ID NO: 30 [or any one of SEQ ID NOs: 6 and 16-21 or any one of SEQ ID NOs: 34-59, 73-91, and 191-193 or any one of SEQ ID NOs:87-91 or SEQ ID NO: 89]; (ii) includes the mutations M51, K53, Q56, D110, and N111, relative to SEQ ID NO: 30, where M51 is K; K53 is G or S; Q56 is G, R, or L; D110 is S, N, or G; and N111 is G or R; and (iii) includes mutations at C38 and C68 (e.g., C38S/C68S, C38S/C68G, C38S/C68A, 8S/C68V, C38S/C68D, C38S/C68E, or C38S/C68N—in some cases C38S/C68G, C38S/C68A, C38S/C68V, C38S/C68D, C38S/C68E, or C38S/C68N—in some cases C38S/C68S, C38S/C68G, C38S/C68A, C38S/C68D, or C38S/C68N—in some cases C38S/C68G, C38S/C68A, C38S/C68D, or C38S/C68N—in some cases C38S/C68D—in some cases C38S/C68G—in some cases C38S/C68A—in some cases C38S/C68N).

In some cases, in addition to the mutations of the previous paragraph the DR IL-18 variant also includes mutations at positions P57 and M60, and in some cases S105 as well. For example, in some cases P57 is A, K, G or L; M60 is L or R—and in some such case S105 is A, N, or D. In some cases, P57 is A (i.e., P57A) and M60 is L (i.e., M60L)—and in some such case S105 is A, N, or D (in some cases S105D).

In some cases a subject DR IL-18 variant (i) includes mutations C38S/C68S, C38S/C68G, C38S/C68A, C38S/C68V, C38S/C68D, C38S/C68E, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutations C38S/C68S, C38S/C68G, C38S/C68A, C38S/C68V, C38S/C68D, C38S/C68E, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutations C38S/C68G, 20 C38S/C68A, C38S/C68V, C38S/C68D, C38S/C68E, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutations C38S/C68G, C38S/C68A, C38S/C68V, C38S/C68D, C38S/C68E, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutations C38S/C68S, C38S/C68G, C38S/C68A, C38S/C68D, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutations C38S/C68S, C38S/C68G, C38S/C68A, C38S/C68D, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutations C38S/C68G, C38S/C68A, C38S/C68D, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutations C38S/C68G, C38S/C68A, C38S/C68D, or C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutation C38S/C68D (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutation C38S/C68D (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutation C38S/C68G (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutation C38S/C68G (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutation C38S/C68A (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutation C38S/C68A (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some cases a subject DR IL-18 variant (i) includes mutation C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30. In some such cases the variant further includes mutations at positions P57 and M60. In some such cases the variant further includes a mutation at position S105.

In some cases a subject DR IL-18 variant (i) includes mutation C38S/C68N (relative to SEQ ID NO: 30); (ii) has 90% or more sequence identity (e.g., 92% or more, 93% or more, 94% or more, 95% or more, 96% or more, 97% or more, 98% or more, or 99% or more sequence identity) with the wild type human IL-18 amino acid sequence set forth as SEQ ID NO: 30; and (iii) includes mutations as positions M51, K53, Q56, D110, and N111 relative to SEQ ID NO: 30, where M51 is K; K53 is G or S; Q56 is G, R, or L; D110 is S, N, or G; and N111 is G or R. In some such cases the variant further includes mutations at positions where P57 is A, K, G or L; and M60 is L or R. In some such cases the variant further includes a mutation at position S105 where S105 is A, N, or D.

In some embodiments, an IL-18 polypeptide (e.g., DR IL-18) disclosed herein does not contain a cysteine at residue 78 (e.g., relative to SEQ ID NO: 30, 89, and/or 19). In some embodiments, an IL-18 polypeptide (e.g., DR IL-18) disclosed herein does not contain a mutation at residue N78 (e.g., relative to SEQ ID NO: 30, 89, and/or 19).

In some embodiments, an IL-18 polypeptide (e.g., DR IL-18) disclosed herein does not contain a cysteine at residue 121 (e.g., relative to SEQ ID NO: 30, 89, and/or 19). In some embodiments, an IL-18 polypeptide (e.g., DR IL-18) disclosed herein does not contain a mutation at residue E121 (e.g., relative to SEQ ID NO: 30, 89, and/or 19).

In some embodiments, an IL-18 polypeptide (e.g., DR IL-18) disclosed herein does not contain a cysteine at residue 144 (e.g., relative to SEQ ID NO: 30, 89, and/or 19). In some embodiments, an IL-18 polypeptide (e.g., DR IL-18) disclosed herein does not contain a mutation at residue L144 (e.g., relative to SEQ ID NO: 30, 89, and/or 19).

In some embodiments, an IL-18 polypeptide (e.g., DR IL-18) disclosed herein does not contain a cysteine at residue 157 (e.g., relative to SEQ ID NO: 30, 89, and/or 19). In some embodiments, an IL-18 polypeptide (e.g., DR IL-18) disclosed herein does not contain a mutation at residue D157 (e.g., relative to SEQ ID NO: 30, 89, and/or 19).

In some embodiments, an IL-18 polypeptide (e.g., DR IL-18) disclosed herein does not contain a cysteine at residue 78, residue 121, residue 144, or residue 157 (e.g., relative to SEQ ID NO: 30, 89, and/or 19). In some embodiments, an IL-18 polypeptide (e.g., DR IL-18) disclosed herein does not contain a mutation at residue N78, residue E121, residue L144, or residue D157 (e.g., relative to SEQ ID NO: 30, 89, and/or 19).

An IL-18 polypeptide (e.g., DR IL-18) of the disclosure can comprise mutations to C38 and C68 as disclosed herein, and can lack any mutations that introduce non-native cysteine residues into the polypeptide sequence. For example, in some embodiments, an IL-18 polypeptide (e.g., DR IL-18) contains cysteines only at position 76 and/or 127 (e.g., relative to SEQ ID NO: 30, 89, or 19). In some embodiments, an IL-18 polypeptide (e.g., DR IL-18) does not contain any cysteines except at position(s) 76 and/or 127 (e.g., relative to SEQ ID NO: 30, 89, or 19). A lack of non-native cysteine residues can contribute to advantageous properties of IL-18 polypeptides of the disclosure, for example, because cysteine residues can negatively impact the stability and/or biological activity of IL-18, e.g., by allowing formation of intramolecular or intermolecular disulfide bonds, dimers, aggregates, and the like.

An IL-18 polypeptide (e.g., DR IL-18) of the disclosure can lack or substantially-lack surface-exposed or solvent-exposed cysteine residues. A lack of surface-exposed or solvent-exposed cysteine residues can contribute to advantageous properties of IL-18 polypeptides of the disclosure, for example, because surface-exposed or solvent-exposed cysteine residues can negatively impact the stability and/or biological activity of IL-18, e.g., by allowing formation of intramolecular or intermolecular disulfide bonds, dimers, aggregates, and the like. An IL-18 polypeptide (e.g., DR IL-18) of the disclosure can lack or substantially-lack surface-exposed or solvent-exposed cysteine residues as determined by, for example, structural modeling, or an assay to detect free thiols (such as Ellman's titration). An IL-18 polypeptide (e.g., DR IL-18) of the disclosure can lack or substantially-lack free or surface-exposed thiols.

An IL-18 polypeptide disclosed herein (e.g., a DR IL-18) can be characterized by its molecular weight. For example, an IL-18 polypeptide can have a molecular weight of about 18 kDa. In some embodiments, an IL-18 polypeptide disclosed herein has a molecular weight of about 13 kDa, about 14 kDa, about 15 kDa, about 16 kDa, about 17 kDa, about 18 kDa, about 19 kDa, about 20 kDa, about 21 kDa, about 22 kDa, or about 23 kDa. In some embodiments, an IL-18 polypeptide disclosed herein has a molecular weight of at least about 10 kDa, at least about 11 kDa, at least about 12 kDa, at least about 13 kDa, at least about 14 kDa, at least about 15 kDa, at least about 16 kDa, at least about 17 kDa, at least about 18 kDa, at least about 19 kDa, or at least about 20 kDa. In some embodiments, an IL-18 polypeptide disclosed herein has a molecular weight of at most about 17 kDa, at most about 18 kDa, at most about 19 kDa, at most about 20 kDa, at most about 21 kDa, at most about 22 kDa, at most about 23 kDa, at most about 24 kDa, at most about 25 kDa, at most about 30 kDa, at most about 40 kDa, at most about 50 kDa, or at most about 100 kDa. In some embodiments, an IL-18 polypeptide disclosed herein has a molecular weight of about 18.15153 kDa, about 18.1515 kDa, about 18.152 kDa, about 18.15 kDa, about 18.2 kDa, or about 18 kDa.

An IL-18 polypeptide disclosed herein (e.g., a DR IL-18) can comprise, for example, about 130, about 135, about 140, about 145, about 150, about 151, about 152, about 153, about 154, about 155, about 156, about 157, about 158, about 159, about 160, about 161, about 162, about 163, about 1645, about 165, about 170, about 175, about 180, about 185, or about 190 amino acids.

In some embodiments, an IL-18 polypeptide disclosed herein (e.g., a DR IL-18) comprises at least about 130, at least about 135, at least about 140, at least about 145, at least about 150, at least about 151, at least about 152, at least about 153, at least about 154, at least about 155, at least about 156, at least about 157, at least about 158, at least about 159, or at least about 160 amino acids. In some embodiments, an IL-18 polypeptide disclosed herein (e.g., a DR IL-18) comprises at most about 155, at most about 156, at most about 157, at most about 158, at most about 159, at most about 160, at most about 161, at most about 162, at most about 163, at most about 1645, at most about 165, at most about 170, at most about 175, at most about 180, at most about 185, or at most about 190 amino acids. In some embodiments, an IL-18 polypeptide disclosed herein (e.g., a DR IL-18) comprises about 150 to about 170, about 152 to about 162, about 155 to about 159, about 156 to about 158, or 157 amino acids.

An IL-18 polypeptide disclosed herein (e.g., a DR IL-18, such as a DR IL-18 in a formulation of the disclosure) can have a level of biological activity or potency that can be measured by an assay for biological activity. A non-limiting example of an assay that can be used to measure a level of potency or biological activity of an IL-18 polypeptide disclosed herein is an IL-18 HEK-Blue potency assay. HEK-Blue IL-18 cells are designed to detect bioactive IL-18 by monitoring activation of the NFκβ and AP-1 pathways. These reporter cells were generated by stable transfection of HEK293-derived cells with genes encoding IL-18Rα and IL-18Rβ. Responses to human TNF-α and IL-1β have also been blocked, so the cells specifically respond to IL-18. These cells express a secreted embryonic alkaline phosphatase (SEAP) reporter gene under control of the IFN-β minimal promoter fused to five NFκβ and five AP-1 binding sites. Binding of bioactive IL-18 to the heterodimeric IL-18 receptor on the surface of HEK-Blue IL-18 cells triggers a signaling cascade that leads to production of SEAP, which can be quantified with a colorimetric assay.

The biological activity or potency of an IL-18 polypeptide disclosed herein (e.g., a DR IL-18, such as a DR IL-18 in a formulation of the disclosure) can be compared to a reference, for example, a wild type IL-18, or a reference standard of the same IL-18 polypeptide produced and characterized previously. In some embodiments, an IL-18 polypeptide disclosed herein (e.g., a DR IL-18, such as a DR IL-18 in a formulation of the disclosure) has a biological activity or potency (e.g., EC50) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the reference value. In some embodiments, an IL-18 polypeptide disclosed herein (e.g., a DR IL-18, such as a DR IL-18 in a formulation of the disclosure) has a biological activity or potency (e.g., EC50) that is at most 105%, at most 110%, at most 115%, at most 120%, at most 125%, at most 130%, at most 135%, at most 140%, at most 145%, at most 150%, at most 155%, at most 160%, at most 165%, at most 170%, at most 175%, at most 180%, at most 185%, at most 190%, at most 195%, at most 200%, at most 250%, or at most 300% of the reference value. In some embodiments, an IL-18 polypeptide disclosed herein (e.g., a DR IL-18, such as a DR IL-18 in a formulation of the disclosure) has a biological activity or potency (e.g., EC50) that is about 30% to about 500%, about 30% to about 250%, about 30% to about 200%, about 30% to about 175%, about 30% to about 150%, about 30% to about 140%, about 30% to about 130%, about 30% to about 120%, about 30% to about 110%, about 30% to about 105%, about 50% to about 500%, about 50% to about 250%, about 50% to about 200%, about 50% to about 175%, about 50% to about 150%, about 50% to about 140%, about 50% to about 130%, about 50% to about 120%, about 50% to about 110%, about 50% to about 105%, about 60% to about 500%, about 60% to about 260%, about 60% to about 200%, about 60% to about 175%, about 60% to about 160%, about 60% to about 140%, about 60% to about 130%, about 60% to about 120%, about 60% to about 110%, about 60% to about 105%, about 70% to about 500%, about 70% to about 250%, about 70% to about 200%, about 70% to about 175%, about 70% to about 150%, about 70% to about 140%, about 70% to about 130%, about 70% to about 120%, about 70% to about 110%, about 70% to about 105%, about 90% to about 500%, about 90% to about 250%, about 90% to about 200%, about 90% to about 175%, about 90% to about 150%, about 90% to about 140%, about 90% to about 130%, about 90% to about 120%, about 90% to about 110%, or about 90% to about 105% of the reference value. In some embodiments, the biological activity or potency (e.g., EC50) at least 60% and at most 140% of the reference value.

In some embodiments, an IL-18 polypeptide disclosed herein (e.g., a DR IL-18, such as a DR IL-18 in a formulation of the disclosure) has a biological activity or potency (e.g., EC50) that is at least 65%, at least 70%, at least 75%, at least 80%, at least 85%, at least 90%, or at least 95%, at least 97.5%, at least 100%, at least 102.5%, at least 105%, at least 110%, at least 115%, at least 120%, at least 125%, at least 130%, at least 140%, at least 150%, or at least 200%, at least 3-fold, at least 4-fold, at least 5-fold, at least 6-fold, at least-fold, at least 8-fold, at least 9-fold, or at least 10-fold more potent than of the biological activity of human wild type IL-18, e.g., as determined by an IL-18 HEK-Blue potency assay.

In some embodiments, an IL-18 polypeptide disclosed herein exhibits an EC50 of less than about 100 μM, less than about 10 μM, less than about 1 μM, less than about 900 nM, less than about 800 nM, less than about 700 nM, less than about 600 nM, less than about 500 nM, less than about 400 nM, less than about 300 nM, less than about 200 nM, less than about 100 nM, less than about 50 nM, less than about 30 nM, less than about 10 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 50 pM, less than about 10 pM, or less than about 1 pM, e.g., as determined by an IL-18 HEK-Blue potency assay.

In some embodiments, an IL-18 polypeptide disclosed herein exhibits an EC50 of about 1 pM to about 1 μM, about 1 pM to about 500 nM, about 1 pM to about 400 nM, about 1 pM to about 300 nM, about 1 pM to about 200 nM, about 1 pM to about 100 nM, about 1 pM to about 50 nM, about 1 pM to about 10 pM, about 10 pM to about 1 μM, about 10 pM to about 500 nM, about 10 pM to about 400 nM, about 10 pM to about 300 nM, about 10 pM to about 200 nM, about 10 pM to about 100 nM, about 10 pM to about 50 nM, about 50 pM to about 1 μM, about 50 pM to about 500 nM, about 50 pM to about 400 nM, about 50 pM to about 300 nM, about 50 pM to about 200 nM, about 50 pM to about 100 nM, about 100 pM to about 1 μM, about 100 pM to about 500 nM, about 100 pM to about 400 nM, about 100 pM to about 300 nM, or about 100 pM to about 200 nM, for example, as determined by an IL-18 HEK-Blue potency assay.

Nucleic Acids

Also provided herein are nucleic acids encoding any of the proteins described herein (e.g., IL-18 protein having a mutation at C38 and C68). Such nucleic acids can take any convenient form (e.g. a PCR product, a vector such as a viral vector, plasmid, cosmid, minicircle, and the like). In some cases the nucleotide sequence encoding the subject IL-18 protein is operably linked to (under the control of) a promoter (e.g., that is functional in a prokaryotic cell, or in some cases that is functional in a eukaryotic cell such as yeast or immune cells such as T cells, NK cells, TILs, and the like).

Also provided herein are cells comprising such nucleic acids and/or comprising the subject IL-18 proteins (e.g., stabilized proteins). In some cases the cell is a prokaryotic cell such as a bacterial cell (e.g., for the purpose of propagating the nucleic acid or for the purpose of producing a subject protein), in some cases the cell is a eukaryotic such as a yeast cell (e.g., for the purpose of producing a subject protein), and in some cases the cell is an immune cell such as a T-cell (e.g., a CAR-T cell such as a TRUCK cell), TIL, TCR-T cell (a T cell with an engineered TCR, e.g., engineered to bind to a target antigen with increased affinity compared to a natural TCR), or NK-cell (e.g., a CAR-NK cell), e.g., such cells can be engineered to express (e.g., secrete) a subject IL-18 protein (e.g., stabilized proteins such as SEQ ID NO: 19).

Cytokine Inhibitors

In some embodiments, the composition of the present disclosure comprises an inhibitor of one or more cytokines. In some embodiments, the inhibitor of one or more cytokines comprises a chemical compound, a protein, a peptide, a peptidomimetic, an antibody, a ribozyme, a small molecule chemical compound, or an antisense nucleic acid molecule (e.g., siRNA, miRNA, etc.) that inhibits the expression, activity, or both of one or more cytokines. In some embodiments, the inhibitor inhibits the expression, activity, or both of IL-17, IL-5, or IL-3. In some embodiments, the cytokine inhibitor decreases toxicity. In some embodiments, the cytokine inhibitor increases efficacy of an administered IL-18 variant polypeptide (e.g., stabilized IL-18 variants, DR IL-18 variants, D2D IL-18 variants, stabilized DR IL-18 variants, and stabilized D2D IL-18 variants).

Treatment

In various embodiments, the present disclosure includes compositions comprising an activator of IL-18 activity (e.g., stabilized IL-18 variants, DR IL-18 variants, D2D IL-18 variants, stabilized DR IL-18 variants, and stabilized D2D IL-18 variants) for use in methods such as stimulating signaling activity through at least one IL-18R, in a cell, tissue, organ, system, or subject in need thereof. In various embodiments, the activator of IL-18 activity compositions, and methods of treatment of the invention, increase the amount of IL-18R signaling, the amount of immune cell activity, or both. In various embodiments, the diseases and disorders in which an increase in IL-18R signaling may improve therapeutic outcomes include, but are not limited to cancer, infectious diseases, macular degeneration, and metabolic diseases or disorders.

Various IL-18 polypeptides are discussed above (e.g., IL-18 polypeptides with C38/C68 mutations) and are not repeated here—because any of the proteins discuss above can be used in the methods discussed herein. For example, in some cases a stabilized IL-18 polypeptide (e.g., stabilized IL-18 variant polypeptides such as stabilized DR IL-18 variants and stabilized D2D IL-18 variants) is used, e.g., to treat a disease or disorder such as cancer or an infection (e.g., a cancer that is resistant to immune checkpoint inhibitors, a cancer associated with a tumor that has reduced or absent expression of MHC class I, a cancer associated with high levels of IL-18BP (e.g., circulating or expressed by tumors), a cancer associated with a tumor in which IL-18R is expressed on infiltrating T cells or NK cells, a metabolic disease or disorder, an infectious disease, a viral infection such as HIV, and the like).

In some cases, the administered polypeptide is a wild type IL-18 polypeptide (e.g., a wild type human IL-18 protein). In some cases, the administered polypeptide is a subject stabilized IL-18 polypeptide (e.g., one that includes amino acid mutations at positions C38 and C68 relative to SEQ ID NO: 30). In some cases, the administered polypeptide is an IL-18 variant polypeptide such as a DR IL-18 variant or a D2D IL-18 variant. In some cases, the administered polypeptide is a stabilized IL-18 variant polypeptide (e.g., a stabilized DR IL-18 variant or a stabilized D2D IL-18 variant—see, e.g., the stabilized DR IL-18 variant polypeptides discussed above).

Fusions/Conjugations

In some embodiments, an IL-18 polypeptide (e.g., a stabilized IL-18 such as a stabilized DR IL-18 variant or stabilized D2D IL-18 variant, and the like) (e.g., SEQ ID NO: 19) of the present disclosure is conjugated to another molecule (e.g., fused to another protein), i.e., an IL-18 variant polypeptide can be fused in frame with a second polypeptide (a fusion partner). In some embodiments, the second polypeptide (the fusion partner) is capable of increasing the overall size of the fusion protein, e.g., so that the fusion protein will not be cleared from the circulation rapidly. In some cases, an IL-18 polypeptide (e.g., a stabilized IL-18 such as a stabilized DR IL-18 variant or stabilized D2D IL-18 variant, and the like) (e.g., SEQ ID NO: 19) is not fused to a second polypeptide.

In some embodiments, the second polypeptide (the fusion partner for a IL-18 variant polypeptide or a fragment thereof) is part or whole of an immunoglobulin Fc region (i.e., an antibody Fc sequence). In other embodiments, the second polypeptide is any suitable polypeptide that is substantially similar to Fc, e.g., providing increased size, multimerization domains, and/or additional binding or interaction with Ig molecules. In some embodiments, the second polypeptide is part or whole of Human Serum Albumin (HSA). In some embodiments, the second polypeptide is part or whole of an antibody, antibody fragment, camelid antibody or "nanobody" or other affinity reagent that binds to or interacts with HSA. These fusion proteins can facilitate purification, multimerization, and show an increased half-life in vivo. Fusion proteins having disulfide-linked multimeric structures can also, in some cases, be more efficient in binding and neutralizing other molecules.

When fused to a heterologous polypeptide, the portion corresponding to the IL-18 polypeptide (e.g., a stabilized IL-18 such as a stabilized DR IL-18 variant or stabilized D2D IL-18 variant, and the like) (e.g., SEQ ID NO: 19) can be referred to as the "IL-18 variant polypeptide portion" of a subject IL-18 variant polypeptide.

In some cases, the second polypeptide is a marker sequence (e.g., an affinity tag), such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37: 767, 1984. The addition of peptide moieties to facilitate handling of polypeptides are familiar and routine techniques in the art. A subject IL-18 polypeptide (e.g., a stabilized IL-18 such as a stabilized DR IL-18 variant or stabilized D2D IL-18 variant, and the like) (e.g., SEQ ID NO: 19) can be modified, e.g., joined/conjugated to a wide variety of other oligopeptides, proteins, and/or non-protein moieties for a variety of purposes. For example, post-translationally modified, for example by prenylation, acetylation, amidation, carboxylation, glycosylation, PEGylation (covalent attachment of polyethylene glycol (PEG) polymer chains), etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, a subject IL-18 variant polypeptide has one or more phosphorylated amino acid residues, e.g. phosphotyrosine, phosphoserine, or phosphothreonine.

In some embodiments, an IL-18 polypeptide disclosed herein is glycosylated. In some embodiments, an IL-18 polypeptide disclosed herein is non-glycosylated.

In some embodiments, an IL-18 polypeptide disclosed herein is conjugated to a water-soluble polymer. In some embodiments, an IL-18 polypeptide disclosed herein is pegylated. In some embodiments, an IL-18 polypeptide disclosed herein is conjugated to a polyethylene glycol homopolymer, polyethylene glycol copolymer, polypropylene glycol homopolymer, poly(N-vinylpyrrolidone), poly(vinyl alcohol), poly(ethylene glycol-co-propylene glycol), poly(N-2-(hydroxypropyl)methacrylamide), poly(sialic acid), poly(N-acryloyl morpholine), or dextran.

In some embodiments, an IL-18 polypeptide disclosed herein is not conjugated to a water-soluble polymer. In some embodiments, an IL-18 polypeptide disclosed herein is not pegylated. In some embodiments, an IL-18 polypeptide disclosed herein is not conjugated to a polyethylene glycol homopolymer, polyethylene glycol copolymer, polypropylene glycol homopolymer, poly(N-vinylpyrrolidone), poly(vinyl alcohol), poly(ethylene glycol-co-propylene glycol), poly(N-2-(hydroxypropyl)methacrylamide), poly(sialic acid), poly(N-acryloyl morpholine), or dextran.

In some other embodiments, an IL-18 polypeptide (e.g., a stabilized IL-18 such as a stabilized DR IL-18 variant or stabilized D2D IL-18 variant, and the like) (e.g., SEQ ID NO: 19) of the disclosure include reagents further modified to improve their resistance to proteolytic degradation or to optimize solubility properties or to render them more suitable as a therapeutic agent. For example, variants of the present disclosure further include analogs containing residues other than naturally occurring L-amino acids, e.g. D-amino acids or non-naturally occurring synthetic amino acids. D-amino acids may be substituted for some or all of the amino acid residues.

Co-Administration and Multispecific IL-18 Variant Polypeptides

In some cases a subject IL-18 polypeptide (e.g., a stabilized IL-18 such as a stabilized DR IL-18 variant or stabilized D2D IL-18 variant, and the like) (e.g., SEQ ID NO:19) is administered with an additional agent. The terms "co-administration", "co-administer", and "in combination with" include the administration of two or more therapeutic agents (e.g., a subject stabilized IL-18) either simultaneously, concurrently or sequentially within no specific time limits. In some embodiments, the agents are present in the cell or in the subject's body at the same time or exert their biological or therapeutic effect at the same time. In some embodiments, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject IL IL-18 polypeptide (e.g., a stabilized IL-18 such as a stabilized DR IL-18 variant or stabilized D2D IL-18 variant, and the like) (e.g., SEQ ID NO: 19) (e.g., formulated as a pharmaceutical composition) is co-administered with a cancer therapeutic drug, therapeutic drug to treat an infection, or cancer-directed antibody. Such administration may involve concurrent (i.e. at the same time), prior, or subsequent administration of the drug/antibody with respect to the administration of an agent or agents of the disclosure. A person of ordinary skill in the art would have no difficulty determining the appropriate timing, sequence and dosages of administration for particular drugs and compositions of the present disclosure.

In some embodiments, treatment is accomplished by administering a combination (co-administration) of a subject IL-18 polypeptide (e.g., a stabilized IL-18 such as a stabilized DR IL-18 variant or stabilized D2D IL-18 variant, and the like) (e.g., SEQ ID NO: 19) with another agent (e.g., an immune stimulant, an agent to treat chronic infection, a cytotoxic agent, an anti-cancer agent, etc.). One example class of cytotoxic agents that can be used are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

A subject IL-18 polypeptide (e.g., a stabilized IL-18 such as a stabilized DR IL-18 variant or stabilized D2D IL-18 variant, and the like) (e.g., SEQ ID NO: 19) need not be, but is optionally formulated with one or more agents that potentiate activity, or that otherwise increase the therapeutic effect. In some embodiments, treatment is accomplished by administering a combination (co-administration) of a subject IL-18 polypeptide (e.g., a stabilized IL-18 such as a stabilized DR IL-18 variant or stabilized D2D IL-18 variant, and the like) (e.g., SEQ ID NO: 19) and an agent that opsonizes a target cell. Thus, also envisioned herein are compositions (and methods that use the compositions) that include: (a) a subject IL-18 polypeptide (e.g., a stabilized IL-18 such as a stabilized DR IL-18 variant or stabilized D2D IL-18 variant, and the like) (e.g., SEQ ID NO: 19); and (b) an agent that opsonizes the target cell. In some cases, that agent that opsonizes the target cell is Rituximab. In some cases, that agent that opsonizes the target cell is Cetuximab.

An "agent that opsonizes a target cell" (an "opsonizing agent") is any agent that can bind to a target cell (e.g., a cancer cell, a cell harboring an intracellular pathogen, etc.) and opsonize the target cell (e.g., mark the target cell for phagocytosis and/or for antibody-dependent cell mediated cytotoxicity (ADCC)). For example, any antibody that can bind to a target cell (e.g., a cancer cell such as a tumor cell), where the antibody has an FC region, is considered to be an agent that opsonizes a target cell. In some cases, the agent that opsonizes a target cell is an antibody that binds to a target cell (e.g., an anti-tumor antibody, an anti-cancer antibody, an anti-infection antibody, and the like).

For example antibodies selective for tumor cell markers, radiation, surgery, and/or hormone deprivation, see Kwon et al., Proc. Natl. Acad. Sci U.S.A., 96: 15074-9, 1999.

Angiogenesis inhibitors can also be combined with the methods of the invention. A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer.

Monoclonal antibodies useful in the methods of the disclosure that have been used in solid tumors include, without limitation, edrecolomab and trastuzumab (herceptin). Edrecolomabtargets the 17-1A antigen seen in colon and rectal cancer, and has been approved for use in Europe for these indications. Trastuzumab targets the HER-2/neu antigen. Cetuximab (Erbitux) is also of interest for use in the methods of the disclosure. The antibody binds to the EGF receptor (EGFR), and has been used in the treatment of solid tumors including colon cancer and squamous cell carcinoma of the head and neck (SCCHN).

A subject IL-18 polypeptide (e.g., a stabilized IL-18 such as a stabilized DR IL-18 variant or stabilized D2D IL-18 variant, and the like) can be combined with any of the above mentioned agents (e.g., agents such as antibodies that opsonize a target cell). Thus, in some cases, a subject IL-18 polypeptide (e.g., a stabilized IL-18 such as a stabilized DR IL-18 variant or stabilized D2D IL-18 variant, and the like) is used in a combination therapy (is co-administered) with one or more opsonizing agents selective for cancer cells, e.g., tumor cells. In some cases, a subject IL-18 polypeptide (e.g., a stabilized IL-18 such as a stabilized DR IL-18 variant or stabilized D2D IL-18 variant, and the like) is used in a combination therapy (is co-administered) with one or more of: cetuximab (binds EGFR), panitumumab (binds EGFR), rituximab (binds CD20), trastuzumab (binds HER2), pertuzumab (binds HER2), alemtuzumab (binds CD52), brentuximab (binds CD30), tositumomab, ibritumomab, gemtuzumab, ibritumomab, and edrecolomab (binds 17-1A), or a combination thereof.

In some cases, a subject IL-18 polypeptide (e.g., a stabilized IL-18 such as a stabilized DR IL-18 variant or stabilized D2D IL-18 variant, and the like) (e.g., SEQ ID NO: 19) is co-administered with a cancer cell opsonizing agent (e.g., one that comprises an antigen binding region that targets CD19, CD20, CD22, CD24, CD25, CD30, CD33, CD37, CD38, CD44, CD45, CD47, CD51, CD52, CD56, CD62L, CD70, CD74, CD79, CD80, CD96, CD97, CD99, CD123, CD134, CD138, CD152 (CTLA-4), CD200, CD213A2, CD221, CD248, CD276 (B7H3), B7H4, CD279 (PD-1), CD274 (PD-L1), CD319, SIRPa, EGFR, EPCAM, 17-1A, HER1, HER2, HER3, CD117, C-Met, HGFR, PDGFRA, AXL, TWEAKR, PTHR2, HAVCR2 (TIM3), GD2 ganglioside, MUC1, mucin CanAg, mesothelin, endoglin, Lewis-Y antigen, CEA, CEACAM1, CEACAM5, CA-125, PSMA, BAFF, FGFR2, TAG-72, gelatinase B, glypican 3, nectin-4, BCMA, CSF1R, SLAMF7, integrin αvβ3, TYRP1, GPNMB, CLDN18.2, FOLR1, CCR4, CXCR4, MICA, C242 antigen, DLL3, DLL4, EGFL7, vimentin, fibronectin extra domain-B, TROP-2, LRRC15, FAP, SLITRK6, NOTCH2, NOTCH3, Tenascin-3, STEAP1, or NRP1, or any combination thereof).

In some cases, a subject IL-18 polypeptide (e.g., a stabilized IL-18 such as a stabilized DR IL-18 variant or stabilized D2D IL-18 variant, and the like) (e.g., SEQ ID NO: 19) is co-administered with and agent that targets one or more antigens selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

In some cases, a subject IL-18 polypeptide (e.g., a stabilized IL-18 such as a stabilized DR IL-18 variant or stabilized D2D IL-18 variant, and the like) (e.g., SEQ ID NO: 19) is used in a combination therapy (is co-administered) with a convenient immunomodulatory agent (e.g., an immune checkpoint inhibitor or immune agonist). As noted above, examples of targets of immune checkpoint inhibitors include but are not limited to: PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, and LILRB2. Thus, examples of immune checkpoint inhibitors include agents (e.g., antibodies) that inhibit proteins such as: PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, and LILRB2. In some cases, a subject stabilized IL-18 variant polypeptide (e.g., a DR-IL-18 variant, a D2D-IL-18 variant) (e.g., SEQ ID NO: 19) is co-administered with an immune checkpoint inhibitor (e.g., an antibody) that inhibits PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, LILRB2, or any combination thereof.

In some cases, a subject stabilized IL-18 variant polypeptide (e.g., a DR-IL-18 variant, a D2D-IL-18 variant) (e.g., SEQ ID NO: 19) is co-administered with an immune agonist. Examples of immune agonists include agents (e.g., agonizing antibodies) that agonize a protein such as: a tumor necrosis factor receptor superfamily (TNFRSF) protein (e.g., GITR, 41BB, OX40, CD27, CD40, HVEM); an immunoglobulin superfamily (IgSF) protein (e.g., CD28, ICOS, CD226, NKG2D); a TLR (e.g., TLR2, TLR4, TLR5, TLR7, TLR9); a nucleic acid sensor (e.g., STING, cGAS, RIG-I (DDX58)). Examples of immune agonists also include, but are not limited to: inflammasome activators (agonists), T cell engagers (e.g., a multispecific agent that cross-links CD3 and/or CD28 with a tumor antigen, e.g., a BiTE), and cytokines or cytokine variants (e.g., IL-2, IL-7, IL-10, IL-12, IL-15, IL-21, IL-23, IL-27, IL-33, TNF, TL1A, IFNA, IFNB, IFNG).

Thus, In some cases, a subject stabilized IL-18 variant polypeptide (e.g., a DR-IL-18 variant, a D2D-IL-18 variant) (e.g., SEQ ID NO: 19) is co-administered with an immune agonist such as: an agent (e.g., antibody) that agonizes a tumor necrosis factor receptor superfamily (TNFRSF) protein (e.g., GITR, 41BB, OX40, CD27, CD40, HVEM); an agent (e.g., antibody) that agonizes an immunoglobulin superfamily (IgSF) protein (e.g., CD28, ICOS, CD226, NKG2D); an agent that agonizes a TLR (e.g., TLR2, TLR4, TLR5, TLR7, TLR9); an agent that agonizes a nucleic acid sensor (e.g., STING, cGAS, RIG-I (DDX58)); an inflammasome activator; a T cell engager (e.g., a multispecific agent that cross-links CD3 and/or CD28 with a tumor antigen, e.g., a BiTE); a cytokine or cytokine variant (e.g., IL-2, IL-7, IL-10, IL-12, IL-15, IL-21, IL-23, IL-27, IL-33, TNF, TL1A, IFNA, IFNB, IFNG); or any combination thereof.

In some cases, a subject stabilized IL-18 variant polypeptide (e.g., a DR-IL-18 variant, a D2D-IL-18 variant) (e.g., SEQ ID DO: 19) is co-administered with a TGFbeta antagonist such as an anti-TGFbeta antibody; an interferon such as Interferon alpha, Interferon beta, or Interferon gamma; a TNF; TRAIL; a lymphotoxin; LIGHT/TNSF14; and the like.

In some cases, a subject IL-18 polypeptide (e.g., a stabilized IL-18 such as a stabilized DR IL-18 variant or stabilized D2D IL-18 variant, and the like) (e.g., SEQ ID NO: 19) is used in a combination therapy (is co-administered) with an inhibitor of BTLA and/or CD160. In some cases, a subject IL-18 polypeptide (e.g., a stabilized IL-18 such as a stabilized DR IL-18 variant or stabilized D2D IL-18 variant, and the like) (e.g., SEQ ID NO: 19) is used in a combination therapy (is co-administered) with an anti-CD47/SIRPA agent (e.g., anti-CD47, anti-SIRPA, a high affinity CD47 binding agent, a high affinity SIRPA binding agent, and the like). In some cases, a subject IL-18 polypeptide (e.g., a stabilized IL-18 such as a stabilized DR IL-18 variant or stabilized D2D IL-18 variant, and the like) (e.g., SEQ ID NO: 19) is used in a combination therapy (is co-administered) with an inhibitor of TIM3 and/or CEACAM1.

In some cases a subject IL-18 polypeptide (e.g., a stabilized IL-18 such as a stabilized DR IL-18 variant or stabilized D2D IL-18 variant, and the like) (e.g., SEQ ID NO: 19) is fused to another protein (i.e., a "fusion partner", a "second polypeptide"). In some embodiments, the second polypeptide (the fusion partner for a subject IL-18 variant polypeptide) specifically binds to a target molecule other than the target molecule bound by the IL-18 variant polypeptide portion of the fusion protein (e.g., other than IL-18R for variants that bind IL-18R; or other than IL-18BP for variants that bind to IL-18BP).

Thus, in some embodiments, a subject IL-18 polypeptide (e.g., a stabilized IL-18 such as a stabilized DR IL-18 variant or stabilized D2D IL-18 variant, and the like) (e.g., SEQ ID NO:19) is multispecific (e.g., bispecific). The terms "multispecific" or "bispecific" are commonly used when referring to agents (e.g., ligands or antibodies) that recognize two or more different antigens by virtue of possessing at least one region (e.g., a ligand or a Fab of a first antibody) that is specific for a first target, and at least a second region (e.g., a ligand or a Fab of a second antibody) that is specific for a second target. A bispecific agent specifically binds to two targets and is thus one type of multispecific agent.

In some embodiments, a subject IL-18 polypeptide (e.g., a stabilized IL-18 such as a stabilized DR IL-18 variant or stabilized D2D IL-18 variant, and the like) (e.g., SEQ ID NO: 19) is multispecific (e.g., bispecific), such that a first region of the polypeptide includes a subject IL-18 variant polypeptide sequence (i.e., the first region includes a IL-18 variant polypeptide), and a second region that specifically binds to another target molecule (e.g., an antigen). For example, in some cases, a IL-18 polypeptide (e.g., a stabilized IL-18 such as a stabilized DR IL-18 variant or stabilized D2D IL-18 variant, and the like) (e.g., SEQ ID NO: 19) is fused to a second polypeptide that binds specifically to a target molecule other than the target molecule bound by the IL-18 variant polypeptide.

Any one of the agents discussed above in the context of co-administration can be conjugated to a subject IL-18 polypeptide (e.g., a stabilized IL-18 such as a stabilized DR IL-18 variant or stabilized D2D IL-18 variant, and the like) (e.g., SEQ ID NO: 19). The term "co-administration" as used herein is meant to encompass such conjugated compounds. For example, when agent 1 is co-administered with agent 2, the term is meant to encompass embodiments where agent 1 and agent 2 are not conjugated to one another, and is also meant to encompass embodiments where agent 1 and agent 2 are conjugated to one another (e.g., where agent 1 and agent 2 are both proteins and agent 1 is fused to agent 2).

In some cases, the second region of a multispecific IL-18 polypeptide (e.g., a stabilized IL-18 such as a stabilized DR IL-18 variant or stabilized D2D IL-18 variant, and the like) (e.g., SEQ ID NO: 19) includes a checkpoint inhibitor. In some cases, the second region of a multispecific IL-18 variant polypeptide inhibits one or more proteins selected from: PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, and LILRB2.

In some cases, the second region of a multispecific IL-18 polypeptide (e.g., a stabilized IL-18 such as a stabilized DR IL-18 variant or stabilized D2D IL-18 variant, and the like) (e.g., SEQ ID NO: 19) includes an immune agonist. In some cases, the second region of a multispecific IL-18 variant polypeptide agonizes one or more proteins selected from: ICOS, GITR, 41BB, OX40, and CD40. Additional examples of immune agonists that can be used as (or used as part of) a second region of a multispecific IL-18 polypeptide (e.g., a stabilized IL-18 such as a stabilized DR IL-18 variant or stabilized D2D IL-18 variant, and the like) (e.g., SEQ ID NO: 19) include, but are not limited to: an agent (e.g., antibody or antigen binding region thereof) that agonizes a tumor necrosis factor receptor superfamily (TNFRSF) protein (e.g., GITR, 41BB, OX40, CD27, CD40, HVEM); an agent (e.g., antibody or antigen binding region thereof) that agonizes an immunoglobulin superfamily (IgSF) protein (e.g., CD28, ICOS, CD226, NKG2D); an agent that agonizes a TLR (e.g., TLR2, TLR4, TLR5, TLR7, TLR9); an agent that agonizes a nucleic acid sensor (e.g., STING, cGAS, RIG-I (D DX58)); an inflammasome activator; a T cell engager (e.g., a multispecific agent that cross-links CD3 and/or CD28 with a tumor antigen, e.g., a BiTE); a cytokine or cytokine variant (e.g., IL-2, IL-7, IL-10, IL-12, IL-15, IL-21, IL-23, IL-27, IL-33, TNF, TL1A, IFNA, IFNB, IFNG); and the like.

In some cases, the second region of a multispecific IL-18 polypeptide (e.g., a stabilized IL-18 such as a stabilized DR IL-18 variant or stabilized D2D IL-18 variant, and the like) (e.g., SEQ ID NO: 19) is a cancer cell opsonizing agent. In some cases, the second region of a multispecific IL-18 variant polypeptide targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3). In some cases, the second region of a multispecific IL-18 polypeptide (e.g., a stabilized IL-18 such as a stabilized DR IL-18 variant or stabilized D2D IL-18 variant, and the like) (e.g., SEQ ID NO: 19) is an opsonizing agent that targets one or more proteins selected from: CD19, CD20, CD22, CD24, CD25, CD30, CD33, CD38, CD44, CD47, SIRPA, CD52, CD56, CD70, CD96, CD97, CD99, CD123, CD279 (PD-1), CD274 (PD-L1), EGFR, 17-1A, HER2, CD117, C-Met, PTHR2, and HAVCR2 (TIM3).

For example, in some cases, the second region of a multispecific IL-18 polypeptide (e.g., a stabilized IL-18 such as a stabilized DR IL-18 variant or stabilized D2D IL-18 variant, and the like) (e.g., SEQ ID NO: 19) includes an ectodomain, e.g., an ectodomain from PD-1, PD-L1, CD47 (e.g., a high affinity CD47 variant/polypeptide), or SIRPA. (e.g., a high affinity SIRPA variant/polypeptide). In some cases, the second region of a multispecific IL-18 variant polypeptide specifically binds an antigen selected from: CTLA-4, Lag-3, BTLA, Tim-3, CD244, CD40, CD40L, CD47, SIRPA, PD-1, and PD-L1.

In some embodiments, the IL-18 variant polypeptide has increased biological activity relative to wild type IL-18. In some embodiments, the IL-18 variant comprises no cysteine residues relative to those natively occurring in wild type IL-18. In some embodiments, the IL-18 variant polypeptide comprises an amino acid sequence with no pegylated amino acids.

In some embodiments, a subject IL-18 variant polypeptide (e.g., a stabilized IL-18) includes a linker (e.g., a linker polypeptide). For example, in some embodiments, a subject IL-18 variant polypeptide and a fusion partner are separated by a linker (e.g., a linker polypeptide). A linker polypeptide may have any of a variety of amino acid sequences. Proteins can be joined by a linker polypeptide can be of a flexible nature (e.g., a flexible linker polypeptide), although other chemical linkages are not excluded. Suitable linkers include polypeptides of between about 6 amino acids and about 40 amino acids in length, or between about 6 amino acids and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that the in some case, linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use.

In some embodiments the IL-18 variant polypeptide (e.g., a stabilized IL-18) is co-administered with an immune cell such as a tumor-infiltrating lymphocyte (TIL), a CAR-T, TCR-T cell (a T cell with an engineered TCR, e.g., engineered to bind to a target antigen with increased affinity compared to a natural TCR), CAR-NK cell, or T or NK cell transduced with an engineered T cell receptor. In other embodiments, the IL-18 variant polypeptide is co-administered with an oncolytic virus.

In some embodiments, a nucleic acid encoding an IL-18 variant polypeptide (e.g., a stabilized IL-18) is included within an engineered ("altered") immune cell such as a CAR-T, TCR-T cell, or CAR-NK cell or T or NK cell transduced with an engineered T cell receptor or a Tumor-infiltrating Lymphocyte (TIL). In this instance, the engineered cell (e.g., altered T cell, altered NK cell, altered TIL) would secrete the IL-18 variant polypeptide. The ability to secrete the IL-18 variant peptide can be regulated in a contextual manner (e.g., turned on within the tumor microenvironment), for instance, by a synthetic NOTCH receptor.

In some embodiments, a nucleic acid encoding an IL-18 variant polypeptide (e.g., a stabilized IL-18) is included within an oncolytic virus. In this instance, cells infected by the oncolytic virus would secrete the IL-18 variant polypeptide.

In some embodiments, an IL-18 variant polypeptide (e.g., a stabilized IL-18) is administered to a cell, tissue, organ, system, or subject to treat a disease or disorder. In some embodiments, a human IL-18 variant polypeptide is administered to a cell, tissue, organ, system, or subject. In some embodiments, a nucleic acid (e.g., DNA, cDNA, mRNA, etc.) encoding at least one human IL-18 variant polypeptide (e.g., a stabilized IL-18) is administered to a cell, tissue, organ, system, or subject.

In some embodiments, a composition of the invention is administered to a murine cell, tissue, organ, system, or subject to treat or prevent a disease or disorder. In some embodiments, a murine IL-18 variant polypeptide, or a fragment thereof, is administered to a cell, tissue, organ, system, or subject (e.g., a human cell, tissue, organ, system, or subject). In some embodiments, a nucleic acid (e.g., DNA, cDNA, mRNA, etc.) encoding at least one murine IL-18 variant polypeptide is administered to a cell, tissue, organ, system, or subject. As noted elsewhere herein, examples of murine IL-18 variant polypeptides (in this case DR IL-18 variants) include but are not limited to: SEQ ID NOs: 60-72. Also as noted elsewhere herein, examples of murine IL-18 variants (in this case D2D IL-18 variants, which bind to IL-18BP but have reduced binding to IL-18R) include but are not limited to SEQ ID NOs: 126-190.

In some embodiments, the method comprises administering to a subject, cell, or tissue, an isolated nucleic acid molecule encoding on or more of the IL-18 variant polypeptides (e.g., a stabilized IL-18) described herein. Increased level of IL-18 signaling, including by using an IL-18 variant polypeptide (e.g., a stabilized IL-18), can be assessed using a wide variety of methods, including those disclosed herein, as well as methods known in the art or to be developed in the future. That is, the routineer would appreciate, based upon the disclosure provided herein, that increasing the level or activity of IL-18 signaling can be readily assessed using methods that assess the level of a nucleic acid (e.g., mRNA) encoding IL-18 or an IL-18 variant polypeptide or fragment thereof, the level of IL-18 or an IL-18 variant polypeptide or fragment polypeptide, and/ or the level of IL-18 or an IL-18 variant polypeptide or fragment activity in a biological sample obtained from a subject.

One skilled in the art, based upon the disclosure provided herein, would understand that the compositions of the disclosure (IL-18 variant polypeptides such as stabilized IL-18)) is useful in subjects who, in whole (e.g., systemically) or in part (e.g., locally, cell, tissue, organ), are being or will be, treated for a disease or disorder where an increase in IL-18 signaling activity would be beneficial. The skilled artisan will appreciate, based upon the teachings provided herein, that the diseases and disorders treatable by the compositions and methods described herein encompass any disease or disorder wherein an increase in IL-18 signaling will promote a positive biologic, physiologic, clinical or therapeutic outcome.

In some embodiments, a method comprises administering to a subject in need thereof a composition comprising at least one IL-18 polypeptide (e.g., a stabilized IL-18 such as a stabilized DR IL-18 variant or stabilized D2D IL-18 variant, and the like) (e.g., SEQ ID NO: 19), and administering to the subject a composition comprising an additional agent. In one such embodiment, the additional agent comprises an immunotherapeutic agent comprising at least one selected from the group including, but not limited to an altered T-cell, a chimeric antigen receptor T-cell (CAR-T), an armored CAR-T cell, a chimeric antigen receptor NK-cell (CAR-NK), a TCR-T cell, a Tumor-infiltrating Lymphocyte (TIL), a virus, an antigen, a vaccine, an antibody, an immune checkpoint inhibitor, a small molecule, a chemotherapeutic agent, and a stem cell. In some embodiments, a composition comprising at least one IL-18 polypeptide (e.g., a stabilized IL-18 such as a stabilized DR IL-18 variant or stabilized D2D IL-18 variant, and the like)(e.g., SEQ ID NO: 19) is used in a method to increase immune system activity before, during, or after infection by a bacterium, virus, or other pathogen. In some embodiments, a composition comprising at least one IL-18 variant polypeptide is used in a method to increase the number and/or activity of immune cells in vitro, in vivo or ex vivo, such as the number and/or activity of T cells, NK cells, and/or myeloid cells.

In some embodiments, the additional agent comprises an inhibitor of one or more cytokines. In some embodiments, the inhibitor of one or more cytokines comprises a chemical compound, a protein, a peptide, a peptidomimetic, an antibody, a ribozyme, a small molecule chemical compound, or an antisense nucleic acid molecule (e.g., siRNA, miRNA, etc.) that inhibits the expression, activity, or both of one or more cytokines. In some embodiments, the inhibitor inhibits the expression, activity, or both of IL-17, IL-5, or IL-3. In some embodiments, the administration of a cytokine inhibitor decreases toxicity. In some embodiments, the administration of a cytokine inhibitor increases efficacy of an administered IL-18 polypeptide (e.g., a stabilized IL-18 such as a stabilized DR IL-18 variant or stabilized D2D IL-18 variant, and the like) (e.g., SEQ ID NO: 19).

As used herein, the term "pharmaceutically-acceptable carrier" means a chemical composition with which an appropriate IL-18 polypeptide (e.g., a stabilized IL-18 such as a stabilized DR IL-18 variant or stabilized D2D IL-18 variant, and the like) (e.g., SEQ ID NO: 19) may be combined and which, following the combination, can be used to administer the IL-18 polypeptide (e.g., a stabilized IL-18 such as a stabilized DR IL-18 variant or stabilized D2D IL-18 variant, and the like) (e.g., SEQ ID NO: 19) to a subject.

Production of IL-18 Variants
SUMO Protease

Provided are compositions and methods for making a polypeptide of interest (e.g., inactive protein) by using a SUMO (small ubiquitin-like modifier) protease to cleave a SUMO tag off of a polypeptide of interest. The SUMO tag can be place N-terminal to the protein of interest and the SUMO protease (e.g., ULP1) can provide for scarless removal of the SUMO tag via a cleavage reaction. In some cases, the cleavage will occur in a cell (e.g., in a bacterial cell, in a yeast cell) and in other cases the cleavage will occur cell-free in vitro.

For example, in some cases a fusion protein (that includes a protein of interested fused at its N-terminus to a SUMO tag) will be introduced into a bacterial cell (e.g., via a nucleic acid encoding the fusion protein) and SUMO protease will also be introduced into the same cell (in such cases, both proteins can be said to be exogenously introduced)—and the cleavage reaction will therefore occur inside of the cell. In some cases, the protease will be encoded by a nucleic acid that is integrated into the cell's genome and in some cases the nucleic acid will not be integrated (e.g. can be a plasmid). The SUMO protease can be expressed from a constitutive promoter or can be operably linked (under the control of) an inducible promoter such as a rhamnose-inducible promoter. Any convenient inducible promoter can be used. As such, in some such cases contacting a fusion protein with a SUMO protease in a cell (e.g., bacterial cell) can comprise inducing expression of the SUMO protease.

In some cases, the fusion protein and SUMO protease are encoded by the same nucleic acid (e.g. plasmid). In some such cases both proteins are operably linked to the same promoter (e.g., they can be translated from a bicistronic mRNA), and in other cases the two proteins are operably linked to separate promoters.

In some cases, the fusion protein is contacted with the SUMO protease in a cell-free in vitro environment. For example, a fusion protein can be purified/isolated and then contacted with a purified SUMO protease (which is readily available).

When the polypeptide of interest is an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19), such proteins are not fully active when the N-terminal amino acid is a methionine (e.g., human wild type IL-18 protein is normally cleaved by caspase-1 to reveal the N-terminal tyrosine, thus obtaining the active mature form). Thus, methods of this disclosure can be used to produce active IL-18 polypeptides. In such cases, a SUMO (small ubiquitin-like modifier) tag can be used to facilitate production of large amounts of fusion protein (IL-18 plus SUMO tag), followed by removal of the SUMO tag to reveal an activated IL-18 protein (e.g., one with a non-methionine, e.g., a tyrosine) at the N-terminus. The SUMO tag can be removed by contacting the fusion protein with SUMO protease (e.g., yeast ULP1), which cleaves off the tag to reveal the native N-terminal amino acid (Tyr in the case of human IL-18). In some cases, the contacting is performed inside of a cell such as a bacterial cell. In some such cases, the produced active protein can then be purified, e.g., from a cell lysate (see further details below).

Any convenient SUMO tag can be used—and one such example is set forth as SEQ ID NO: 26. In some cases, e.g., for purposes of subsequent purification (see below), it is desirable to include an additional tag (e.g., a 6×His tag) on the SUMO tag. SEQ ID NO: 27 provides one non-limiting example of such a tagged SUMO tag.

Purification Steps

In some embodiments, the subject 'methods of making'/ 'producing' further include purifying the polypeptide of interest after the SUMO tag has been removed (e.g., an IL-18 polypeptide such as a stabilized IL-18 variant, a DR IL-18 variant, a D2D IL-18 variant, a stabilized DR IL-18 variant, a stabilized D2D IL-18 variant, and the like) (e.g., SEQ ID NO: 19). In some such cases the cleavage (SUMO tag removal) occurs cell-free in vitro and the purification can include removal of the SUMO tag and SUMO protease. For example, in some cases the SUMO protease and/or the SUMO tag can be tagged (e.g., His tagged), which can in some cases facilitate removal of these components after cleavage, e.g., for purification of the polypeptide of interest, e.g., using immobilized metal affinity chromatography (IMAC) such as a nickel column.

In some cases, the cleavage (SUMO tag removal) occurs in a cell (e.g., a bacterial cell as discussed above) and the polypeptide of interested is purified from a cell lysate. In some cases, the polypeptide of interested is secreted into the medium (e.g., in some cases when using yeast cells)—and is then purified from the medium. Any convenient step or series of steps can be used to purify proteins from, e.g., bacterial lysates or media into which proteins have been secreted. In some cases (e.g., in some cases in which the polypeptide of interest is an IL-18 polypeptide such as a stabilized IL-18 variant, a DR IL-18 variant, a D2D IL-18 variant, a stabilized DR IL-18 variant, a stabilized D2D IL-18 variant, and the like) (e.g., SEQ ID NO: 19), purification includes ion-exchange chromatography (e.g., Capto Q), IMAC (e.g., to remove any residual his-tagged SUMO, uncleaved protein, and/or protease), multimodal chromatography (e.g., Capto MMC chromatography-Capto MMC is a multimodal salt-tolerant resin for capture and intermediate purification of proteins from large feed volumes by packed bed chromatography) and hydrophobic interaction chromatography (HIC) (e.g., in some cases phenyl sepharose HIC). In some cases, high-performance Q chromatography is also performed. In some such cases, ultrafiltration (UF) and diafiltration (DF) steps are performed prior to each chromatography step. As an example of one possible purification process, see FIG. 48.

It will be appreciated by one of skill in the art, when armed with the present disclosure including the methods detailed herein, that the invention is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit. Therefore, the present invention, as described more fully herein, includes a method for preventing diseases and disorders in a subject, in that an activator of IL-18 activity as discussed elsewhere herein, can be administered to a subject prior to the onset of the disease or disorder, thereby preventing the disease or disorder from developing.

Pharmaceutical Compositions of the Disclosure

Compositions comprising a polypeptide, a polypeptide fragment, an IL-18 polypeptide (e.g., a stabilized IL-18 such as a stabilized DR IL-18 variant or stabilized D2D IL-18 variant, and the like) (e.g., SEQ ID NO: 19) as described elsewhere herein can be formulated and administered to a subject, as now described. By way of non-limiting examples, a IL-18 polypeptide (e.g., a stabilized IL-18 such as a stabilized DR IL-18 variant or stabilized D2D IL-18 variant, and the like) (e.g., SEQ ID NO: 19) for the treatment and/or prevention of a disease or disorder can be formulated and administered to a subject, in any convenient way, e.g., as now described.

The disclosure encompasses the preparation and use of pharmaceutical compositions comprising a composition useful for the treatment or prevention of a disease or disorder, disclosed herein as an active ingredient (an IL-18 polypeptide, e.g., a stabilized IL-18 such as a stabilized DR IL-18 variant or stabilized D2D IL-18 variant, and the like) (e.g., SEQ ID NO: 19). Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically-acceptable carrier" means a chemical composition with which an appropriate IL-18 polypeptide (e.g., a stabilized IL-18 such as a stabilized DR IL-18 variant or stabilized D2D IL-18 variant, and the like) (e.g., SEQ ID NO: 19), may be combined and which, following the combination, can be used to administer to a subject.

In some embodiments, pharmaceutical compositions can include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

The pharmaceutical compositions useful for practicing the subject methods (e.g., the IL-18 polypeptide such as a wild type IL-18, a stabilized IL-18, a DR IL-18, a D2D IL-18, a stabilized DR IL-18, a stabilized D2D IL-18, and the like) (e.g., SEQ ID NO: 19) may be administered to deliver a dose of between about 0.1 ng and 100 mg per kg (e.g., 1 ng to 100 mg, 100 ng to 100 mg, 1 ug to 100 mg, 100 ug to 100 mg, 1 mg to 100 mg, 25 mg to 100 mg, 50 mg to 100 mg, 1 ng to 80 mg, 100 ng to 80 mg, 1 ug to 80, 100 ug to 80 mg, 1 mg to 80 mg, 25 mg to 80 mg, 50 mg to 80 mg, 1 ng to 50 mg, 100 ng to 50 mg, 1 ug to 50 mg, 100 ug to 50 mg, 1 mg to 50 mg, 25 mg to 50 mg, 50 mg to 50 mg, 1 ng to 50 mg, 100 ng to 50 mg, 1 ug to 50 mg, 100 ug to 50 mg, 1 mg to 50 mg, or 25 mg to 50 mg per kg). Dosing is described in more detail elsewhere herein.

In various embodiments, the pharmaceutical compositions useful in the methods of the invention may be administered, by way of example, systemically, parenterally, subcutaneously, intraperitoneally, or topically, such as, in oral formulations, inhaled formulations, including solid or aerosol, and by topical or other similar formulations, or intraocularly. In addition to the appropriate therapeutic composition, such pharmaceutical compositions may contain pharmaceutically acceptable carriers and other ingredients known to enhance and facilitate drug administration. Other possible formulations, such as nanoparticles, liposomes, other preparations containing the active ingredient, and immunologically based systems may also be used to administer an appropriate modulator thereof, according to the methods of the invention.

A carrier may bear a subject agent (e.g., IL-18 variant polypeptide) in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear a IL-18 polypeptide (e.g., a stabilized IL-18 such as a stabilized DR IL-18 variant or stabilized D2D IL-18 variant, and the like) (e.g., SEQ ID NO: 19) by non-covalent associations, such as non-covalent bonding or by encapsulation. The nature of the carrier can be either soluble or insoluble for purposes of the invention.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, transdermal, intralesional, subcutaneous, intramuscular, ophthalmic, intrathecal and other known routes of administration. Other contemplated formulations include projected nanoparticles, liposomal preparations, other preparations containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

Pharmaceutically acceptable excipients used in the manufacture of pharmaceutical compositions include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Liquid formulations of a pharmaceutical composition of the invention may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and 15 hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques. In some cases, a subject IL-18 polypeptide (e.g., a stabilized IL-18 such as a stabilized DR IL-18 variant or stabilized D2D IL-18 variant, and the like) (e.g., SEQ ID NO: 19) is administered subcutaneously.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Example Formulations

In some embodiments, the formulation comprises an active ingredient comprising an IL-18 polypeptide, one or more of a buffering agent to control pH, one or more of a stabilizer, one or more of a solvent, a surfactant, a reagent for preventing oxidation, and a stabilizer. In some embodiments, formulations of a IL-18 polypeptide comprise one or more of: L-Histidine (His), L-Histidine Hydrochloride (His-HCl), sucrose, Polysorbate 80, L-Methionine and disodium salt of EDTA.

One example of an appropriate formulation for a IL-18 polypeptide (e.g., a stabilized IL-18 such as a stabilized DR IL-18 variant or stabilized D2D IL-18 variant, and the like) (e.g., SEQ ID NO: 19) that was arrived at via experimentation includes: (1) an IL-18 polypeptide (e.g., a wild type IL-18, a stabilized IL-18, a DR IL-18, a D2D IL-18, a stabilized DR IL-18, a stabilized D2D IL-18, and the like) (e.g., SEQ ID NO: 19); (2) a buffering agent to maintain to pH between 6.2 and 6.8 (e.g., in some cases 6.5)(e.g., His/His-HCl at 8-12 mM, e.g., at 10 mM); (3) a sugar (e.g., sucrose, e.g., at 6-10%; in some cases 8%); (4) a chelating agent (e.g., EDTA, e.g., at 0.05-1.5 mM, e.g., in some cases 0.1 mM); (5) an agent to prevent oxidation (e.g., L-methionine, e.g., at 4-6 mM, e.g., in some cases 5 mM), and (6) an agent to prevent protein adsorption (e.g., PS80, e.g., at 0.01-0.03% w/v, e.g., 0.02%).

As such, in some cases a formulation includes: (1) an IL-18 polypeptide (e.g., a wild type IL-18, a stabilized IL-18, a DR IL-18, a D2D IL-18, a stabilized DR IL-18, a stabilized D2D IL-18, and the like) (e.g., SEQ ID NO: 19); (2) about 10 mM His/His-HCl; (3) about 8% sucrose; (4) about 0.1 mM EDTA; (5) about 5 mM L-Methionine; and (6) about 0.02% (w/v) PS80.

In some of the above embodiments (e.g., if the formulation is to be administered subcutaneously), the IL-18 polypeptide (e.g., a wild type IL-18, a stabilized IL-18, a DR IL-18, a D2D IL-18, a stabilized DR IL-18, a stabilized D2D IL-18, and the like) (e.g., SEQ ID NO: 19) will be present at a concentration in a range of from 10-100 mg/ml (e.g., 10-90, 10-75, 10-60, 10-50, 10-40, 10-30, 25-100, 25-90, 25-75, 25-60, 25-50, 25-40, 25-30, 30-100, 30-90, 30-75, 30-60, 30-50, 30-40, 40-100, 40-90, 40-75, 40-60, 40-50, 50-100, 50-90, 50-75, or 50-60 mg/ml). In some of the above embodiments (e.g., if the formulation is to be administered subcutaneously), the IL-18 polypeptide (e.g., a wild type IL-18, a stabilized IL-18, a DR IL-18, a D2D IL-18, a stabilized DR IL-18, a stabilized D2D IL-18, and the like) (e.g., SEQ ID NO: 19) will be present at a concentration in a, or 50-60 mg/ml). In some of the above embodiments (e.g., if the formulation is to be administered subcutaneously), the IL-18 polypeptide (e.g., a wild type IL-18, a stabilized IL-18, a DR IL-18, a D2D IL-18, a stabilized DR IL-18, a stabilized D2D IL-18, and the like) (e.g., SEQ ID NO: 19) will be present at a concentration in a range of from 20-30 mg/ml.

In some embodiments, the drug product is formulated in batches. In some embodiments, batches are 1.5 L. In other embodiments, batches are 10.5 L. Batches may include, for example, the IL-18 polypeptide of SEQ ID NO: 19, L-Histidine, L-Histidine Hydrochloride, sucrose, polysorbate 80, L-Methionine, disodium salt of EDTA, and water for injections. In some embodiments, a batch comprises between 40 and 50 g SEQ ID NO: 19, between 1.00 and 2.00 g of L-Histidine; between 0.25 and 1.00 g L-Histidine Hydrochloride, between 100.00 and 150.00 g of sucrose; between 0.01 and 0.60 g polysorbate 80; between 1 and 1.5 g L-Methionine; between 0.005 and 0.1 g disodium salt of EDTA; and a quantity sufficient to about 1.5 L of water. In some embodiments, a batch comprises about 45 g SEQ ID NO: 19, about 1.91 g of L-Histidine; about 0.57 g L-Histidine Hydrochloride, about 120.0 g of sucrose; about 0.30 g polysorbate 80; about 1.13 g L-Methionine; about 0.06 g disodium salt of EDTA; and a quantity sufficient to about 1.5 L of water. In some embodiments, a 10.5 L batch comprises between 300 and 350 g SEQ ID NO: 19, between 10.00 and 15.00 g of L-Histidine; between 3.50 and 4.50 g L-Histidine Hydrochloride, between 800.00 and 900.00 g of sucrose; between 1.5 and 2.5 g polysorbate 80; between 7.00 and 8.00 g L-Methionine; between 0.1 and 0.6 g disodium salt of EDTA; and a quantity sufficient to about 10.5 L of water. In some embodiments, a 10.5 L batch comprises about 315 g SEQ ID NO: 19, about 13.34 g of L-Histidine; about 3.99 g L-Histidine Hydrochloride, about 840.0 g of sucrose; about 2.1 g polysorbate 80; about 7.88 g L-Methionine; about 0.42 g disodium salt of EDTA; and a quantity sufficient to about 1.5 L of water.

A formulation of the disclosure can be maintained at a pH, for example, to help stabilize or maintain activity of a compound or polypeptide disclosed herein. The pH of the disclosed formulation can range, for example, from about 3 to about 12. The pH of the composition can be, for example, from about 3 to about 4, from about 4 to about 5, from about 5 to about 6, from about 6 to about 7, from about 7 to about 8, from about 8 to about 9, from about 9 to about 10, from about 10 to about 11, or from about 11 to about 12 pH units. The pH of the composition can be, for example, about 3, about 4, about 5, about 6, about 7, about 8, about 9, about 10, about 11, or about 12 pH units. The pH of the composition can be, for example, at least 3, at least 4, at least 5, at least 6, at least 7, at least 8, or at least 9 pH units. The pH of the composition can be, for example, at most 5, at most 6, at most 7, at most 8, at most 9, at most 10, at most 11, or at most 12 pH units.

A formulation disclosed herein can have a pH of from about 5.5 to about 8. For example, a formulation of the present disclosure can have a pH of about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some embodiments, the pH is 6.5±0.6, 6.5±0.5, 6.5±0.4, 6.5±0.3, 6.5±0.2, 6.5±0.1, about 6.5, or 6.5. In some embodiments, the pH is 6.2±0.6, 6.2±0.5, 6.2±0.4, 6.2±0.3, 6.2±0.2, 6.2±0.1, about 6.2, or 6.2. In some embodiments, the pH is 6.8±0.6, 6.8±0.5, 6.8±0.4, 6.8±0.3, 6.8±0.2, 6.8±0.1, about 6.8, or 6.8. In some embodiments, the pH is 7.4±0.6, 7.4±0.5, 7.4±0.4, 7.4±0.3, 7.4±0.2, 7.4±0.1, about 7.4, or 7.4. In some embodiments, the pH is about 6.2 to about 6.8. If the pH is outside the range desired by the formulator, the pH can be adjusted by using sufficient pharmaceutically-acceptable acids and bases.

In some embodiments, a formulation disclosed herein can comprise a buffering agent. In some embodiments, the buffering agent serves to maintain a stable pH and to help stabilize a compound or polypeptide disclosed herein. In some embodiments, a buffer system comprises at least one buffering agent that has a buffering range that overlaps fully or in part the range of pH 5.5-7.4. In some embodiments, the buffer has a pKa of about 6.5±0.5, or 6.2±0.5.

Dosing

Typically dosages of an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) which may be administered to an animal, preferably a human, range in amount from 0.001 mg to about 10 mg per kilogram (mpk) of body weight of the animal. In some embodiments, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual at a dose in a range of from 0.01-4 mpk (e.g., 0.01-3.5, 0.01-3.3, 0.01-3, 0.01-1.5, 0.01-2, 0.01-1.5, 0.01-1, 0.01-0.5, 0.01-0.35, 0.025-4, 0.025-3.5, 0.025-3.3, 0.025-3, 0.025-1.5, 0.025-2, 0.025-1.5, 0.025-1, 0.0250.5, 0.025-0.35, 0.05-4, 0.05-3.5, 0.05-3.3, 0.05-3, 0.05-1.5, 0.05-2, 0.05-1.5, 0.05-1, 0.05-0.5, 0.05-0.35, 0.1-4, 0.1-3.5, 0.1-3.3, 0.1-3, 0.1-1.5, 0.1-2, 0.1-1.5, 0.1-1, 0.1-0.5, 0.1-0.35, 0.25-4, 0.25-3.5, 0.25-3.3, 0.25-3, 0.25-1.5, 0.25-2, 0.25-1.5, 0.25-1, 0.25-0.5, 0.25-0.35, 0.5-4, 0.5-3.5, 0.5-3.3, 0.5-3, 0.5-1.5, 0.5-2, 0.5-1.5, or 0.5-1 mpk). In some embodiments, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual at a dose in a range of from 0.05-3.5 mpk (e.g., 0.05-3.3, 0.05-3, 0.05-1.5, 0.05-2, 0.05-1.5, 0.05-1, 0.05-0.5, 0.05-0.35, 0.1-3.5, 0.1-3.3, 0.1-3, 0.1-1.5, 0.1-2, 0.1-1.5, 0.1-1, 0.1-0.5, 0.1-0.35, 0.25-3.5, 0.25-3.3, 0.25-3, 0.25-1.5, 0.25-2, 0.25-1.5, 0.25-1, 0.25- 0.5, 0.25-0.35, 0.5-3.5, 0.5-3.3, 0.5-3, 0.5-1.5, 0.5-2, 0.5-1.5, or 0.5-1 mpk). In some cases the compound can be administered to an animal as frequently as several times daily, or it can be administered less frequently, such as once a day, once a week, once every two weeks, once a month, or even less frequently, such as once every several months or even once a year or less.

However, as noted above, in some cases it is delivered once per week or less.

Methods of Administration

Frequency of Administration

One of skill in the art will appreciate that the IL-18 proteins discussed herein can be administered acutely (e.g., over a short period) or chronically (e.g., over a long period of time, such as several months or a year or more). One of skill in the art will appreciate that they can be administered singly or in any combination with other agents. Further, the IL-18 proteins described herein can be administered singly or in any combination in a temporal sense, in that they may be administered concurrently, and/or before, and/or after each other. One of ordinary skill in the art will appreciate, based on the disclosure provided herein, that IL-18 protein compositions can be used to treat a disease or disorder in a subject in need thereof, and that such proteins can be used alone or in any combination with another agent to affect a therapeutic result.

As surprisingly demonstrated in the working examples below, administration of an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) can in some cases be detrimental (e.g., toxic—can cause anemia) if it is administered too frequently, e.g., more than once per week. For example, the working examples below demonstrated that administrations of DR-18 of twice per week in primates (monkeys) had a dose-dependent reduction in hemoglobin relative to saline-treated monkeys. In contrast, once weekly administration did not result in decreased hemoglobin levels relative to saline treatment.

Thus, in some embodiments, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual at a frequency of once per week (one dose per week) or less (e.g., once per two weeks or less, once per month or less). In some cases an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) is administered to an individual at a frequency in a range of from once per week to once per 6 months (e.g., once per week to once per 4 months, once per week to once per 2 months, or once per week to once per month). In some cases an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual at a frequency in a range of from once per week to once per month.

In some cases, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual about once per week. In some cases, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual about once every two weeks. In some cases, an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) (e.g., SEQ ID NO: 19) is administered to an individual about once per month. In some cases an IL-18 polypeptide (e.g., a wild type IL-18, a stabilized IL-18 variant, a DR IL-18 variant, a D2D IL-18 variant, a stabilized DR IL-18 variant, a stabilized D2D IL-18 variant, and the like) is not administered to an individual more frequently than once per week.

Diseases

In some embodiments, the method of the present disclosure is useful for treating or preventing a tumor or cancer tumors that have lost surface expression of MHC class I; such as a tumor that has lost B2m, the MHC locus, or has mutations in other members of the antigen presentation and/or antigen loading complex, such as tapasin.

Metabolic diseases and disorders include various metabolic and endocrine-related diseases and disorders. The following are non-limiting examples of metabolic and endocrine-related diseases and disorders that can be treated or prevented by the methods and compositions of the invention: obesity, diabetes, prediabetes, type II diabetes, mature onset diabetes of the young (MODY), hyperglycemia, metabolic syndrome, dyslipidemia, hypertriglyceridemia, and hypercholesterolemia.

Non-limiting examples of other diseases and disorders that can be treated or prevented using the compositions and methods of the invention include viral infections, bacterial infections, parasitic infections, and low immune activity. In some embodiments, the viral infection is at least one of a pox viruses, a smallpox virus, molluscum contagiosum, HPV infection, and warts caused by a virus. In some embodiments, the infection is a systemic infection. In some embodiments, the viral infection is a vaccinia virus infection. In some embodiments, the viral infection is a systemic vaccinia virus infection. In some embodiments, the bacterial infection is sepsis. In some embodiments, the low immune activity is neutropenia, for example, as may occur with chemotherapy.

Non-limiting examples of other diseases and disorders that can be treated or prevented using the compositions and methods of the invention include macular degeneration. For example, in some cases the disease or disorder is wet macular degeneration, and in some cases the disease or disorder is wet age-related macular degeneration. In some such cases, the IL-18 variant polypeptide (e.g., a stabilized IL-18) can be used as an anti-angiogenic. For example, a subject IL-18 variant polypeptide (e.g., a stabilized IL-18) can in some cases attenuate choroidal neovascularization.

In some embodiments, an IL-18 polypeptide (e.g., a stabilized IL-18 such as a stabilized DR IL-18 variant or stabilized D2D IL-18 variant, and the like) (e.g., SEQ ID NO: 19) are useful for the treatment or prevention of a disease or disorder. In various embodiments, the disease or disorder is cancer or a metabolic disease or disorder, including obesity and diabetes (e.g., a subject method can cause a decrease in body fat). Thus, in some embodiments, a composition comprises at least one IL-18 polypeptide (e.g., a stabilized IL-18 such as a stabilized DR IL-18 variant or stabilized D2D IL-18 variant, and the like) (e.g., SEQ ID NO: 19). In other embodiments, a method of administering at least one IL-18 polypeptide (e.g., a stabilized IL-18 such as a stabilized DR IL-18 variant or stabilized D2D IL-18 variant, and the like) (e.g., SEQ ID NO: 19), is performed to treat a disease or disorder, such as, but not limited to, cancer or a metabolic disease or disorder.

The following are non-limiting examples of cancers that can be treated or prevented by the methods and compositions of the disclosure: acute lymphoblastic leukemia, acute myeloid leukemia, adrenocortical carcinoma, appendix cancer, basal cell carcinoma, bile duct cancer, bladder cancer, bone cancer, brain and spinal cord tumors, brain stem glioma, brain tumor, breast cancer, bronchial tumors, burkitt lymphoma, carcinoid tumor, central nervous system atypical teratoid/rhabdoid tumor, central nervous system embryonal tumors, central nervous system lymphoma, cerebellar astrocytoma, cerebral astrocytoma/malignant glioma, cerebral astrocytoma/malignant glioma, cervical cancer, childhood visual pathway tumor, chordoma, chronic lymphocytic leukemia, chronic myelogenous leukemia, chronic myeloproliferative disorders, colon cancer, colorectal cancer, craniopharyngioma, cutaneous cancer, cutaneous t-cell lymphoma, endometrial cancer, ependymoblastoma, ependymoma, esophageal cancer, ewing family of tumors, extracranial cancer, extragonadal germ cell tumor, extrahepatic bile duct cancer, extrahepatic cancer, eye cancer, fungoides, gallbladder cancer, gastric (stomach) cancer, gastrointestinal cancer, gastrointestinal carcinoid tumor, gastrointestinal stromal tumor (gist), germ cell tumor, gestational cancer, gestational trophoblastic tumor, glioblastoma, glioma, hairy cell leukemia, head and neck cancer, hepatocellular (liver) cancer, histiocytosis, hodgkin lymphoma, hypopharyngeal cancer, hypothalamic and visual pathway glioma, hypothalamic tumor, intraocular (eye) cancer, intraocular melanoma, islet cell tumors, kaposi sarcoma, kidney (renal cell) cancer, langerhans cell cancer, langerhans cell histiocytosis, laryngeal cancer, leukemia, lip and oral cavity cancer, liver cancer, lung cancer, lymphoma, macroglobulinemia, malignant fibrous histiocytoma of bone and osteosarcoma, medulloblastoma, medulloepithelioma, melanoma, merkel cell carcinoma, mesothelioma, metastatic squamous neck cancer with occult primary, mouth cancer, multiple endocrine neoplasia syndrome, multiple myeloma, mycosis, myelodysplastic syndromes, myelodysplastic/myeloproliferative diseases, myelogenous leukemia, myeloid leukemia, myeloma, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma, osteosarcoma and malignant fibrous histiocytoma of bone, ovarian, ovarian cancer, ovarian epithelial cancer, ovarian germ cell tumor, ovarian low malignant potential tumor, pancreatic cancer, papillomatosis, paraganglioma, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm, plasma cell neoplasm/multiple myeloma, pleuropulmonary blastoma, primary central nervous system cancer, primary central nervous system lymphoma, prostate cancer, rectal cancer, renal cell (kidney) cancer, renal pelvis and ureter cancer, respiratory tract carcinoma involving the nut gene on chromosome 15, retinoblastoma, rhabdomyosarcoma, salivary gland cancer, sarcoma, sezary syndrome, skin cancer (melanoma), skin cancer (nonmelanoma), skin carcinoma, small cell lung cancer, small intestine cancer, soft tissue cancer, soft tissue sarcoma, squamous cell carcinoma, squamous neck cancer, stomach (gastric) cancer, supratentorial primitive neuroectodermal tumors, supratentorial primitive neuroectodermal tumors and pineoblastoma, T-cell lymphoma, testicular cancer, throat cancer, thymoma and thymic carcinoma, thyroid cancer, transitional cell cancer, transitional cell cancer of the renal pelvis and ureter, trophoblastic tumor, urethral cancer, uterine cancer, uterine sarcoma, vaginal cancer, visual pathway and hypothalamic glioma, vulvar cancer, waldenstrom macroglobulinemia, and Wilms Tumor.

In some non-limiting examples, the cancer is defined not by the histological tissue of origin, but by its molecular features. For example, tumors with high tumor mutational burden (TMB), tumors with microsatellite instability (MSI), tumors that lack or have diminished surface expression of MHC Class I (e.g., due to deletion of Beta-2 microglobulin or Tapasin), or tumors that express high levels of IL-18BP. In some cases, those molecular features are determined through next-generation sequencing (e.g., using TMB/MSI). In some cases, those molecular features are determined through immunohistochemistry, immunofluorescence, or flow cytometry. Thus, non-limiting examples of cancers that can be treated or prevented by the methods and compositions of the disclosure include solid tumor cancers, liquid cancers, blood cancers, teratomas, sarcomas, and carcinomas.

In some embodiments, the compositions and methods of the disclosure are useful for treating a tumor or cancer that is resistant to immune checkpoint inhibitors (ICIs). Examples of immune checkpoint inhibitors include, but are not limited to: anti-PD1 agents such as an anti-PD1 antibody (e.g., nivolumab), anti-PD-L1 agents such as an anti-PD-L1 antibody, anti-CTLA4 (e.g., ipilimumab), anti-TIM3, anti-TIGIT, anti-LAG3, anti-B7H3, anti-B7H4, anti-VISTA, anti-BTLA, anti-CD47, anti-SIRP alpha, anti-CD48, anti-CD155, anti-CD160, anti-TREM2, anti-IDO1, anti-Adenosine 2A receptor, anti-Aryl hydrocarbon receptor, anti-KIR, and anti-LILRB2. Examples of targets of immune checkpoint inhibitors include but are not limited to: PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, and LILRB2.

Thus, examples of immune checkpoint inhibitors include agents that inhibit proteins such as: PD-L1, PD1, CTLA4, TIM3, TIGIT, LAG3, B7H3, B7H4, VISTA, BTLA, CD47, SIRP alpha, CD48, CD155, CD160, TREM2, IDO1, Adenosine 2A receptor, Aryl hydrocarbon receptor, KIR, and LILRB2. In some cases, a subject stabilized IL-18 variant polypeptide (e.g., a DR-IL-18 variant, a D2D-IL-18 variant) (e.g., SEQ ID NO: 19) is co-administered with an immune checkpoint inhibitor (e.g., an agent that inhibits PD-L1, PD1, CTLA4, TIM3, TIGIT, LAGS, B7H3, B7H4, VISTA, BTLA, CD47, SIRP alpha, CD48, CD155, CD160, TREM2, IDO1, Adenosine 2A receptor, Aryl hydrocarbon receptor, KIR, LILRB2, or any combination thereof).

In some embodiments, the compositions and methods of the disclosure are useful for treating a cancer that is associated with high levels of IL-18BP (e.g., circulating or expressed by tumors) or a cancer associated with a tumor in which IL-18R is expressed on infiltrating T cells or NK cells.

Thus, the present invention relates to the prevention and treatment of a disease or disorder by administration of a therapeutically effective amount of an IL-18 variant polypeptide (e.g., a stabilized IL-18), a recombinant IL-18 variant polypeptide, an active IL-18 variant polypeptide fragment (e.g., IL-18 variant peptide, etc.), to a cell, tissue, organ, or subject in need thereof, for the treatment of a disease or disorder, or its associated signs, symptoms or pathologies. In one embodiment, the prevent invention provides a method of administering a therapeutically effective amount of an IL-18 variant polypeptide (e.g., a stabilized IL-18), a recombinant IL-18 variant polypeptide, an active IL-18 variant polypeptide fragment (e.g., IL-18 variant peptide, etc.), to a subject having, suspecting of having, or at risk for having, a disease or disorder described herein. In one embodiment, the prevent invention provides a method of administering a therapeutically effective amount of an IL-18 variant polypeptide (e.g., a stabilized IL-18), a recombinant IL-18 variant polypeptide, an active IL-18 variant polypeptide fragment (e.g., IL-18 variant peptide, etc.), to a cell, tissue or organ of a subject having, suspecting of having, or at risk for having, a disease or disorder described herein.

Kits

The present invention also pertains to kits useful in the methods of the invention. Such kits comprise various combinations of components useful in any of the methods described elsewhere herein, including for example, a IL-18 polypeptide (e.g., a stabilized IL-18 such as a stabilized DR IL-18 variant or stabilized D2D IL-18 variant, and the like) (e.g., SEQ ID NO: 19) and/or materials for quantitatively analyzing IL-18 variant polypeptide or IL-18 variant nucleic acid, and/or materials for assessing the activity of an IL-18 variant polypeptide or an IL-18 variant nucleic acid, and/or instructional material. For example, in some embodiments, the kit comprises components useful for the quantification of IL-18 variant nucleic acid in a biological sample. In another embodiment, the kit comprises components useful for the quantification of IL-18 variant polypeptide in a biological sample. In a further embodiment, the kit comprises components useful for the assessment of the activity (e.g., enzymatic activity, ligand binding activity, etc.) of an IL-18 variant polypeptide in a biological sample.

In a further embodiment, the kit comprises the components of an assay for monitoring the effectiveness of a treatment administered to a subject in need thereof, containing instructional material and the components for determining whether the level of IL-18 signaling in a biological sample obtained from the subject is modulated during or after administration of the treatment. In various embodiments, to determine whether the level of IL-18 signaling is modulated in a biological sample obtained from the subject, the level of IL-18 signaling is compared with the level of at least one comparator control contained in the kit, such as a positive control, a negative control, a historical control, a historical norm, or the level of another reference molecule in the biological sample. In certain embodiments, the ratio of IL-18 signaling and a reference molecule is determined to aid in the monitoring of the treatment.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: IL-18 Variant Polypeptides

IL-18 is a pro-inflammatory cytokine that can stimulate T, NK, and myeloid cells. It has been proposed as an immunotherapeutic agent for cancer given its ability to stimulate anti-tumor immune cells. As demonstrated herein, the therapeutic efficacy of recombinant IL-18 treatment can be greatly limited by upregulation of its natural endogenous soluble inhibitor IL-18BP. The present disclosure is based, in part, on the development of variants of both human and mouse IL-18 that exhibit minimal binding to IL-18BP. The cytokine variants exhibit altered relative preference for the receptors (IL-18Rα and IL-18BP) by hundreds of thousands to over a million-fold. These variants have potent anti-tumor activity in preclinical tumor models, both as monotherapies and in combination with immune checkpoint inhibitors such as anti-PD-1. As an additional application, IL-18 also has a well-established anti-obesity role and it is demonstrated herein that administration of the variants greatly reduces body fat composition compared to WT IL-18 treatment. The new variants thus have indications in endocrinology/metabolism/obesity in addition to tumor immunotherapies.

Also described herein are an additional set of IL-18 variants that act as IL-18BP antagonists by exclusively binding IL-18BP with absent or greatly reduced binding to IL-18Ra. It is envisaged that these proteins could be used to enhance the activity of endogenous IL-18 by neutralizing IL-18BP.

The materials and methods employed in these experiments are now described.

Protein Expression and Purification

Human IL-18, mouse IL-18 (amino acids 1-157) and variants thereof, were assembled as gBlocks (Integrated DNA Technologies, IDT) and cloned into a pET28a-smt vector for expression of N-terminal sumo-tagged and C-terminal hexahistidine-tagged proteins in *E. coli* BL21 (DE3) Rosetta strain. Protein expression was induced with 0.5 mM IPTG at 16° C. for 20 hours. The fusion proteins were first purified using Ni-chelating resins, followed by cleavage of the sumo tag with sumo protease. Proteins were then separated from aggregates by successive ammonium sulfate cuts, with aggregates precipitating at 20% ammonium sulfate and the target proteins at 70% ammonium sulfate. Protein pellets were resuspended and applied to Ni-chelating resins again to remove sumo tags, and were subjected to an endotoxin removal wash with 0.1% Triton X-114. Finally, eluted protein was buffer exchanged to PBS by PD-10 column (GE Healthcare). Protein sample was tested for monodispersity by size exclusion chromatography using an FPLC (Bio-Rad) and SEC650 column (Bio-Rad).

Human IL-18Rα ectodomain (amino acids 19-329), IL-18Rβ ectodomain (amino acids 15-356), and IL-18BP (amino acids 31-194), were secreted and purified via a baculovirus expression system. In brief, all construct sequences were cloned into the pAcBN-BH3 vector (BD Biosciences) with an N-terminal gp67 signal peptide and a C-terminal AviTag™ and hexahistidine tag. *Spodoptera frugiperda* (Sf9) insect cells cultured at 27° C. in SF900 II SFM medium (Invitrogen) were transfected with the plasmid constructs to establish high-titer recombinant virus, which was subsequently amplified. Trichopulsia ni (High-Five) insect cells (Invitrogen) grown in Insect Xpress medium (Lonza) at 27° C. were infected with the viruses to express recombinant protein. Three days after infection, proteins were extracted via Ni-NTA (QIAGEN) affinity chromatography, concentrated, and purified to >98% homogeneity with SEC650 sizing column (Bio-Rad) equilibrated in 10 mM HEPES (pH 7.5) and 150 mM NaCl.

Mouse IL-18Rα ectodomain (amino acids 19-329) and IL-18BP (amino acids 31-194) were produced as secreted proteins using the Expi293 expression system (Thermo Fisher). In brief, all construct sequences were cloned into the BacMam expression vector pEZT_D_Lux with an N-terminal H7 signal peptide and a C-terminal AviTag™ and hexahistidine tag. Expi293 cells cultured at 37° C. in Expi293 expression medium (Thermo Fisher) were transfected with plasmids using the ExpiFectamine 293 Transfection Kit (Thermo Fisher) according to the manufacturer's instructions. Cells were harvested 3-5 days after transfection. Protein purification procedures were the same as with the human proteins.

For protein biotinylation, a C-terminal biotin acceptor peptide (AviTag)-GLNDIFEAQKIEWHE was fused to all IL-18 receptor constructs. Protein biotinylation was carried out with soluble BirA ligase enzyme in 0.1 mM Bicine (pH 8.3), 10 mM ATP, 10 mM magnesium acetate, and 0.5 mM biotin (Sigma). Proteins were purified by size exclusion on a SEC650 column, as described above.

Yeast Display of IL-18

Human and mouse IL-18 gene block (IDT) were synthesized and cloned into the vector pYAL and displayed on the *Saccharomyces cerevisiae* strain EBY100. Individual colonies of IL-18 yeast were grown overnight at 30° C. in SDCAA liquid media and induced in SGCAA liquid media for 1 day at 20° C. IL-18 display levels on yeast were verified by flow cytometry using an anti-cMyc tag antibody (anti-myc-PE; Cell Signaling Technologies). Receptor staining with biotinylated IL-18Rα (with or without IL-18R β) or biotinylated IL-18BP was performed in PBS supplemented with 0.5% BSA and 2 mM EDTA (PBE) on ice. All analysis was performed on a Sony SA3800 flow cytometer.

Human IL-18 Library Construction and Selection

For the first human decoy-resistant IL-18 library, fourteen hIL-18Rα and hIL-18BP contact residues in hIL-18 (Table 1) were identified from homologous positions by aligning the structure of hIL-18/hIL-18Ra/hIL-18Rβ complex (Protein Data Bank (PDB ID) code 3OW4) to the structure of IL-18/IL-18BP (PDB ID 3F62). A library randomizing these residues was constructed using assembly PCR with the degenerate primers listed in Table 2. The library had a theoretical diversity of $\sim 1.96\times 10^{11}$ unique protein sequences. The PCR products were further amplified with primers having homology to the pYAL vector and co-electroporated together with linearized pYAL into EBY100 yeast. The resulting library contained $2.5\times 10^{8}$ transformants. For the second V2.0 human decoy-resistant IL-18 library, eleven hIL-18Rα and hIL-18BP contact residues in hIL-18 were selected to randomize, with a theoretical diversity of $3.44\times 10^{9}$ variants (described in FIG. 7A). A library randomizing these residues was constructed using assembly PCR with the degenerate primers and co-electroporated with pYAL into EBY100 yeast. The resulting library had a diversity of $6\times 10^{8}$ transformants.

Table 1 shows the First Human IL-18 library design

| Residue | Codon | Potential residues |
|---|---|---|
| 1Y | YNT | Y, F, S, C, L, P, H, R |
| L5 | NWT | L, F, I, Y, H, N, V, D |
| 8K | MRA | K, R, R, Q |

-continued

| Residue | Codon | Potential residues |
|---|---|---|
| 51M | RNS | M, I, T, N, K, S, R, V, A, D, E, G |
| 53S | ARA | K, R |
| 55S | RRW | S, R, G, G, N, K, D, E |
| 59G | RNA | G, E, A, V, I, T, K, R |
| 60M | VDG | M, K, R, L, Q, R, V, E, G |
| 103Q | VAW | Q, K, E, D, N, H |
| 105S | RRW | S, K, R, N, D, E, G, G |
| 110D | VAW | D, E, K, N, Q, H |
| 111N | NAT | N, D, H, Y |
| 153V | RHT | V, A, D, I, T, N |
| 155N | VAW | N, K, D, E, Q, H |

Table 2 shows the First human IL-18 library assembly primers

| Primer | Sequence (5' to 3') |
|---|---|
| hIL18Lib1 | CATTTTCATTAAGATGCAGTTACTTCGCTGTTTTTCA ATATTTTCTGTTATTGCTAGC (SEQ ID NO: 194) |
| hIL18Lib2 | AATTACGGATGACCGAAAGTYKGGATTCAWNCTTGCC GAAANRTGCTAAAACGCTAGCAATAACAGAAAATATT GAAAAA (SEQ ID NO: 195) |
| hIL18Lib3 | ACTTTCGGTCATCCGTAATTTGAACGACCAAGTCCTT TTTATTGACCAGGG (SEQ ID NO: 196) |
| hIL18Lib4 | ACTATCCGTCATATCCTCGAATAAGGGACGATTGCCC TGGTCAATAAAAAGGACT (SEQ ID NO: 197) |
| hIL18Lib5 | CTTATTCGAGGATATGACGGATAGTGATTGCCGTGAC AACGCCC (SEQ ID NO: 198) |
| hIL18Lib6 | ACTGAGATTGTTACCGCCHBTNYACGGGGTTGWYYAT CTYTATASNYAGAGATGATGAAAATTGTACGAGGGGC GTTGTCACGG (SEQ ID NO: 199) |
| hIL18Lib7 | GGCGGTAACAATCTCAGTTAAGTGCGAAAAAATCTCG ACACTTTCTTGTGAA (SEQ ID NO: 200) |
| hIL18Lib8 | GGTTCATTTCCTTGAACGAAATGATCTTGTTTTCACA AGAAAGTGTCGAGATT (SEQ ID NO: 201) |
| hIL18Lib9 | CATTTCGTTCAAGGAAATGAACCCGCCGGATAATATC AAGGATACAAAATCAGATATTATTT (SEQ ID NO: 202) |
| hIL18Lib10 | TGATGAGCTCTCGAATTGCATCTTATNWTBGTGTCCA GGCACWYYACGWTBGAAGAAAATAATATCTGATTTTG TATCCTTGATATTA (SEQ ID NO: 203) |
| hIL18Lib11 | ATAAGATGCAATTCGAGAGCTCATCATACGAAGGTTA CTTTTTAGCCTGCG (SEQ ID NO: 204) |
| hIL18Lib12 | AATTAACTTAAACAGGTCGCGCTCCTTCTCGCAGGCT AAAAAGTAACCTT (SEQ ID NO: 205) |
| hIL18Lib13 | GCGACCTGTTTAAGTTAATTCTTAAGAAAGAAGATGA GTTGGGGGATCG (SEQ ID NO: 206) |
| hIL18Lib14 | CCAGAACCACCGTCCTCWTBCTGADYGGTAAACATGA TGCTACGATCCCCCAACTCATCTT (SEQ ID NO: 207) |
| hIL18Lib15 | GAGGACGGTGGTTCTGGATCCGAACAAAAGCTTATCT CCGAAGAAGACTTGG (SEQ ID NO: 208) |
| hIL18Lib16 | CCACCAGATCCACCACCACCCAAGTCTTCTTCGGAGA TA AG (SEQ ID NO: 209) |

For both libraries, transformed yeast were recovered and expanded in liquid synthetic dextrose medium with casamino acids (SDCAA) medium at 30° C. and induced by dilution 1:10 into liquid synthetic galactose medium with casamino acids (SGCAA) medium and cultured at 20° C. for 24 hours. Appropriate numbers of induced yeast were used in each round to ensure at least 10-fold coverage of the expected diversity of the library at each step, and not less than $10^8$ cells. All selection steps were carried out at 4° C. using PBE buffer (PBS with 0.5% BSA and 2 mM EDTA). For the first generation library, each round's selection reagents are listed in Table 3. For round 1, yeast were counter-selected with anti-Cy5/AlexaFluor 647 microbeads (Miltenyi) and an LS MACS column (Miltenyi) to remove non-specific bead binders. Positive selection was performed by labeling yeast with 1 µM biotinylated hIL-18Rα for 1 hour at 4° C., followed by magnetic selection with SA/AlexaFluor 647 microbeads and an LS MACS column. For round 2, counter-selection was performed with 1 µM biotinylated IL-18BP, with positive selection identical to round 1. For rounds 3-5, selection was performed by incubating yeast with 100 nM (rounds 3-4) or 10 nM (round 5) biotinylated IL-18Rα and 250 nM pre-formed, biotin-capped hIL-18BP/SA-PE tetramers. After competition binding, yeast were washed and labeled with SA AlexaFluor 647 to detect IL-18Ra. Display levels were determined by staining with AlexaFluor 488-conjugated anti-cMyc (Cell Signaling Technologies), and the top 1% of display-normalized IL-18Rα binders (out of IL-18BP non-binders) were isolated using FACS with a Sony SA3800 cell sorter. After each round of selection, recovered yeast were expanded in SDCAA medium at 30° C. overnight and later induced at 20° C. by a 1:10 dilution into SGCAA medium for 24 hours.

The V2.0 human DR-IL-18 library was selected in a similar fashion, with specific selection steps elaborated in FIG. 7B.

Mouse IL-18 Library Construction and Selection

Construction and selection procedures are similar to human IL-18, with the following changes. Library construction was informed by an in-silico modeled mouse IL-18/receptor complex structure (predicted by Phyer2.0). Thirteen positions were chosen for randomization (Table 3) using primers described in Table 4. Co-electroporation with pYAL yielded a library of $4 \times 10^8$ transformants. Selection reagents used for each round are listed in Table 5.

Table 3 shows the Mouse IL-18 library design

| Residue | Codon | Potential residues |
|---|---|---|
| 1N | NWT | F, Y, L, H, I, N, V, D |
| 50M | RNS | M, I, T, N, K, S, R, V, A, D, E, G |
| 51Y | NRN | Y, K, R, D, E |
| 52K | VNS | L, P, H, Q, R, I, M, T, N, K, S, V, A, D, E, |
| 54S | RRW | S, R, G, G, N, K, D, E |
| 55E | VRN | E, K, N, R, S, R, H |
| 56V | VNV | V, S, P, T, A, K, R |
| 57R | RVW | R, D, E, S, T |
| 58G | RNA | G, E, A, V, I, T, K, R |

-continued

| Residue | Codon | Potential residues |
|---------|-------|---------------------|
| 59L | VDR | L, K, R, Q, R, V, E, G |
| 104R | NDH | R, D, E, N, Y, F, I, L, V |
| 109N | NAT | N, D, H, Y |
| 151L | VHY | L, V, A, D, I, T, N |

Table 4 shows the Mouse IL-18 library assembly primers

| Primer | Sequence (5' to 3') |
|--------|---------------------|
| mIL18lib1 | CATTTTCATTAAGATGCAGTTACTTCGCTGTTTTTCAATATTTT CTGT TATTGCTAGCGTTT (SEQ ID NO: 210) |
| mIL18lib2 | TTGTACAGTGAAGTCGGCCAAAAWNTGCTAAAACGCTAGCA ATAAC AGAAAATAT (SEQ ID NO: 211) |
| mIL18lib3 | GCCGACTTCACTGTACAACCGCAGTAATACGGAATATAAATG ACCA AGTTCTCTTCGTT (SEQ ID NO: 212) |
| mIL18lib4 | TTGATCAATATCAGTCATATCCTCGAACACAGGCTGTCTTTTG TCAA CGAAGAGAACTTGGTCATTT (SEQ ID NO: 213) |
| mIL18lib5 | GTGTTCGAGGATATGACTGATATTGATCAAAGTGCCAGTGAA CCCCA GACCAGA (SEQ ID NO: 214) |
| mIL18lib6 | TCACAGAGAGGGTCACAGCYHBTNYWBYBNBNBNYBWYYGTCS NBNY NSNYGTATATTATCAGTCTGGTCTGGGGTTCAC (SEQ ID NO. 215) |
| mIL18lib7 | GCTGTGACCCTCTCTGTGAAGGATAGTAAAATGTCTACCCTCT CCTG TAAGAACAAGA (SEQ ID NO: 216) |
| mIL18lib8 | GTATATCATCAATATTTTCAGGTGGATCCATTTCCTCAAAGGA AATG ATCTTGTTCTTACAGGAGAGGG (SEQ ID NO: 217) |
| mIL18lib9 | AATGGATCCACCTGAAAATATTGATGATATACAAAGTGATCT CATAT TCTTTCAGAAANDHGTTCCAGGACACNATAAGATGGAGTTTG |
| mIL18lib9 | AATGGATCCACCTGAAAATATTGATGATATACAAAGTGATCT CATATTCTTTCAGAAANDHGTTCCAGGACACNATAAGATGGA GTTTGAATCT TCACT (SEQ ID NO: 218) |
| mIL18lib10 | CCTTTTGGCAAGCAAGAAAGTGTCCTTCATACAGTGAAGATT CAAAC TCCATCTTAT (SEQ ID NO: 219) |
| mIL18lib11 | CTTTCTTGCTTGCCAAAAGGAAGATGATGCTTTCAAACTCATT CTGA AAAAAAGGATGA (SEQ ID NO: 220) |
| mIL18lib12 | CCACCACTTTGATGTAAGTTAGTRDBAGTGAACATTACAGATT TATC CCCATTTTCATCCTTTTTTTTCAGAATGAG (SEQ ID NO: 221) |
| mIL18lib13 | ACTAACTTACATCAAAGTGGTGGTTCTGGATCCGAACAAAAG CTTAT CTCCGAAGAAGA (SEQ ID NO: 222) |

Table 5 shows the summary of library selection reagents

| | Human IL-18 library selection | | Mouse IL-18 library selection | |
|---|---|---|---|---|
| | Counter-selection | Positive Selection | Counter-selection | Positive Selection |
| Round1 | SA-beads alone | 1 μM hIL-18Rα-SA-beads | — | 1000 nM IL-18Rα-SA-beads |
| Round2 | 1 μM IL-18BP | 1 μM IL-18Rα-SA-beads | — | 1 μM IL-18Rα |
| Round3 | 1 μM IL-18BP | 100 nM hIL-18Rα | 1 μM IL-18BP | 1 μM IL-18Rα |
| Round4 | 1 μM IL-18BP | 10 nM hIL-18Rα | 1 μM IL-18BP | 100 nM IL-18Rα |
| Round5 | 250 nM IL-18BP tetramer | 10 nM hIL-18Rα | 1 μM IL-18BP | 10 nM IL-18Rα |
| Round6 | — | — | 250 nM IL-18BP tetramer | 200 nM IL-18Rα |

Surface Plasmon Resonance

Experiments were conducted using a Biacore T100 and carried out at 25° C. Biotinylated IL-18Rα or IL-18BP were immobilized onto a Biacore biotin capture chip (Series S CAP sensor chip, GE Healthcare) to yield an Rmax of ~50 RU (IL-18Rα) or ~10 RU (IL-18BP). Measurements were made with serial dilutions of the IL-18 variants in HEPES buffered Saline-P+ buffer (10 mM HEPES pH 7.4, 150 mM NaCl, 0.005% surfactant P20). The surface was regenerated by three 60-sec injections of regeneration buffer (3/4 (v/v) 8M guanidine hydrochloride with 1/4 (v/v) 1M sodium hydroxide). Experiments were performed in multiple channels simultaneously for increased observations. All data were analyzed with the Biacore T100 evaluation software version 2.0 with a 1:1 Langmuir binding model.

Cell Lines

HEK-Blue IL-18 sensor cells (InvivoGen) were maintained in complete media (DMEM containing 10% heat-inactivated FBS, 2 mM L-glutamine, 50 U/mL penicillin, and 50 μg/mL streptomycin) supplemented with 100 μg/mL Normocin, 30 μg/mL Blasticidin, 180 μg/mL Zeocin, and 200 μg/mL Hygromycin. YUMMER1.7 melanoma cells were cultured and prepared as previously described (Wang et al., 2017, Pigment Cell Melanoma Res., 30(4):428-435).

HEK-Blue Cytokine Activity Assay

For cytokine activity measurements, 50,000 HEK-Blue IL-18 sensor cells per well of a flat-bottom 96-well plate were incubated with recombinant human IL-18 at successively decreasing concentrations in a total volume of 200 μL of complete media. After 20-24 hours of incubation at 37° C. and 5% $CO_2$, 30 μL of cell culture supernatant was mixed with 170 μL QUANTI-Blue detection media (InvivoGen) and incubated at 37° C. and 5% CO2 until a color change from pink to blue was detectable (0.5-4 hours). Levels of alkaline phosphatase were quantified using a spectrophotometer at 655 nm wavelength. Cytokine activity was determined by calculating the relative absorbance value (percentage of the maximal absorbance value measured at 655 nm) for each cytokine in the assay.

For IL-18BP blockade experiments, a fixed concentration of recombinant human IL-18 was pre-incubated with recombinant human IL-18BP at successively decreasing concentrations for 1 hour at 4° C. Subsequently, the protein mixture was added to the HEK-Blue IL-18 sensor cells and the assay was performed as described.

Mice

C57BL/6 wild type mice (6-9 weeks old) from Jackson Laboratory were used for in vivo mouse experiments. Experimental groups were matched by weight, sex, and age. All animal experiments were conducted in compliance with approval from the Yale Institutional Animal Care and Use Committee.

In Vivo Pharmacodynamic and Pharmacokinetic Studies

Mice (n=9 per group) received daily intraperitoneal (i.p.) injections of 1 mg/kg recombinant IL-18 (WT or variant SEQ ID NO: 61), or PBS as vehicle control. On day 1, day 4, and day 7 of the experiment, 3 mice per group were sacrificed 5 hours post-injection for blood collection via cardiac puncture, and subsequent analysis of blood plasma or white blood cells (see mouse IL-18BP ELISA, Luminex-based multiplex immunoassay for mouse cytokine analysis, as well as immunophenotyping via flow cytometry) was performed. Throughout the 7 days of the experiment, body temperatures were monitored daily using the Rodent thermometer BIO-TK8851 (Bioseb) and the RET 3 rectal probe for mice (Braintree Scientific Inc.). Body weights were monitored daily.

Plasma Preparation from Whole Blood

Plasma preparation from whole blood was performed using EDTA-coated Microtainer Plasma Separator Tubes (BD) according to manufacturer's instruction. Plasma samples were frozen once at −20° C. before being used for analytical assays.

IFN-γ and IL-18BP ELISA

To measure levels of human IFN-γ in cell culture supernatant, the Human IFN-γ ELISA MAX Deluxe Set (BioLegend) with a sensitivity of 4 pg/mL and a detection range of 7.8-500 pg/mL was used according to the manufacturer's instructions. For quantification of human IL-18BP in cell culture supernatant, the Quantikine Human IL-18BP Immunoassay (R&D Systems) with a sensitivity of 7.52 pg/mL and a detection range of 26.6-1,700 pg/mL was used. Mouse IL-18BP levels in blood plasma were quantified using the Mouse IL-18BP ELISA Kit (R&D systems) with a sensitivity of 0.156 ng/mL and a detection range of 0.156-10 ng/mL. All assays including sample preparation were performed according to manufacturer's instructions.

Luminex-Based Multiplex Immunoassay for Mouse Cytokine Analysis

To quantify a variety of mouse cytokine levels in blood plasma including IFN-γ and IL-12, the luminex-based Bio-Plex Pro multiplex immunoassay (Bio-Rad) was performed using the Bio-Plex 200 System (Bio-Rad). Cytokines of interest were analyzed using the Bio-Plex Pro Mouse Cytokine Standard 23-Plex (Group I) reconstituted in DMEM, following the manufacturer's instructions.

Immunophenotyping Via Flow Cytometry

For white blood cell analysis, 100 μL of whole blood were collected into an EDTA-coated Microtainer Plasma Separator Tube (BD) additionally containing 50 μL Heparin-solution, and mixed by inverting several times. Red blood cell lysis was performed by adding ACK Lysing Buffer (VWR) and incubating for 3-5 minutes at room temperature. After adding MACS buffer (2 mM EDTA, 2% FBS, in PBS), white blood cells were collected by centrifugation (5 minutes, 400×g, 4° C.) and aspiration of the supernatant. White blood cells were washed once with cold MACS buffer, and collected again as described. The cell pellet was resuspended in 200 μL MACS buffer containing 10% (v/v) rat serum (STEMCELL Technologies Inc.) and specific fluorescently-labeled antibodies to stain for subsequent flow cytometric analysis. Staining was performed for 30 minutes at 4° C. using the following antibodies: αCD4-AF700 (BioLegend), αCD8-APC (BioLegend), B220-APC-Cy7 (BioLegend), CD11b-PB (BioLegend), NK1.1-PE (BioLegend), NKp46-PE (BioLegend), and CD69-FITC (BioLegend). Thereafter, white blood cells were washed twice with MACS buffer as described before. Finally, the cells were resuspended in 100 μL MACS buffer and samples were acquired using the flow cytometer (Sony SA3800). An aliquot of 10 μL was taken to perform cell counting using the Invitrogen Countess II Automated Cell Counter (Thermo Fisher Scientific). FlowJo v10.3 software was used for data analysis, and cells were gated for leukocytes and single events using the forward and side scatter.

Tumor Treatment Experiments $0.5 \times 10^6$ YUMMER1.7 cells were implanted subcutaneously into C57BL/6J mice. 7 days after implantation, when tumors were approximately 50 mg, treatment was initiated. Mice were divided into treatment cohorts which included: 1) vehicle (saline), 2) anti-PD1 (rat clone RMP1-14, Bio X Cell, West Lebanon, New Hampshire, US), 3) wildtype IL-18, 4) SEQ ID NO: 61, 5) wild type IL-18+anti-PD-1, and 6) SEQ ID NO: 61 IL-18+anti-PD1. Anti PD-1, wild type IL-18, and SEQ ID NO: 61 IL-18 were administered via intraperitoneal injection twice weekly at 8 mg/kg, 0.32 mg/kg, and 0.32 mg/kg, respectively. Mice were monitored for signs of clinical toxicity, and tumor growth was tracked twice weekly using caliper measurements. Mice were euthanized when the tumor diameter reached or exceeded 1.5 cm in greatest dimension; this was considered the endpoint for survival analyses.

B2m-deficient YUMMER1.7 studies were conducted in a similar fashion, with the minor changes. $1.0 \times 10^6$ cells were engrafted, as tumors grew slower than the parental strain. Treatments consisted of saline, anti-PD1 plus anti-CTLA4, and SEQ ID NO: 61 given at the same schedule and dose as the studies above.

The results of the experiments are now described.

The IL-18 Axis as a Target for Cancer Immunotherapy

To identify potential signaling nodes for immunotherapeutic intervention, single cell RNAseq data from tumor infiltrating lymphocytes was analyzed for the expression of cytokine pathway components (Singer et al., 2016, Cell, 166:1500-1511, e1509). The receptor subunits for IL-18-IL-18Rα (i.e., IL-18R1) and IL-18Rβ (i.e., IL-18RAP)—as well as IL-18 itself were upregulated in both activated and dysfunctional lymphocyte programs (FIG. 1A).

Figure 1B:
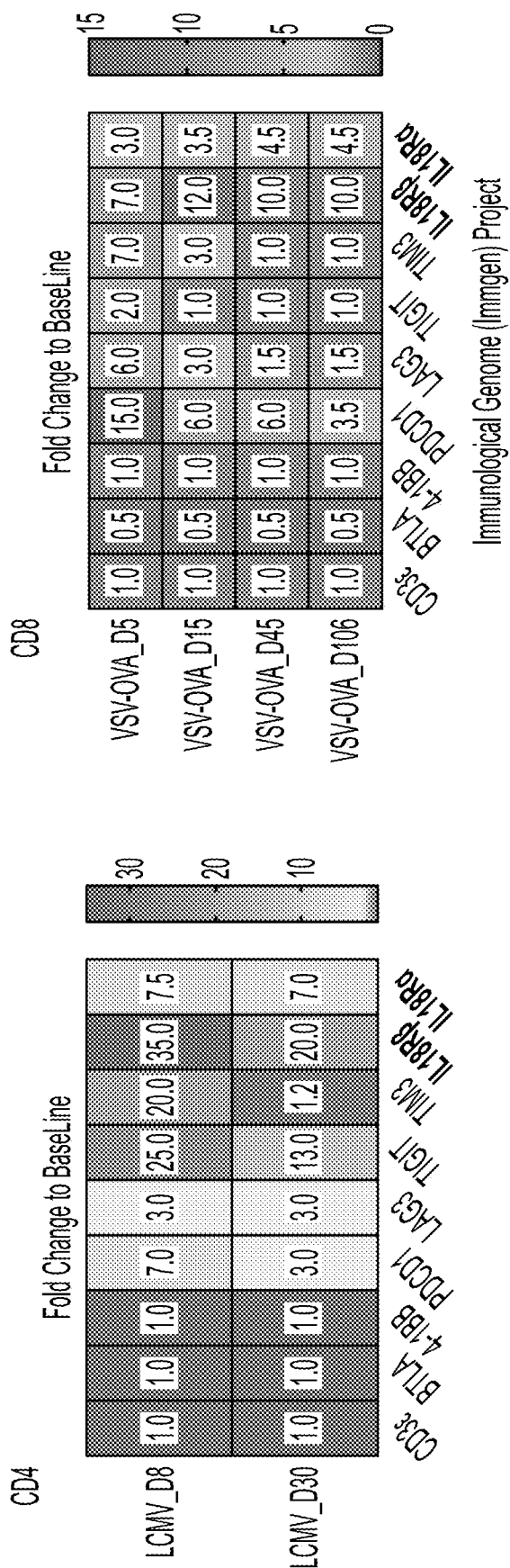
Figure 2A:
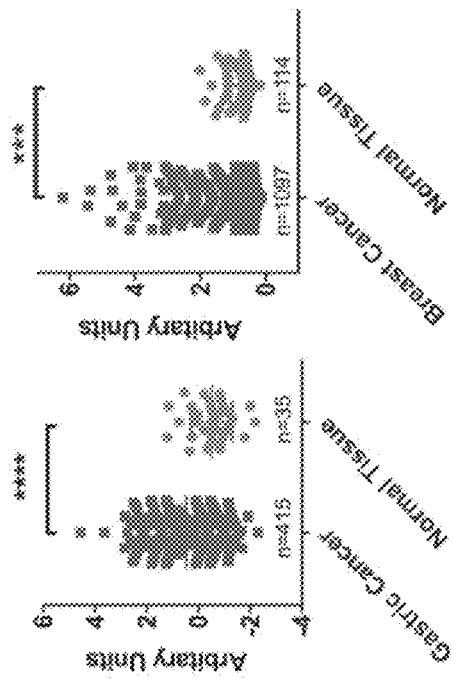
FIG. 2A through FIG. 2C depict results from example experiments, demonstrating IL-18BP has features of a "soluble immune checkpoint".
Figure 2B:
Figure 2C:
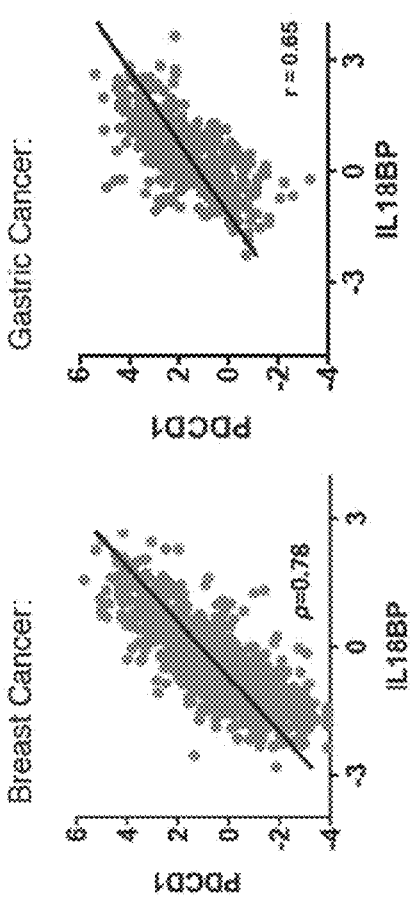

Further analysis of the Immunological Genome (ImmGen) database revealed that expression of both IL-18 receptor subunits correlated with expression of T cell "exhaustion" markers in CD4 and CD8 cells including PD-1, Tim3, Lag3, and TIGIT following chronic antigen exposure as shown in FIG. 1B. These expression features suggested that the IL-18 pathway could be used to selectively stimulate activated and dysfunctional/exhausted T cells within tumors as an immunotherapeutic paradigm. IL-18 is a Th1 cytokine initially termed "interferon-gamma-inducing-factor" (IGIF) for its ability to robustly stimulate release of interferon gamma (IFN-γ) by T and NK cells. Feedback inhibition of IL-18 is achieved by IFN-γ-driven induction of IL-18BP, a high-affinity secreted decoy receptor for IL-18 that sterically hinders IL-18's ability to bind and activate its receptor (FIG. 2A). Without wishing to be bound by any particular theory, this mechanism is reminiscent of the induction of PD-L1 by IFN-γ, suggesting that IL-18BP may act as a "soluble immune checkpoint." Consistent with this hypothesis, it was found that IL-18BP is unregulated in several types of cancer, most notably breast, gastric, and brain cancer in the TCGA and Oncomine databases (FIG. 2B). Furthermore, IL-18BP expression strongly correlates with expression of the crucial immune checkpoint PD-1 in tumors (r=0.65 and 0.78 in gastric and breast cancer respectively, FIG. 2C), suggesting that IL-18BP may also contribute to tumor immune evasion and lymphocyte exhaustion.

Recombinant IL-18 has been administered to cancer patients in multiple clinical trials. It was found to be well-tolerated even at high doses of 2 mg/kg, with robust pharmacodynamics outputs including expansion of activated $CD69^+$ natural killer (NK) cells and dramatic increases in serum IFN-γ levels. However, a phase II trial of melanoma patients was discontinued due to lack of efficacy. Examination of the reported pharmacodynamics results from these clinical trials reveals that the effectiveness of rIL-18 wanes with repeated dosing, with tachyphylaxis seen with respect to peripheral NK cell activation/expansion and cytokine release (including IFN-γ and GM-CSF). The waning effectiveness of rIL-18 coincides with a profound increase in the serum levels of IL-18BP, more than two orders of magnitude over pre-treatment levels and often exceeding 100 ng/mL. Without wishing to be bound by any particular theory, it was hypothesized that IL-18BP limits the effectiveness of rIL-18 therapy and that IL-18 variants that are impervious to IL-18BP inhibition could be effective tumor immunotherapies. Additionally, inhibitors of IL-18BP will likely be effective for tumor immunotherapy.

Engineering IL-18 Variants that are Resistant to IL-18BP Inhibition (Human DR-IL-18 Variants)

Figure 3A:
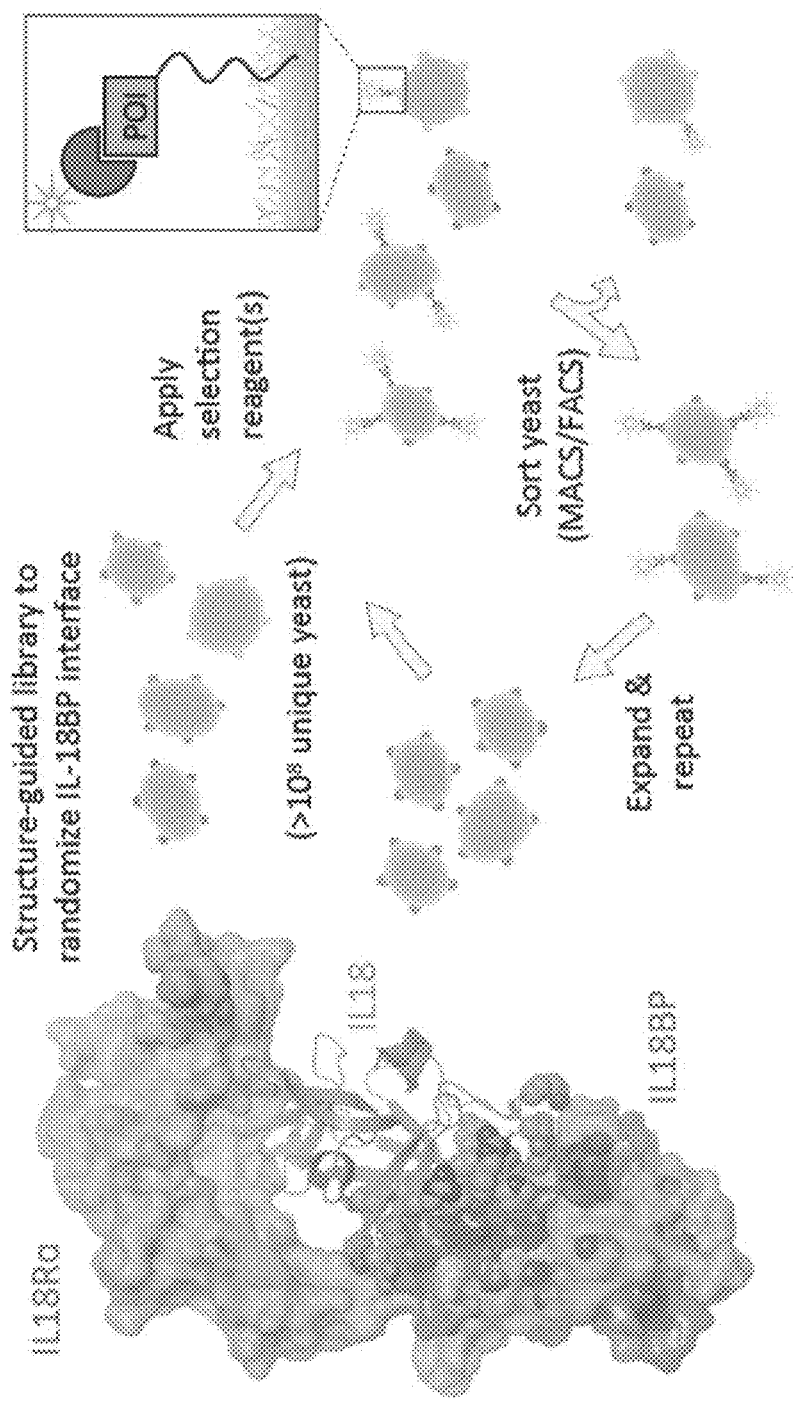
FIG. 3A through FIG. 3C depict results from example experiments, demonstrating engineering human IL-18 variants for independence to IL-18BP using yeast display.
Figure 3C:
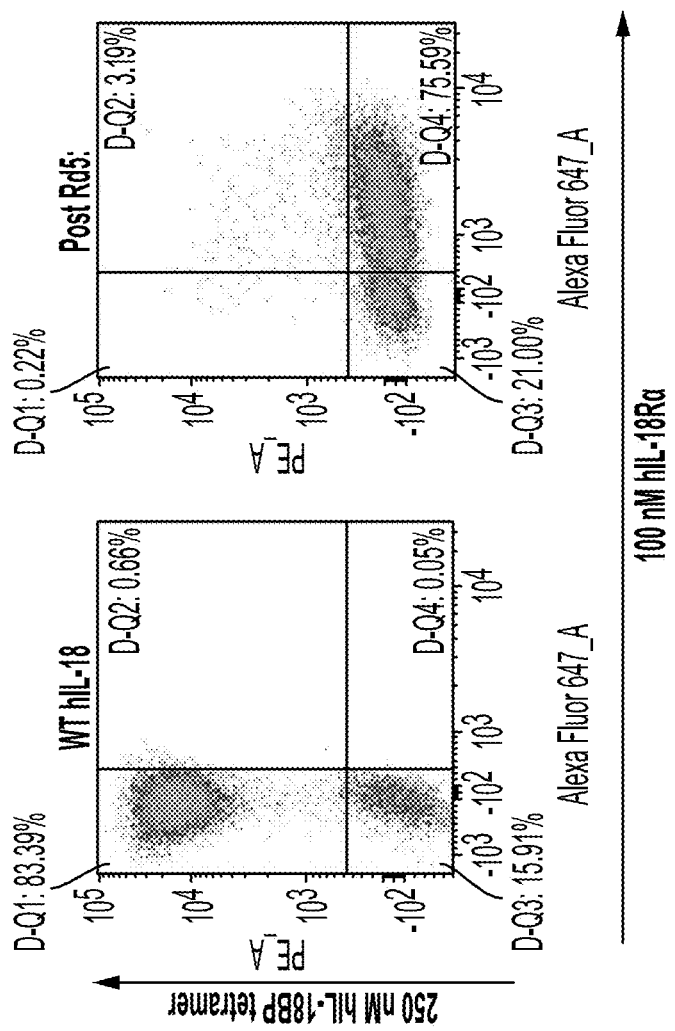
Figure 3B:
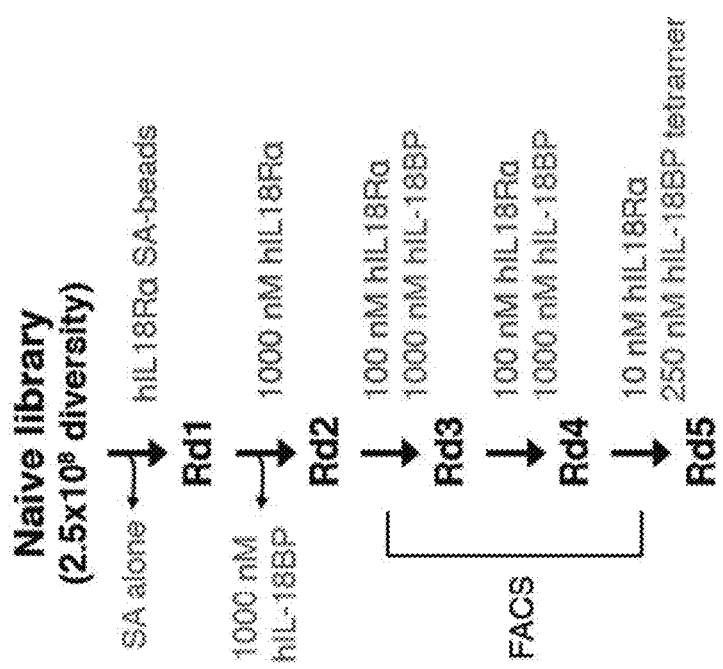

To obtain variants of IL-18 that can signal through IL-18Rα/IL-18Rf3, but are impervious to inhibition by IL-18BP, directed evolution with yeast surface display was utilized. The structure of the ternary signaling complex of human IL-18:IL-18Rα:IL-18Rf3 (PDB=30W4) was first analyzed, and residues of IL-18 that have a shared interface with the signaling complex and IL-18BP were identified (FIG. 3A). As the structure of hIL-18:hIL-18BP has not been determined, a related complex between IL-18 and a viral (ectromelia virus) orthologue of IL-18BP was utilized (PDB=3F62). A combinatorial library randomizing this set of residues to a defined set of alternatives (see Table 1) was created using degenerate oligonucleotide primers and assembly PCR. This library was electroporated into yeast together with the N-terminal yeast display vector pYAL to obtain a library with $2.5 \times 10^8$ transformants. Using this library, directed evolution was performed by conducting successive rounds of selection using magnetic and fluorescent cell sorting (FACS) with recombinant hIL-18Rα and counterselection with hIL-18BP, as summarized in FIG. 3B. After five rounds of selection, the clear majority of the library clones had completely swapped their relative preference for hIL-18BP and hIL-18Rα as compared to WT hIL-18 (FIG. 3C). These clones were designated as "DR-hIL-18" variants, where "DR" stands for "decoy-resistant."

Figure 4:
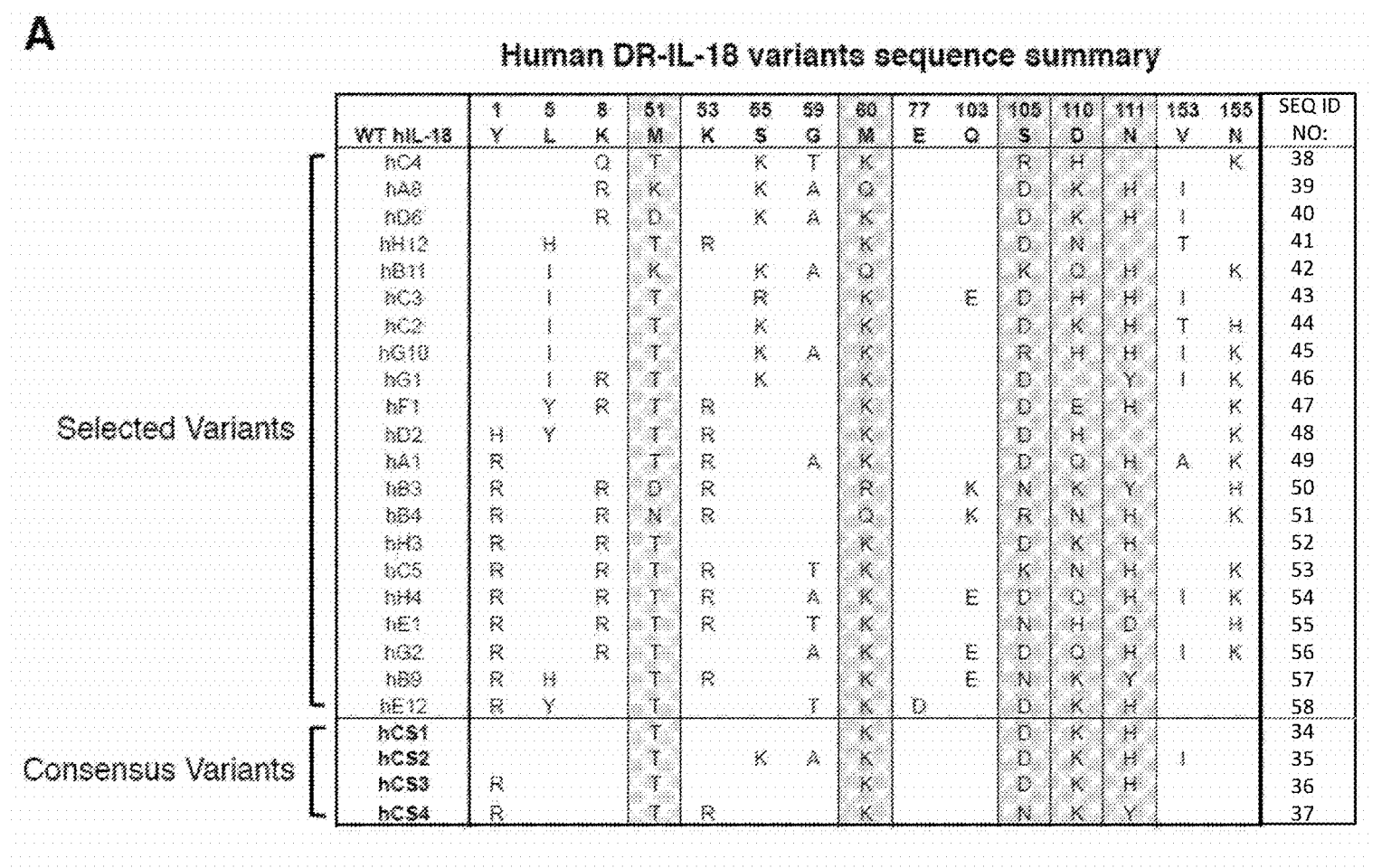
Figure 5A:
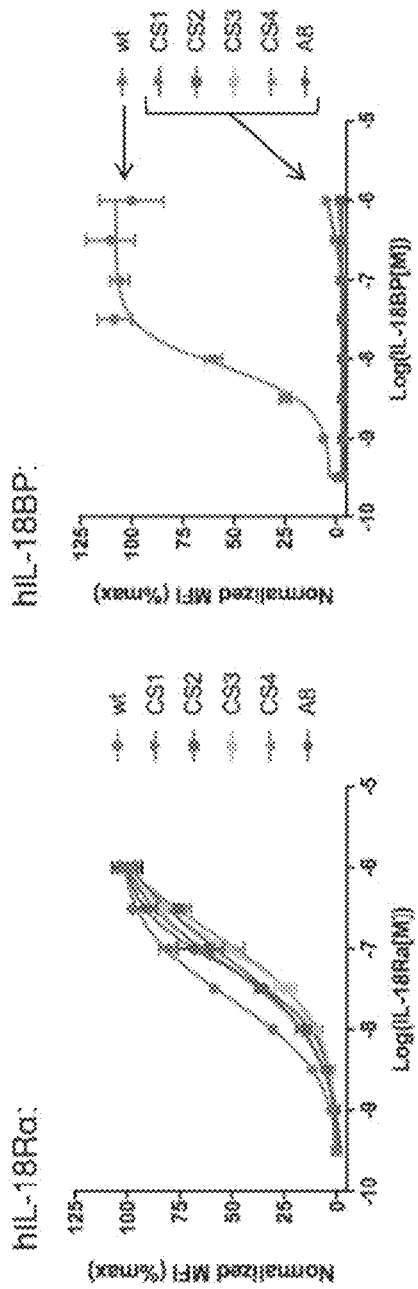
FIG. 5A and FIG. 5B depict results from example experiments, demonstrating biophysical characterization of human DR-IL-18 variants.
Figure 5B:
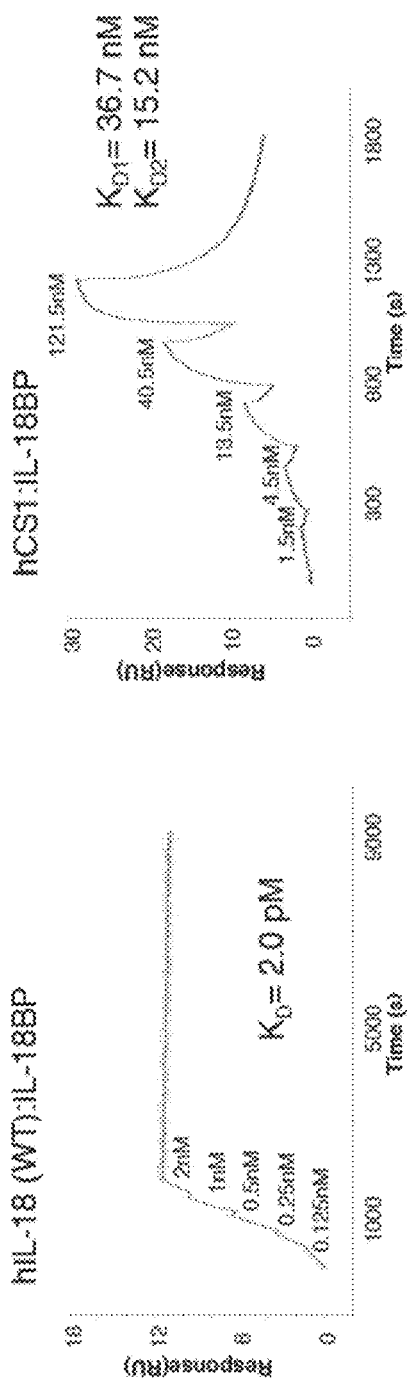

Sequencing of 96 clones from the post-round five pool revealed 21 unique sequences, which were analyzed to create four "consensus sequences", SEQ ID NO: 34-37 (FIG. 4). To estimate the binding affinities of these variants for hIL-18Rα and hIL-18BP, binding isotherms were established for hIL-18Rα and IL-18BP binding using yeast-displayed cytokine variants and flow cytometry. As seen in FIG. 5A, the DR-hIL-18 variants bound hIL-18Rα with comparable affinity to WT IL-18, but showed severely attenuated binding to hIL-18BP, with apparent binding EC50 values significantly greater than 1 μM. To additionally characterize the receptor binding activities of the DR-IL-18 variants, the cytokines were expressed recombinantly and surface plasmon resonance for IL-18Rα and IL-18BP was performed (see FIG. 5B for representative traces). These results are summarized in Tables 6 and 7 and demonstrate that the DR-hIL-18 variants have a dramatically decreased preference for IL-18BP compared to IL-18Rα, by several orders of magnitude.

Table 6 depicket IL-18Rα and IL-18BP binding affinites of human IL-18 variants by on-yeast binding isotherms.

| IL-18 Variant | KD IL-18Rα (M) | KD IL-18BP (M) | KDratio: IL-18BP/IL-18Rα | Dissociation Constant Ratio normalized to WT IL-18 |
|---|---|---|---|---|
| hIL-18 WT | 2.40E– | 7.08E–09 | 2.95E–01 | 1 |
| SEQ ID NO: 39 | 5.77E– | NBD | >3.47E+02 | >1.17E+03 |
| SEQ ID NO: 52 | 8.38E– | NBD | >2.39E+02 | >8.09E+02 |
| SEQ ID NO: 57 | 1.27E– | NBD | >1.57E+02 | >5.34E+02 |
| SEQ ID NO: 34 | 6.44E– | 1.93E–05 | 3.00E+02 | 1.02E+03 |
| SEQ ID NO: 35 | 9.15E– | NBD | >2.19E+02 | >7.41E+02 |
| SEQ ID NO: 36 | 1.13E– | 1.16E–05 | 1.03E+02 | 3.48E+02 |
| SEQ ID NO: 37 | 1.60E– | NBD | >1.25E+02 | >4.24E+02 |
| SEQ ID NO: 87 | 4.1E– | NBD | 4.9E+02 | >7.2E+03 |
| SEQ ID NO: 88 | N.D. | 3.4E–07 | — | — |
| SEQ ID NO: 89 | 1.7E– | NBD | 1.2E+03 | >1.7E+04 |
| SEQ ID NO: 90 | 4.2E– | NBD | 4.8E+02 | >7.0E+03 |
| SEQ ID NO: 91 | 3.7E– | NBD | 5.4E+02 | >8.0E+03 |

NBD, no binding detected (20 uM used for ratio calculations), — value not determined

| IL-18 Variant | KD IL-18Rα (M) | KD IL-18BP (M) | KDratio: IL-18BP/ IL-18Rα | Dissociation Constant Ratio normalized to WT IL-18 |
|---|---|---|---|---|
| hIL-18 WT | 2.93E−09 | 1.90E−12 | 6.48E−04 | 1 |
| SEQ ID NO: 39 | — | — | — | — |
| SEQ ID NO: 52 | — | — | — | — |
| SEQ ID NO: 57 | — | — | — | — |
| SEQ ID NO: 34 | 8.05E−09 | 1.94E−08 | 2.41E+00 | 3.72E+03 |
| SEQ ID NO: 35 | 1.31E−08 | | | |
| SEQ ID NO: 36 | 8.18E−09 | 1.86E−08 | 2.27E+00 | 3.50E+03 |
| SEQ ID NO: 37 | 4.38E−09 | 1.83E−07 | 4.18E+01 | 6.45E+04 |

— indicates value not determined

Table 7 depicts IL-18Rα and IL-18BP binding affinities of human IL-18 variants by SPR Functional Characterization of Human DR-IL-18 Variants A previous report from Kim et al (Kim et al., 2001, Proc Natl Acad Sci USA 98(6):3304-9) described 3 hIL-18 variants with enhanced activity and purportedly decreased inhibition by IL-18BP: E42A, K89A, and E42A/K89A. These cytokine variants were displayed on yeast and IL-18BP inhibition of IL-18Rα binding was assessed by flow cytometry. As seen in FIG. 6A, while the DR-hIL-18 variants were impervious to inhibition of hIL-18Rα binding by hIL-18BP, the Kim et al variants showed roughly equivalent hIL-18BP neutralization as compared to WT hIL-18. These results indicate that the DR-hIL-18 variants are IL-18BP independent, whereas the Kim et al variants are highly sensitive to IL-18BP inhibition, similar to WT hIL-18.

To confirm that the DR-hIL-18 could yield productive signaling through the IL-18 receptor in a cellular context, concentration-response experiments were performed using the HEK-blue IL-18 reporter cell line. In this system, IL-18R signaling is read-out by expression of secreted alkaline phosphatase (SEAP) downstream of a Nfκb/AP1 promotor. In the absence of IL-18BP, DR-hIL-18 variants yielded signaling EC50 values commensurate with WT hIL-18. However, the DR-hIL-18 variants demonstrated virtually no inhibition by hIL-18BP, with no detectable inhibition at 1 μM IL-18BP (FIG. 6B). Taken together, these studies establish that the DR-hIL-18 variants are biologically active and impervious to IL-18BP neutralization in a cell signaling context.

Engineering and Characterization of Second-Generation Human IL-18 Variants that are Resistant to IL-18BP Inhibition (Human v2.0 DR-IL-18 Variants)

To obtain additional, potentially enhanced human DR-IL-18 variants, a second library of human IL-18 randomized at 11 positions (FIG. 7A) was designed and yeast was transformed as described above. The resulting library of 6×10$^8$ transformants was selected as outlined in FIG. 7B, yielding a robust preference for IL-18Rα compared to IL-18BP with successive selection steps (FIG. 7C). 17 unique sequences were recovered after 5-6 rounds of selection (FIG. 8). As shown in FIG. 9A, when compared to WT IL-18, clones SEQ ID NO: 89, SEQ ID NO: 90, SEQ ID NO: 91, and SEQ ID NO: 87 had equal or somewhat stronger binding to IL18Rα as measured by yeast-binding isotherms with biotinylated IL18Ra. However as shown in FIG. 9B, these clones did not show any appreciable binding to IL-18BP. FIG. 9C depicts the measurement of thermal stability by applying a range of temperatures to the yeast-displayed clones showed that they were more thermal stable than WT IL-18 by 7-13° C. These results are summarized in FIG. 9D.

Engineering IL-18 Variants that are Resistant to IL-18BP Inhibition (Murine DR-IL-18 Variants)

Figure 10B:
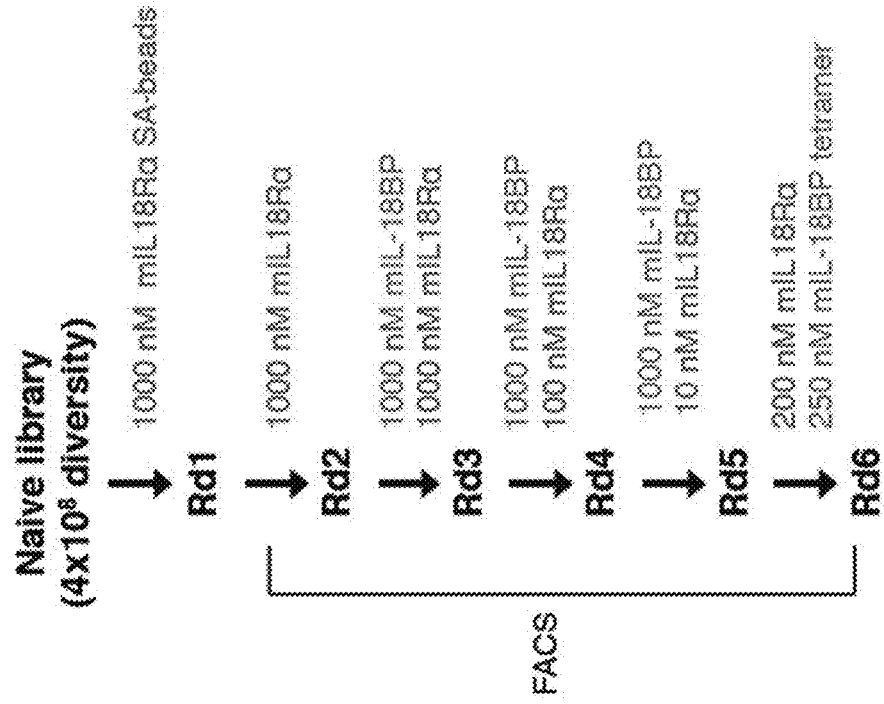
Figure 10A:
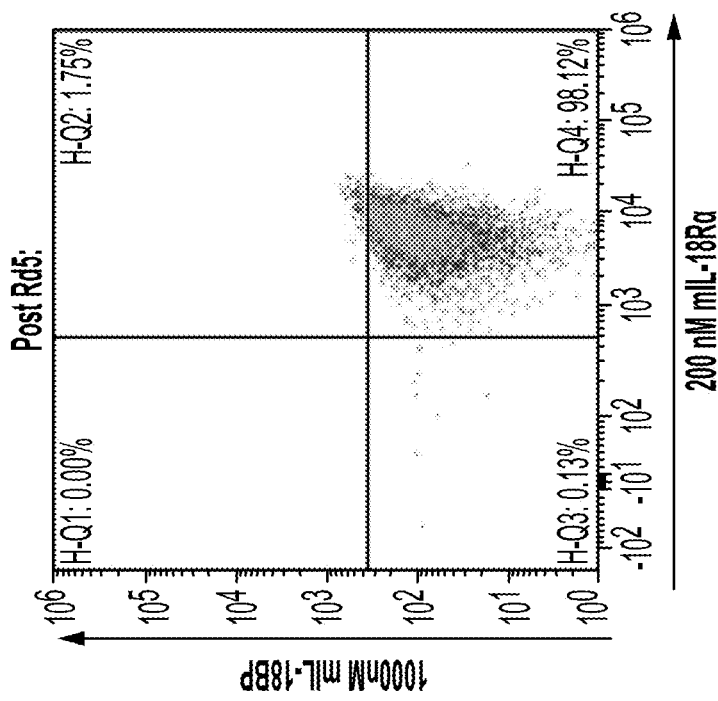
Figure 11A:
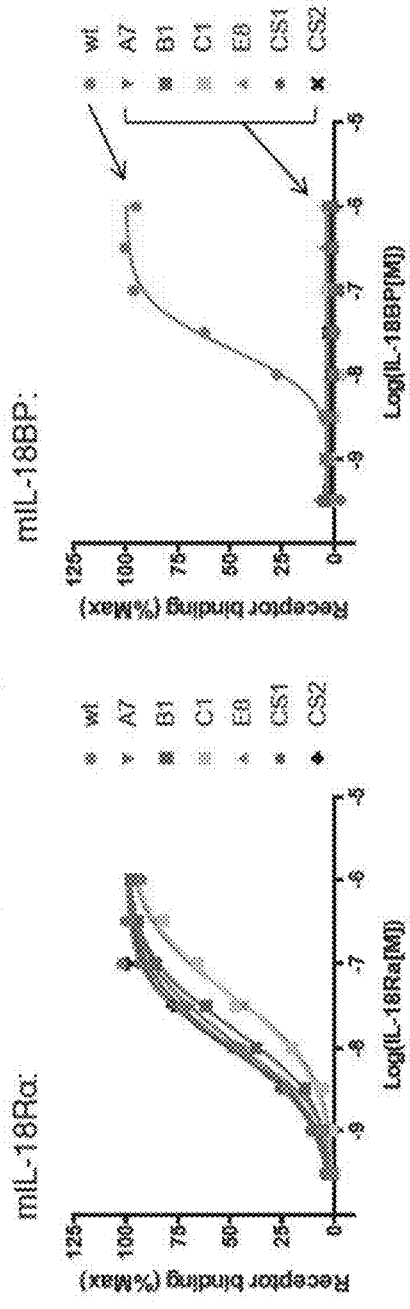
FIG. 11A and FIG. 11B depict results from example experiments, demonstrating biophysical characterization of murine DR-IL-18 variants.
Figure 11B:
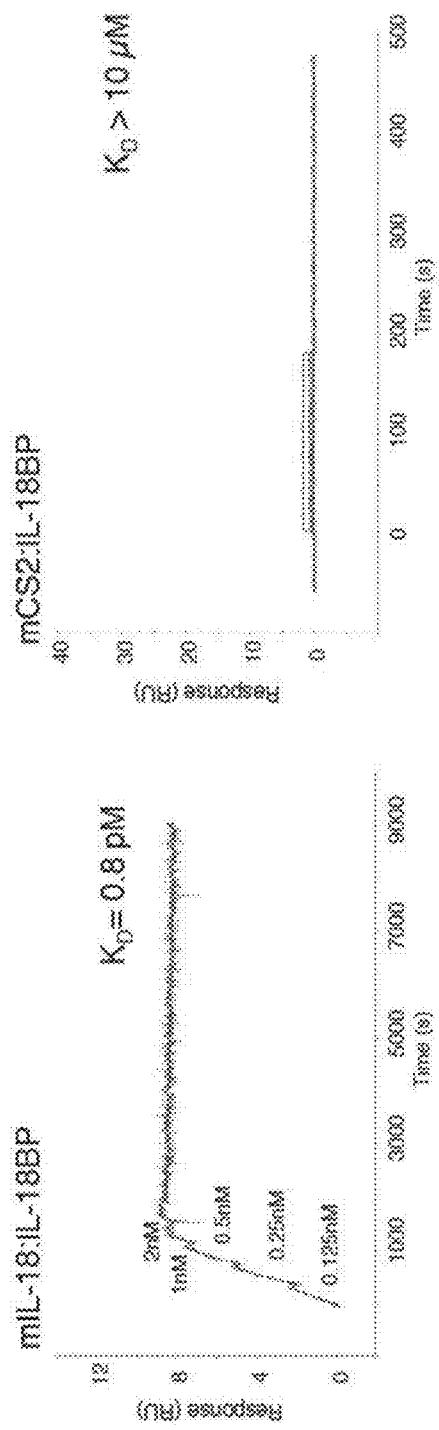

As the human and mouse interspecies cross-reactivity of IL-18 for IL-18Rα is poor, murine equivalents of the DR-IL-18 variants that could be used for studies in mice were created. Similar to the approach taken for hIL-18 above, a combinatorial library of mIL-18 variants randomizing a similar set of mIL-18Rα/mIL-18BP contact residues (Table 3) was created, yielding a library of 4×10$^8$ transformants. Directed evolution was performed on this library similar to how it was performed with the human IL-18 library; the selection strategy is summarized in FIG. 10A. After the completion of six rounds of selection, the remaining clones had a near-complete preference for mIL-18Rα over mIL-18BP (FIG. 10B). Analysis of 96 clones revealed 11 unique sequences, from which were derived two consensus sequences SEQ ID NO: 60 and SEQ ID NO: 61 (FIG. 10C). Yeast binding isotherms and surface plasmon resonance experiments confirmed these DR-IL-18 clones had an even greater independence for IL-18BP than the human IL-18 variants described herein, with the mIL-18BP binding KD's being well above 1 μM, with mIL-18Rα binding remaining roughly equal to WT mIL-18 (FIG. 11A, FIG. 11B, Tables 8 and 9).

Table 8 depicts IL-18Rα and IL-18BP binding affinities of mouse IL-18 variants by on-yeast binding isotherms

| IL-18 Variant | KD IL-18Rα (M) | KD IL-18BP (M) | KD ratio: IL-18BP/ IL-18Rα | Dissociation Constant Ratio normalized to WT IL-18 |
|---|---|---|---|---|
| mIL-18 WT | 1.13E−08 | 2.13E−09 | 1.88E−01 | 1 |
| SEQ ID NO: 70 | 1.35E−08 | NBD | >7.41E+02 | >3.93E+03 |
| SEQ ID NO: 67 | 1.79E−08 | NBD | >5.59E+02 | >2.96E+03 |
| SEQ ID NO: 64 | 4.20E−08 | NBD | >2.38E+02 | >1.26E+03 |
| SEQ ID NO: 62 | 4.30E−08 | NBD | >2.33E+02 | >1.23E+03 |
| SEQ ID NO: 60 | 1.07E−08 | NBD | >9.35E+02 | >4.96E+03 |
| SEQ ID NO: 61 | 1.13E−08 | NBD | >8.85E+02 | >4.69E+03 |

NBD, no binding detected (10 μM used for ratio calculations)

Table 9 depicts IL-18Rα and IL-18BP binding affinities of mouse IL-18 variants by SPR

| IL-18 Variant | KD IL-18Rα (M) | KD IL-18BP (M) | KD ratio: IL-18BP/ IL-18Rα | Dissociation Constant Ratio normalized to WT IL-18 |
|---|---|---|---|---|
| mIL-18 WT | 6.00E−10 | 1.10E−12 | 1.83E−03 | 1 |
| SEQ ID NO:70 | 2.20E−10 | 1.39E−05 | 6.32E+04 | 3.45E+07 |
| SEQ ID NO: 67 | 7.00E−10 | 1.47E−05 | 2.10E+04 | 1.15E+07 |
| SEQ ID NO: 64 | 1.69E−09 | NBD | >1.78E+04 | >9.68E+06 |
| SEQ ID NO: 62 | 1.09E−09 | 2.87E−05 | 2.63E+04 | 1.44E+07 |
| SEQ ID NO: 60 | 5.40E−10 | 3.80E−06 | 7.04E+03 | 3.84E+06 |
| SEQ ID NO: 61 | 7.90E−11 | 1.05E−05 | 1.33E+05 | 7.25E+07 |

NBD, no binding detected (30 μM used for ratio calculations)

In Vivo Pharmacodynamic Studies of DR-IL-18 Variants

Figure 12A:
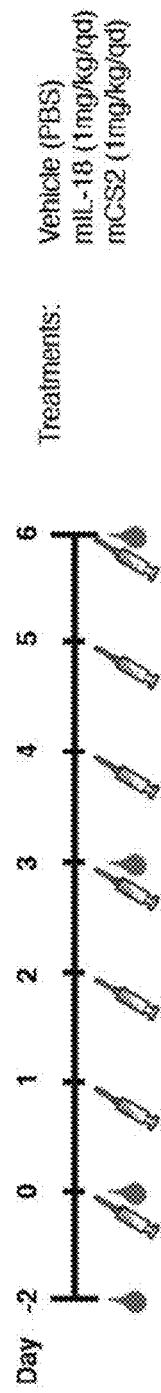
FIG. 12A through FIG. 12D depict results from example experiments, demonstrating pharmacodynamics of DR-IL-18 administered to mice.
Figure 12B:
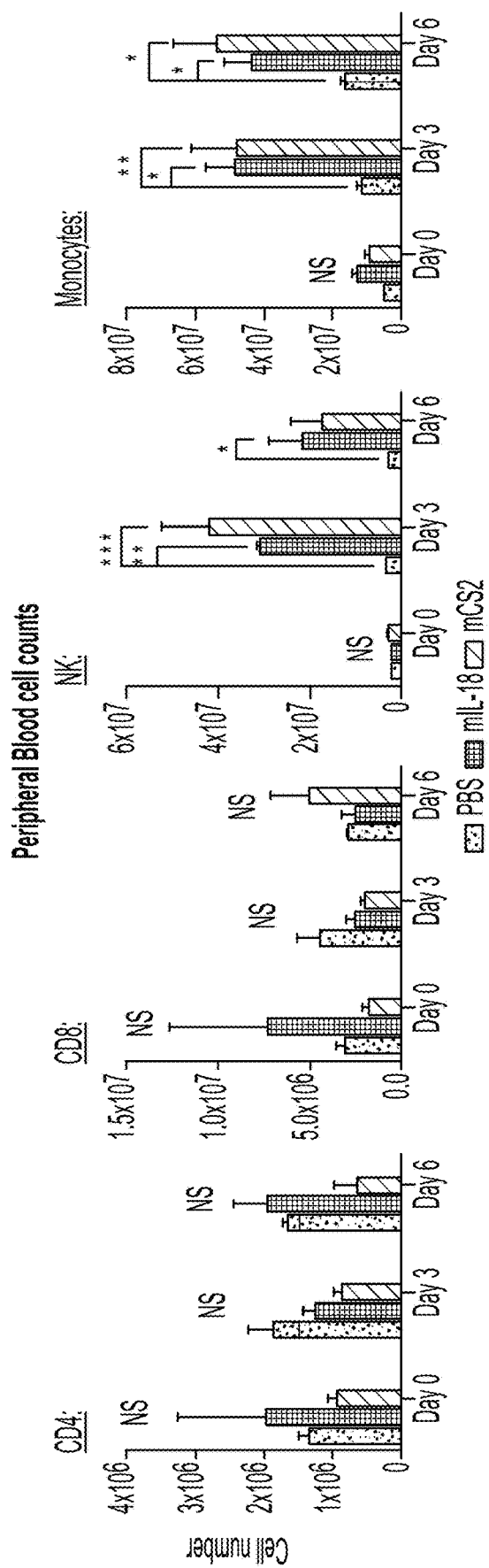
Figure 12C:
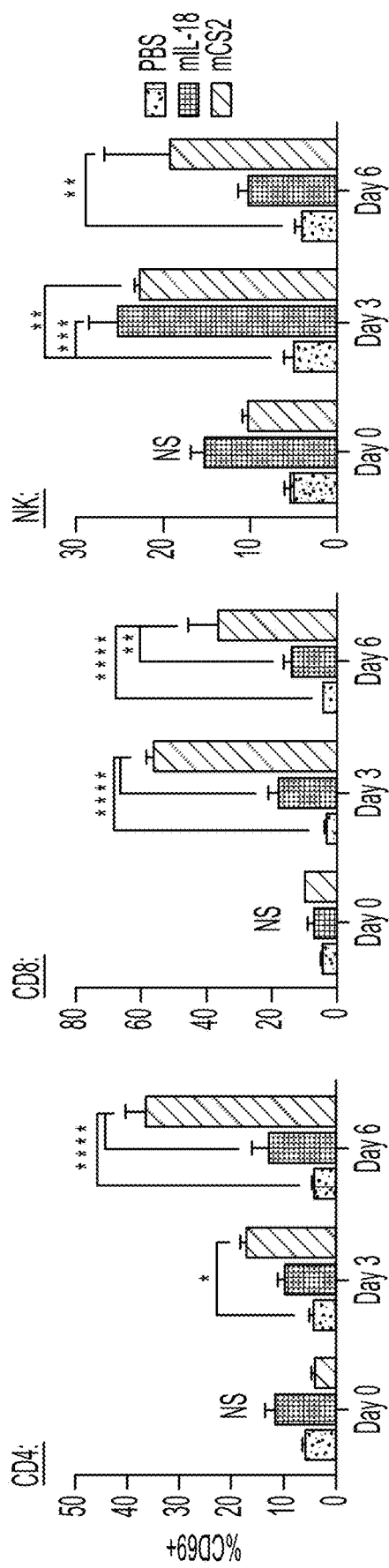
Figure 12D:
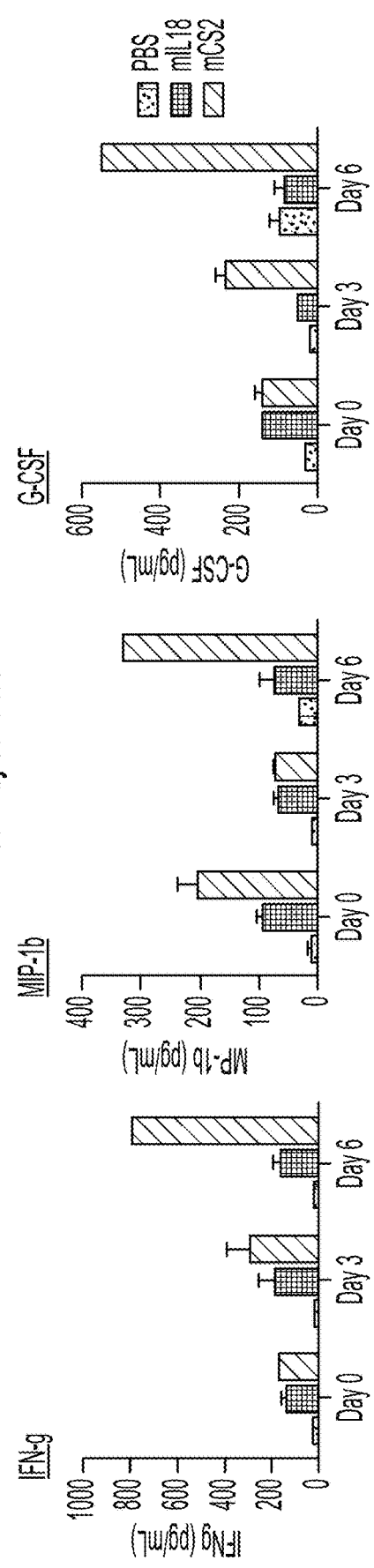

To assess the biologic effects of administration of the DR-IL-18 variants in vivo, pharmacodynamics studies were performed in mice, comparing WT mIL-18 to SEQ ID NO: 61. In the first study, mice were treated with vehicle (PBS), mIL-18 (1 mg/kg/day), or SEQ ID NO: 61 (1 mg/kg/day) for a total of seven injections (FIG. 12A). Analysis of peripheral blood phenotypes by flow cytometry showed that both WT mIL-18 and SEQ ID NO: 61 increased peripheral NK cell numbers by over ten-fold, and peripheral monocyte counts by over five-fold compared to vehicle treatment; total CD4 and CD8 cell counts were not significantly affected (FIG. 12B). Examination of cellular activation status by CD69 induction revealed that SEQ ID NO: 61 treatment dramatically increased CD69 levels on CD4 and CD8 cells compared to mIL-18 or vehicle treatment; reaching over 30% and over 50% positivity for CD4 and CD8 subsets, respectively (FIG. 12C). While both mIL-18 and SEQ ID NO: 61 stimulated CD69 expression on peripheral NK cells to over 20% positive by day 3, the CD69 levels decreased to non-significant levels for mIL-18 by day 6, but remained significantly elevated with SEQ ID NO: 61 treatment (FIG. 12C). Peripheral cytokine levels were also measured with a multiplexed Luminex panel. As seen in FIG. 12D, both mIL-18 and SEQ ID NO: 61 increased serum IFN-g, MIP1b, and G-CSF compared to vehicle treatment, but SEQ ID NO: 61 achieved much higher levels than mIL-18 by day 6 for each of these cytokines, as mIL-18 exhibited tachyphylaxis with plateaued or decreasing induced cytokine levels with subsequent administration.

Effect of SEQ ID NO: 61 on Body Fat Composition

Figure 13:
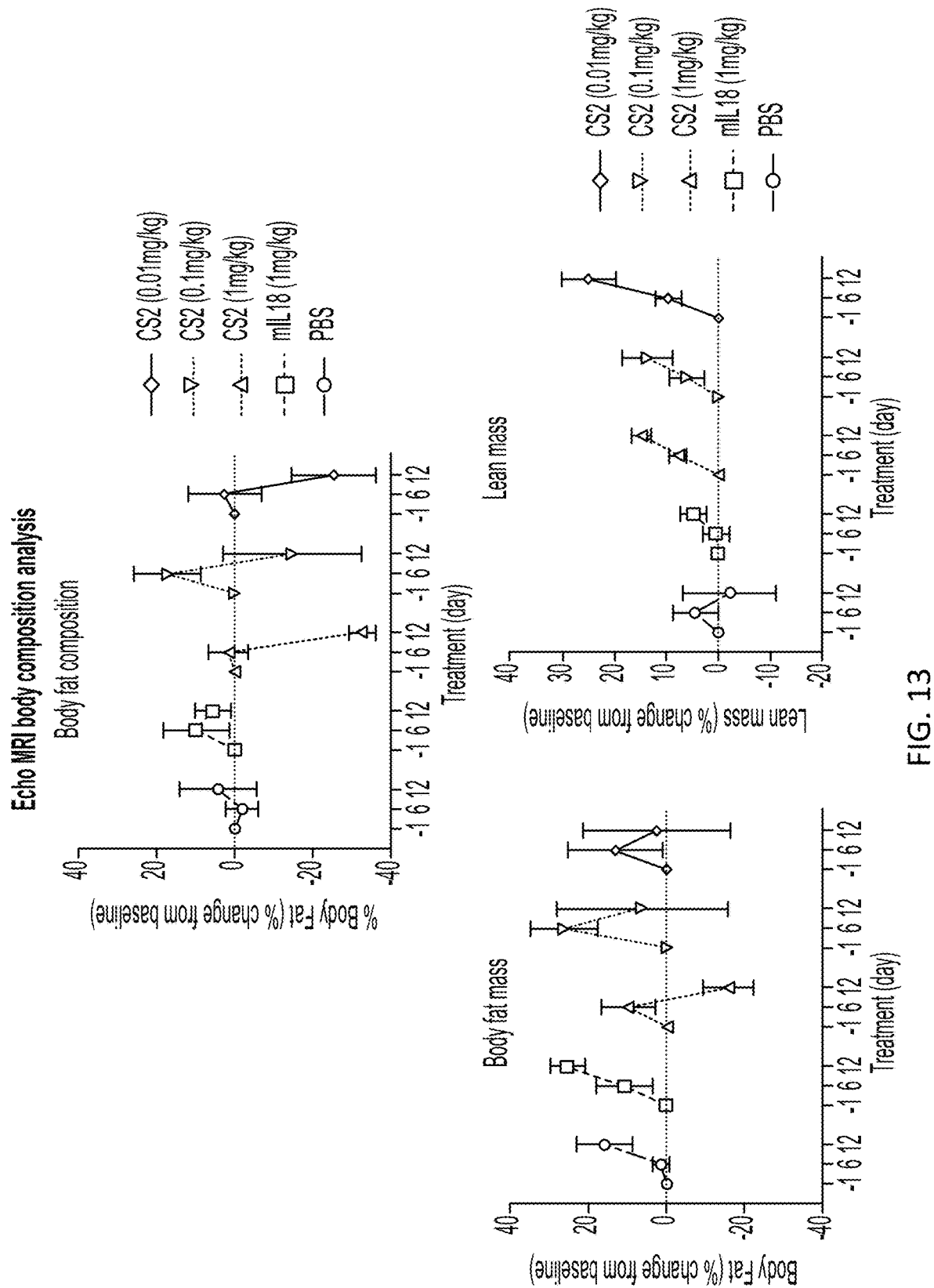
FIG. 13 depicts results from example experiments, demonstrating DR-IL-18 treatment decreases body fat composition in mice. Body fat and lean mass composition were measured in mice treated with 0.01, 0.1, or 1 mg/kg of the DR-IL-18 variant SEQ ID NO: 61 or 1 mg/kg WT mIL-18 every three days. SEQ ID NO: 61 treatment produced a significant decrease in body fat as a total percentage of body mass (top panel). This was manifested by decreases or stable fat mass (left panel), with concordant increases in lean mass (right panel). Vehicle treated and mIL-18 treated mice showed increases in body fat mass and stable lean mass over the same treatment period.

To assess the effect of the DR-IL-18 variants on body fat composition, we administered WT IL-18 at 1 mg/kg or 0.01, 0.1, or 1 mg/kg SEQ ID NO: 61 by intraperitoneal injection to C57BL/6 mice every three days. Body fat and lean mass composition were monitored by echoMRI. All tested doses of SEQ ID NO: 61 (1 mg/kg, 0.1 mg/kg, and 0.01 mg/kg) resulted in striking decreases in the overall percentage of body fat by day 12, while vehicle and mIL-18 treated mice did not have a significant change in total body fat composition (FIG. 13, top). Specifically, SEQ ID NO: 61-treated mice had either reduced or stable levels of total fat mass during the experiment (FIG. 13, bottom left), but substantially increased their total lean mass (FIG. 13, bottom right). These results indicate that SEQ ID NO: 61, and other variants disclosed herein, could be used to therapeutically decrease body fat composition (e.g., for treatment of obesity, diabetes, and/or metabolic syndrome).

Anti-Tumor Efficacy of DR-IL-18 Variants

Figure 14A:
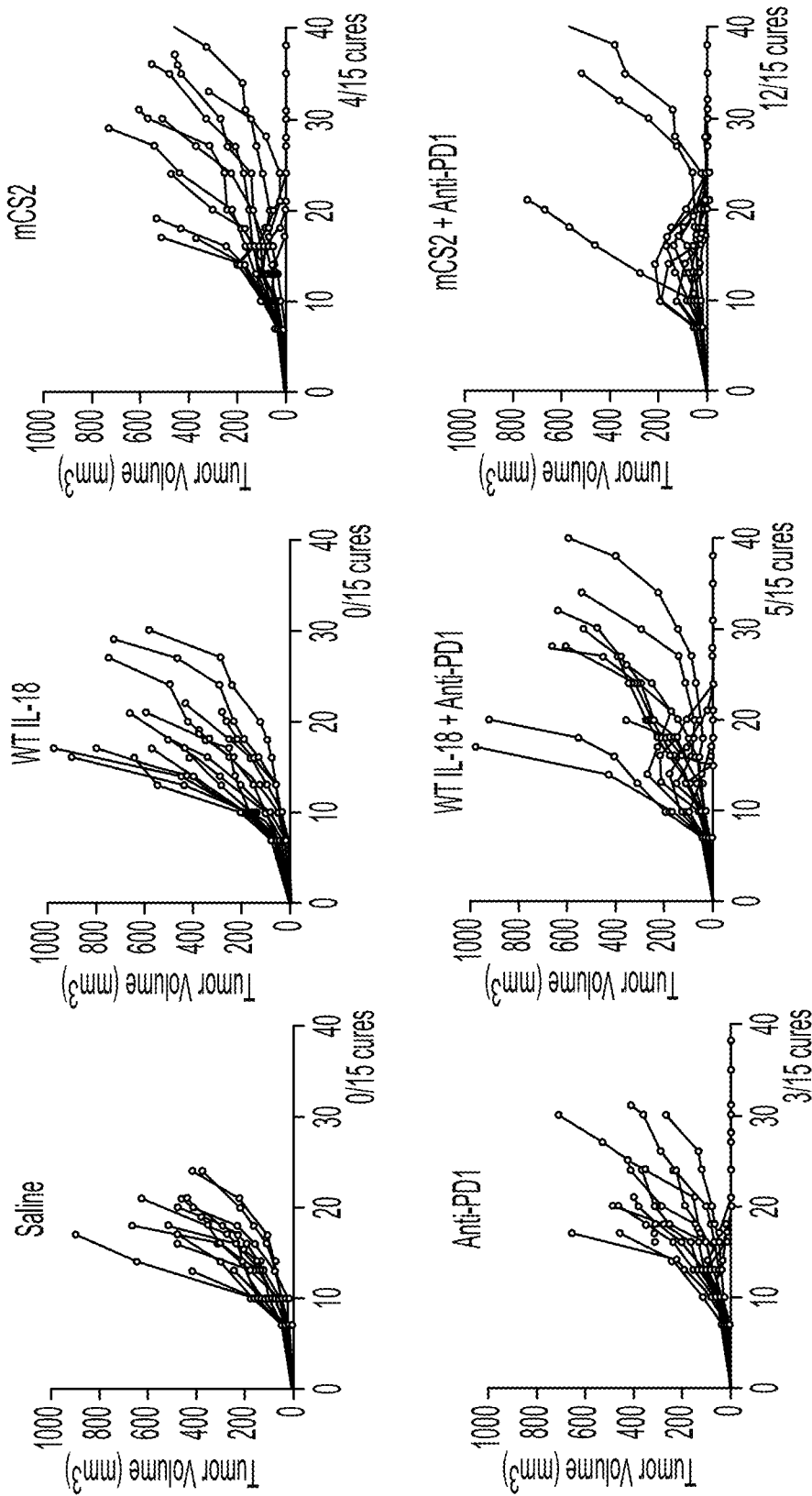
FIG. 14A through FIG. 14B depict results from example experiments, demonstrating DR-IL-18 is an effective immunotherapeutic in a melanoma model.
Figure 14B:
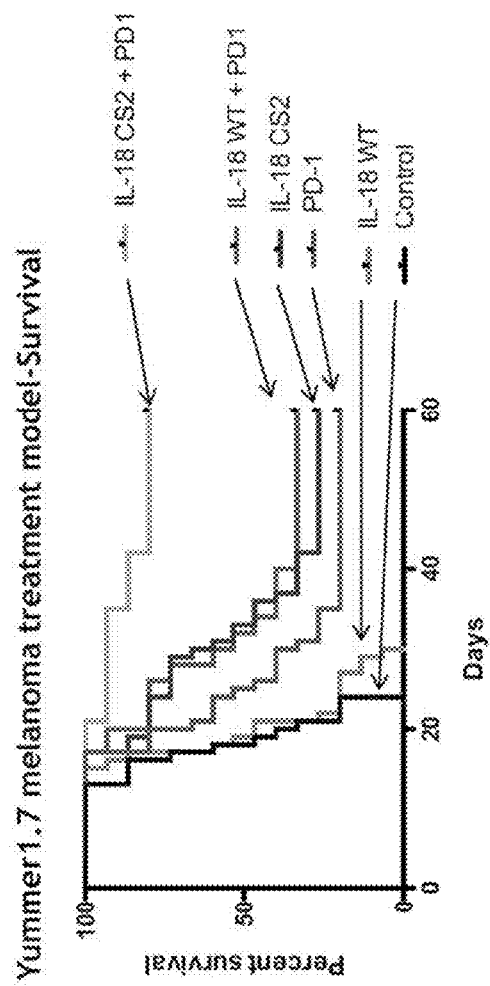

The anti-tumor efficacy of DR-IL-18 (SEQ ID NO: 61) was assessed using the transplantable, syngeneic YUMMER1.7 malignant melanoma tumor model. WT mIL-18 and SEQ ID NO: 61 were administered intraperitoneally to mice bearing YUMMER1.7 tumors biweekly at a dose of 0.32 mg/kg, with or without co-administration of anti-PD1 antibodies (8 mg/kg/q3d). Consistent with previous reports on its use in mice and humans, WT IL-18 did not affect tumor growth or survival compared to vehicle (saline), and only marginally improved the efficacy anti-PD1 when administered in combination. However, SEQ ID NO: 61 cured 27% of treated mice as a monotherapy and produced a partial response in another 27%, an effect commensurate with anti-PD1 treatment. The combination of SEQ ID NO: 61 with anti-PD1 cured 80% of treated mice (FIG. 14A and FIG. 14B).

Figures 15A, 15B:
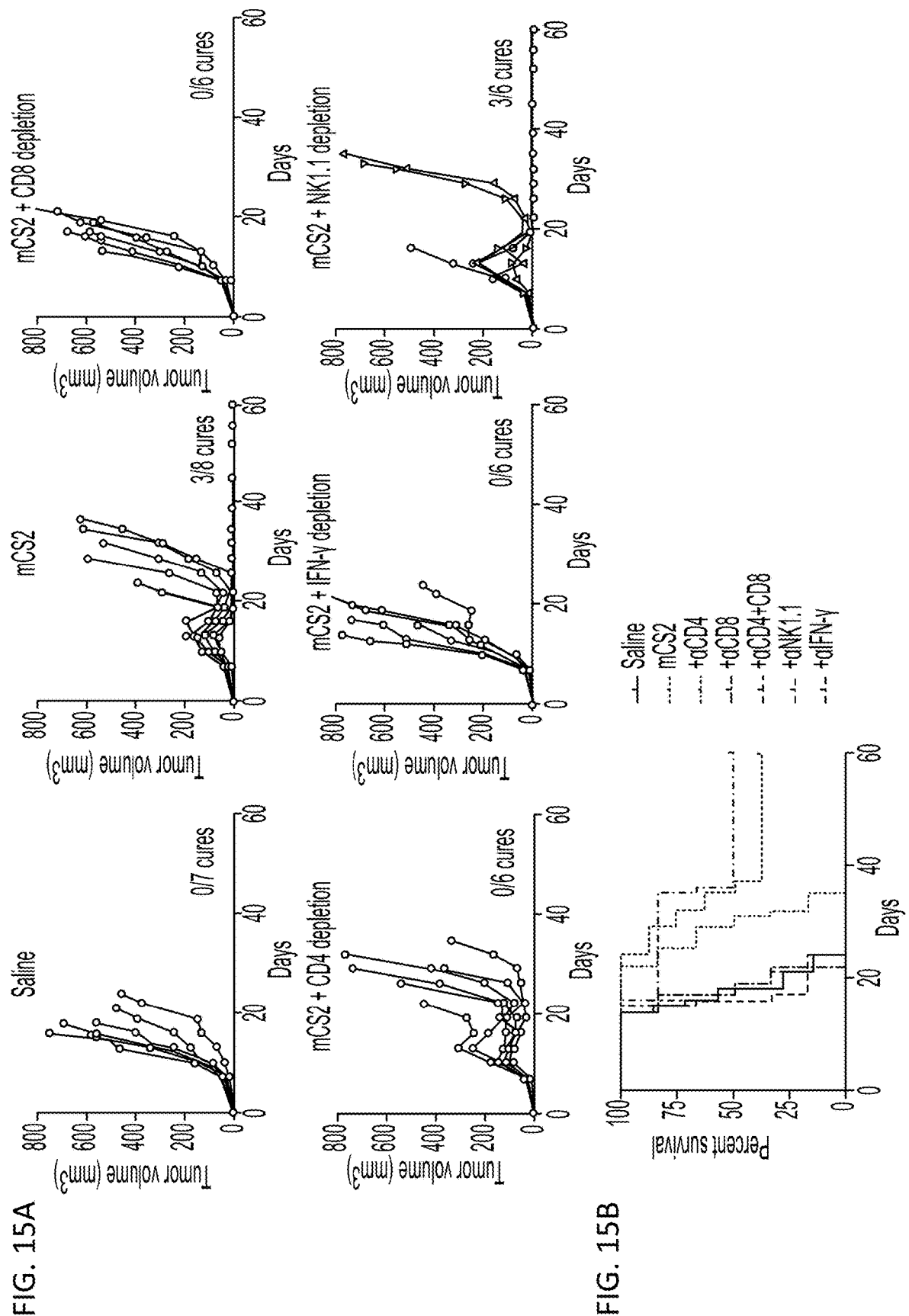
FIG. 15A and FIG. 15B depict results from example experiments that demonstrate that the effectiveness of DR-IL-18 in the melanoma model of FIG. 14 is dependent on CD4 and CD8 lymphocytes and interferon gamma.

To establish the mechanism of action of DR-IL-18 on YUMMER1.7 tumors, cell depletion studies were performed using antibodies against CD8, CD4, NK1.1, and Interferon-gamma. As seen in FIG. 15A and FIG. 15B, depletion of CD8 cells or neutralization of Interferon-gamma completely abrogated the effectiveness of DR-IL-18. Depletion of CD4 cells did not affect the initial activity of DR-IL-18 in terms of tumor growth, however, in CD4 treated mice, therapeutic responses are not sustained, suggesting a role of CD4 cells in supporting and sustaining anti-tumor immunity. Depletion of NK cells did not affect tumor growth or survival in YUMMER1.7 cells.

Figure 16:
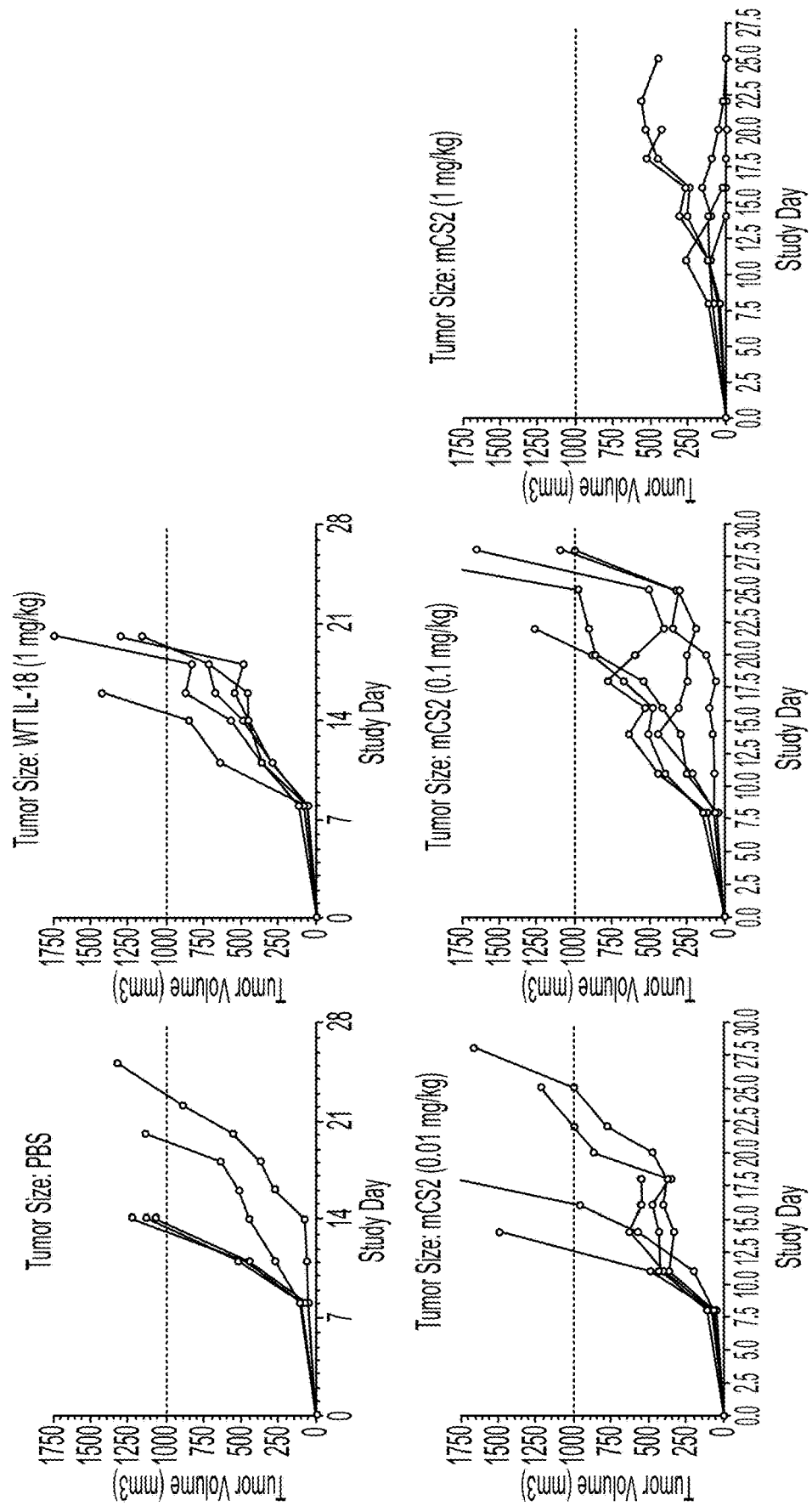
FIG. 16 depicts results from example experiments, demonstrating dose-dependent efficacy of DR-IL-18 in the MC38 tumor model. Tumor growth spider plots from mice bearing MC38 colon cancer tumors treated with PBS (control), 1.0 mg/kg WT IL-18, 1.0 mg/kg SEQ ID NO: 61, 0.1 mg/kg SEQ ID NO: 61, or 0.01 mg/kg SEQ ID NO: 61 every three days. WT IL-18 was not efficacious at 1 mg/kg, whereas SEQ ID NO: 61 showed partial efficacy at 0.1 mg/kg and maximal efficacy at 1.0 mg/kg.
Figure 17:
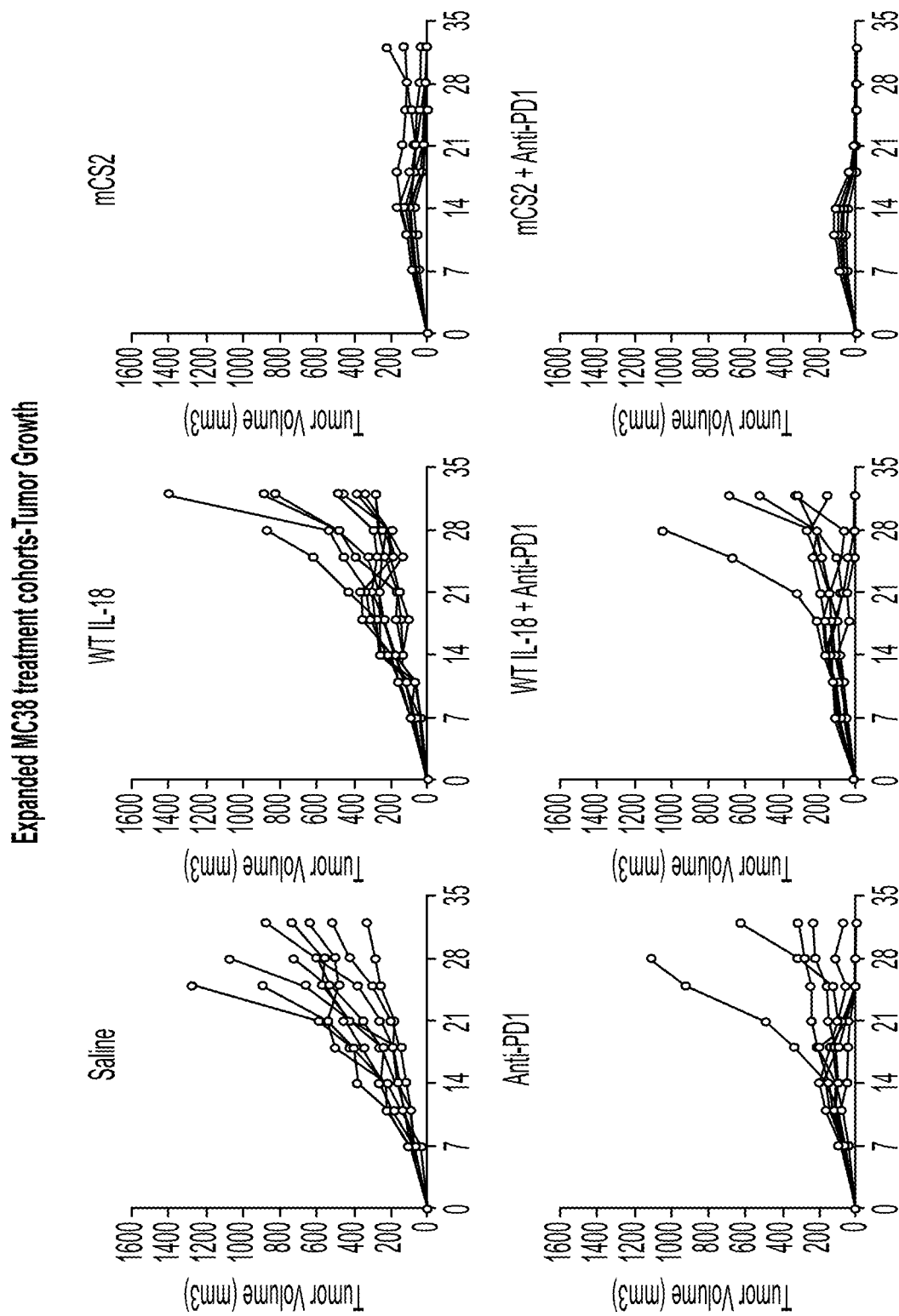
FIG. 17 depicts results from example experiments demonstrating the efficacy of DR-IL-18 alone in combination with the immune checkpoint inhibitor anti-PD1 in the MC38 tumor model. Tumor growth spider plots are shown from mice bearing MC38 colon cancer tumors treated with PBS (control), 0.32 mg/kg WT IL-18, 0.32 mg/kg of the DR-IL-18 variant SEQ ID NO: 61, 5 mg/kg anti-PD1, the combinations of anti-PD1 with WT IL-18, or the combination of anti-PD1 with SEQ ID NO: 61. All agents were dosed intraperitoneally twice per week for up to 6 total doses.

The activity of DR-IL-18 was additionally assessed in the immunogenic MC38 colorectal tumor model. A dose-finding study was first performed, administering saline, WT IL-18 (1 mg/kg twice weekly), or a range of DR-IL-18 doses from 0.01 mg/kg, 0.1 mg/kg, or 1 mg/kg twice weekly. As seen in FIG. 16, WT IL-18 had no effect on tumor growth, whereas DR-IL-18 (SEQ ID NO: 61) showed dose-dependent efficacy, slowing tumor growth at 0.1 mg/kg and producing tumor regression at 1 mg/kg. The cohorts were then expanded and potential synergism with immune checkpoint inhibition was assessed. Again, WT IL-18 had no effect as a monotherapy and showed no enhancement of anti-PD1 efficacy. By contrast, DR-IL-18 showed robust monotherapeutic activity commensurate with or superior to anti-PD1, and the two therapies given together showed exceptional synergism, producing complete regression in all treated mice as seen in FIG. 17.

Figure 18A:
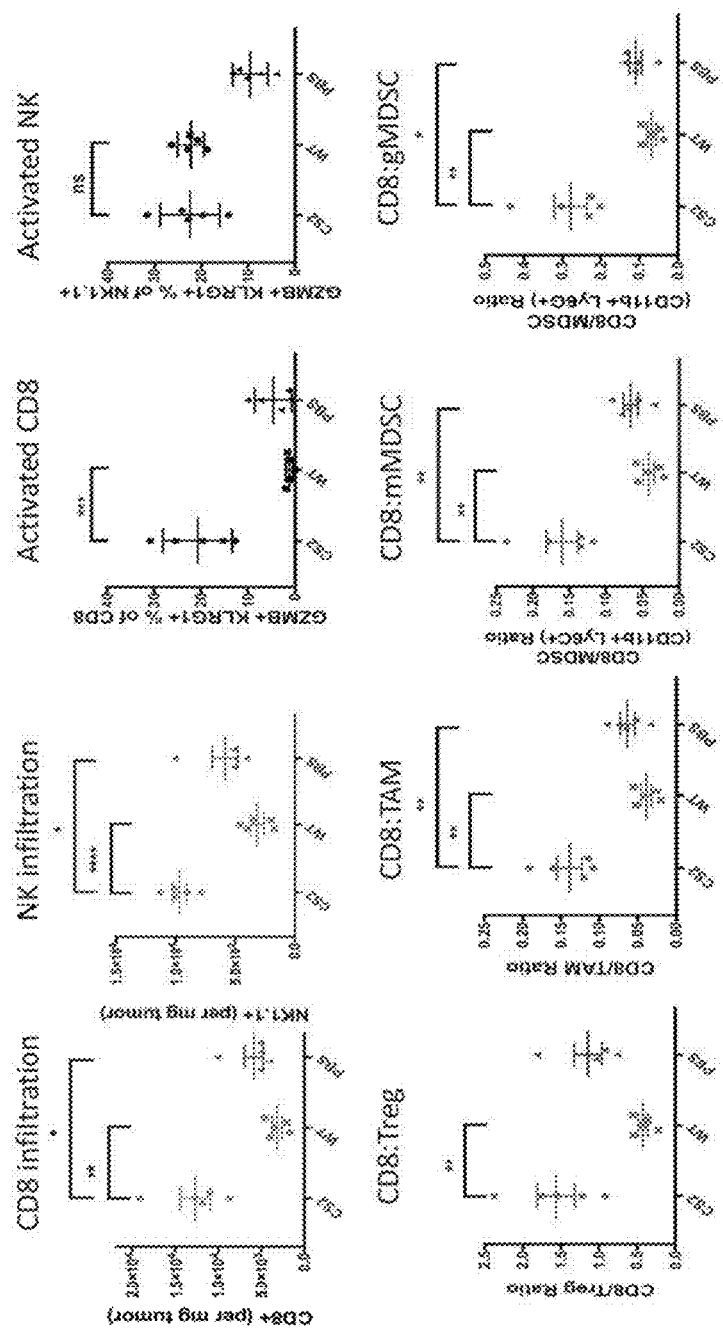
FIG. 18A and FIG. 18B depict results from example experiments that investigate the anti-tumor mechanism of DR-IL-18 in mice bearing MC38 tumors.
Figure 18B:
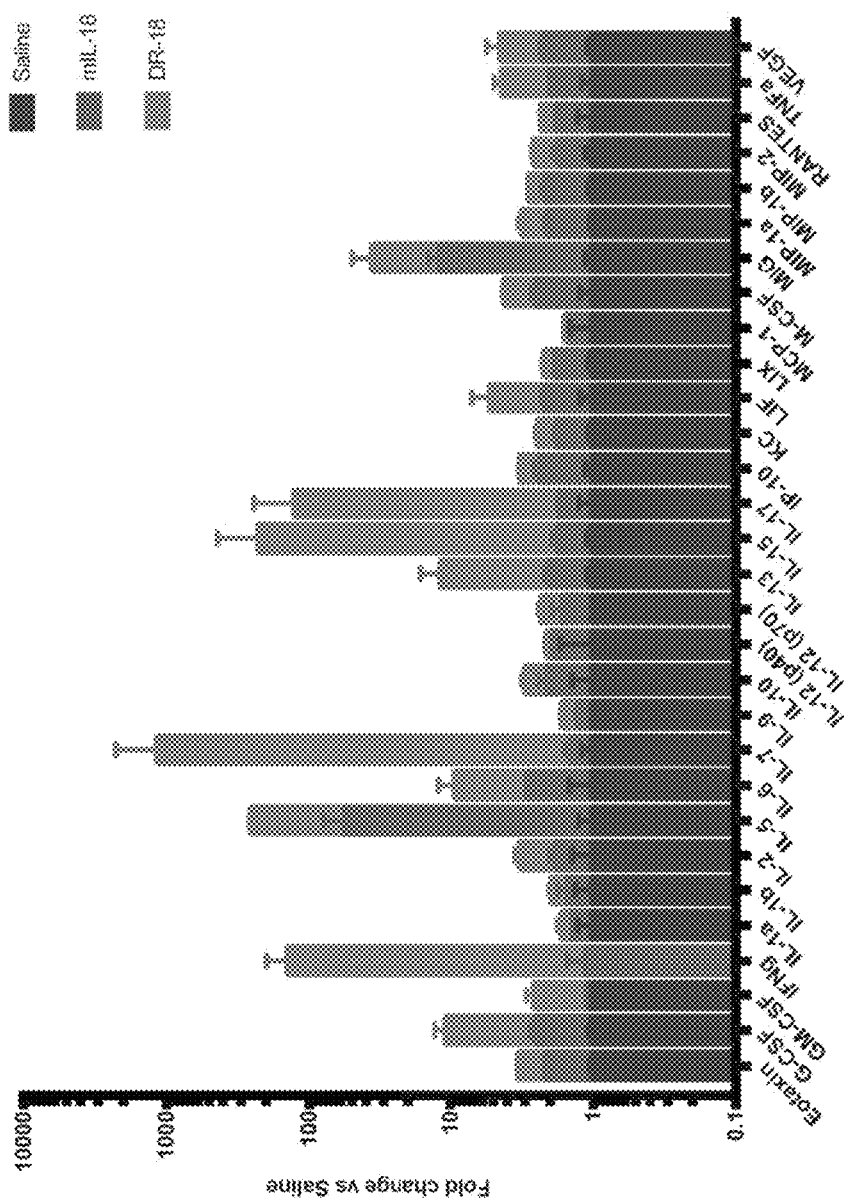

To further characterize the mechanism of DR-IL-18, flow cytometric studies were performed on the immune infiltrate of MC38 tumors from mice treated with saline, WT IL-18, or DR-IL-18 (SEQ ID NO: 61). Relative to saline or WT IL-18, DR-IL-18 treatment increased CD8 and NK cell infiltration per mg of tumor and additionally resulting in upregulation of activation markers of effector cells such as granzyme B and KLRG1 (FIG. 18A, top row). Unlike other cytokine therapies such as IL-2 or IL-15, DR-IL-18 does not increase the CD8:Treg ratio within tumors compared to saline treatment. However, DR-IL-18 treatment leads to a more favorable tumor immune microenvironment, by increasing the ratio of CD8 cells to tumor associated macrophages (TAMs), and monocytic and granulocytic myeloids derived suppressor cells (MDSCs). The secondary cytokine release profile was also measured from serum of the same mice using a Luminex assay. As seen in FIG. 18B, DR-IL-18 treatment increased systemic levels of Interferon-gamma, IL-7, and IL-15 by over 100-fold relative to WT IL-18 treatment. Taken in aggregate, these results indicate that DR-IL-18 produces anti-tumor efficacy through a unique mechanism of action distinct from IL-2, IL-15, or WT IL-18 treatment.

Some of the secondary cytokines induced by DR-IL-18 therapy would be predicted to potentially contribute to toxicity and/or decreased effectiveness. For instance, IL-17 which is upregulated>100-fold by DR-IL-18 contributes to colitis and psoriasis and additionally stimulates granulocytes that can become immunosuppressive myeloid derived suppressor cells. IL-5 and IL-13 are type 2 cytokines also upregulated by DR-IL-18 and could contribute to allergy, exacerbation of asthma, or analphylaxis. Th2 T cells do not contribute to immunotherapeutics responses and may promote immunosuppressive Treg development. As such, in certain instances the effectiveness and safety of DR-IL-18 could be enhanced by selective inhibition of undesired secondary cytokines such as IL-17, IL-5, and IL-13, for instance by a neutralizing antibody.

Figure 19A:
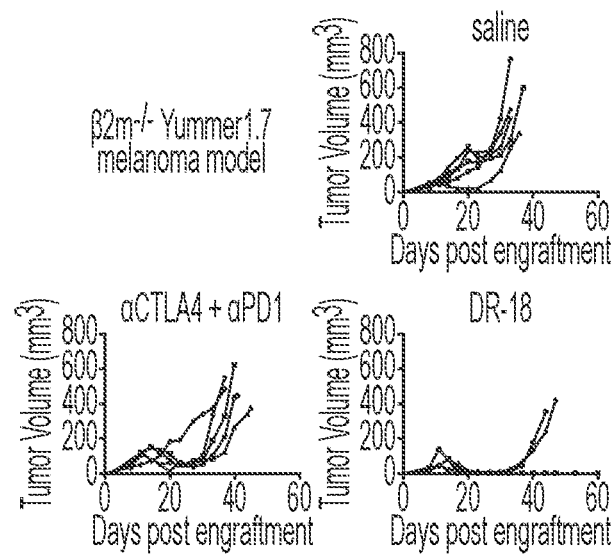
FIG. 19A through FIG. 19C depicts results from example experiments demonstrating the capability of DR-IL-18 to effectively treat tumors that are refractory to immune checkpoint inhibitors through loss of surface MHC class I expression.
Figure 19B:
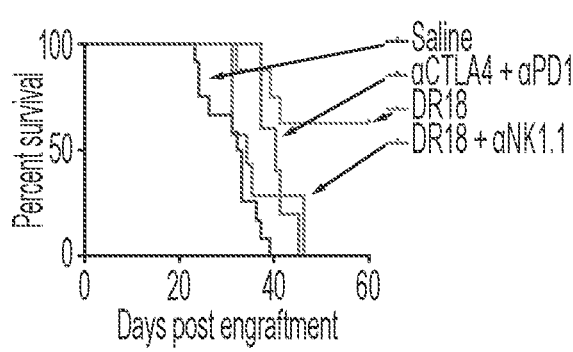
Figure 19C:
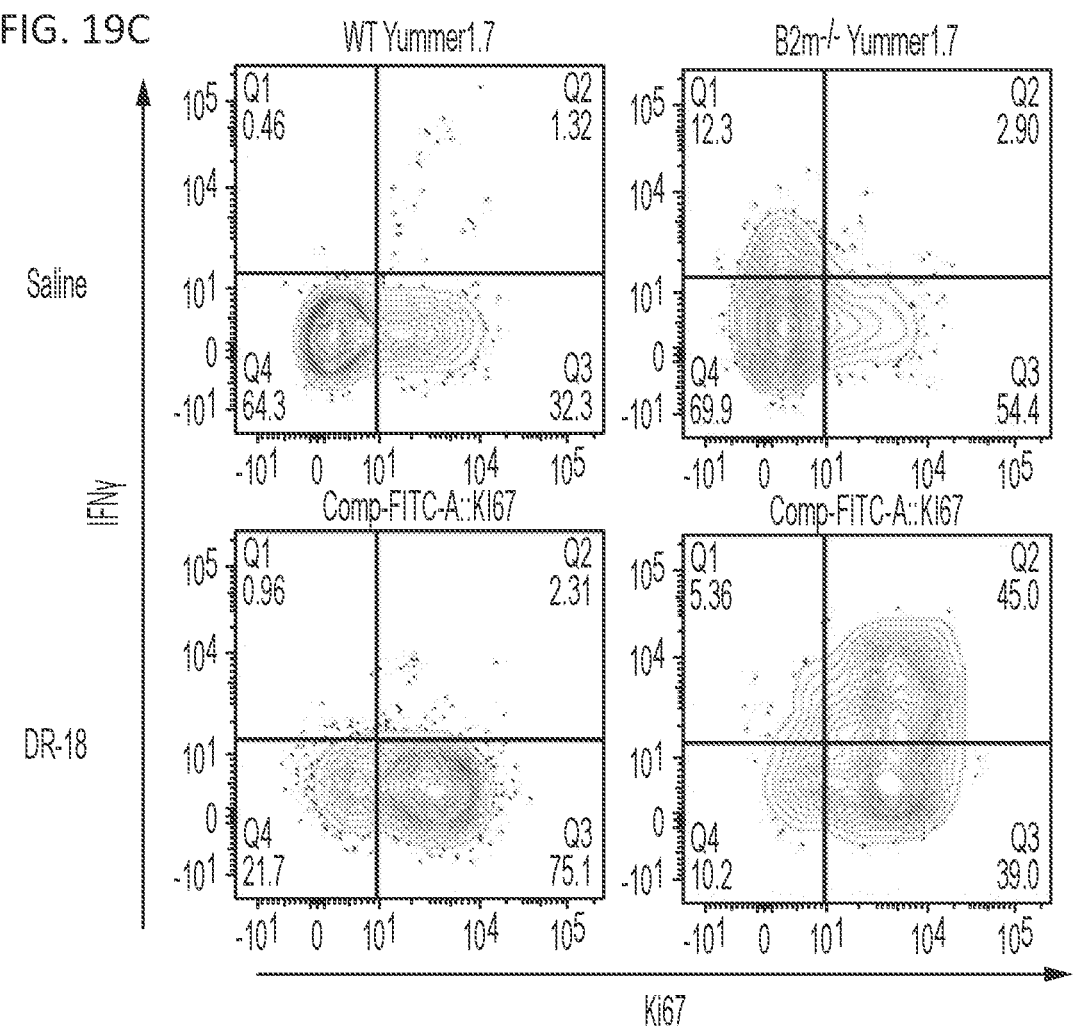

Many tumors are resistant to immune checkpoint inhibition, either at initial presentation (primary resistance) or after an initial response to treatment (secondary resistance). The most prevalent cause of resistance of checkpoint inhibitors is loss of antigen presentation through MHC class I. Loss of surface MHC class I is classically associated with NK-cell mediated cytolysis, however, NK cells can become exhausted within MHC I deficient tumors. As NK cells express the IL-18R and our previous results in MC38 indicated that NK cells are expanded and activated by DR-IL-18, we thus tested whether DR-IL-18 could stimulate NK cell attack against MHC I deficient tumors. We used CRISPR/cas9 to knockout B2m in the Yummer1.7 cell line and found that implanted B2m-deficient YUMMER1.7 tumors were refractory to even combined treatment with both anti-CTLA4 and anti-PD1 (FIG. 19A and FIG. 19B), a combination that routinely cures close to 100% of parental Yummer1.7 tumors. However, single-agent treatment with DR-IL-18 (SEQ ID NO: 61) cured 60% of B2m-deficient Yummer1.7 tumors in an NK-cell dependent fashion, as depletion with anti-NK1.1 abrogated the effect (FIG. 19A and FIG. 19B). Experiments were conducted to understand the effect that DR-IL-18 had on intratumoral NK cells in the setting of an MHC class I deficient tumor. Immunophenotyping studies were performed with flow cytometry on B2m-deficient Yummer.17 tumors from mice treated with saline or DR-IL-18. 24 hours after the 3rd dose of treatment, the mice were sacrificed, tumors were dissociated, and the cell suspension was treated with PMA/ionomycin for four hours. The proliferative index and functional capacity of the NK cells were then analyzed by intracellular flow cytometry with Ki67 and Interferon-gamma. As seen in FIG. 19C, NK cells from saline-treated B2m-deficient Yummer1.7 tumors had scant Interferon-gamma production and Ki67 levels, indicating an exhausted phenotype. By contrast, NK cells from tumors treated with DR-IL-18 had robust Interferon-gamma production and Ki67 levels, with the majority of NK cells being positive for both markers. These results thus establish that DR-IL-18 is effective in the treatment of MHC class I deficient tumors that are refractory to immune checkpoint blockade in an NK cell-dependent manner.

These results establish DR-IL-18 as a highly promising tumor immunotherapeutic, and provide strong evidence that IL-18BP greatly limits the effectiveness of IL-18 therapy, given the greatly improved activity of the SEQ ID NO: 61 DR-IL-18 variant. From these results, it is predicted that other strategies, such as blocking IL-18BP with an antibody, small protein, and/or small molecule could augment IL-18 therapy and other immunotherapeutic regimens.

Figure 21:
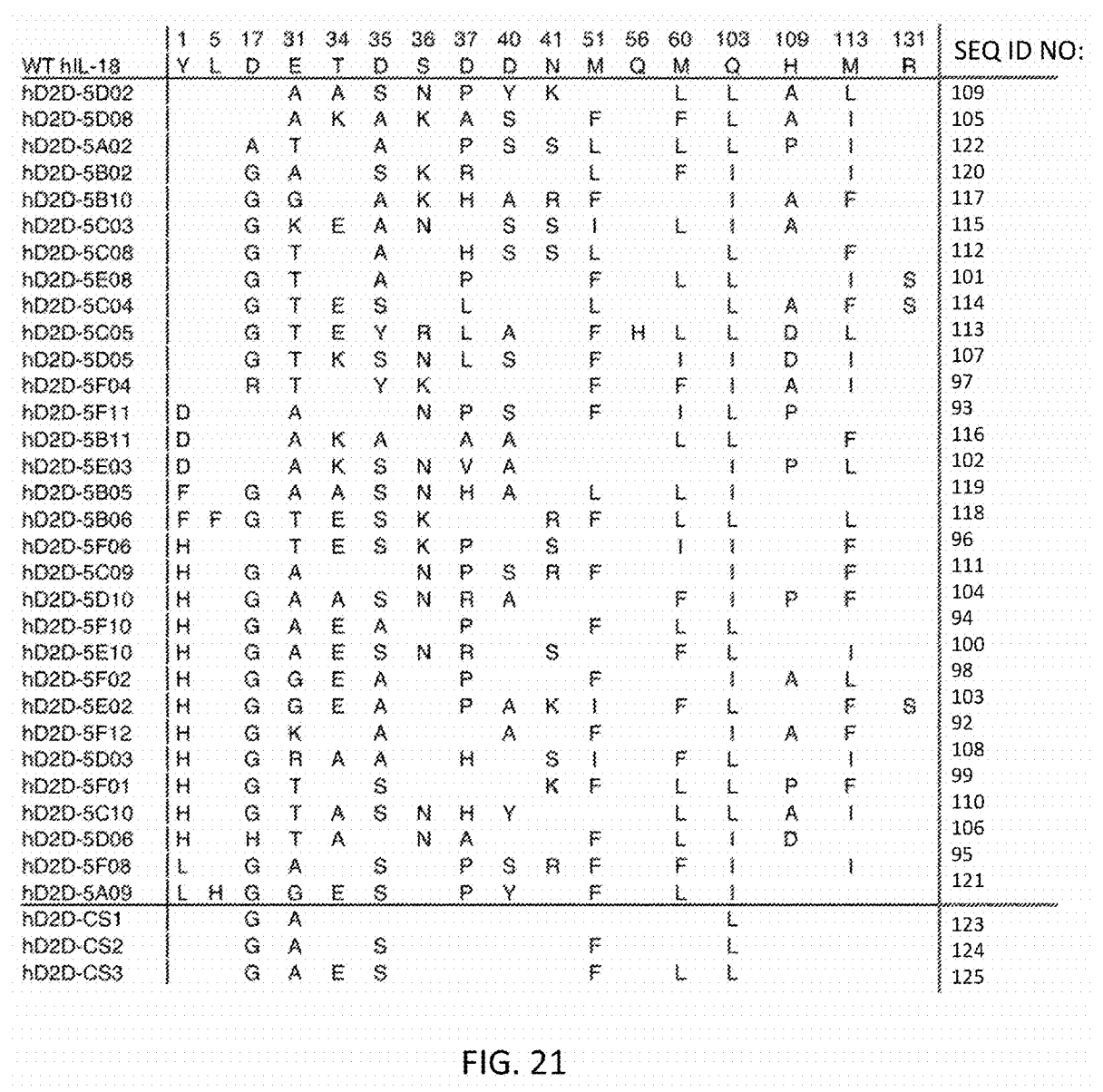

Efforts were undertaken to engineer an IL-18BP antagonist by creating a "decoy-to-the-decoy" (D2D), or IL-18 variants that specifically bind IL-18BP, but do not bind IL-18Rα and thus do not signal. The potential advantage of such an agent is that it would serve to neutralize IL-18BP and enhance the activity of endogenous IL-18, as opposed to driving IL-18R signaling systemically. IL-18 was thus randomized at contact positions for IL-18Rα (FIG. 20A) and a yeast-displayed library was prepared as described previously for human and mouse DR-IL-18. The resulting library of 3.9×10$^8$ transformants was selected for 3 rounds as indicated in FIG. 20B, selecting for retained IL-18BP binding, while counter selecting against IL-18Rα. As seen in FIG. 20C, each round of selection conferred enrichment for binding to IL-18BP (human and mouse), but without acquisition of IL-18Rα binding. 96 clones were sequenced, yielding 31 unique sequences, from which three consensus sequences SEQ ID NO: 123, SEQ ID NO: 124, and SEQ ID NO: 125 were derived (FIG. 21). Biophysical characterization of the resulting clones indicated that they showed similar binding isotherms to IL-18BP as WT IL-18 (FIG. 22A), but with greatly decreased/absent binding to IL-18Rα (FIG. 22B). These data are summarized in FIG. 22C. An identical selection process was performed for murine IL-18, creating a library of 2.0×10$^8$ transformants, which we selected to obtain 51 unique sequences summarized in FIG. 23.

Example 2: Binding Affinity Measurements of Second Generation Variants

Surface Plasmon Resonance (SPR) was used to perform biophysical affinity measurements of second generation DR-IL-18 variants (binding to IL-18R vs IL-18BP). Experiments were conducted using a Biacore T100 instrument and carried out at 25° C. Biotinylated IL-18Rα or IL-18BP were immobilized onto a Biacore biotin capture chip (Series S CAP sensor chip, GE Healthcare) to yield an Rmax of ~50 RU (IL-18Rα) or ~10 RU (IL-18BP). Measurements were made with serial dilutions of the IL-18 variants in HEPES buffered Saline-P+ buffer (10 mM HEPES pH 7.4, 150 mM NaCl, 0.005% surfactant P20). The surface was regenerated by three 60-sec injections of regeneration buffer (3/4 (v/v) 8M guanidine hydrochloride with ¼ (v/v) 1M sodium hydroxide). Experiments were performed in multiple channels simultaneously for increased observations. All data were analyzed with the Biacore T100 evaluation software version 2.0 with a 1:1 Langmuir binding model.

Figure 24:
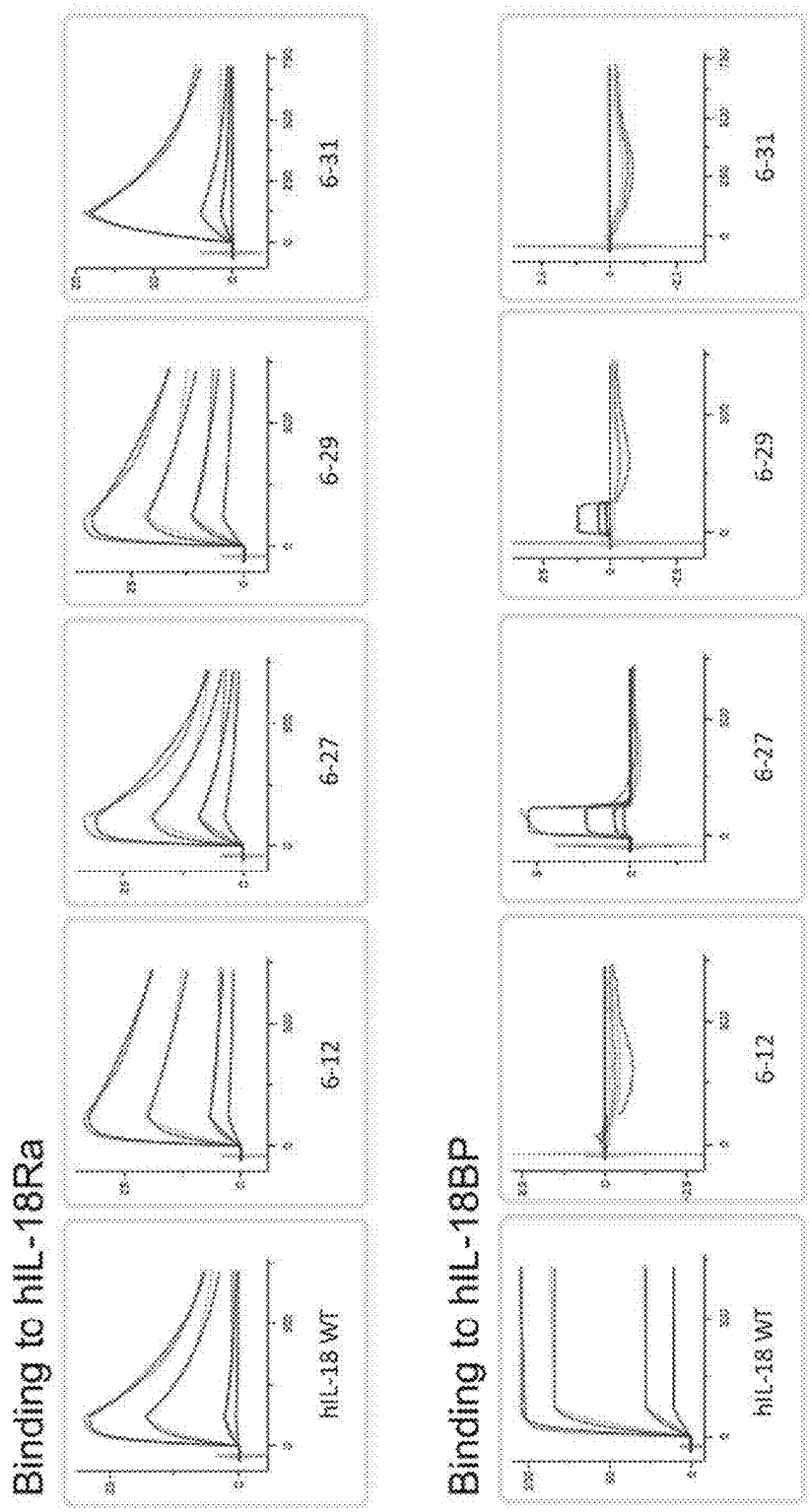
FIG. 24 depicts results from biophysical affinity measurements (sensograms) of the second-generation DR-IL-18 variants for binding to IL-18Rα and IL-18BP using Surface Plasmon Resonance (SPR). Top row: representative sensograms of the indicated IL-18 variants (soluble analytes) for hIL-18Rα (immobilized ligand). Bottom row: representative sensograms of the indicated IL-18 variants for human (hIL-18BP). The x axis is time in seconds and the y axis is Response Units (RU). The curves are the observed data over time for different concentrations (2-fold dilutions starting at 1 nM), superimposed with curves of best fit assuming a 1:1 langmuir binding model.

The results confirmed that DR-IL-18 variants of the disclosure exhibit greatly reduced affinity for IL-18BP, and bind to IL-18Rα with at least comparable affinity as WT IL-18 (See FIG. 24 for the generated sensograms, Table 10 for a summary of the measured kinetics, Table 11 is a summary of the affinity measurements, and Table 12 for a general summary, including results for the dissociation constant ratios of the second generation DR-IL-18 variants).

Table 10 is a summary of SPR data for second generation hDR-IL-18 variants (kinetics)

| Surface Ligand | Analyte | ka (1/Ms) | kd (1/s) | KD (M) Exp 2 | KD (M) Exp 1 | % Rmax |
|---|---|---|---|---|---|---|
| hIL-18Rα | hIL-18 | 5.55E+05 | 2.97E−03 | 5.36E−09 | 5.35E−09 | 32 |
| hIL-18Rα | SEQ ID NO: 89 | 4.95E+05 | 9.10E−04 | 1.84E−09 | 2.24E−09 | 35 |
| hIL-18Rα | SEQ ID NO: 90 | 6.31E+05 | 2.43E−03 | 3.85E−09 | 3.48E−09 | 35 |
| hIL-18Rα | SEQ ID NO: 91 | 5.75E+05 | 1.19E−03 | 2.07E−09 | 2.65E−09 | 36 |
| hIL-18Rα | SEQ ID NO: 87 | 2.18E+05 | 3.32E−03 | 1.52E−08 | 1.94E−08 | 19 |
| hIL-18BP | hIL-18 | 5.18E+05 | 2.23E−07 | 4.30E−13 | 6.94E−13 | 48 |
| hIL-18BP | SEQ ID NO: 89 | | | Too weak to measure | | −1 |
| hIL-18BP | SEQ ID NO: 90 | | | Too weak to measure | | 2 |
| hIL-18BP | SEQ ID NO: 91 | | | Too weak to measure | | 0 |
| hIL-18BP | SEQ ID NO: 87 | | | Too weak to measure | | −1 |

Table 11 is a summary of SPR data for second generation hDR-IL-18 variants (affinity)

| Sample | $KD_{apparent}$hIL-18Rα (nM) | $KD_{apparent}$hIL-18BP (nM) |
|---|---|---|
| hIL-18 | 5.4, 5.4 | <0.1 |
| SEQ ID NO: 89 | 1.8, 2.2 | too weak |
| SEQ ID NO: 90 | 3.9, 3.5 | too weak |
| SEQ ID NO: 91 | 2.1, 2.7 | too weak |
| SEQ ID NO: 87 | 15.2, 19.4 | too weak |

Table 12 is a summary of the SPR affinity measurements of second generation hDR-IL-18 variants for IL-18Rα and IL-18BP. The IL-18 BP:Rα Dissociation Constant Ratio is the ratio of the KD for IL-18BP to the KD for IL-18Rα normalized to the same ratio of WT IL-18. A higher number for this ratio indicates that the IL-18 variant has an enhanced preference for binding IL-18Rα over IL-18BP compared to WT IL-18. *Average of 2 studies. k is a multiple of 1,000. m is a multiple of 1,000,000.

| Protein | SPR: $K_D$ Rα (nM) | SPR: $K_D$BP (nM) | IL-18 BP:Rα Dissociation Constant Ratio |
|---|---|---|---|
| WT hIL-18 | 4.1* | 0.002 | 1 |
| SEQ ID NO: 34 | 8.0* | 11.8* | 3,024 |
| SEQ ID NO: 36 | 9.1* | 19.3* | 4,348 |
| SEQ ID NO: 37 | 7.7* | 121* | 32,215 |
| SEQ ID NO: 89 | 2.2 | >10,000 | >9,318,275 |
| SEQ ID NO: 90 | 3.5 | >10,000 | >5,857,201 |
| SEQ ID NO: 91 | 2.7 | >10,000 | >7,592,669 |
| SEQ ID NO: 87 | 19.4 | >10,000 | >1,056,712 |
| WT mIL-18 | 0.60 | 0.0011 | 1 |
| SEQ ID NO: 61 | 0.08 | 11,000 | >75,000,136 |
| A7, B1, C1, E8 | 0.22-1.7 | 14k-29k | 9.3m-35m |

Example 3: Efficacy for Cancer Treatment

Efficacy of DR-IL-18 variants was tested using multiple different cancer models, including models of colorectal tumors, breast cancer, melanoma, and MHC class I deficient tumors that are resistant to immune checkpoint inhibitors. The results show that DR-IL-18 variants with a bias to bind IL-18R and not IL-18BP can be used to treat a broad range of cancers (not limited to just those that were tested).

Figure 25A:
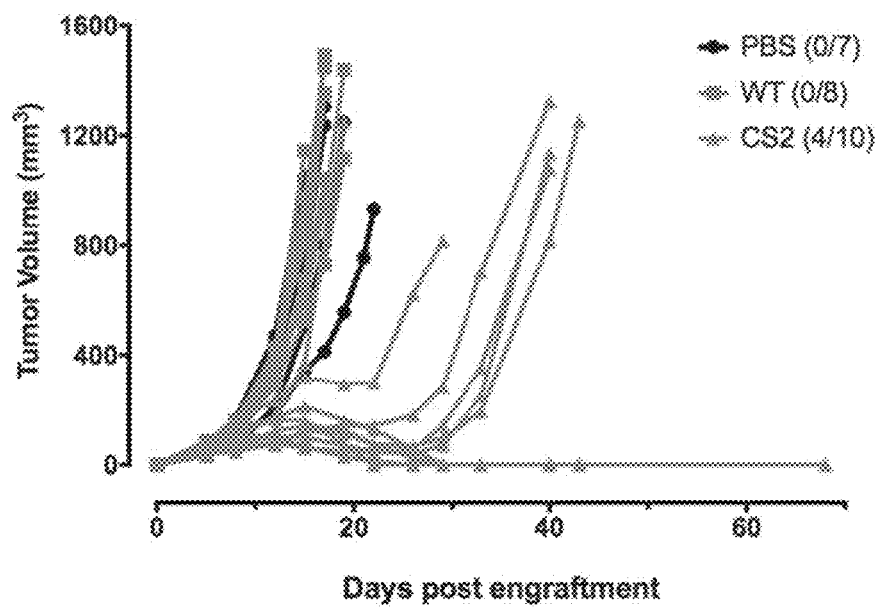
FIG. 25A and FIG. 25B depict data demonstrating efficacy of DR-IL-18 on the CT26 colorectal tumor model. 250,000 CT26 cells were implanted subcutaneously and treatment initiated at day 7 once tumors were ~60 mm$^3$ on average. WT IL-18 and SEQ ID NO: 61 were dosed at 0.32 mg/kg twice weekly for a total of 5 doses. Anti-PD1 was given at 10 mg/kg at the same schedule.
Figure 25B:
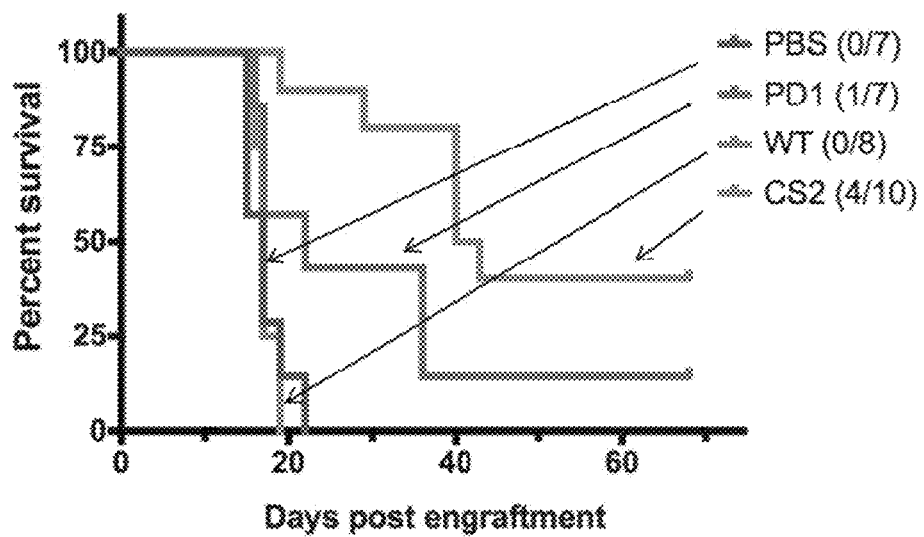

To efficacy of DR-IL-18 in a model of colorectal cancer, 250,000 CT26 cells were implanted subcutaneously and treatment initiated at day 7 once tumors were ~60 mm³ on average. WT IL-18 and SEQ ID NO: 61 were dosed subcutaneously at 0.32 mg/kg twice weekly for a total of 5 doses. Anti-PD1 was given at 10 mg/kg at the same schedule. Only treatment with DR-IL-18, but not WT IL-18, resulted in tumor growth inhibition and tumor clearance in a subset of animals (FIG. 25A, providing an overlay of spider plots showing tumor growth of animals treated with saline (PBS, circles), WT IL-18 (squares), and DR-IL-18 (SEQ ID NO: 61, triangles). DR-IL-18, but not WT IL-18 resulted in prolonged survival (FIG. 25B, showing survival curves for mice treated with anti-PD-1, WT IL-18, or DR-IL-18 (SEQ ID NO: 61); numbers of complete responses are indicated in parentheses). 40% of mice treated with DR-IL-18 exhibited tumor clearance, which was an improvement over the checkpoint inhibitor anti-PD-1. provides survival curves for mice treated with anti-PD-1, WT IL-18, and DR-IL-18 (SEQ ID NO: 61). Numbers of complete responses are indicated in parentheses. and tumor clearance in 40% of mice, an improvement over the checkpoint inhibitor anti-PD-1.

In both the in the 4T1 breast cancer model and B16-F10 melanoma model, only DR-IL-18, but not WT IL-18 resulted in tumor growth inhibition. Treatments were administered after tumors exceeded an average volume 50 mm³ as indicated by the boxes marked with "t".

Figure 26A:
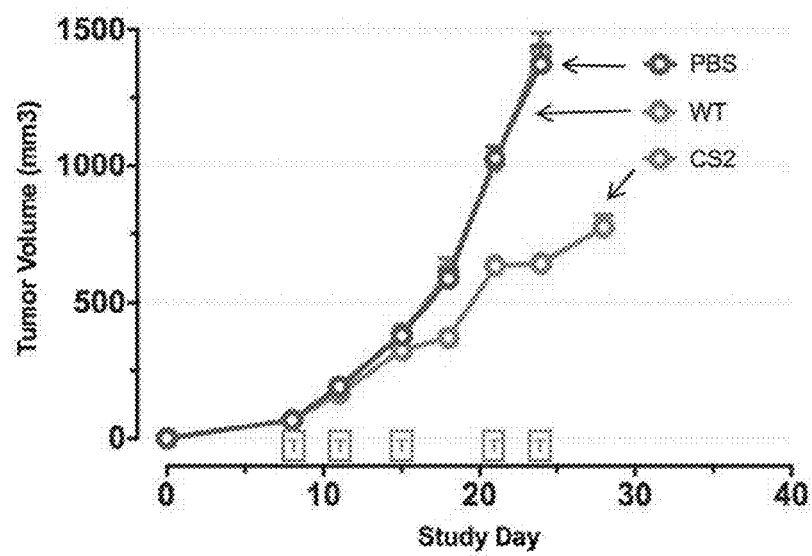
FIG. 26A and FIG. 26B depict data demonstrating efficacy of DR-IL-18 in the 4T1 breast cancer model and B16-F10 melanoma model.
Figure 26B:
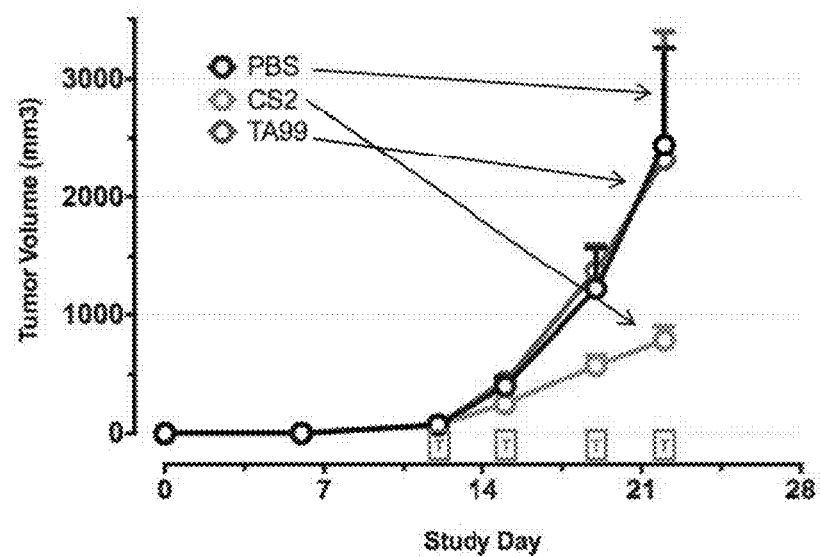
Figure 27A:
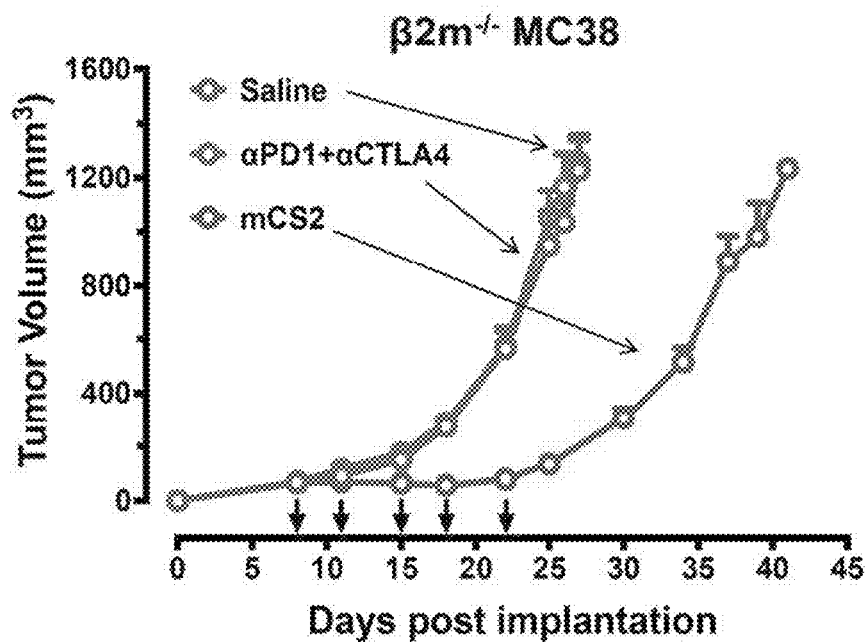
FIG. 27A and FIG. 27B depict data that extend the data of FIG. 19A through 19C. Depicted is data demonstrating efficacy of DR-IL-18 in the treatment of additional MHC class I deficient tumor models that are resistant to immune checkpoint inhibitors.

The 4T1 breast cancer model and B16-F10 melanoma model were used to evaluate the efficacy of DR-IL-18 for additional cancer types. 500,000 4T1 cells were implanted subcutaneously in BALB/C mice, and 500,000B16-F10 cells were implanted subcutaneously in C57BL/6 mice. Treatments were administered after tumors exceeded an average volume 50 mm³. In both models, only DR-IL-18, but not WT IL-18 resulted in tumor growth inhibition as shown in FIG. 26A (4T1 tumors) and FIG. 26B (B16-F10). Treatments were administered after tumors exceeded an average volume 50 mm³ as indicated by the boxes marked with "t". The efficacy of DR-IL-18 was also evaluated in MHC class I deficient tumor models. B2m deficient (and thus MHC class I deficient) MC38 cells were prepared using CRISPR/Cas9 mediated deletion as described for B2m deficient YUMMER cells. B2m−/− MC38 cells were implanted subcutaneously and treatment initiated at day 7 once tumors were ~65 mm³ on average. SEQ ID NO: 61 was dosed at 0.32 mg/kg twice weekly for 5 doses. Anti-PD1 and anti-CTLA4 were given at 8 mg/kg at the same schedule. The MHC class I deficient tumors were resistant to immune checkpoint inhibition with anti-PD1 and anti-CTLA4, however DR-IL-18 treatment resulted in tumor growth inhibition (FIG. 27A).

Figure 27B:
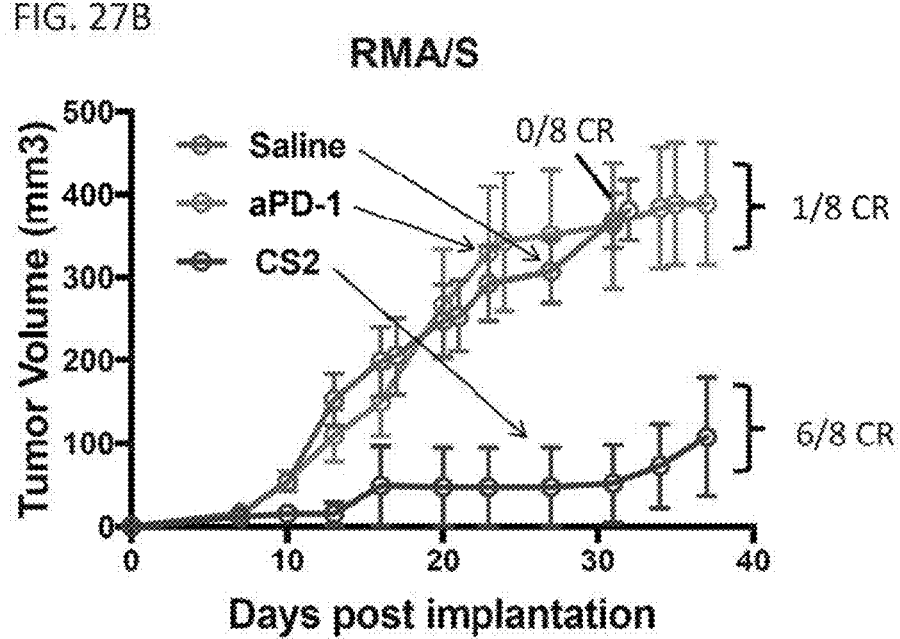

RMA/S is a variant of the RMA lymphoma line that contains a spontaneous mutation in Tapasin, which results in a defect in antigen loading and therefore decreased MHC class I surface expression. Congenic C57BL/6 mice were implanted with 1,000,000 RMA/S cells subcutaneously and treatment initiated at day 7. SEQ ID NO: 61 was dosed at 0.32 mg/kg twice weekly. Anti-PD1 was given at 8 mg/kg at the same schedule. The RMA/S tumors were resistant to immune checkpoint inhibition with anti-PD-1, while treatment with DR-IL-18 resulted in tumor growth inhibition (FIG. 27B).

Figure 28:
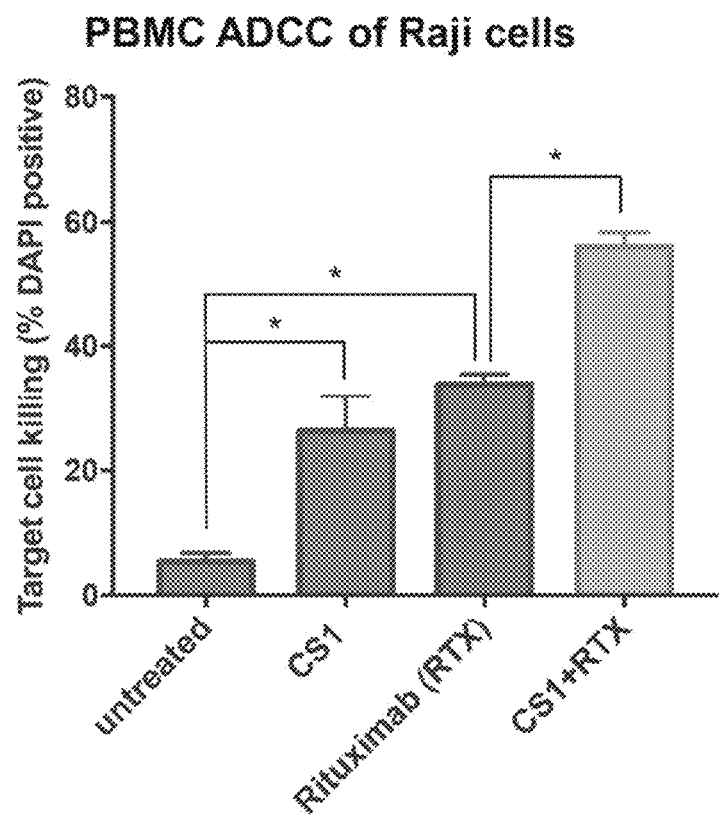
FIG. 28 depicts data demonstrating efficacy of DR-IL-18 to enhance anti-tumor antibody-dependent cell mediated cytotoxicity (ADCC). Ex vivo cytotoxicity studies used CFSE labeled Raji (B cell lymphoma) cells and isolated human peripheral blood mononuclear cells (PBMCs). PBMCs and labeled Raji cells were incubated together at an effector: target (E:T) ratio of 1:10 for 25 hours. The human DR-IL-18 variant hCS-1 (1 μM), rituximab (10 μg/mL), or the combination of both agents were applied to the samples as indicated. Cytotoxicity was measured by flow cytometry and calculated as the fraction of CFSE cells that became DAPI positive. DR-18 stimulated significant tumor cell killing as a single agent and significantly enhanced the killing by the therapeutic antibody rituximab. * p<0.05 by two-way ANOVA with Tukey's correction for multiple comparisons.

Example 4: Promotion of Cancer Cell Killing by DR-IL-18 Alone or in Combination with a Therapeutic Antibody An ex vivo cytotoxicity study was conducted to evaluate the ability of DR-IL-18 to promote killing of cancer cells. CFSE labeled Raji (B cell lymphoma) cells were used as target cells. Human i peripheral blood mononuclear cells (PBMCs) were isolated and incubated with the CFSE labeled Raji cells \ at an effector:target (E:T) ratio of 1:10 for 25 hours. The human DR-IL-18 variant hCS-1 (1 μM), the anti-CD20 antibody rituximab (10 μg/mL), or the combination of both agents. Cytotoxicity was measured by flow cytometry and calculated as the fraction of CFSE cells that became DAPI positive. DR-IL-18 treatment resulted in killing of target cells, and the combination of DR-IL-18 with rituximab resulted in a higher level of cancer cell killing than either agent alone, suggesting DR-IL-18 can enhance anti-tumor antibody-dependent cell mediated cytotoxicity (ADCC; FIG. 28; * p<0.05 by two-way ANOVA with Tukey's correction for multiple comparisons). These data suggest DR-IL-18 can be combined with opsonizing agents, such as tumor-targeting antibodies, to enhance killing of cancer cells.

Example 5: Efficacy of DR-IL18 Against Viral Infections

Figure 29B:
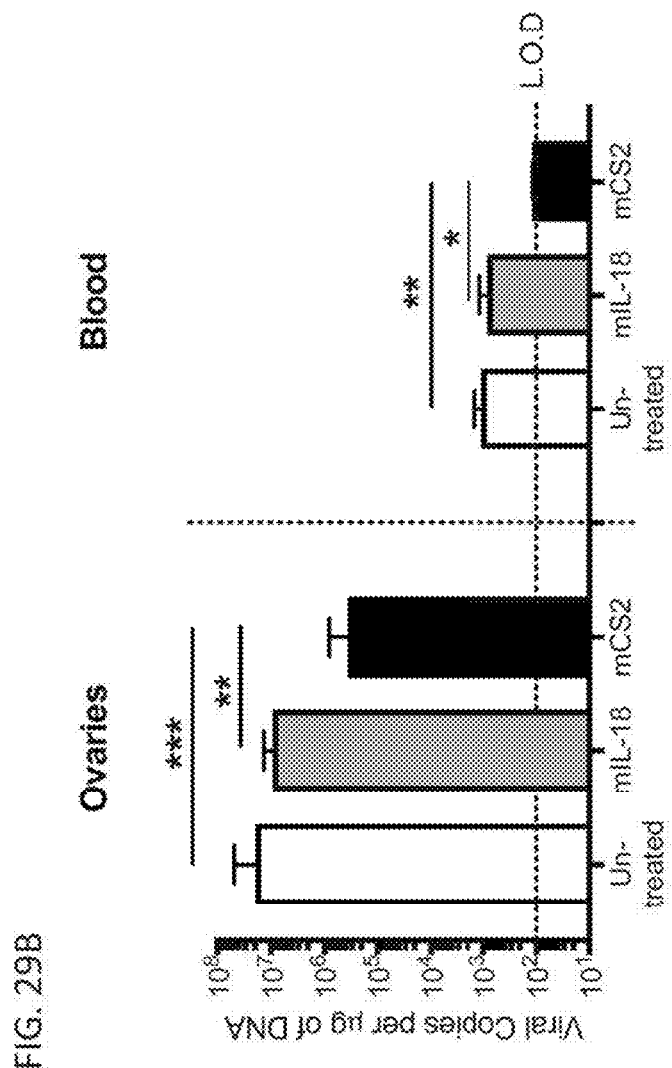

This example demonstrates that DR-IL-18 can be used to treat infectious diseases, such as viral infections. C57BL/6 mice were infected with 106 PFU of Vaccinia virus (VACV) intraperitoneally (IP) and administered 1 mg/kg WT mIL-18 or DR-IL-18 (SEQ ID NO: 61) IP, as summarized in FIG. 29A. Mice were sacrificed and viral titers were measured in the blood and ovaries by RT-PCR on day 3 post-infection. Treatment with DR-IL-18, but not wild type mIL-18, resulted in a significant reduction in viral load in the blood and ovaries (FIG. 29B, * p<0.05,  p<0.01, * p<0.001). The efficacy of DR-IL-18 demonstrated in this model of systemic viral infection suggest that DR-IL-18 can be used to control infectious disease.

Example 6: Second Generation Human DR-IL-18 Variants Induce IL-18R Signaling

The ability of second generation human DR-IL-18 variants SEQ ID NO: 89, SEQ ID NO: 90, SEQ ID NO: 91, and SEQ ID NO: 87 to induce signaling via IL-18 receptor was evaluated using IL-18 HEK-Blue reporter cells. Generation of these DR-IL-18 variants is described in Example 1, and their affinities for IL-18Rα and IL-18BP in Example 2.

HEK-Blue IL-18 sensor cells (InvivoGen) were maintained in complete media (DMEM containing 10% heat-inactivated FBS, 2 mM L-glutamine, 50 U/mL penicillin, and 501.1 g/mL streptomycin) supplemented with 100 μg/mL Normocin, 30 μg/mL Blasticidin, 180 μg/mL Zeocin, and 200 μg/mL Hygromycin. For cytokine activity measurements, 50,000 HEK-Blue IL-18 sensor cells per well of a flat-bottom 96-well plate were incubated with recombinant human IL-18 or the DR-IL-18 variants at successively decreasing concentrations in a total volume of 200 μL of complete media. After 24 hours of incubation at 37° C. and 5% $CO_2$, 30 μL of cell culture supernatant was mixed with 170 μL QUANTI-Blue detection media (InvivoGen) and incubated at 37° C. and 5% $CO_2$ until a color change from pink to blue was detectable (0.5-4 hours). Levels of alkaline phosphatase were quantified using a spectrophotometer at 655 nm wavelength.

Figure 30:
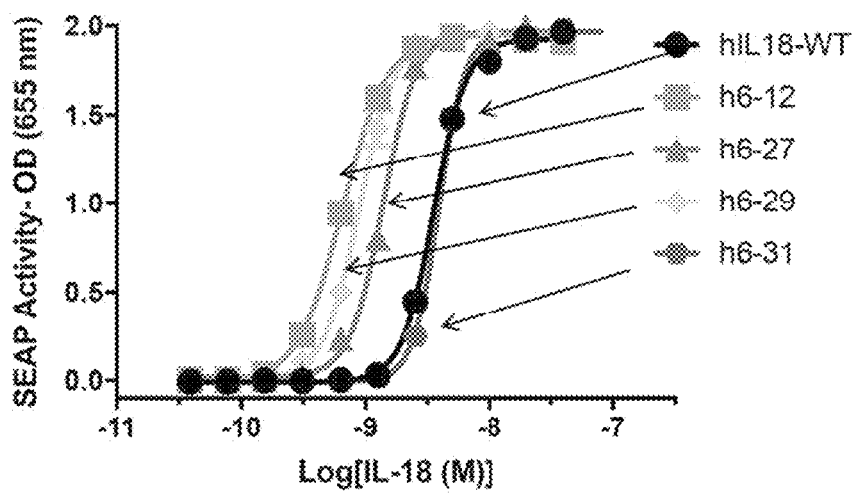
FIG. 30 depicts data demonstrating that the second-generation human DR-IL-18 variants are active.

Human SEQ ID NO: 89, SEQ ID NO: 90, and SEQ ID NO: 91 showed enhanced potency compared to WT hIL-18, whereas SEQ ID NO: 87 exhibited approximately equivalent potency as WT hIL-18 (FIG. 30). The data demonstrate, therefore, that all tested second generation human DR-IL-18 variants actively signal through IL-18R.

Example 7: Cysteine Mutations to Enhance Stability of IL-18 Variants

SEQ ID NO: 89 is more stable than WT IL-18, however, it can form disulfide-linked dimers, as well as intramolecular disulfide bonds. Thus, all combinations of single, double, triple, and quadruple cysteine to serine mutations were generated to test whether mutations at these positions could stabilize IL-18 molecules, and to determine what combination(s) of mutations provided the best stability.

Systematic mutation of all 4 cysteine residues to serine in SEQ ID NO: 89 was performed as shown in Table 13.

Table 13 shows the tested cysteine variants of SEQ ID NO: 89.

| Construct | Cys 38 | Cys 68 | Cys 76 | Cys 127 |
|---|---|---|---|---|
| SEQ ID NO: 89 | C | C | C | C |
| SEQ ID NO: 1 | S | S | S | S |
| SEQ ID NO: 2 | C | S | S | S |
| SEQ ID NO: 3 | S | C | S | S |
| SEQ ID NO: 4 | S | S | C | S |
| SEQ ID NO: 5 | S | S | S | C |
| SEQ ID NO: 6 | S | S | C | C |
| SEQ ID NO: 7 | S | C | S | C |
| SEQ ID NO: 8 | S | C | C | S |
| SEQ ID NO: 9 | C | S | S | C |
| SEQ ID NO: 10 | C | S | C | S |
| SEQ ID NO: 11 | C | C | S | S |
| SEQ ID NO: 12 | S | C | C | C |
| SEQ ID NO: 13 | C | S | C | C |
| SEQ ID NO: 14 | C | C | S | C |
| SEQ ID NO: 15 | C | C | C | S |

Clones SEQ ID NOs: 1-15 (which are variants of SEQ ID NO: 89) were synthesized by Twist and cloned into a *Pichia pastoris* expression vector containing an n-terminal aga2 leader sequence for secretory expression. Plasmids were transformed into *Pichia* and expressed by methanol induction at 30° C. for 60 hours. After induction, supernatants were run on an SDS/PAGE gel and visualized using Spyro-Ruby stain.

Figure 31:
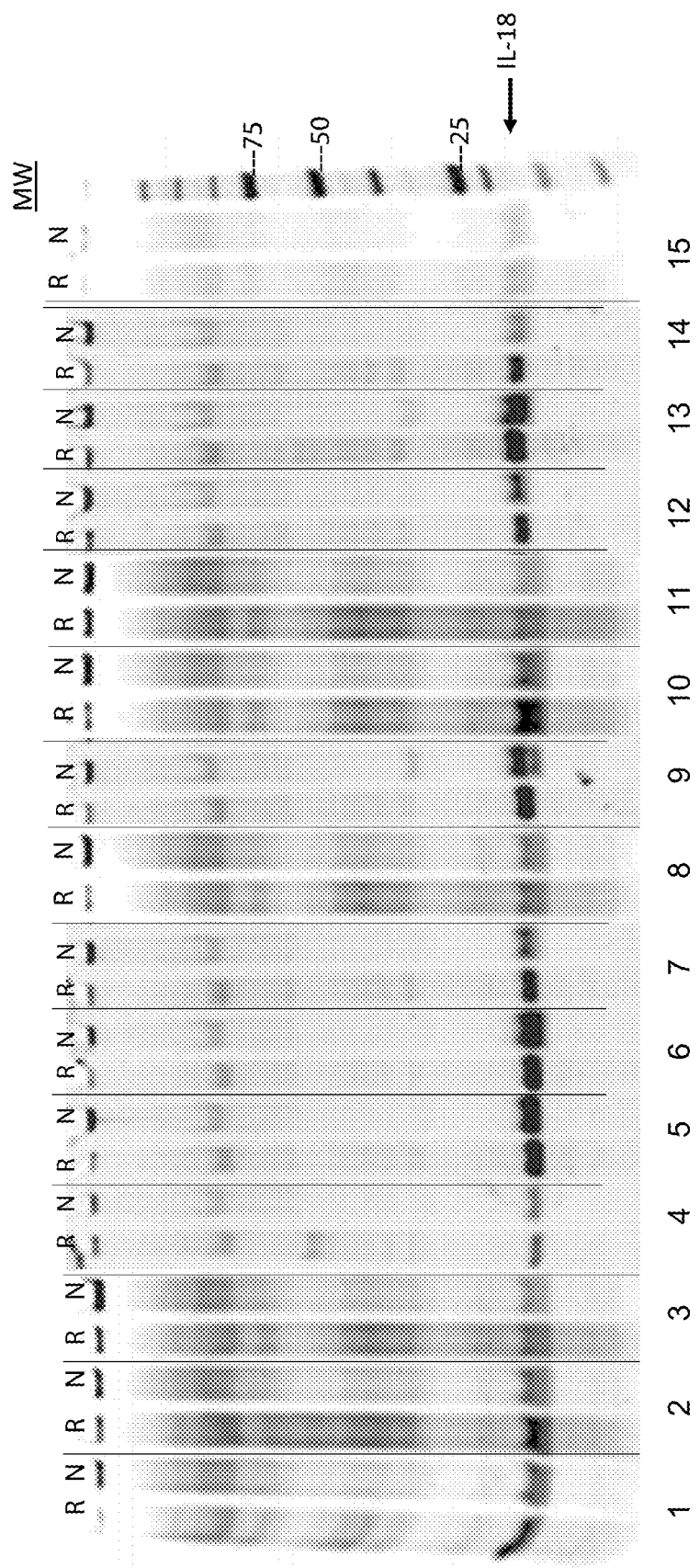
FIG. 31 depicts IL-18 variants with mutations at various cysteine positions that were prepared and then run on an SDS/PAGE gel (visualized using Spyro-Ruby stain). R=Reduced sample; N=Non-reduced sample; MW=Molecular weight. The numbers along the bottom refer to the SEQ ID number (see Table 13).

Clones SEQ ID NO: 5 and SEQ ID NO: 6 gave the best expression without evidence of intermolecular or intramolecular disulfide bond formation (FIG. 31; e.g., dimer band at ~35 kDa in non-reduced samples and lower doublet band below 18 kD, respectively). These two clones contained the combination of C38S and C68S mutations. Any clone with a C127 mutation exhibited lower expression yields. In FIG. 31, R=Reduced sample; N=Non-reduced sample; MW=Molecular weight. The numbers along the bottom refer to the SEQ ID number.

Conclusion: Mutations at positions C38 and C68 (see, e.g., SEQ ID NO: 6) provided the greatest degree of stabilization (e.g., in this case of the DR-IL-18 variant SEQ ID NO: 89). SEQ ID NO: 6 (C38S/C68S) in particularly showed enhanced expression and greatly increased stability, albeit with slightly less (but nevertheless acceptable) potency.

Example 8: Removal of Predicted T Cell Epitope

The C68S mutation generated in Example 7 resulted in a predicted neo-epitope (e.g., T cell epitope). Thus, 6 additional non-immunogenic substitutions at position C68 (SEQ ID NO: 16-21) were constructed and their stability/potency were then tested.

Clones SEQ ID NO: 16-21 containing alternative substitutions (G, A, V, D, E, or N) at C68 were synthesized by Twist and cloned into an *E. coli* cytoplasmic expression vector with an N-terminal 6×His-SUMO tag. *E. coli* were grown in 100 mL Terrific Broth in shake flasks and induced with IPTG at 20° C. for 16 hours. After induction, proteins were purified by an immobilized metal affinity chromatography (IMAC) column; SUMO tag removal was achieved by addition of his-tagged Ulp1 protease. Free his-tagged SUMO and his-tagged Ulp1 were then removed by a second IMAC column. Yields and purity were assessed by SDS/PAGE.

Figure 32:
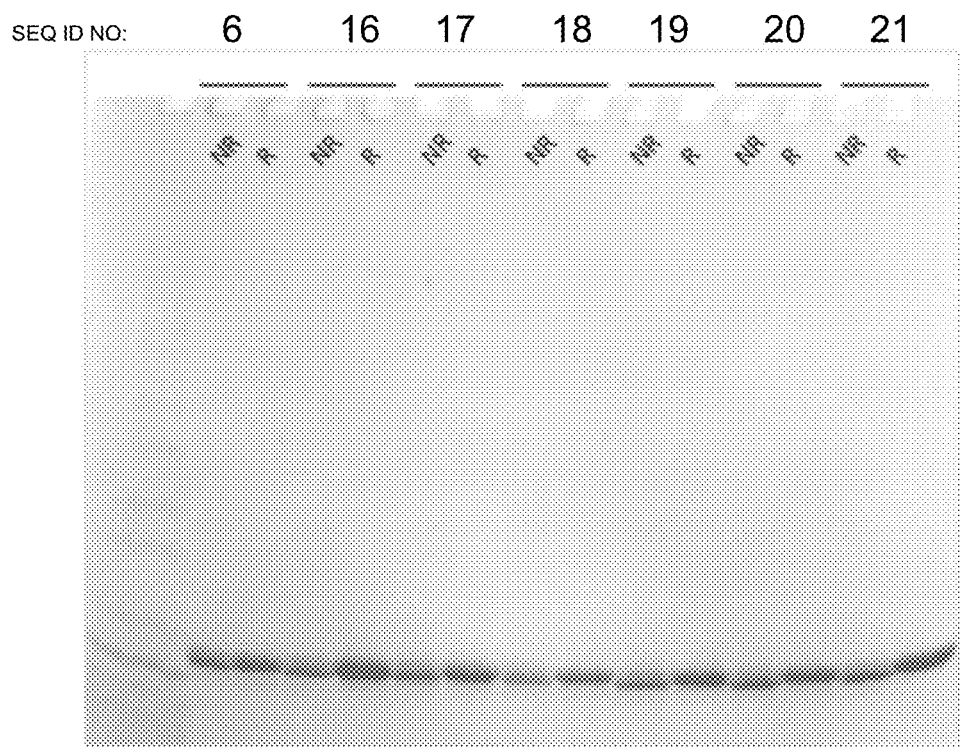
FIG. 32 depicts SDS/PAGE gel analysis of different C38S/C68 mutants that remove a potential T cell epitope on C68S. R=Reduced sample. NR=Non-reduced sample

The variants expressed at high titers (Table 14) and did not show evidence of disulfide bond formation by non-reducing SDS-PAGE gel analysis (FIG. 32; R=Reduced sample; NR=Non-reduced sample).

Table 14 summarizes the additional mutations screened at positions 38 and 68, corresponding sequences, and protein yields of the DR-IL-18 variants.

| Variant | Yield (mg/L) | Rank | SEQ ID NO: |
|---|---|---|---|
| SEQ ID NO: 6 (SEQ ID NO: 89 plus C38S/C68S) | 76 | 7 | 6 |
| SEQ ID NO: 16 (SEQ ID NO: 89 plus C38S/C68G) | 115 | 1 | 16 |
| SEQ ID NO: 17 (SEQ ID NO: 89 plus C38S/C68A) | 93 | 3 | 17 |
| SEQ ID NO: 18 (SEQ ID NO: 89 plus C38S/C68V) | 79 | 6 | 18 |
| SEQ ID NO: 19 (SEQ ID NO: 89 plus C38S/C68D) | 93 | 3 | 19 |
| SEQ ID NO: 20 (SEQ ID NO: 89 plus C38S/C68E) | 91 | 5 | 20 |

-continued

| Variant | Yield (mg/L) | Rank | SEQ ID NO: |
|---|---|---|---|
| SEQ ID NO: 21 (SEQ ID NO: 89 plus C38S/C68N) | 106 | 2 | 21 |

Figure 33:
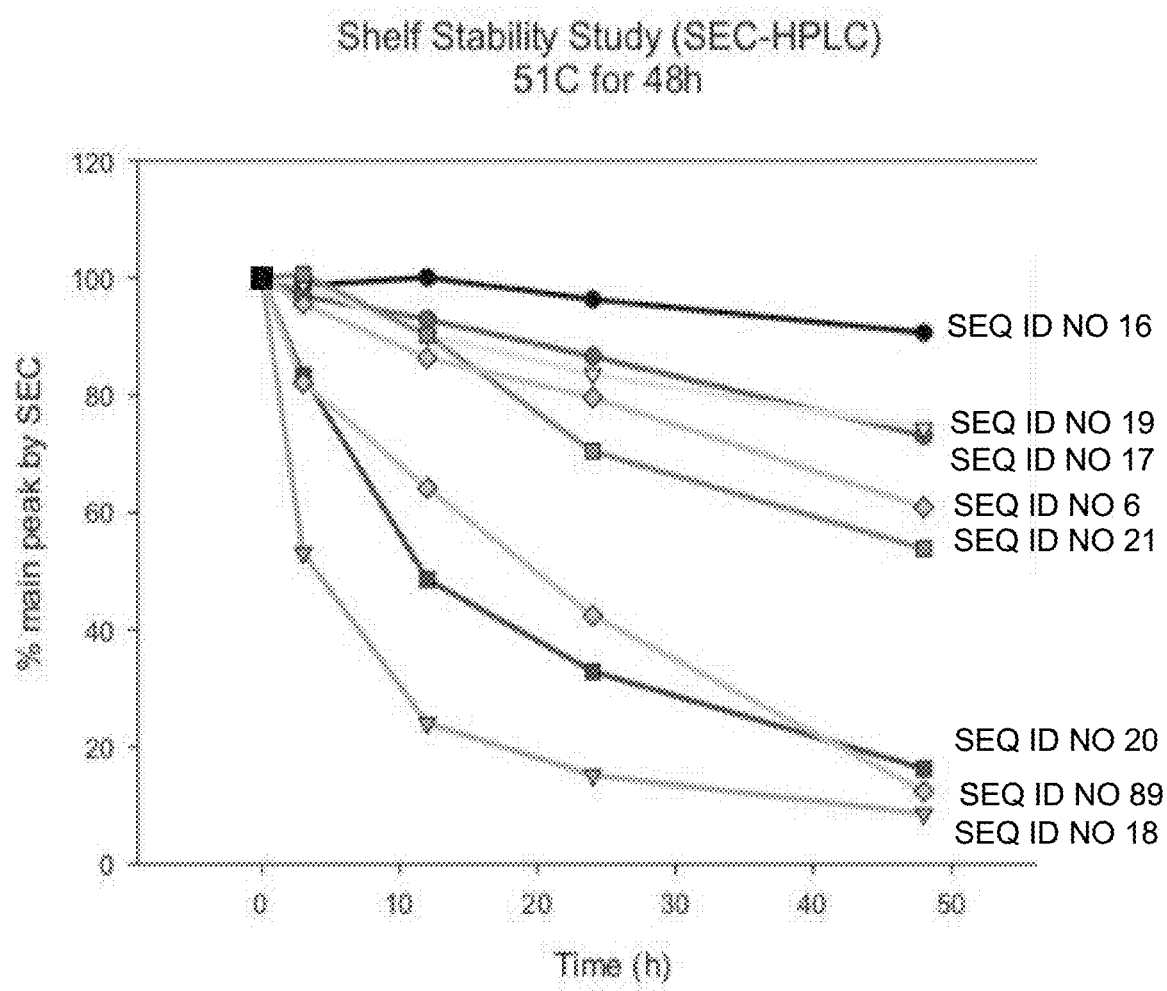
FIG. 33 depicts size-exclusion chromatography data from a shelf stability study for different C38S/C68 mutants that remove a potential T cell epitope on C68S.

As shown in FIG. 33, An accelerated "shelf stability" study was performed to further evaluate the stability of DR-IL-18 variants. Protein preparations were formulated in PBS at 1 mg/mL and held at 51° C. for 48 hours. Samples were taken at several timepoints, filtered through a 0.45 μm filter, and analyzed by size-exclusion chromatography (SEC). The DR-IL-18 variants exhibited a range of stabilities under these conditions, with SEQ ID NO: 16, SEQ ID NO: 19, and SEQ ID NO: 17 showing the greatest retention in the % of the main peak relative to t=0 (FIG. 33). The activity of WT IL-18 versus the DR-IL-18 variants was measured using an IL-18 reporter assay in which IL-18 receptor signaling results in expression of secreted alkaline phosphatase (HEK-Blue IL-18 from InVivoGen). Reporter cells were cultured, stimulated, and secreted alkaline phosphatase levels measured, as described in Example 6. All variants showed increased potency of IL-18R signaling induction compared to WT IL-18, and similar potency to the parent variant SEQ ID NO: 89 (Table 15 and FIG. 34).

Table 15 shows EC50 values of DR-IL18 variants for inducing IL-18R signaling as determined by a HEK-Blue reporter cell line assay (see also FIG. 34)

| Variant | EC50-#1 (M) | EC50-#2 (M) | Rank | SEQ ID NO: |
|---|---|---|---|---|
| hIL-18 WT | 1.45 × 10$^{-9}$ | 1.16 × 10$^{-9}$ | — | 30 |
| SEQ ID NO: 89 | 1.43 × 10$^{-10}$ | 5.44 × 10$^{-11}$ | 2 | 89 |
| SEQ ID NO: 6 | 1.96 × 10$^{-10}$ | 1.30 × 10$^{-10}$ | 7 | 6 |
| SEQ ID NO: 16 | 2.05 × 10$^{-10}$ | 1.54 × 10$^{-10}$ | 8 | 16 |
| SEQ ID NO: 17 | 1.41 × 10$^{-10}$ | 1.09 × 10$^{-10}$ | 4 | 17 |
| SEQ ID NO: 18 | 5.19 × 10$^{-11}$ | 4.48 × 10$^{-11}$ | 1 | 18 |
| SEQ ID NO: 19 | 1.24 × 10$^{-10}$ | 7.90 × 10$^{-11}$ | 3 | 19 |
| SEQ ID NO: 20 | 1.35 × 10$^{-10}$ | 1.62 × 10$^{-10}$ | 6 | 20 |
| SEQ ID NO: 21 | 1.28 × 10$^{-10}$ | 1.24 × 10$^{-10}$ | 5 | 21 |

Table 16 summarizes the rankings of yield, potency, and stability of DR-IL-18 variants determined by the assays in this example

| Variant | Yield | Potency | Stability (51° C. 48 h) | SEQ ID NO: |
|---|---|---|---|---|
| SEQ ID NO: 89 | 8 | 2 | 6 | 89 |
| (SEQ ID NO: 89 plus C38S/C68S) | 7 | 7 | 4 | 6 |
| (SEQ ID NO: 89 plus C38S/C68G) | 1 | 8 | 1 | 16 |
| (SEQ ID NO: 89 plus C38S/C68A) | 3 | 4 | 12 | 17 |
| (SEQ ID NO: 89 plus C38S/C68V) | 6 | 1 | 8 | 18 |
| (SEQ ID NO: 89 plus C38S/C68D) | 3 | 3 | 2 | 19 |
| (SEQ ID NO: 89 plus C38S/C68E) | 5 | 6 | 7 | 20 |
| (SEQ ID NO: 89 plus C38S/C68N) | 2 | 5 | 14 | 21 |

Example 9: Characterization of Stability, Affinity, and Potency of a DR-IL-18 of the Disclosure SEQ ID NO: 19 was selected for further characterization based on its favorable profile of potency, stability, and immunogenicity (see Examples 7 & 8). Additional assays were performed to compare stability, affinity, and potency of SEQ ID NO: 19 (C38S/C68D) to SEQ ID NO: 89 (the parent C38/C68 molecule), and to wild type human IL-18.

Figure 35:
FIG. 35 depicts size-exclusion chromatography data comparing SEQ ID NO: 19 to SEQ ID NO: 89 from a Freeze-thaw study.

The effect of freeze thaw cycles on SEQ ID NO: 19 and SEQ ID NO: 89 was tested. The proteins were formulated in 20 mM acetate pH 5.0, 8% sucrose, 0.1 mM EDTA, and 0.02% Polysorbate (PS) 80. The formulations were then frozen at −80° C. and thawed at 25° C. five times. The proteins were then analyzed by size-exclusion chromatography. A decrease in main peak of SEQ ID NO: 89 was observed, as was an appearance of a dimer peak (indicated by arrow) (FIG. 35, upper panel). In contrast, no or minimal changes were detected for SEQ ID NO: 19 (FIG. 35, lower panel), demonstrating superior stability of this DR-IL-18 variant after exposure to freeze-thaw cycles.

Figure 36:
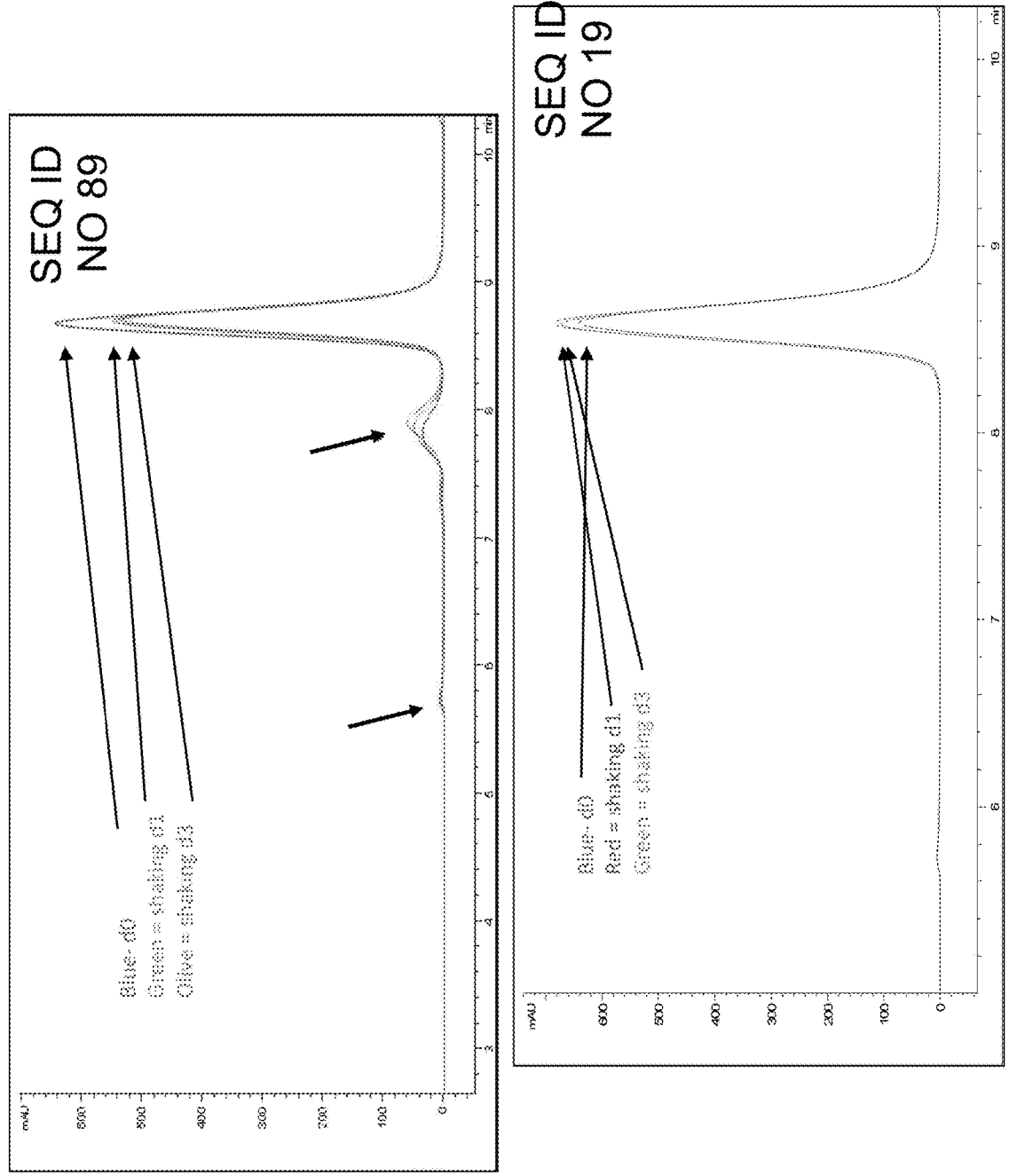
FIG. 36 depicts size-exclusion chromatography data comparing SEQ ID NO: 19 to SEQ ID NO: 89 from an agitation study.

A stability comparison using an agitation study was performed after exposure to agitation at 37° C. SEQ ID NO: 19 and SEQ ID NO: 89 proteins were formulated in 20 mM acetate, pH 5.0, 8% sucrose, 0.1 mM EDTA, and 0.02% PS80. The samples were agitated with shaking at 37° C. for 72 hours. Samples were taken at t=0, 24 (d1), and 72 (d3) hours and analyzed by size exclusion chromatography. A decrease in main peak of SEQ ID NO: 89 was observed, as was a relative increase in dimer/HMW (high molecular weight) species indicated by arrows (FIG. 36, upper panel). In contrast, no or minimal changes were detected for SEQ ID NO: 19. FIG. 36 depicts size-exclusion chromatography data comparing SEQ ID NO: 19 to SEQ ID NO: 89 from the agitation study.

Figure 37A:
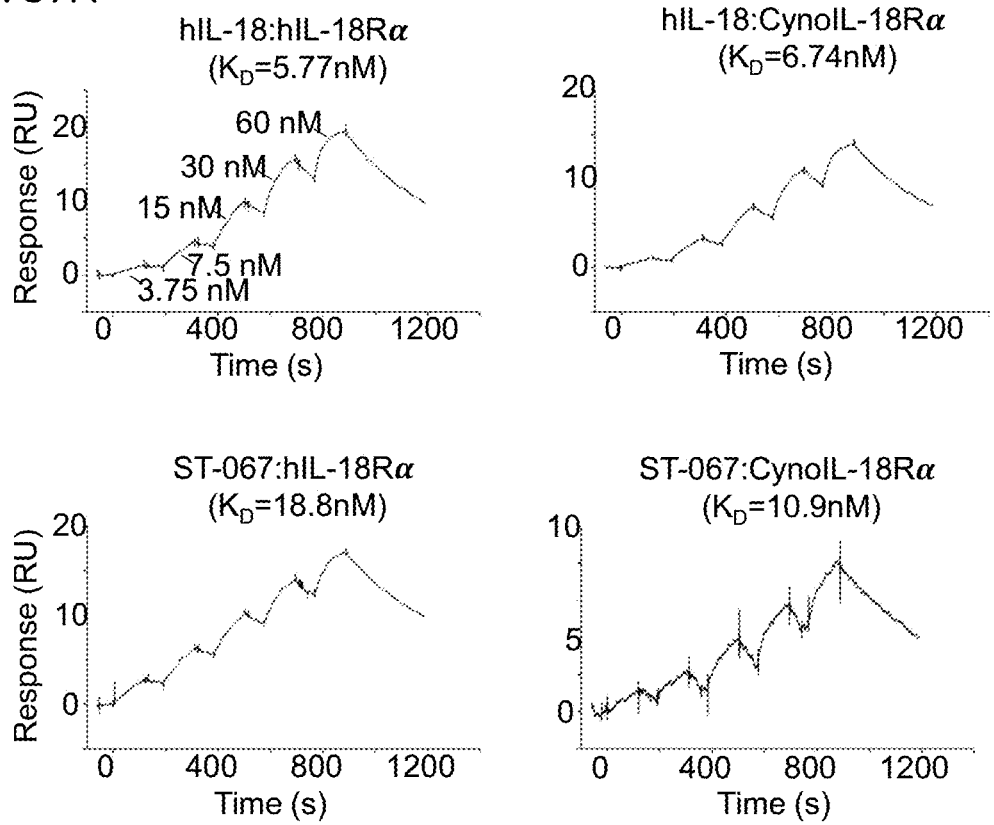
FIG. 37A and FIG. 37B depict results from surface plasmon resonance experiments to test affinity of SEQ ID NO: 19 and wild type human IL-18 for human and cynomolgus monkey IL-18Rα (FIG. 37A) and IL-18BP (FIG. 37B).
Figure 37B:
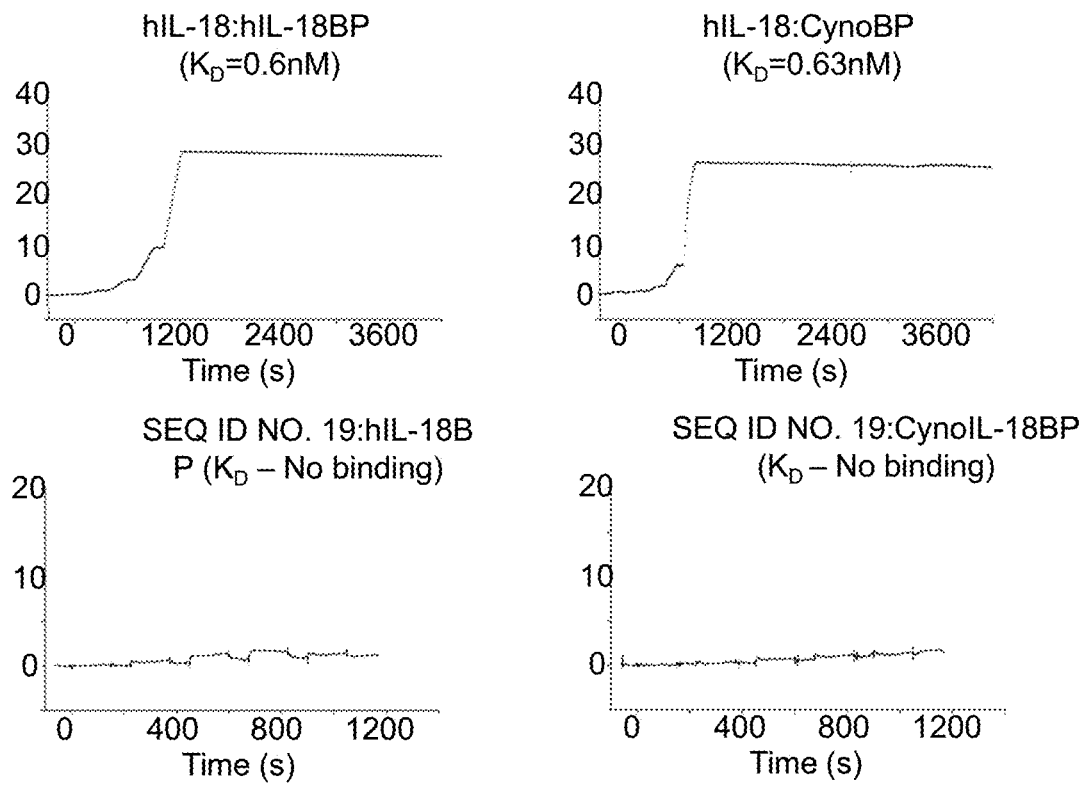

IL-18 receptor affinity. The affinities of human IL-18 and SEQ ID NO: 19 were determined for both human and cynomolgus monkey IL-18Rα and IL-18BP using surface plasmon resonance. Biotinylated receptor proteins were immobilized on a streptavidin capture chip and IL-18 or SEQ ID NO: 19 were applied as the free analyte. Single-cell kinetics were used to determine binding. WT hIL-18 and SEQ ID NO: 19 had similar binding affinity for IL-18Rα in this assay (FIG. 37A). However, WT IL-18 bound IL-18BP with extremely high affinity (<1 nM), whereas SEQ ID NO: 19 exhibited no detectable binding to IL-18BP (FIG. 37B).

Figure 38:
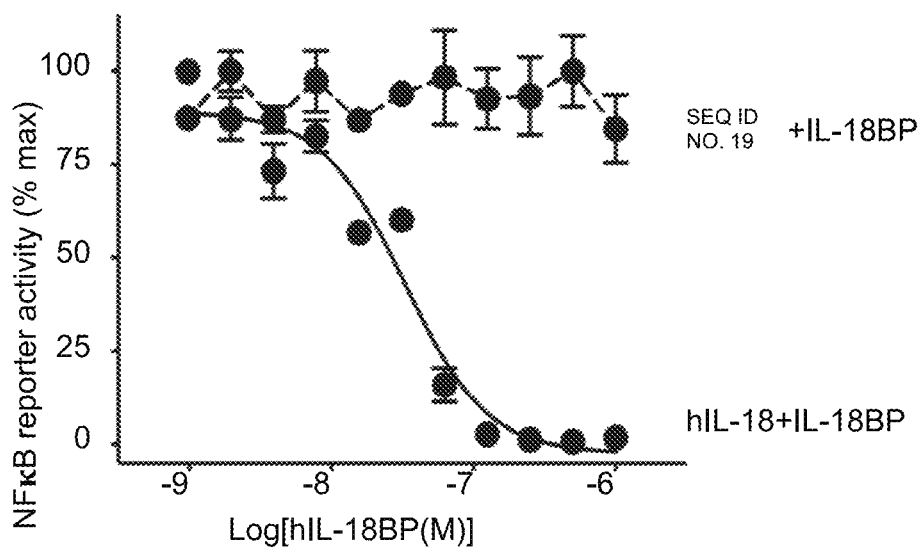
FIG. 38 depicts results from an IL-18BP resistance assay. WT hIL-18 was potently inhibited by addition of IL-18BP, whereas SEQ ID NO: 19 retained strong signaling capacity at all concentrations of IL-18BP.

The activity of WT IL-18 and SEQ ID NO: 19 in the presence of IL-18BP was evaluated using an IL-18 reporter assay in which IL-18 receptor signaling results in expression of secreted alkaline phosphatase (HEK-Blue IL-18 from InVivoGen). Reporter cells were cultured and secreted alkaline phosphatase levels measured as described in Example 6, except that WT IL-18 or SEQ ID NO: 19 were applied to HEK-BLUE IL-18 reporter cells at a fixed concentration of 1.0 or 0.1 ng/mL, respectively, in the presence of a range of IL-18BP concentrations, from 10$^{-6}$ to 10$^{-9}$ M. Downstream secreted embryonic alkaline phosphatase (SEAP) activity was measured according to the manufacturer's instructions. WT hIL-18 was potently inhibited by addition of IL-18BP, whereas SEQ ID NO: 19 retained strong induction of IL-18R signaling at all concentrations of IL-18BP (FIG. 38).

Example 10: Dosing of IL-18 Polypeptides

A first dosing study was performed to compare efficacy and tolerability of dosing with DR-IL-18 once per day, every other day, two times per week, and 1 time per week in a cancer model This study was carried out in mice, and therefore used SEQ ID NO: 61, which is a mouse DR IL-18 variant polypeptide (i.e., a mouse IL-18 that binds to and activates mouse IL-18R but is not inhibited by mouse IL-18BP). The human variants were not used because the human IL-18 protein does not cross-react with mouse IL-18R (i.e., it does not bind to and active mouse IL-18R).

Figure 39:
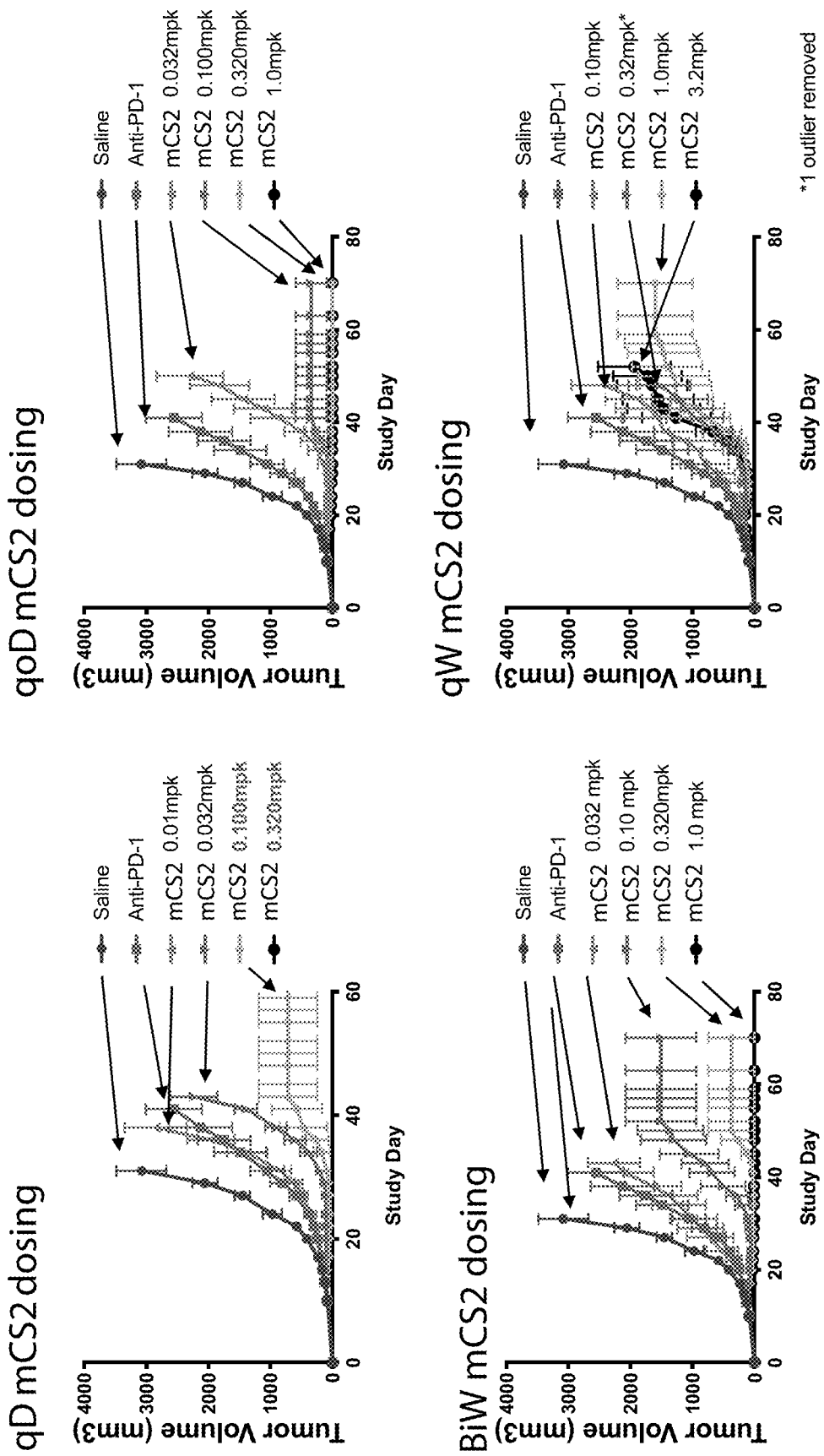
FIG. 39 depicts tumor growth data in mice from dosing experiments (using the mouse DR IL-18 variant SEQ ID NO: 61).

250,000 MC38 cells were implanted subcutaneously and treatment was initiated once tumors were at 80 mm³. Dosing was qD (once daily), qoD (once every other day), BiW (Twice Weekly,), or qW (Once Weekly), given subcutaneously for 2 weeks. All doses and schedules showed efficacy (FIG. 39). Most regimens were well tolerated. However, daily dosing showed toxicity at 0.1 mpk (mg/kg) and higher. Tumor outgrowth generally occurred after treatment was discontinued. Tumor growth curves are depicted with the last point carried forward once endpoint was reached. Curves were terminated once 50% or more animals reached endpoint. Results: Daily dosing at 0.1 mpk (mg/kg) and higher appeared to be toxic and was associated with weight-loss. DR-IL-18 was effective at all other dosing schedules. Efficacy was superior to anti-PD-1 therapy, which was evident at all doses tested and even at once-weekly dosing.

A second dosing experiment was performed to compare dosing once per week versus twice per week in a cancer model. As above, SEQ ID NO: 61 was used because these studies were carried out in mice. 250,000 MC38 cells were implanted subcutaneously and treatment was initiated once tumors reached 100 mm³ (day 7). Animals were administered four doses at a frequency of once per week (qW) or two doses at a frequency of once every two weeks (q2W) by subcutaneous injection. A 100-fold range of doses (from 0.01 to 1.0 mg/kg) was tested. All doses and schedules showed efficacy, even at 0.01 mg/kg. The maximum effective dose (MaxED) was about 0.32 mg/kg at both qW and q2W dosing (FIG. 40). Strong DR IL-18 efficacy was observed even with infrequent pulse-dosing. ven once every 2 week dosing was more effective that twice per week anti-PD-1 treatment. This was very surprising given the dosing requirements of other interleukins, (e.g., IL-2/IL-15, IL-10) that require half-life extension or frequent dosing (e.g., TID dosing of IL-2).

Figure 41A:
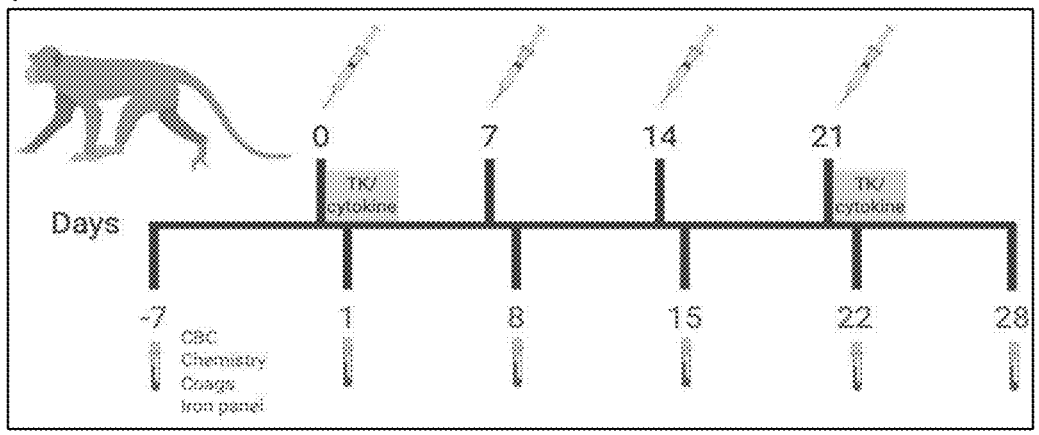
FIG. 41A and FIG. 41B depict dosing toleration experiments in primates (Cynomolgus macques) using a DR IL-18 variant (SEQ ID NO: 89 in this case).
Figure 41B:
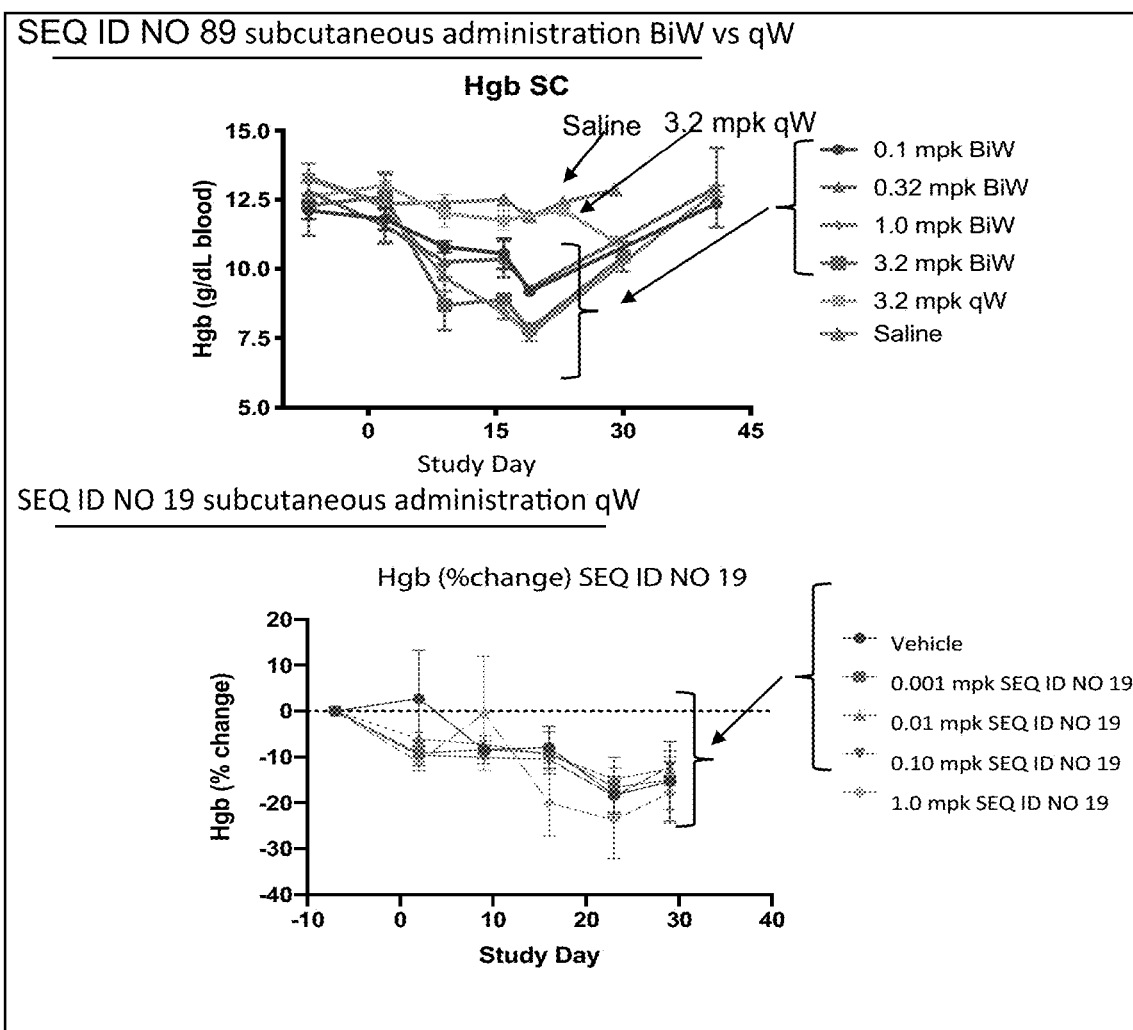

Monkey tolerability assays were performed to determine how well tolerated DR-IL-18 was at various doses, and using once weekly (qW) or twice weekly (BiW) dosing schedules. Cynomolgus macques were treated with DR-IL-18 (SEQ ID NO: 89 or SEQ ID NO: 19) subcutaneously, weekly (qW) or twice weekly (BiW), with doses ranging from 0.001 mg/kg to 3.2 mg/kg. Blood was drawn periodically and hemoglobin levels in the blood measured. An illustrative dosing and sampling regimen is provided in FIG. 41A. The results showed dosing frequencies more than 1x/week elicited undesirable decreases in hemoglobin concentrations in the study. Cynomolgus macques treated with SEQ ID NO: 89 subcutaneously twice per week exhibited a dose-dependent reduction in hemoglobin relative to saline-treated monkeys (FIG. 41B, upper panel). By contrast, once weekly treatment with DR-18 (SEQ ID NO: 89 or SEQ ID NO: 19), even up to 3.2 mg/kg, did not result in decreased hemoglobin levels relative to control saline treatment (FIG. 41B, upper panel and lower panel).

Example 11: Producing DR-IL-18 Variant in Bacteria (*E. coli*)

Process 1: Cell-Free In Vitro Cleavage with SUMO-Protease

In this example, DR-IL-18 (SEQ ID NO: 89 in this case) was tagged with a His-tagged SUMO tag, expressed in *E. coli*, and a His-tagged SUMO protease was used to cleave the SUMO tag, producing an active IL-18 protein.

Figure 42A:
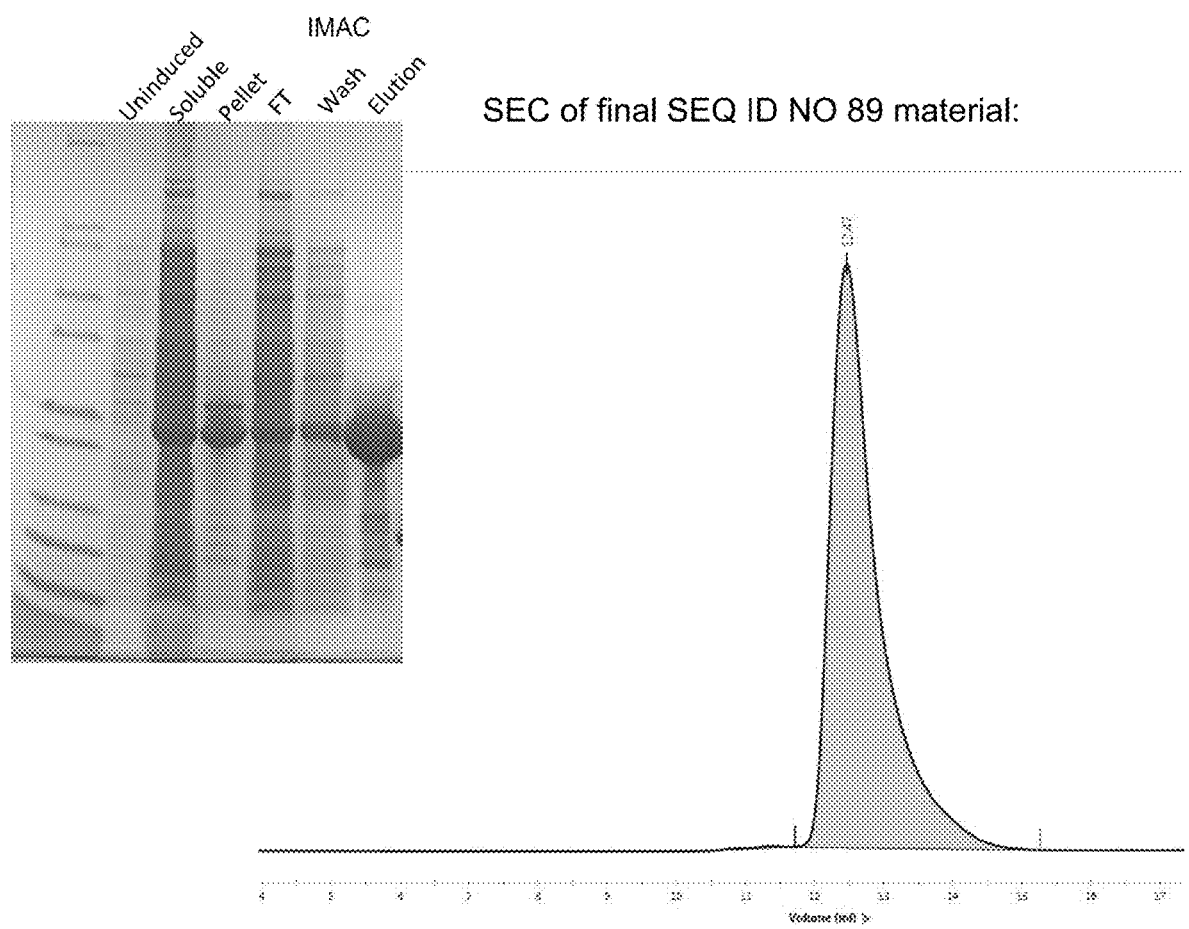
FIG. 42A and FIG. 42B depicts production and purification of IL-18 polypeptides (in this case DR IL-18 SEQ ID NO: 89) using cell-free SUMO protease to cleave an N-terminal SUMO tag off of the IL-18 protein.
Figure 42B:
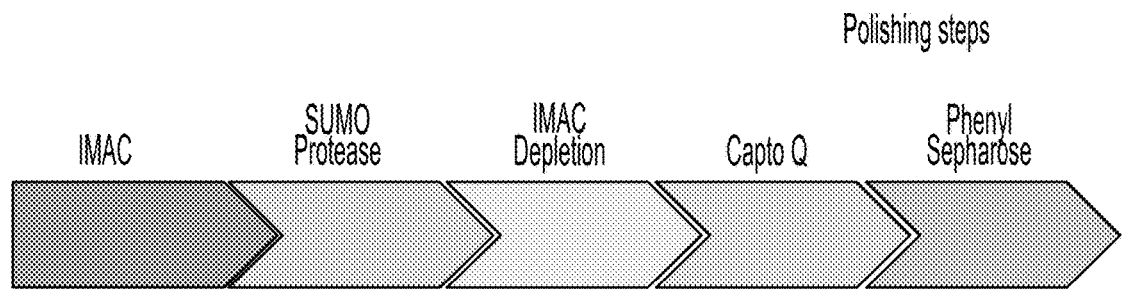

DR-IL-18 was cloned into an *E. coli* cytoplasmic expression vector with an N-terminal 6×His-SUMO tag. *E. coli* were grown in 100 mL Terrific Broth in shake flasks and induced with IPTG at 20° C. for 16 hours. Initial capture of the fusion protein (His-tagged SUMO tag fused to the DR-IL-18) from bacterial lysate was performed using immobilized metal affinity chromatography (IMAC). This was efficient, with high step-yield at >90% purity. After the cleavage reaction with His-tagged Ulp1 SUMO protease to remove the SUMO tag, the removed His-tagged SUMO tag and the His-tagged SUMO protease were efficiently removed using IMAC in depletion mode. Yields and purity were assessed by SDS/PAGE. The resulting protein was >90% pure after this step (often >95%) (FIG. 42A). Cleavage was efficient and can be conducted at ratios of 1:500 or greater. Note: Expression at lower temperature (21° C.) greatly increases soluble yields (this particular study was performed at 26° C.). FIG. 42B summarizes the processing and purification steps.

Figure 43A:
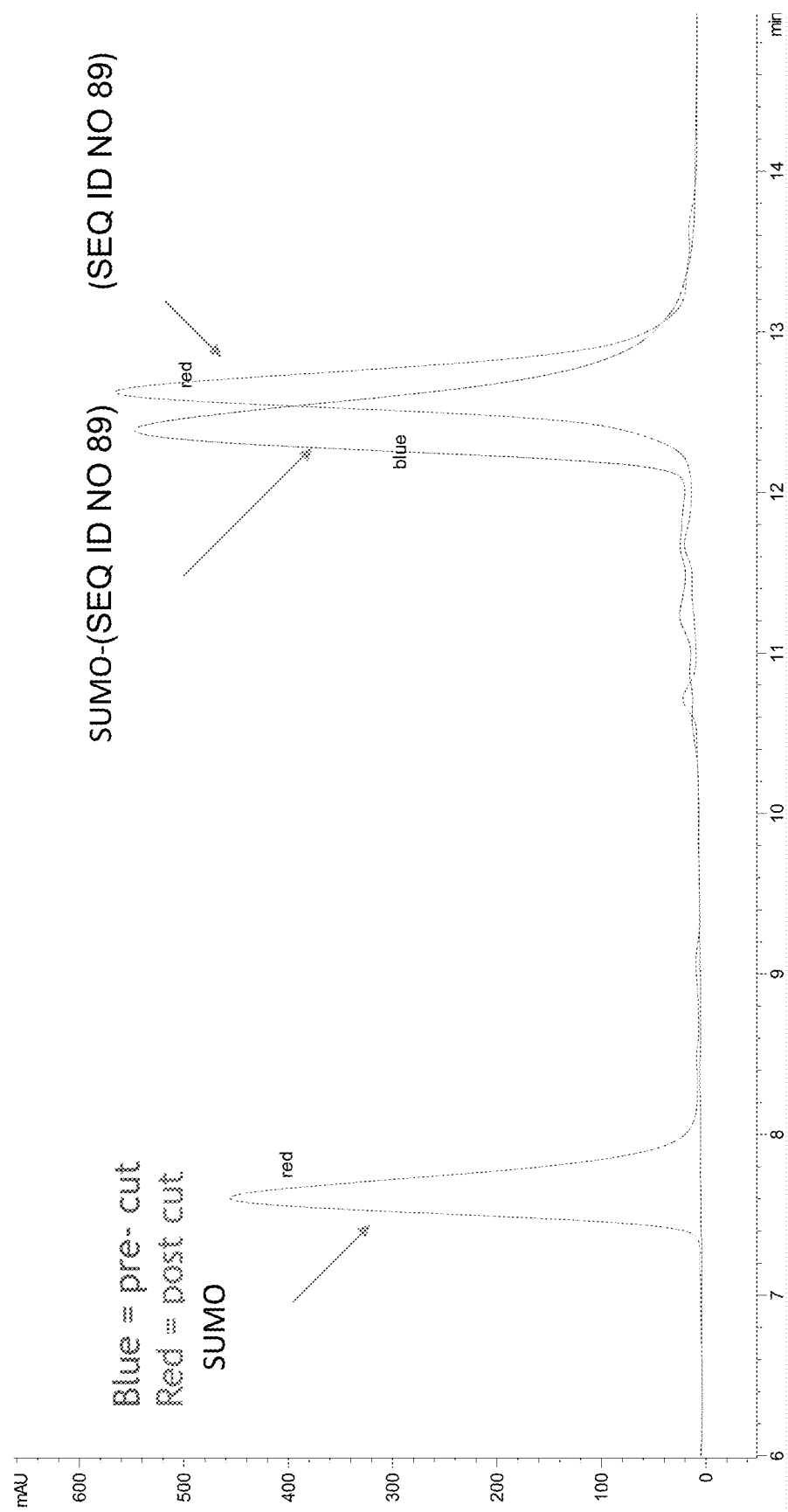
FIG. 43A and FIG. 43B depicts results from monitoring SUMO protease cleavage by RP-HPLC.
Figure 43B:
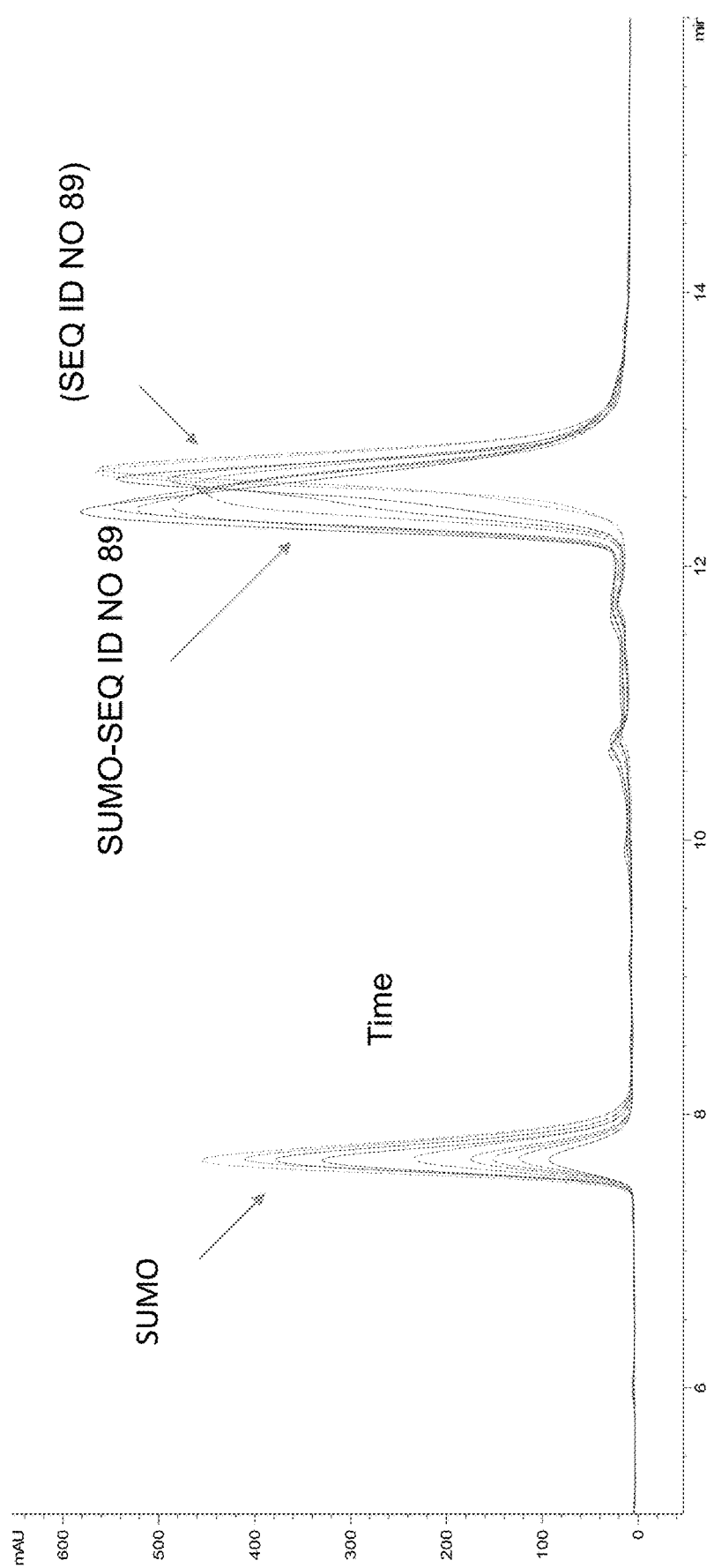

FIG. 43A and FIG. 43B provide results of the cleavage reaction, as monitored by RP-HPLC assays. The RP-HPLC assay can be used to calculate step-yield and titers, as well.

Process 2: Cleavage Inside of a Bacterial Cell with Co-Expressed SUMO-Protease

Figure 44:
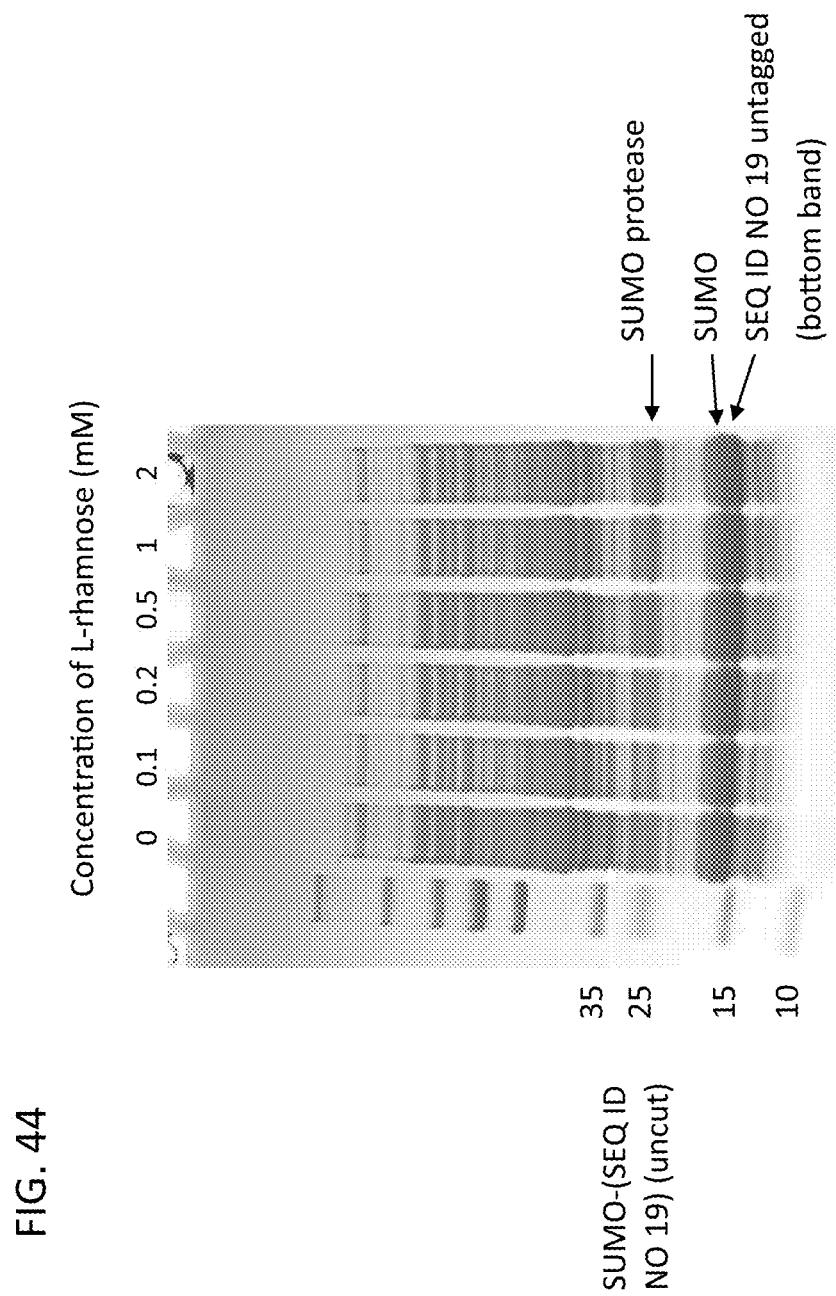
FIG. 44 depicts production and purification of IL-18 polypeptides (in this case DR IL-18 SEQ ID NO: 19) using exogenously provided SUMO protease to cleave the N-terminal SUMO tag off of the IL-18 protein inside of a bacterial cell (in this case *E. coli*).

This example demonstrates that SUMO tagged IL-18 (in this case the stabilized DR IL-18 SEQ ID NO: 19) and SUMO-protease can be co-expressed in bacteria (in this case *E. coli*), resulting in removal of the SUMO tag via cleavage inside of the bacterial cells. The SUMO protease was expressed under control of a rhamnose-inducible promoter. Rhamnose induction of the protease allowed for separate timing and tunable induction of the protease relative to the IL-18 (e.g., DR-IL-18). *E. coli* expressing the SUMO-tagged DR-IL-18 were treated with 0.1 to 2 mM L-rhamnose, resulting in induction of SUMO protease expression, and cleavage of the SUMO tag to liberate untagged SEQ ID NO: 19 (FIG. 44). Note: On a non-reducing gel, the SUMO tag runs above DR-18; some cleavage can be observed without rhamnose treatment due to promoter "leakiness".

Figure 45:
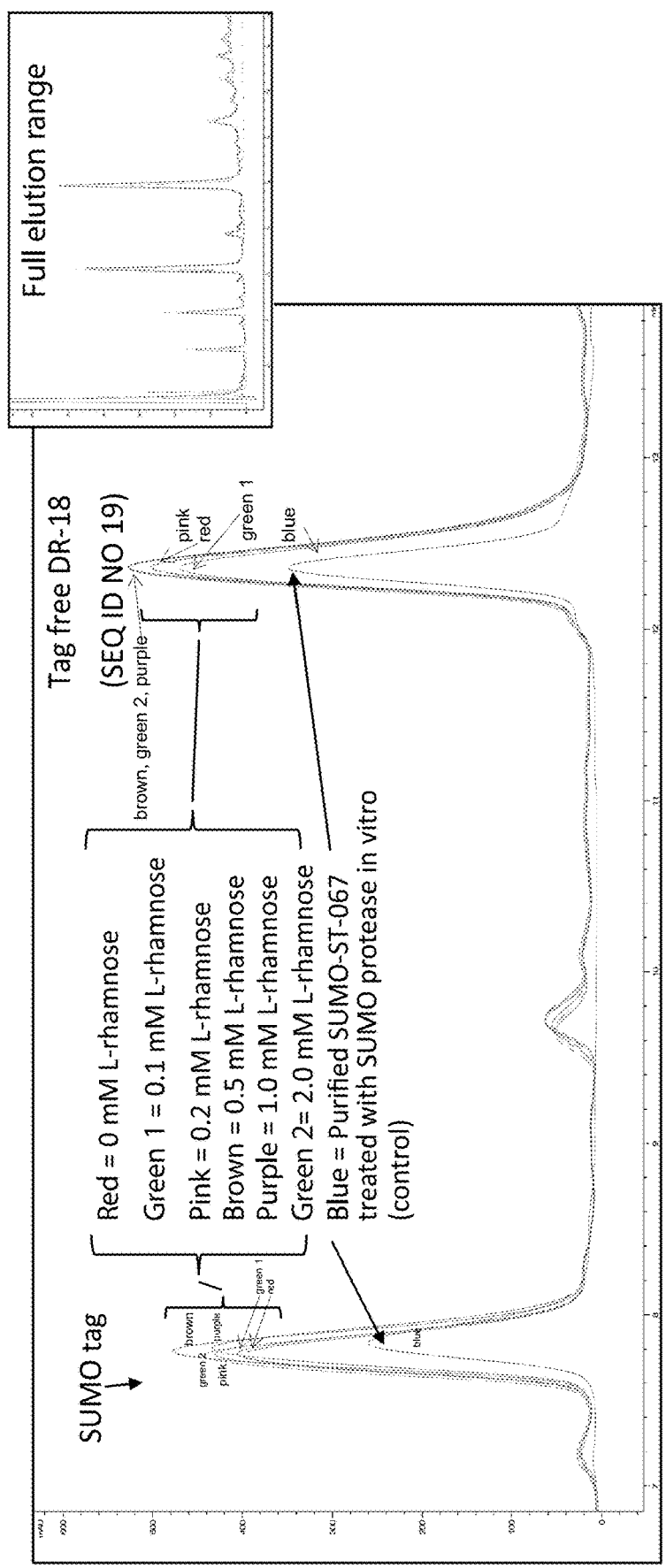
FIG. 45 depicts RP-HPLC data from monitoring the SUMO protease cleavage reaction inside of bacterial cells.

Total expression of the cleaved product was comparable to the SUMO-fusion (after accounting for SUMO mass). In vivo (in bacterial cells) cleavage was monitored using RP-HPLC (FIG. 45, showing cleavage of the SUMO tag for rhamnose-treated cultures). 0.2-0.5 mM L-rhamnose appeared to provide good results in these particular experiments.

Successful results have been obtained by placing SUMO-protease downstream of the IL-18 (e.g., DR-IL-18) in a bicistronic format, as well as by expressing the SUMO protease from a separate promoter (e.g., from a separate plasmid), e.g., under an inducible promoter such as the rhamnose-inducible promoter, as in this example.

A downstream process can be used to capture and purify the cleaved product (i.e., the active DR-IL-18 protein) (see, e.g., Example 12).

In vivo (in bacterial cells) cleavage was monitored using RP-HPLC. FIG. 45 provides the chromatographs for in vivo (in bacterial cells) cleavage. Note: "Leakiness" of the rhamnose promotor created enough SUMO protease to cleave most of the fusion protein. 0.2-0.5 mM L-rhamnose appeared to be the optimal concentration range in these particular experiments.

Example 12: Producing IL-18 Variant Using Yeast (*P. pastoris*)

Figure 46:
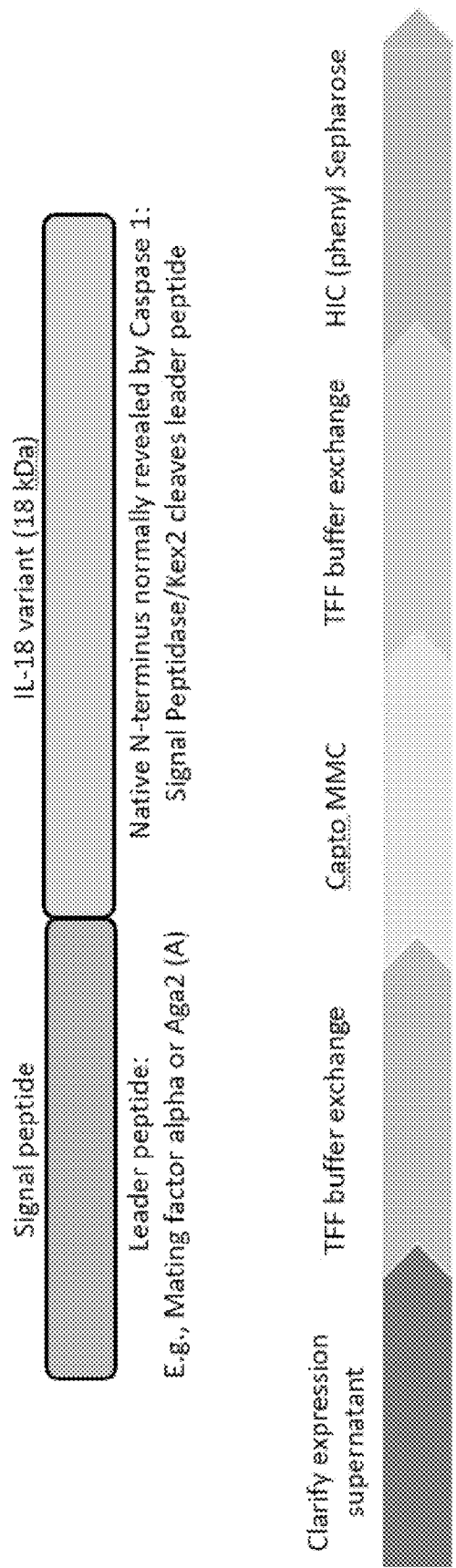
FIG. 46 depicts a Schematic of a yeast (e.g., *Pichia pastoris*) secretion system to produce IL-18 variants.

A system for expression and secretion of DR-IL-18 was developed using *Pichia Pastoris* (yeast). A signal peptide was added to the DR-IL-18 and cloned into an expression vector (FIG. 46, top). This system results in secretion of the DR-IL-18 and cleavage of the signal peptide by Signal Peptidase/Kex2, avoiding the need for a protease to remove a tag.

Figure 47:
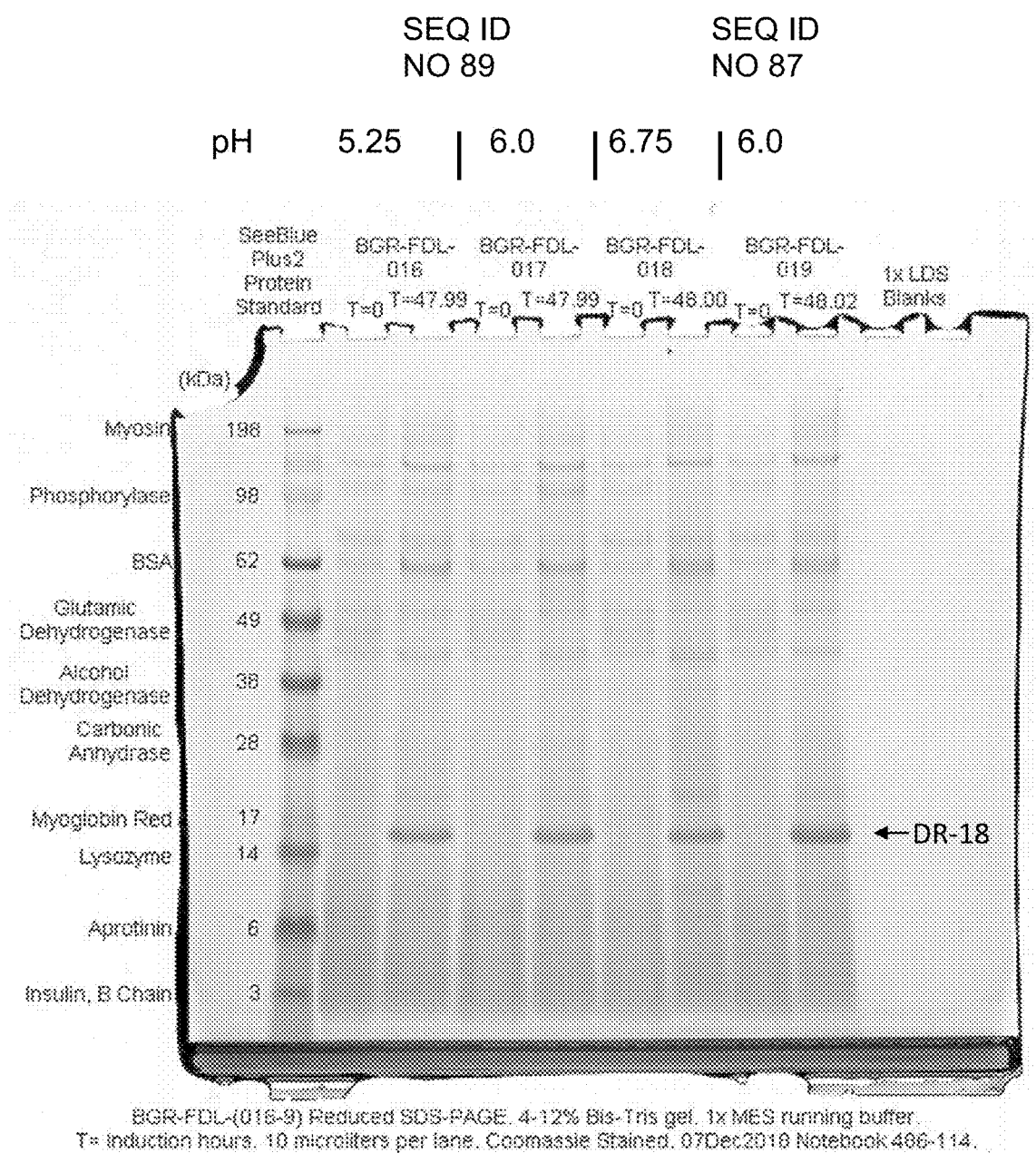
FIG. 47 depicts a representative reduced SDS-PAGE gel showing expression of DR-18 (IL-18 variants—in this case SEQ ID NO: 89 and SEQ ID NO: 87.

In this illustrative example, the DR-IL-18 variants SEQ ID NO: 89 and SEQ ID NO:87 were tested. The DR-IL-18 variants were synthesized by Twist Biosciences and cloned into a *Pichia pastoris* expression vector containing an n-terminal aga2 leader sequence for secretory expression. Plasmids were transformed into *Pichia* and expressed by methanol induction at 30° C. for 60 hours, resulting in production of DR-IL-18 at high titers, including >1 g/L in some cases. DR-IL-18 with the active native N-terminus (tyrosine in the case of human IL-18) was directly secreted into the media (FIG. 47).

Figure 48:
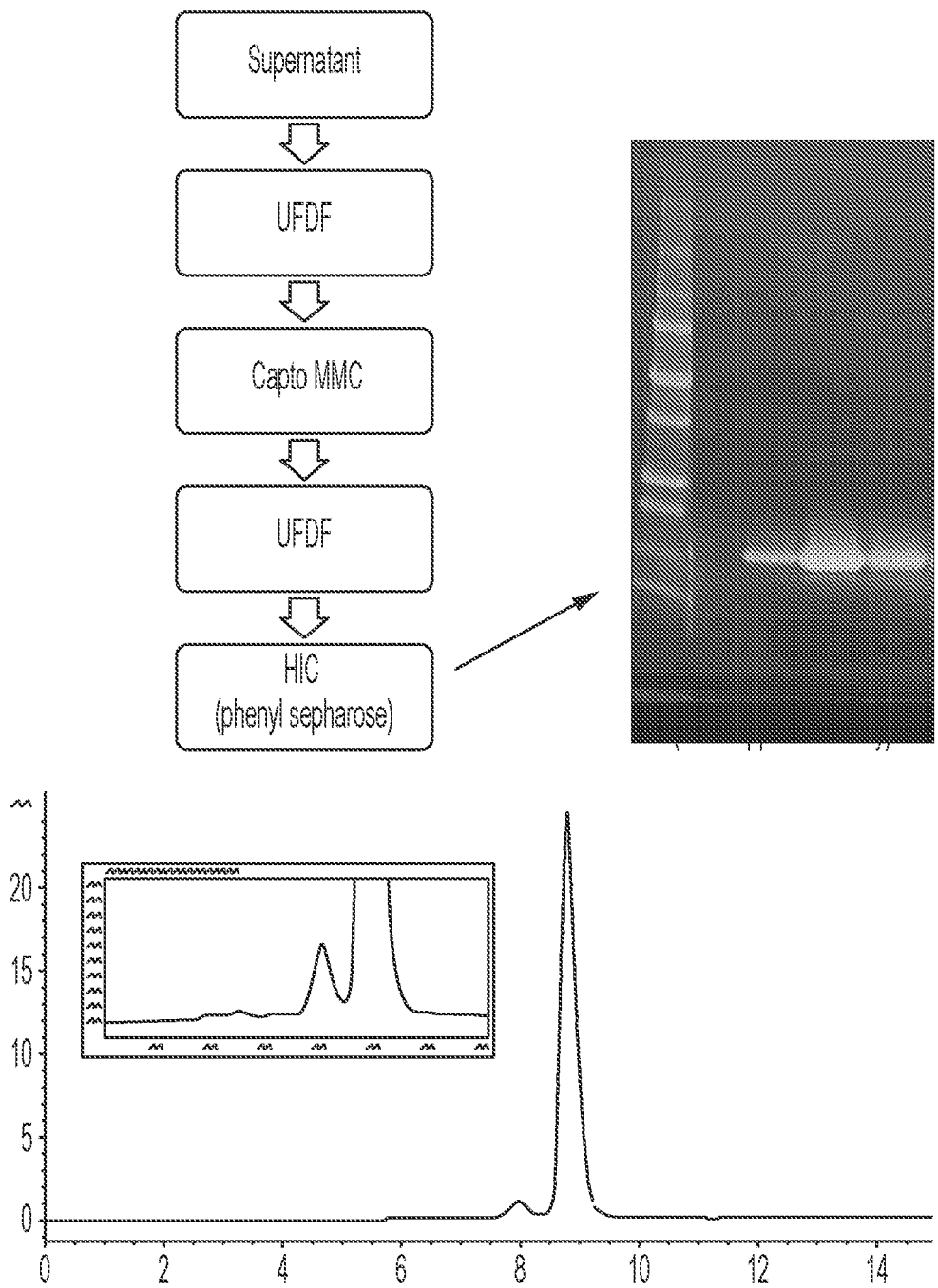
FIG. 48 depicts a 2-chromatographic-step process (and associated data) that facilitated tagless purification of IL-18 from a yeast secretion expression system (in this case *P. Pastoris*).

A 2-chromatographic-step process was used for tagless purification of IL-18 (in this case the DR IL-18 SEQ ID NO: 89) to >97% purity, 96% monodispersity, <2 EU/mg (FIG. 46 and FIG. 48; UFDF=Ultrafiltration (UF) and diafiltration (DF). "Capto MMC" is a multimodal salt-tolerant resin for capture and intermediate purification of proteins from large feed volumes by packed bed chromatography. HIC=Hydrophobic Interaction Chromatography (e.g., depicted in this figure is phenyl sepharose HIC).

DR-18 purification was performed. FIG. 48 shows SDS-PAGE gel showing purification of DR-18 (e.g., from P. Pastoris or from bacteria). A 2-chromatographic-step process facilitated tagless purification of IL-18 (in this case the DR IL-18 SEQ ID NO: 89) to >97% purity, 96% monodispersity, <2 EU/mg. UFDF=Ultrafiltration (UF) and diafiltration (DF). "Capto MMC" is a multimodal salt-tolerant resin for capture and intermediate purification of proteins from large feed volumes by packed bed chromatography. HIC=Hydrophobic Interaction Chromatography (e.g., depicted in this figure is phenyl sepharose HIC).

Example 13: Generation of a Cell Bank for Production of a DR IL-18 Variant

This example demonstrates generation of a plasmid system and cell bank for production of SEQ ID NO: 19, a DR IL-18 variant of the disclosure with mutations at positions C38 and C68.

A dual plasmid system was generated for expression of SEQ ID NO: 19 in *E. coli*. For full activity, IL-18 (e.g., DR IL-18, such as SEQ ID NO: 19) can require its native N-terminus rather than an N-terminal methionine. Accordingly, a plasmid was designed using a small ubiquitin-related modifier (SUMO) expression system which utilizes a SUMO leader sequence from *Saccharomyces cerevisiae* at the N-terminus, such that the SUMO leader can be cleaved off by the SUMO protease, ULP1.

Expression of the DR IL-18 with SUMO leader peptide was driven by a T7 promotor in a high copy plasmid to maximize expression. A pD451-SR plasmid backbone was used. This plasmid contains a kanamycin resistance gene, a pUC origin of replication, and has the T7 promotor present to express the SEQ ID NO: 19 protein after isopropyl (3-d-1-thiogalactopyranoside (IPTG) induction.

A second lower copy number plasmid was used for expression of the SUMO protease driven by a rhamnose promoter, which is relatively weak, such that expression can be tuned by varying the amount of rhamnose added to the culture. The SUMO protease gene was cloned into the plasmid pD883-SR. This plasmid contains a chloramphenicol resistance gene, a p15a origin of replication, and has the rhamnose promoter as part of the rhaBAD regulatory sequence to enable controlled expression of the SUMO protease after rhamnose induction.

Both plasmids were transformed simultaneously into the *E. coli* strain T7 Express, and clones with the plasmids were selected using agar plates containing both kanamycin and chloramphenicol. The T7 Express is a strain that allows for very high expression of genes utilizing the T7 promotor after IPTG induction. It contains the T7 polymerase in the lactose operon and contains no lambda prophage. The system of two plasmids with different origins of replication and different antibiotic resistance genes allows both plasmids to be maintained in a stable manner and tested for independently. The SUMO protease and the SUMO leader peptide both have N-terminal His-tags, thereby allowing their removal by immobilized metal affinity chromatography. This expression system was designed to allow very high expression of correctly processed SEQ ID NO: 19 that has been properly cleaved by the SUMO protease, for example, at 2-3 g/L.

*E. coli* strain T7 Express competent cells were transformed with 1 μL of each of the two plasmids. The transformed cells were grown overnight on LB agar plates supplemented with 50 μg/mL of kanamycin (KAM) and 50 μg/mL of chloramphenicol (CAM) at 37° C. A single, well grown colony, was inoculated into 10 mL of medium and grown overnight at 30° C. A cell bank was prepared by mixing equal volumes of overnight culture with 30% (v/v) sterile glycerol solution, then the mixed solution was aliquoted into suitable vials (at 200 μL), and stored at −20° C.

One vial was thawed, subcultured onto TBA (Terrific Broth Agar) plates containing 50 μg/mL of KAM and 50 μg/mL of CAM, and incubated at 30° C. for 20 to 24 hours. A single colony was inoculated into 50 mL of medium and incubated in a shaker-incubator overnight at 30° C., 220 rpm. This culture was inoculated at 0.2 to 0.3 OU at OD600 nm and incubated in a shaker incubator at 30° C., 220 rpm. The final culture OD600 nm was 1.9 (before glycerol). A new cell bank was prepared by mixing of 56 mL of cell culture with 8 mL of 80% sterile glycerol (10% final concentration) and aliquoting into 50 cryo-vials (1 mL each). The vials were labeled and stored directly in a −80° C. freezer. This cell bank was tested before and after freezing, demonstrating stability of the plasmids and retention of a high concentration of viable cells (Table 17).

TABLE 17

Viability, purity, and plasmid stability of cell bank samples before and after freezing

|  | Before freezing | After freezing |
| --- | --- | --- |
| Viable cell count | 7.7 × 10^8 CFU/mL | 7.3 × 10^8 CFU/mL |
| Purity | Conforms | Conforms |
| Plasmid stability | 98% | 97% |

One vial was gently thawed at 2° C. to 8° C. for ≤30 min. After thawing, 1 mL of cell suspension was transferred into a 0.5 L shake flask with prepared TB medium with added salt and antibiotics (kanamycin and chloramphenicol). This culture was incubated for 15 to 18 h at 37° C. with an agitation rate of 300 rpm until target optical density of ≥5.0 OU was reached. After that, the required amount of cell suspension from the first growth was transferred to a 1 L shake flask for further cultivation for at least 3 to 4 hours until a required optical density of 1.50 OU to 3.50 OU was reached. 160 mL of the second growth cell culture was combined and mixed with 160 mL of 50% glycerol solution and 1.0 mL of cell suspension was aliquoted into sterile cryogenic vials and labelled appropriately. Vials from this second cell bank were frozen at −80±10° C. In-process controls of the cell bank preparation were culture purity after freezing, total viable cell count after freezing, and plasmid stability after freezing. The tests showed that no bacteriophage contamination was present, and a a plasmid copy number of 288.15. The IL-18 encoding plasmid retained 100% sequence identity to the originally designed sequences, and restriction enzyme digestion yielded expected plasmid fragment sizes indicating no changes to the plasmid structure or insert sequences.

Example 14: Ellman's Titration for Free Thiols

This example demonstrates that native SEQ ID NO: 19, a DR IL-18 variant of the disclosure with mutations at positions C38 and C68, contains very little free cysteine.

Ellman's Reagent (5,5'-dithio-bis-[2-nitrobenzoic acid]/DTNB) was used to estimate sulfhydryl groups in a sample by comparing to a standard curve of a sulfhydryl-containing compound. DTNB, upon reaction with free thiols of proteins, generates a colored product, 2-nitro-5-thiobenzoate (TNB) that absorbs at 412 nm. For every mole of thiol that reacts with DTNB, one mole of TNB is produced, and by quantifying the amount of TNB, the number of free cysteines present per mole of protein can be estimated. The results of the assay show that very little free cysteine is present in native SEQ ID NO: 19 (Table 18), consistent with mutation of C38 and C68 to other residues, a lack of solvent exposure of the two remaining cysteines in SEQ ID NO: 19, and reduced formation of intramolecular and intermolecular disulfide bonds observed for polypeptides with such mutations in Examples 7 and 8.

TABLE 18

Free thiol group determination in samples of SEQ ID NO: 19.

| Sample | Avg intensity | Protein, mol/ sample | Free thiol groups, mol/protein, mol | SD | CV, % | Protein, mol/free thiol, mol |
|---|---|---|---|---|---|---|
| RS, dilution −3.0 | 3804.5 | 1.8E−08 | 0.0041 | 71.4 | 1.88 | 242.96 |
| RS, dilution −2.0 | 5756.5 | 2.69E−08 | 0.0042 | 154.9 | 2.69 | 239.15 |
| RS, dilution −1.5 | 7220.5 | 3.59E−08 | 0.0039 | 143.5 | 1.99 | 253.50 |
| Mean | | | 0.0041 | | | 245.20 |

Example 15: Formulation Development

Formulation development was performed to select drug substance and drug product formulation for toxicology and clinical studies. The SEQ ID NO: 19 drug substance formulation development process included evaluation of optimal pH, protein concentration, and excipient screening. Formulation was intended to support the following product attributes: liquid form, sterility, suitability for subcutaneous injection, and a shelf life of at least 24 months at 2° C. to 8° C. or −20° C. temperature. Formulations were assessed through stability studies. The details of stability studies are mentioned below:

1. Stressed samples were compared to initial samples for possible alterations of protein integrity at selected pH value. Stress conditions were 40±2° C./25% RH for up to 3 weeks.
2. Freeze-thaw cycles were performed to assess sensitivity of the protein to repeated freezing and thawing. Up to five freeze-thaw cycles were performed at the following conditions: −80° C. for up to 16 hours, then at room temperature for 8 hours.
3. Agitation with shaking was performed to assess protein degradation pathways and rates (25° C./60% RH for up to 2 weeks at 150 rpm). SEQ ID NO: 19 drug substance formulation development studies are summarized in Table 19.

TABLE 19

| Step | Formulation Composition | pH | Protein concentration (mg/mL) | Material batch No. | Stability study types | Quality attributes |
|---|---|---|---|---|---|---|
| | | Study No. 1 | | | | |
| Selection of an optimal pH | 10 mM L-Histidine/L-Histidine-HCl, 240 mM Sucrose, 0.2% (w/v) Polysorbate 20, pH 6.0 | 6<br>6.5<br>7 | 10<br>20<br>15<br>20<br>10<br>20 | P57-BTPH-097-2004M-262 | Stressed conditions (40 degrees C.) for 1 and 3 weeks | Fragments/soluble aggregates by SE-HPLC and non-reducing SDS-PAGE Protein concentration measured at A280 Oxidation by RP-HPLC |

TABLE 19-continued

| Step | Formulation Composition | pH | Protein concentration (mg/mL) | Material batch No. | Stability study types | Quality attributes |
|---|---|---|---|---|---|---|
| | | Study No. 2 | | | | |
| Lead formulation selection | 10 mM His/His-HCl, 8% sucrose, 0.1 mM EDTA, 5 mM L-Methionine, 0.02% (w/v) Polysorbate 80 | 6.5 | 30 | P57-BTPH-097-2006M-402 | Accelerated conditions (25 degrees Celsius) 3. Freeze-thaw 5 cycles | Protein concentration turbidity, measured at A280, A340/A4350 Charge isoforms by AEX-HPLC Oxidation by RP-HPLC Sub-visible particles by MFI |
| | 10 mM L-Histidine/L-Histidine-HCl, 8% Sucrose, 5 mM L-Methionine, 0.1 mM EDTA, 0.02% w/v Polysorbate 80 | 6.5 | 20 | | | |
| | 10 mM L-Histidine/L-Histidine-HCl, 8% Sucrose, 5 mM L-Methionine, 0.1 mM EDTA, 0.02% w/v Polysorbate 80 | 7 | 30 | | | |

Abbreviations:
AEX-HPLC = anion exchange liquid chromatography;
MFI = micro-flow imaging;
RP-HPLC = reverse phase high performance liquid chromatography;
PS80—polysorbate 80;
SDS-PAGE = sodium dodecyl sulphate polyacrylamide gel electrophoresis;
SE-HPLC = size exclusion liquid chromatography.

During Study 1, six formulations with different concentration and pH were compared at thermal stress conditions. Formulations with lower pH were less stable after 3 weeks at 40±2° C./25% RH. Thus, pH 6.5 and 7.0 were chosen for Study 2. Also, protein purity during Study 1 did not show a dependency on protein concentration. Thus, protein concentrations of 20 mg/mL and 30 mg/mL were used in Study 2. During Study 2, additional excipients were added to the formulations, ethylenediaminetetraacetic acid and L-methionine, to maintain optimal protein stability and prevent its oxidation. No differences between the formulations were observed at all tested conditions. According to the formulation development results, the final selected composition was 30 mg/mL of SEQ ID NO: 19 protein in 10 mM L-histidine/L-histidine-HCl, 8% sucrose, 0.02% (w/v) polysorbate 80 at pH-6.5.

Example 16: Human Administration to Determine Treatment Dose

The primary objective of this study is to determine the MTD and the RP2D of SEQ ID NO: 19 in patients with relapsed or refractory solid tumors. The secondary objectives are to evaluate the overall safety and tolerability of SEQ ID NO: 19 and to characterize the pharmacokinetic (PK) profile of SEQ ID NO: 19 as a single agent. Investigators monitor the safety of the study by looking at: the incidence of DLTs and adverse effects (AEs), changes in clinical laboratory parameters, vital signs, ECG testing and parameters, physical examination, and incidence of anti-SEQ ID NO: 19 antibodies. Investigators additionally monitor the possibility of patients developing cytokine storms, since SEQ ID NO: 19 is an immune agonist.

Patients with relapsed or refractory solid tumors are enrolled in a dose escalation study to determine the maximum tolerated dose (MTD) and the recommended Phase 2 dose (RP2D) of SEQ ID NO: 19. Eligible patients are 18 years or older and diagnosed with solid tumors that have disease progression through standard therapy or for whom standard of care therapy that prolongs survival is unavailable or unsuitable. Patients receive a subcutaneous (SC) dose of SEQ ID NO: 19 once a week for 28 days (one cycle). The dose can range from 30 µg of SEQ ID NO: 19 per kg of patient (µg/kg) to 1200 µg/kg. Further dose escalations can include ranges from 1200 µg/kg to 1.5 mg/kg. The initial testing dose is 30 µg/kg. Any dose within those two ranges is testable within the study to determine the MTD and RP2D. Dose escalation follows an mTPI model with cohorts of 2 patients initially with a primary dose limiting toxicities (DLT) monitoring period of 28 days following the first dose. Patients are monitored for 7 days after the first dose of a new dose before new patients may receive that new dose amount.

The mTPI model uses a simple beta-binomial hierarchical model, where the decision rules are based on calculating the unit probability mass (UPM) of 3 dosing intervals corresponding to under, proper, and over-dosing. The mTPI method calculates the UPMs for the 3 dosing intervals, and the one with the largest UPM implies the corresponding dose-finding decision and that decision provides the dose level to be used for future patients. The target toxicity probability rate is 25% with an acceptable DLT interval of 20-30%. If the initial two patients in the first cycle experience no DLTs then the enrollment of the next cohort begins at the next dose level in the next cycle. If one of the two initial patients experience a DLT, then the dose will be lowered to the next lowest dose. If no additional DLTs are observed at the lower dose level when the cohort expands to 6 patients, dose escalation will be resumed. Once the first DLT is observed, only ≤33% dose increments will be applied to all the remaining cohorts.

The estimation of the MTD at the end of study derives from isotonic regression. Specifically, the MTD estimate is the dose level which isotonic estimate of DLT rates is less than or equal to 25% and it is the dose level for which the isotonic estimate of the DLT rate is closest to the target DLT rate. Dose escalation is stopped if the maximum sample size of 42 patients has been achieved, 6 to 12 patients have been enrolled at a dose level that is predicted to be the MTD, or all doses explored appear to be overly toxic and the MTD cannot be determined.

Blood samples for PK analysis are collected from all and investigators use these samples to calculate the PK parameters. Blood samples are collected on days 1, 2, 3, 8, 15, and 22 of cycle 1, days 1 and 15 of cycle 2, and on day 1 of alternate cycles staring with cycle 3 until study completion. Patients also provide a blood sample 30 days after the last dose of SEQ ID NO: 19 and before the patients start anew therapy. PK parameters $C_{max}$, $t_{max}$, $AUC_{0-1}$, $AUC_\tau$, $AUC_{0-\infty}$, and $t_{1/2}$ are estimated from plasma concentration-time data using non-compartmental analysis if possible. Additional PK parameters may be considered if appropriate. Investigators also monitor patients are the development of anti-drug antibodies using the blood samples.

Example 17: Efficacy Testing in Patients with Solid Tumors

The primary objective of this study is to evaluate the anti-tumor activity of SEQ ID NO: 19 at the RP2D in relapsed solid tumor cohorts. The primary efficacy endpoint for this study is confirmed objective response looking at patients that have a complete response (CR) or partial response (PR) by RECIST 1.1. Secondary efficacy endpoints will include: best objective response, disease control rate (DCR) (CR, PR, or stable disease (SD) for >12 weeks), duration of response (DOR), time to response (ToR), progression free survival (PFS), and overall survival (OS).

Patients with distinct solid tumor types are enrolled in a study to evaluate the efficiency of SEQ ID NO: 19 treatment in these tumor types. Eligible patients are 18 years or older and have one the of following solid tumor types: melanoma, renal cell carcinoma (RCC), triple-negative breast cancer (TNBC), non-small cell lung cancer (NSCLC), squamous cell carcinoma of the head and neck (SCCHN), or Microsatellite Instable High (MSI-Hi) tumors. Within 28 days of the first dose, patients undergo a mandatory tumor biopsy. For RCC, TNBC, NSCLC, and MSI-Hi, up to 25 patients may be enrolled for each tumor type; metastatic melanoma and SCCHN cancer types can enroll up to 28 patients per cancer type. If investigators do not observe any objective response in a cancer type cohort, then no additional patients will be enrolled into that cohort.

Patients receive one subcutaneous dose of SEQ ID NO: 19 once a week for 28 days (one cycle). The dose is the RP2D from the human dose escalation study. Patients undergo disease assessments every 8 or 12 weeks during the study and may include computed tomography (CT) scans, magnetic resonance imaging (MRI) scans, and/or positron emission tomography (PET) scans. Investigators evaluate all target and nontarget lesions from the scans using Response Evaluation Criteria in Solid Tumors (RECIST 1.1). Prior to the start of cycle 2, patients undergo a second mandatory tumor biopsy. If disease progression occurs while in the study, patients may request an optional biopsy at the time of disease progression.

Blood samples for PK analysis are collected from all patients and investigators use these samples to calculate the PK parameters. Blood samples are collected on days 1 and 15 of cycle 1, days 1 and 15 of cycle 2, and on day 1 of alternate cycles staring with cycle 3 until study completion. Patients also provide a blood sample 30 days after the last dose of SEQ ID NO: 19 and before the patients start a new therapy. PK parameters $C_{max}$, $t_{max}$, $AUC_{0-1}$, $AUC_\tau$, $AUC_{0-\infty}$, and $t_{1/2}$ are estimated from plasma concentration-time data using non-compartmental analysis if possible. Additional PK parameters may be considered if appropriate. Investigators also monitor patients are the development of anti-drug antibodies using the blood samples.

Amino Acid Sequences

```
Wild-type IL-18 amino acid sequences
HUMAN Interleukin-18 (mature form)
                                  (SEQ ID NO: 30)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED

MOUSE Interleukin-18 (mature form)
                                  (SEQ ID NO: 31)
NFGRLHCTTAVIRNINDQVLFVDKRQPVFEDMTDIDQSASEPQTRLIIY

MYKDSEVRGLAVTLSVKDSKMSTLSCKNKIISFEEMDPPENIDDIQSDL

IFFQKRVPGHNKMEFESSLYEGHFLACQKEDDAFKLILKKKDENGDKSV

MFTLTNLHQS

Q14116|IL18_HUMAN Interleukin-18 (uncleaved
precursor)
                                  (SEQ ID NO: 32)
MAAEPVEDNCINFVAMKFIDNTLYFIAEDDENLESDYFGKLESKLSVIR

NLNDQVLFIDQGNRPLFEDMTDSDCRDNAPRTIFIISMYKDSQPRGMAV

TISVKCEKISTLSCENKIISFKEMNPPDNIKDTKSDIIFFQRSVPGHDN

KMQFESSSYEGYFLACEKERDLFKLILKKEDELGDRSIMFTVQNED

P70380|IL18_MOUSE Interleukin-18 (uncleaved
precursor)
                                  (SEQ ID NO: 33)
MAAMSEDSCVNFKEMMFIDNTLYFIPEENGDLESDNFGRLHCTTAVIRN

INDQVLFVDKRQPVFEDMTDIDQSASEPQTRLIIYMYKDSEVRGLAVTL

SVKDSKMSTLSCKNKIISFEEMDPPENIDDIQSDLIFFQKRVPGHNKME

FESSLYEGHFLACQKEDDAFKLILKKKDENGDKSVMFTLTNLHQS
```

Generation 1 Human Interleukin-18 Decoy-Resistant Variants Amino Acid Sequences

```
hCS1    YFGKLESKLSVIRNLNDQVLFIDQGNRPLFEDMTDSDCRDNAPRTIFIIS
        TYKDSQPRGKAVTISVKCEKISTLSCENKIISFKEMNPPDNIKDTKSDIIF
        FQRDVPGHKHKMQFESSSYEGYFLACEKERDLFKLILKKEDELGDRSI
        MFTVQNED (SEQ ID NO: 34)
```

| | |
|---|---|
| hCS2 | YFGKLESKLSVIRNLNDQVLFIDQGNRPLFEDMTDSDCRDNAPRTIFIIS<br>TYKDKQPRAKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTIQNED (SEQ ID NO: 35) |
| hCS3 | RFGKLESKLSVIRNLNDQVLFIDQGNRPLFEDMTDSDCRDNAPRTIFIIS<br>TYKDSQPRGKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTVQNED (SEQ ID NO: 36) |
| hCS4 | RFGKLESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FQRNVPGHKYKMQFESSSYEGYFLACEKERDLFKLILKKEDELGDRSI<br>MFTVQNED (SEQ ID NO: 37) |
| hC4 | YFGKLESQLSVIRNLNDQVLFIDQGNRPLFEDMTDSDCRDNAPRTIFIIS<br>TYKDQPRTKAVTISVKCEKISTLSCENKIISFKEMNPPDNIKDTKSDIIF<br>FORRVPGHHNKMQFESSSYEGYFLACEKERDLFKLILKKEDELGDRSI<br>MFTVQKED (SEQ ID NO: 38) |
| hA8 | YFGKLESRLSVIRNLNDQVLFIDQGNRPLFEDMTDSDCRDNAPRTIFIIS<br>KYKDKQPRAQAVTISVKCEKISTLSCENKIISFKEMNPPDNIKDTKSDIIF<br>FQRDVPGHKHKMQFESSSYEGYFLACEKERDLFKLILKKEDELGDRSI<br>MFTIQNED (SEQ ID NO: 39) |
| hD6 | YFGKLESRLSVIRNLNDQVLFIDQGNRPLFEDMTDSDCRDNAPRTIFIIS<br>DYKDKQPRAXAVTISVKCEKISTLSCENKIISFKEMNPPDNIKDTKSDIIF<br>FQRDVPGHKHKMQFESSSYEGYFLACEKERDLFKLILKKEDELGDRSI<br>MFTIQNED (SEQ ID NO: 40) |
| hH12 | YFGKHESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FQRDVPGHNNKMQFESSSYEGYFLACEKERDLFKLILKKEDELGDRSI<br>MFTTQNED (SEQ ID NO: 41) |
| hB11 | YFGKIESKLSVIRNLNDQVLFIDQGNRPLFEDMTDSDCRDNAPRTIFIIS<br>KYKDKQPRAQAVTISVKCEKISTLSCENKIISFKEMNPPDNIKDTKSDIIF<br>FQRKVPGHQHKMQFESSSYEGYFLACEKERDLFKLILKKEDELGDRSI<br>MFTVQKED (SEQ ID NO: 42) |
| hC3 | YFGKIESKLSVIRNLNDQVLFIDQGNRPLFEDMTDSDCRDNAPRTIFIIST<br>YKDRQPRGKAVTISVKCEKISTLSCENKIISFKEMNPPDNIKDTKSDIIFF<br>ERDVPGHHHKMQFESSSYEGYFLACEKERDLFKLILKKEDELGDRSIM<br>FTIQNED (SEQ ID NO: 43) |
| hC2 | YFGKIESKLSVIRNLNDQVLFIDQGNRPLFEDMTDSDCRDNAPRTIFIIST<br>YKDKQPRGKAVTISVKCEKISTLSCENKIISFKEMNPPDNIKDTKSDIIFF<br>QRDVPGHKHKMQFESSSYEGYFLACEKERDLFKLILKKEDELGDRSIM<br>FTTQHED (SEQ ID NO: 44) |
| hG10 | YFGKIESKLSVIRNLNDQVLFIDQGNRPLFEDMTDSDCRDNAPRTIFIIST<br>YKDKQPRAKAVTISVKCEKISTLSCENKIISFKEMNPPDNIKDTKSDIIFF<br>QRRVPGHHHKMQFESSSYEGYFLACEKERDLFKLILKKEDELGDRSIM<br>FTIQKED (SEQ ID NO: 45) |
| hG1 | YFGKIESRLSVIRNLNDQVLFIDQGNRPLFEDMTDSDCRDNAPRTIFIIST<br>YKDKQPRGKAVTISVKCEKISTLSCENKIISFKEMNPPDNIKDTKSDIIFF<br>QRDVPGHDYKMQFESSSYEGYFLACEKERDLFKLILKKEDELGDRSIM<br>FTIQKED (SEQ ID NO: 46) |
| hF1 | YFGKYESRLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FQRDVPGHEHKMQFESSSYEGYFLACEKERDLFKLILKKEDELGDRSI<br>MFTVQKED (SEQ ID NO: 47) |
| hD2 | HFGKYESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FQRDVPGHHNKMQFESSSYEGYFLACEKERDLFKLILKKEDELGDRSI<br>MFTVQKED (SEQ ID NO: 48) |
| hA1 | RFGKLESKLSVIRNLNDQVLFIDQGNRPLFEDMTDSDCRDNAPRTIFIIS<br>TYRDSQPRAKAVTISVKCEKISTLSCENKIISFKEMNPPDNIKDTKSDIIF<br>FQRDVPGHQHKMQFESSSYEGYFLACEKERDLFKLILKKEDELGDRSI<br>MFTAQKED (SEQ ID NO: 49) |
| hB3 | RFGKLESRLSVIRNLNDQVLFIDQGNRPLFEDMTDSDCRDNAPRTIFIIS<br>DYRDSQPRGRAVTISVKCEKISTLSCENKIISFKEMNPPDNIKDTKSDIIF<br>FKRNVPGHKYKMQFESSSYEGYFLACEKERDLFKLILKKEDELGDRSI<br>MFTVQHED (SEQ ID NO: 50) |

-continued

| | |
|---|---|
| hB4 | RFGKLESRLSVIRNLNDQVLFIDQGNRPLFEDMTDSDCRDNAPRTIFIIS<br>NYRDSQPRGQAVTISVKCEKISTLSCENKIISFKEMNPPDNIKDTKSDIIF<br>FKRRVPGHNHKMQFESSSYEGYFLACEKERDLFKLILKKEDELGDRSI<br>MFTVQKED (SEQ ID NO: 51) |
| hH3 | RFGKLESRLSVIRNLNDQVLFIDQGNRPLFEDMTDSDCRDNAPRTIFIIS<br>TYKDSQPRGKAVTISVKCEKISTLSCENKIISFKEMNPPDNIKDTKSDIIF<br>FQRDVPGHKHKMQFESSSYEGYFLACEKERDLFKLILKKEDELGDRSI<br>MFTVQNED (SEQ ID NO: 52) |
| hH5 | RFGKHESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FERNVPGHKYKMQFESSSYEGYFLACEKERDLFKLILKKEDELGDRSI<br>MFTVQNED (SEQ ID NO: 53) |
| hH4 | RFGKLESRLSVIRNLNDQVLFIDQGNRPLFEDMTDSDCRDNAPRTIFIIS<br>TYRDSQPRAKAVTISVKCEKISTLSCENKIISFKEMNPPDNIKDTKSDIIF<br>FERDVPGHQHKMQFESSSYEGYFLACEKERDLFKLILKKEDELGDRSI<br>MFTIQXED (SEQ ID NO: 54) |
| hE1 | RFGKLESRLSVIRNLNDQVLFIDQGNRPLFEDMTDSDCRDNAPRTIFIIS<br>TYRDSQPRTKAVTISVKCEKISTLSCENKIISFKEMNPPDNIKDTKSDIIF<br>FQRNVPGHHDKMQFESSSYEGYFLACEKERDLFKLILKKEDELGDRSI<br>MFTVQHED (SEQ ID NO: 55) |
| hG2 | RFGKLESRLSVIRNLNDQVLFIDQGNRPLFEDMTDSDCRDNAPRTIFIIS<br>TYKDSQPRAKAVTISVKCEKISTLSCENKIISFKEMNPPDNIKDTKSDIIF<br>FERDVPGHQHKMQFESSSYEGYFLACEKERDLFKLILKKEDELGDRSI<br>MFTIQKED (SEQ ID NO: 56) |
| hB9 | RFGKHESKLSVIRNLNDQVLFIDQGNRPLFEDMTDSDCRDNAPRTIFIIS<br>TYRDSQPRGKAVTISVKCEKISTLSCENKIISFKEMNPPDNIKDTKSDIIF<br>FERNVPGHKYKMQFESSSYEGYFLACEKERDLFKLILKKEDELGDRSI<br>MFTVQNED (SEQ ID NO: 57) |
| hE12 | RFGKYESKLSVIRNLNDQVLFIDQGNRPLFEDMTDSDCRDNAPRTIFIIS<br>TYKDSQPRTKAVTISVKCEKISTLSCDNKIISFKEMNPPDNIKDTKSDIIF<br>FQRDVPGHKHKMQFESSSYEGYFLACEKERDLFKLILKKEDELGDRSI<br>MFTVQNED (SEQ ID NO: 58) |
| hC5 | RFGKLESRLSVIRNLNDQVLFIDQGNRPLFEDMTDSDCRDNAPRTIFIIS<br>TYRDSQPRTKAVTISVKCEKISTLSCENKIISFKEMNPPDNIKDTKSDIIF<br>FQRKVPGHNHKMQFESSSYEGYFLACEKERDLFKLILKKEDELGDRSI<br>MFTVQKED (SEQ ID NO: 59) |

Generation 2 Human Interleukin-18 Decoy-Resistant Variants Amino Acid Sequences

| | |
|---|---|
| 5-18 | YFGKLESKLSVIRNLNDQVLFIDQGNRPLFEDMTDSDCRDNAPRTIFIIS<br>EYKDSELRGRAVTISVKCEKISTLSCENKIISFKEMNPPDNIKDTKSDIIF<br>FPRAVPGHNRKVQFESSSYEGYFLACEKERDLFKLILKKEDELGDRSIM<br>FTVQNED (SEQ ID NO: 73) |
| 5-29 | YFGKLESKLSVIRNLNDQVLFIDQGNRPLFEDMTDSDCRDNAPRTIFIIS<br>KYKDSAGRGLAVTISVKCEKISTLSCENKIISFKEMNPPDNIKDTKSDIIF<br>FERDVPGHSNKVQFESSSYEGYFLACEKERDLFKLILKKEDELGDRSIM<br>FTVQNED (SEQ ID NO: 74) |
| 5-8 | YFGKLESKLSVIRNLNDQVLFIDQGNRPLFEDMTDSDCRDNAPRTIFIIS<br>KYGDSAARGLAVTISVKCEKISTLSCENKIISFKEMNPPDNIKDTKSDIIF<br>FQRSVPGHKRKMQFESSSYEGYFLACEKERDLFKLILKKEDELGDRSI<br>MFTVQNED (SEQ ID NO: 75) |
| 5-6 | YFGKLESKLSVIRNLNDQVLFIDQGNRPLFEDMTDSDCRDNAPRTIFIIS<br>KYGDSRGRGLAVTISVKCEKISTLSCENKIISFKEMNPPDNIKDTKSDIIF<br>FERDVPGHNSKRQFESSSYEGYFLACEKERDLFKLILKKEDELGDRSIM<br>FTVQNED (SEQ ID NO: 76) |
| 5-27 | YFGKLESKLSVIRNLNDQVLFIDQGNRPLFEDMTDSDCRDNAPRTIFIIS<br>KYGDSVPRGLAVTISVKCEKISTLSCENKIISFKEMNPPDNIKDTKSDIIF<br>FARAVPGHSRKTQFESSSYEGYFLACEKERDLFKLILKKEDELGDRSIM<br>FTVQNED (SEQ ID NO: 77) |

-continued

| | |
|---|---|
| 5-20 | YFGKLESKLSVIRNLNDQVLFIDQGNRPLFEDMTDSDCRDNAPRTIFIIS<br>KYSDSGARGLAVTISVKCEKISTLSCENKIISFKEMNPPDNIKDTKSDIIF<br>FARAVPGHGRKTQFESSSYEGYFLACEKERDLFKLILKKEDELGDRSIM<br>FTVQNED (SEQ ID NO: 78) |
| 5-2 | YFGKLESKLSVIRNLNDQVLFIDQGNRPLFEDMTDSDCRDNAPRTIFIIS<br>KYSDSKARGMAVTISVKCEKISTLSCENKIISFKEMNPPDNIKDTKSDIIF<br>FARDVPGHSSKRQFESSSYEGYFLACEKERDLFKLILKKEDELGDRSIM<br>FTVQNED (SEQ ID NO: 79) |
| 5-9 | YFGKLESKLSVIRNLNDQVLFIDQGNRPLFEDMTDSDCRDNAPRTIFIIS<br>KYSDSLARGLAVTISVKCEKISTLSCENKIISFKEMNPPDNIKDTKSDIIF<br>FQRDVPGHSRKMQFESSSYEGYFLACEKERDLFKLILKKEDELGDRSI<br>MFTVQNED (SEQ ID NO: 80) |
| 5-42 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FQRNVPGHGRKMQFESSSYEGYFLACEKERDLFKLILKKEDELGDRSI<br>MFTVQNED (SEQ ID NO: 81) |
| 5-13 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FARSVPGHGRKTQFESSSYEGYFLACEKERDLFKLILKKEDELGDRSIM<br>FTVQNED (SEQ ID NO: 82) |
| 5-12 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FARDVPGHSGKRQFESSSYEGYFLACEKERDLFKLILKKEDELGDRSIM<br>FTVQNED (SEQ ID NO: 83) |
| 5-1 | YFGKLESKLSVIRNLNDQVLFIDQGNRPLFEDMTDSDCRDNAPRTIFIIS<br>KYTDSRPRGLAVTISVKCEKISTLSCENKIISFKEMNPPDNIKDTKSDIIF<br>FERDVPGHSSKKQFESSSYEGYFLACEKERDLFKLILKKEDELGDRSIM<br>FTVQNED (SEQ ID NO: 84) |
| 5-33 | YFGKLESKLSVIRNLNDQVLFIDQGNRPLFEDMTDSDCRDNAPRTIFIIS<br>KYTDSRARGMAVTISVKCEKISTLSCENKIISFKEMNPPDNIKDTKSDIIF<br>FERDVPGHNDKRQFESSSYEGYFLACEKERDLFKLILKKEDELGDRSIM<br>FTVQNED (SEQ ID NO: 85) |
| 5-21 | YFGKLESKLSVIRNLNDQVLFIDQGNRPLFEDMTDSDCRDNAPRTIFIIS<br>RYKDSGKRGLAVTISVKCEKISTLSCENKIISFKEMNPPDNIKDTKSDIIF<br>FRRSVPGHSRKVQFESSSYEGYFLACEKERDLFKLILKKEDELGDRSIM<br>FTVQNED (SEQ ID NO: 86) |
| 6-31 | YFGKLESKLSVIRNLNDQVLFIDQGNRPLFEDMTDSDCRDNAPRTIFIIS<br>KYGDSGARGLAVTISVKCEKISTLSCENKIISFKEMNPPDNIKDTKSDIIF<br>FERDVPGHSGKVQFESSSYEGYFLACEKERDLFKLILKKEDELGDRSIM<br>FTVQNED (SEQ ID NO: 87) |
| 6-20 | YFGKLESKLSVIRNLNDQVLFIDQGNRPLFEDMTDSDCRDNAPRTIFIIS<br>KYGDSRPRGMAVTISVKCEKISTLSCENKIISFKEMNPPDNIKDTKSDIIF<br>FQRAVPGHNRKMQFESSSYEGYFLACEKERDLFKLILKKEDELGDRSI<br>MFTVQNED (SEQ ID NO: 88) |
| 6-12 | YFGKLESKLSVIRNLNDQVLFIDQGNRPLFEDMTDSDCRDNAPRTIFIIS<br>KYSDSLARGLAVTISVKCEKISTLSCENKIISFKEMNPPDNIKDTKSDIIF<br>FQRDVPGHSRKMQFESSSYEGYFLACEKERDLFKLILKKEDELGDRSI<br>MFTVQNED (SEQ ID NO: 89) |
| 6-27 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FARSVPGHGRKTQFESSSYEGYFLACEKERDLFKLILKKEDELGDRSIM<br>FTVQNED (SEQ ID NO: 90) |
| 6-29 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FQRNVPGHGRKMQFESSSYEGYFLACEKERDLFKLILKKEDELGDRSI<br>MFTVQNED (SEQ ID NO: 91) |
| 5-26 | YFGKLESKLSVIRNLNDQVLFIDQGNRPLFEDMTDSDCRDNAPRTIFIIS<br>KYGDSVPRGLAVTISVKCEKISTLSCENKIISFKEMNPPDNIKDTKSDIIF<br>FARAVPGHSRKTQFESSSYEGYFLACEKERDLFKLILKKEDELGDRSIM<br>FTVQNED (SEQ ID NO: 191) |
| 5-17 | YFGKLESKLSVIRNLNDQVLFIDQGNRPLFEDMTDSDCRDNAPRTIFIIS<br>KYSDSRARGLAVTISVKCEKISTLSCENKIISFKEMNPPDNIKDTKSDIIF<br>FARSVPGHGRKTQFESSSYEGYFLACEKERDLFKLILKKEDELGDRSIM<br>FTVQNED (SEQ ID NO: 192) |

-continued

| | |
|---|---|
| 5-41 | YFGKLESKLSVIRNLNDQVLFIDQGNRPLFEDMTDSDCRDNAPRTIFIIS KYSDSRARGLAVTISVKCEKISTLSCENKIISFKEMNPPDNIKDTKSDIIF FARDVPGHSGKRQFESSSYEGYFLACEKERDLFKLILKKEDELGDRSIM FTVQNED (SEQ ID NO: 193) |

Mouse Interleukin-18 Decoy-Resistant Variants Amino Acid Sequences

| | |
|---|---|
| mCS1 | NFGRLHCTTAVIRNINDQVLFVDKRQPVFEDMTDIDQSASEPQTRLIIY GYADSRVRGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 60) |
| mCS2 | HFGRLHCTTAVIRNINDQVLFVDKRQPVFEDMTDIDQSASEPQTRLIIY AYGDSRARGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 61) |
| mC1 | NFGRLHCTTAVIRNINDQVLFVDKRQPVFEDMTDIDQSASEPQTRLIIY AYVDRRLRGKAVTLSVKDSKMSTLSCKNKIISFEEMDPPENIDDIQSDL IFFQKKVPGHNKMEFESSLYEGHFLACQKEDDAFKLILKKKDENGDKS VMFTLTNLHQS (SEQ ID NO: 62) |
| mA12 | NFGRLHCTTAVIRNINDQVLFVDKRQPVFEDMTDIDQSASEPQTRLIIYS YSDKHMRGKAVTLSVKDSKMSTLSCKNKIISFEEMDPPENIDDIQSDLI FFQKLVPGHNKMEFESSLYEGHFLACQKEDDAFKLILKKKDENGDKS VMFTLTNLHQS (SEQ ID NO: 63) |
| mE8 | NFGRLHCTTAVIRNINDQVLFVDKRQPVFEDMTDIDQSASEPQTRLIIY VYTDGRRRGKAVTLSVKDSKMSTLSCKNKIISFEEMDPPENIDDIQSDL IFFQKKVPGHDKMEFESSLYEGHFLACQKEDDAFKLILKKKDENGDKS VMFTLTNLHQS (SEQ ID NO: 64) |
| mC10 | HFGRLHCTTAVIRNINDQVLFVDKRQPVFEDMTDIDQSASEPQTRLIIY AYGDSHMRGKAVTLSVKDSKMSTLSCKNKIISFEEMDPPENIDDIQSDL IFFQKQVPGHNKMEFESSLYEGHFLACQKEDDAFKLILKKKDENGDKS VMFTVTNLHQS (SEQ ID NO: 65) |
| mB7 | HFGRLHCTTAVIRNINDQVLFVDKRQPVFEDMTDIDQSASEPQTRLIIY AYGDSNAGGRAVTLSVKDSKMSTLSCKNKIISFEEMDPPENIDDIQSDL IFFQKKVPGHNKMEFESSLYEGHFLACQKEDDAFKLILKKKDENGDKS VMFTLTNLHQS (SEQ ID NO: 66) |
| mB1 | HFGRLHCTTAVIRNINDQVLFVDKRQPVFEDMTDIDQSASEPQTRLIIY GYADSDARAKAVTLSVKDSKMSTLSCKNKIISFEEMDPPENIDDIQSDL IFFQKSVPGHNKMEFESSLYEGHFLACQKEDDAFKLILKKKDENGDKS VMFTVTNLHQS (SEQ ID NO: 67) |
| mD1 | HFGRLHCTTAVIRNINDQVLFVDKRQPVFEDMTDIDQSASEPQTRLIIY GYSDRGSKGKAVTLSVKDSKMSTLSCKNKIISFEEMDPPENIDDIQSDLI FFQKQVPGHNKMEFESSLYEGHFLACQKEDDAFKLILKKKDENGDKS VMFTLTNLHQS (SEQ ID NO: 68) |
| mH7 | YFGRLHCTTAVIRNINDQVLFVDKRQPVFEDMTDIDQSASEPQTRLIIY MYADRRARGKAVTLSVKDSKMSTLSCKNKIISFEEMDPPENIDDIQSD LIFFQKKVPGHDKMEFESSLYEGHFLACQKEDDAFKLILKKKDENGDK SVMFTVTNLHQS (SEQ ID NO: 69) |
| mA7 | YFGRLHCTTAVIRNINDQVLFVDKRQPVFEDMTDIDQSASEPQTRLIIY AYGDNRVRGKAVTLSVKDSKMSTLSCKNKIISFEEMDPPENIDDIQSDL IFFQKRVPGHNKMEFESSLYEGHFLACQKEDDAFKLILKKKDENGDKS VMFTLTNLHQS (SEQ ID NO: 70) |
| mE1 | YFGRLHCTTAVIRNINDQVLFVDKRQPVFEDMTDIDQSASEPQTRLIIY GYGDSERGGRAVTLSVKDSKMSTLSCKNKIISFEEMDPPENIDDIQSDLI FFQKRVPGHDKMEFESSLYEGHFLACQKEDDAFKLILKKKDENGDKS VMFTLTNLHQS (SEQ ID NO: 71) |
| mH3 | YFGRLHCTTAVIRNINDQVLFVDKRQPVFEDMTDIDQSASEPQTRLIIY TRTDGGQKGVAVTLSVKDSKMSTLSCKNKIISFEEMDPPENIDDIQSDL IFFQKRVPGHDKMEFESSLYEGHFLACQKEDDAFKLILKKKDENGDKS VMFTLTNLHQS (SEQ ID NO: 72) |

Human Decoy-to-the-Decoy (D2D) Variants Amino Acid Sequences

```
hD2D-5F12    HFGKLESKLSVIRNLNGQVLFIDQGNRPLFKDMTASDCRANAPR
             TIFIISFYKDSQPRGMAVTISVKCEKISTLSCENKIISFKEMNPPDNI
             KDTKSDIIFFIRSVPGADNKFQFESSSYEGYFLACEKERDLFKLIL
             KKEDELGDRSIMFTVQNED (SEQ ID NO: 92)

hD2D-5F11    DFGKLESKLSVIRNLNDQVLFIDQGNRPLFADMTDNPCRSNAPR
             TIFIISFYKDSQPRGIAVTISVKCEKISTLSCENKIISFKEMNPPDNIK
             DTKSDIIFFLRSVPGPDNKMQFESSSYEGYFLACEKERDLFKLILK
             KEDELGDRSIMFTVQNED (SEQ ID NO: 93)

hD2D-5F10    HFGKLESKLSVIRNLNGQVLFIDQGNRPLFADMEASPCRDNAPR
             TIFIISFYKDSQPRGLAVTISVKCEKISTLSCENKIISFKEMNPPDNI
             KDTKSDIIFFLRSVPGHDNKMQFESSSYEGYFLACEKERDLFKLIL
             KKEDELGDRSIMFTVQNED (SEQ ID NO: 94)

hD2D-5F08    LFGKLESKLSVIRNLNGQVLFIDQGNRPLFADMTSSPCRSRAPRTI
             FIISFYKDSQPRGFAVTISVKCEKISTLSCENKIISFKEMNPPDNIKD
             TKSDIIFFIRSVPGHDNKIQFESSSYEGYFLACEKERDLFKLILKKE
             DELGDRSIMFTVQNED (SEQ ID NO: 95)

hD2D-5F06    HFGKLESKLSVIRNLNDQVLFIDQGNRPLFTDMESKPCRDSAPRT
             IFIISMYKDSQPRGIAVTISVKCEKISTLSCENKIISFKEMNPPDNIK
             DTKSDIIFFIRSVPGHDNKFQFESSSYEGYFLACEKERDLFKLILK
             KEDELGDRSIMFTVQNED (SEQ ID NO: 96)

hD2D-5F04    YFGKLESKLSVIRNLNRQVLFIDQGNRPLFTDMTYKDCRDNAPR
             TIFIISFYKDSQPRGFAVTISVKCEKISTLSCENKIISFKEMNPPDNI
             KDTKSDIIFFIRSVPGADNKIQFESSSYEGYFLACEKERDLFKLILK
             KEDELGDRSIMFTVQNED (SEQ ID NO: 97)

hD2D-5F02    HFGKLESKLSVIRNLNGQVLFIDQGNRPLFGDMEASPCRDNAPR
             TIFIISFYKDSQPRGMAVTISVKCEKISTLSCENKIISFKEMNPPDNI
             KDTKSDIIFFIRSVPGADNKLQFESSSYEGYFLACEKERDLFKLIL
             KKEDELGDRSIMFTVQNED (SEQ ID NO: 98)

hD2D-5F01    HFGKLESKLSVIRNLNGQVLFIDQGNRPLFTDMTSSDCRDKAPRT
             IFIISFYKDSQPRGLAVTISVKCEKISTLSCENKIISFKEMNPPDNIK
             DTKSDIIFFLRSVPGPDNKFQFESSSYEGYFLACEKERDLFKLILK
             KEDELGDRSIMFTVQNED (SEQ ID NO: 99)

hD2D-5E10    HFGKLESKLSVIRNLNGQVLFIDQGNRPLFADMESNRCRDSAPRT
             IFIISMYKDSQPRGFAVTISVKCEKISTLSCENKIISFKEMNPPDNIK
             DTKSDIIFFLRSVPGHDNKIQFESSSYEGYFLACEKERDLFKLILK
             KEDELGDRSIMFTVQNED (SEQ ID NO: 100)

hD2D-5E08    YFGKLESKLSVIRNLNGQVLFIDQGNRPLFTDMTASPCRDNAPRT
             IFIISFYKDSQPRGLAVTISVKCEKISTLSCENKIISFKEMNPPDNIK
             DTKSDIIFFLRSVPGHDNKIQFESSSYEGYFLACEKERSLFKLILKK
             EDELGDRSIMFTVQNED (SEQ ID NO: 101)

hD2D-5E03    DFGKLESKLSVIRNLNDQVLFIDQGNRPLFADMKSNVCRANAPR
             TIFIISMYKDSQPRGMAVTISVKCEKISTLSCENKIISFKEMNPPDN
             IKDTKSDIIFFIRSVPGPDNKLQFESSSYEGYFLACEKERDLFKLIL
             KKEDELGDRSIMFTVQNED (SEQ ID NO: 102)

hD2D-5E02    HFGKLESKLSVIRNLNGQVLFIDQGNRPLFGDMEASPCRAKAPR
             TIFIISIYKDSQPRGFAVTISVKCEKISTLSCENKIISFKEMNPPDNIK
             DTKSDIIFFLRSVPGHDNKFQFESSSYEGYFLACEKERSLFKLILK
             KEDELGDRSIMFTVQNED (SEQ ID NO: 103)

hD2D-5D10    HFGKLESKLSVIRNLNGQVLFIDQGNRPLFADMASNRCRANAPR
             TIFIISMYKDSQPRGFAVTISVKCEKISTLSCENKIISFKEMNPPDNI
             KDTKSDIIFFIRSVPGPDNKFQFESSSYEGYFLACEKERDLFKLILK
             KEDELGDRSIMFTVQNED (SEQ ID NO: 104)

hD2D-5D08    YFGKLESKLSVIRNLNDQVLFIDQGNRPLFADMKAKACRSNAPR
             TIFIISFYKDSQPRGFAVTISVKCEKISTLSCENKIISFKEMNPPDNI
             KDTKSDIIFFLRSVPGADNKIQFESSSYEGYFLACEKERDLFKLIL
             KKEDELGDRSIMFTVQNED (SEQ ID NO: 105)

hD2D-5D06    HFGKLESKLSVIRNLNHQVLFIDQGNRPLFTDMADNACRDNAPR
             TIFIISFYKDSQPRGLAVTISVKCEKISTLSCENKIISFKEMNPPDNI
             KDTKSDIIFFIRSVPGDDNKMQFESSSYEGYFLACEKERDLFKLIL
             KKEDELGDRSIMFTVQNED (SEQ ID NO: 106)
```

-continued

| | |
|---|---|
| hD2D-5D05 | YFGKLESKLSVIRNLNGQVLFIDQGNRPLFTDMKSNLCRSNAPRT<br>IFIISFYKDSQPRGIAVTISVKCEKISTLSCENKIISFKEMNPPDNIK<br>DTKSDIIFFIRSVPGDDNKIQFESSSYEGYFLACEKERDLFKLILKK<br>EDELGDRSIMFTVQNED (SEQ ID NO: 107) |
| hD2D-5D03 | HFGKLESKLSVIRNLNGQVLFIDQGNRPLFRDMAASHCRDSAPR<br>TIFIISIYKDSQPRGFAVTISVKCEKISTLSCENKIISFKEMNPPDNIK<br>DTKSDIIFFLRSVPGHDNKIQFESSSYEGYFLACEKERDLFKLILK<br>KEDELGDRSIMFTVQNED (SEQ ID NO: 108) |
| hD2D-5D02 | YFGKLESKLSVIRNLNDQVLFIDQGNRPLFADMASNPCRYKAPR<br>TIFIISMYKDSQPRGLAVTISVKCEKISTLSCENKIISFKEMNPPDNI<br>KDTKSDIIFFLRSVPGADNKLQFESSSYEGYFLACEKERDLFKLIL<br>KKEDELGDRSIMFTVQNED (SEQ ID NO: 109) |
| hD2D-5C10 | HFGKLESKLSVIRNLNGQVLFIDQGNRPLFTDMASNHCRYNAPR<br>TIFIISMYKDSQPRGLAVTISVKCEKISTLSCENKIISFKEMNPPDNI<br>KDTKSDIIFFLRSVPGADNKIQFESSSYEGYFLACEKERDLFKLIL<br>KKEDELGDRSIMFTVQNED (SEQ ID NO: 110) |
| hD2D-5C09 | HFGKLESKLSVIRNLNGQVLFIDQGNRPLFADMTDNPCRSRAPRT<br>IFIISFYKDSQPRGMAVTISVKCEKISTLSCENKIISFKEMNPPDNIK<br>DTKSDIIFFIRSVPGHDNKFQFESSSYEGYFLACEKERDLFKLILK<br>KEDELGDRSIMFTVQNED (SEQ ID NO: 111) |
| hD2D-5C08 | YFGKLESKLSVIRNLNGQVLFIDQGNRPLFTDMTASHCRSSAPRT<br>IFIISLYKDSQPRGMAVTISVKCEKISTLSCENKIISFKEMNPPDNIK<br>DTKSDIIFFLRSVPGHDNKFQFESSSYEGYFLACEKERDLFKLILK<br>KEDELGDRSIMFTVQNED (SEQ ID NO: 112) |
| hD2D-5C05 | YFGKLESKLSVIRNLNGQVLFIDQGNRPLFTDMEYRLCRANAPR<br>TIFIISFYKDSHPRGLAVTISVKCEKISTLSCENKIISFKEMNPPDNI<br>KDTKSDIIFFLRSVPGDDNKLQFESSSYEGYFLACEKERDLFKLIL<br>KKEDELGDRSIMFTVQNED (SEQ ID NO: 113) |
| hD2D-5C04 | YFGKLESKLSVIRNLNGQVLFIDQGNRPLFTDMESSLCRDNAPRT<br>IFIISLYKDSQPRGMAVTISVKCEKISTLSCENKIISFKEMNPPDNIK<br>DTKSDIIFFLRSVPGADNKFQFESSSYEGYFLACEKERSLFKLILK<br>KEDELGDRSIMFTVQNED (SEQ ID NO: 114) |
| hD2D-5C03 | YFGKLESKLSVIRNLNGQVLFIDQGNRPLFKDMEANDCRSSAPR<br>TIFIISIYKDSQPRGLAVTISVKCEKISTLSCENKIISFKEMNPPDNIK<br>DTKSDIIFFIRSVPGADNKMQFESSSYEGYFLACEKERDLFKLILK<br>KEDELGDRSIMFTVQNED (SEQ ID NO: 115) |
| hD2D-5B11 | DFGKLESKLSVIRNLNDQVLFIDQGNRPLFADMKASACRANAPR<br>TIFIISMYKDSQPRGLAVTISVKCEKISTLSCENKIISFKEMNPPDNI<br>KDTKSDIIFFLRSVPGHDNKFQFESSSYEGYFLACEKERDLFKLIL<br>KKEDELGDRSIMFTVQNED (SEQ ID NO: 116) |
| hD2D-5B10 | YFGKLESKLSVIRNLNGQVLFIDQGNRPLFGDMTAKHCRARAPR<br>TIFIISFYKDSQPRGMAVTISVKCEKISTLSCENKIISFKEMNPPDNI<br>KDTKSDIIFFIRSVPGADNKFQFESSSYEGYFLACEKERDLFKLIL<br>KKEDELGDRSIMFTVQNED (SEQ ID NO: 117) |
| hD2D-5B06 | FFGKFESKLSVIRNLNGQVLFIDQGNRPLFTDMESKDCRDRAPRT<br>IFIISFYKDSQPRGLAVTISVKCEKISTLSCENKIISFKEMNPPDNIK<br>DTKSDIIFFLRSVPGHDNKLQFESSSYEGYFLACEKERDLFKLILK<br>KEDELGDRSIMFTVQNED (SEQ ID NO: 118) |
| hD2D-5B05 | FFGKLESKLSVIRNLNGQVLFIDQGNRPLFADMASNHCRANAPR<br>TIFIISLYKDSQPRGLAVTISVKCEKISTLSCENKIISFKEMNPPDNI<br>KDTKSDIIFFIRSVPGHDNKMQFESSSYEGYFLACEKERDLFKLIL<br>KKEDELGDRSIMFTVQNED (SEQ ID NO: 119) |
| hD2D-5B02 | YFGKLESKLSVIRNLNGQVLFIDQGNRPLFADMTSKRCRDNAPR<br>TIFIISLYKDSQPRGFAVTISVKCEKISTLSCENKIISFKEMNPPDNI<br>KDTKSDIIFFIRSVPGHDNKIQFESSSYEGYFLACEKERDLFKLILK<br>KEDELGDRSIMFTVQNED (SEQ ID NO: 120) |
| hD2D-5A09 | LFGKHESKLSVIRNLNGQVLFIDQGNRPLFGDMESSPCRYNAPRT<br>IFIISFYKDSQPRGLAVTISVKCEKISTLSCENKIISFKEMNPPDNIK<br>DTKSDIIFFIRSVPGHDNKMQFESSSYEGYFLACEKERDLFKLILK<br>KEDELGDRSIMFTVQNED (SEQ ID NO: 121) |
| hD2D-5A02 | YFGKLESKLSVIRNLNAQVLFIDQGNRPLFTDMTASPCRSSAPRTI<br>FIISLYKDSQPRGLAVTISVKCEKISTLSCENKIISFKEMNPPDNIK<br>DTKSDIIFFLRSVPGPDNKIQFESSSYEGYFLACEKERDLFKLILKK<br>EDELGDRSIMFTVQNED (SEQ ID NO: 122) |

-continued

| | |
|---|---|
| hD2D-CS1 | YFGKLESKLSVIRNLNGQVLFIDQGNRPLFADMTDSDCRDNAPR<br>TIFIISMYKDSQPRGMAVTISVKCEKISTLSCENKIISFKEMNPPDN<br>IKDTKSDIIFFLRSVPGHDNKMQFESSSYEGYFLACEKERDLFKLI<br>LKKEDELGDRSIMFTVQNED (SEQ ID NO: 123) |
| hD2D-CS2 | YFGKLESKLSVIRNLNGQVLFIDQGNRPLFADMTSSDCRDNAPR<br>TIFIISFYKDSQPRGMAVTISVKCEKISTLSCENKIISFKEMNPPDNI<br>KDTKSDIIFFLRSVPGHDNKMQFESSSYEGYFLACEKERDLFKLIL<br>KKEDELGDRSIMFTVQNED (SEQ ID NO: 124) |
| hD2D-CS3 | YFGKLESKLSVIRNLNGQVLFIDQGNRPLFADMESSDCRDNAPR<br>TIFIISFYKDSQPRGLAVTISVKCEKISTLSCENKIISFKEMNPPDNI<br>KDTKSDIIFFLRSVPGHDNKMQFESSSYEGYFLACEKERDLFKLIL<br>KKEDELGDRSIMFTVQNED (SEQ ID NO: 125) |

Mouse Decoy-to-the-Decoy (D2D) Variants Amino Acid Sequences

| | |
|---|---|
| mD2D-A5 | YFGRYHCTTAVIRNINQQVLFVDKRQPVFADMGYTVQSASEPQT<br>RLIIYMYKDSEVRGLAVTLSVKDSKMSTLSCKNKIISFEEMDPPE<br>NIDDIQSDLIFFLKEVPGHRKLEFESSLYEGHFLACQKEDEAFKLI<br>LKKKDENGDKSVMFTLTNLHQS (SEQ ID NO: 126) |
| mD2D-A6 | DFGRLHCTTAVIRNINDQVLFVDKRQPVFADMGSIAQSASEPQT<br>RLIIYFYKDSEVRGLAVTLSVKDSKMYTLSCKNKIISFEEMDPPE<br>NIDDIQSDLIFFLKAVPGDNKIEFESSLYEGHFLACQKEATAFKLI<br>LKKKDENGDKSVMFTLTNLHQS (SEQ ID NO: 127) |
| mD2D-A7 | YFGRLHCTTAVIRNINGQVLFVDKRQPVFRDMADTVQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEAGAFKLIL<br>KKKDENGDKSVMFTLTNLHQS (SEQ ID NO: 128) |
| mD2D-A8 | HFGRLHCTTAVIRNINDQVLFVDKRQPVFKDMEYTVQSASEPQT<br>RLIIYMYKDSEVRGLAVTLSVKDSKMSTLSCKNKIISFEEMDPPE<br>NIDDIQSDLIFFIKAVPGDRKIEFESSLYEGHFLACQKEDNAFKLIL<br>KKKDENGDKSVMFTLTNLHQS (SEQ ID NO: 129) |
| mD2D-A9 | YFGRLHCTTAVIRNINAQVLFVDKRQPVFADMADKGQSASEPQT<br>RLIIYMYKDSEVRGLAVTLSVKDSKMSTLSCKNKIISFEEMDPPE<br>NIDDIQSDLIFFLKPVPGDTKMEFESSLYEGHFLACQKEFGAFKLI<br>LKKKDENGDKSVMFTLTNLHQS (SEQ ID NO: 130) |
| mD2D-A11 | YFGRLHCTTAVIRNINEQVLFVDKRQPVFADMGDRHQSASEPQT<br>RLIIYMYKDSEVRGLAVTLSVKDSKMSTLSCKNKIISFEEMDPPE<br>NIDDIQSDLIFFIKPVPGASKLEFESSLYEGHFLACQKEDDAFKLIL<br>KKKDENGDKSVMFTLTNLHQS (SEQ ID NO: 131) |
| mD2D-A12 | HFGRLHCTTAVIRNINDQVLFVDKRQPVFRDMGAIGQSASEPQT<br>RLIIYFYKDSEVRGLAVTLSVKDSKMSTLSCKNKIISFEEMDPPEN<br>IDDIQSDLIFFIKPVPGDSKLEFESSLYEGHFLACQKEVDAFKLILK<br>KKDENGDKSVMFTLTNLHQS (SEQ ID NO: 132) |
| mD2D-B4 | HFGRLHCTTAVIRNINSQVLFVDKRQPVFTDMGSIVQSASEPQTR<br>LIIYMYKDSEVRGLAVTLSVKDSKMSTLSCKNKIISFEEMDPPENI<br>DDIQSDLIFFIKGVPGDNKIEFESSLYEGHFLACQKEDRAFKLILK<br>KKDENGDKSVMFTLTNLHQS (SEQ ID NO: 133) |
| mD2D-B7 | YFGRLHCTTAVIRNINSQVLFVDKRQPVFRDMEDTPQSASEPQTR<br>LIIYFYKDSEVRGLAVTLSVKDSKMSTLSCKNKIISFEEMDPPENI<br>DDIQSDLIFFIKRVPGDSKLEFESSLYEGHFLACQKEFEAFKLILK<br>KKDENGDKSVMFTLTNLHQS (SEQ ID NO: 134) |
| mD2D-B11 | HFGRLHCTTAVIRNINAQVLFVDKRQPVFGDMTATVQSASEPQT<br>RLIIYFYKDSEVRGLAVTLSVKDSKMSTLSCKNKIISFEEMDPPEN<br>IDDIQSDLIFFIKPVPGDSKLEFESSLYEGHFLACQKEDNAFKLILK<br>KKDENGDKSVMFTLTNLHQS (SEQ ID NO: 135) |
| mD2D-B12 | NFGRLHCTTAVIRNINNQVLFVDKRQPVFKDMEYTLQSASEPQT<br>RLIIYFYKDSEVRGLAVTLSVKDSKMSTLSCKNKIISFEEMDPPEN<br>IDDIQSDLIFFIKPVPGDNKLEFESSLYEGHFLACQKEYEAFKLILK<br>KKDENGDKSVMFTLTNLHQS (SEQ ID NO: 136) |

| | |
|---|---|
| mD2D-C1 | YFGRLHCTTAVIRNINGQVLFVDKRQPVFADMEATRQSASEPQT<br>RLIIYFYKDSEVRGLAVTLSVKDSKMSTLSCKNKIISFEEMDPPEN<br>IDDIQSDLIFFIKGVPGANKMEFESSLYEGHFLACQKEDGAFKLIL<br>KKKDENGDNSVMFTLTNLHQS (SEQ ID NO: 137) |
| mD2D-C3 | NFGRLHCTTAVIRNINGQVLFVDKRQPVFADMRAILQSASEPQT<br>RLIIYFYKDSEVRGLAVTLSVKDSKMSTLSCKNKIISFEEMDPPEN<br>IDDIQSDLIFFLKGVPGDNKLEFESSLYEGHFLACQKEDRAFKLIL<br>KKKDENGDKSVMFTLTNLHQS (SEQ ID NO: 138) |
| mD2D-C5 | YFGRLHCTTAVIRNINAQVLFVDKRQPVFADMEATAQSASEPQT<br>RLIIYFYKDSEVRGLAVTLSVKDSKMSTLSCKNKIISFEEMDPPEN<br>IDDIQSDLIFFIKGVPGASKMEFESSLYEGHFLACQKEDGAFKLIL<br>KKKDENGDKSVMFTLTNLHQS (SEQ ID NO: 139) |
| mD2D-C6 | LFGRLHCTTAVIRNINGQVLFVDKRQPVFADMGATLQSASEPQT<br>RLIIYMYKDSEVRGLAVTLSVKDSKMSTLSCKNKIISFEEMDPPE<br>NIDDIQSDLIFFLKPVPGDTKMEFESSLYEGHFLACQKEASAFKLI<br>LKKKDENGDKSVMFTLTNLHQS (SEQ ID NO: 140) |
| mD2D-C9 | NFGRLHCTTAVIRNINGQVLFVDKRQPVFEDMAYTVQSASEPQT<br>RLIIYFYKDSEVRGLAVTLSVKDSKMSTLSCKNKIISFEEMDPPEN<br>IDDIQSDLIFFIKGVPGDSKMEFESSLYEGHFLACQKEYDAFKLIL<br>KKKDENGDKSVMFTLTNLHQS (SEQ ID NO: 141) |
| mD2D-C10 | DFGRLHCTTAVIRNINDQVLFVDKRQPVFKDMESKPQSASEPQT<br>RLIIYFYKDSEVRGLAVTLSVKDSKMSTLSCKNKIISFEEMDPPEN<br>IDDIQSDLIFFLKAVPGASKLEFESSLYEGHFLACQKEANAFKLIL<br>KKKDENGDKSVMFTLTNLHQS (SEQ ID NO: 142) |
| mD2D-C11 | LFGRLHCTTAVIRNINGQVLFVDKRQPVFADMGDKVQSASEPQT<br>RLIIYMYKDSEVRGLAVTLSVKDSKMSTLSCKNKIISFEEMDPPE<br>NIDDIQSDLIFFIKPVPGDNKLEFESSLYEGHFLACQKEDEAFKLIL<br>KTKDENGDKSVMFTLTNLHQS (SEQ ID NO: 143) |
| mD2D-D1 | YFGRHHCTTAVIRNINQQVLFVDKRQPVFRDMAATRQSASEPQT<br>RLIIYMYKDSEVRGLAVTLSVKDSKMSTLSCKNKIISFEEMDPPE<br>NIDDIQSDLIFFLKGVPGDNKMEFESSLYEGHFLACQKEDDAFKL<br>ILKKKDENGDKSVMFTLTNLHQS (SEQ ID NO: 144) |
| mD2D-D9 | NFGRLHCTTAVIRNINQQVLFVDKRQPVFTDMESIGQSASEPQTR<br>LIIYFYKDSEVRGLAVTLSVKDSKMSTLSCKNKIISFEEMDPPENI<br>DDIQSDLIFFLKAVPGANKLEFESSLYEGHFLACQKEDSAFKLILK<br>KKDENGDKSVMFTLTNLHQS (SEQ ID NO: 145) |
| mD2D-D12 | FFGRHHCTTAVIRNINGQVLFVDKRQPVFGDMGDRVQSASEPQT<br>RLIIYMYKDSEVRGLAVTLSVKDSKMSTLSCKNKIISFEEMDPPE<br>NIDDIQSDLIFFIKAVPGDSKIEFESSLYEGHFLACQKEDGAFKLIL<br>KKKDENGDKSVMFTLTNLHQS (SEQ ID NO: 146) |
| mD2D-E3 | VFGRHHCTTAVIRNINGQVLFVDKRQPVFKDMTYIDQSASEPQT<br>RLIIYMYKDSEVRGLAVTLSVKDSKMSTLSCKNKIISFEEMDPPE<br>NIDDIQSDLIFFLKAVPGDTKMEFESSLYEGHFLACQKEAQAFKLI<br>LKKKDEIGDKSVMFTLTNLHQS (SEQ ID NO: 147) |
| mD2D-E4 | NFGRLHCTTAVIRNINGQVLFVDKRQPVFADMTATRQSASEPQT<br>RLIIYMYKDSEVRGLAVTLSVKDSKMSTLSCKNKIISFEEMDPPE<br>NIDDIQSDLIFFIKQVPGANKIEFESSLYEGHFLACQKEFRAFKLIL<br>KKKDENGDKSVMFTLTNLHQS (SEQ ID NO: 148) |
| mD2D-E5 | DFGRLHCTTAVIRNINGQVLFVDKRQPVFGDMAYIGQSASEPQT<br>RLIIYFYKDSEVRGLAVTLSVKDSKMSTLSCKNKIISFEEMDPPEN<br>IDDIQSDLIFFIKAVPGHSKIEFESSLYEGHFLACQKESGAFKLILK<br>KKDENGDKSVMFTLTNLHQS (SEQ ID NO: 149) |
| mD2D-E7 | YFGRLHCTTAVIRNINDQVLFVDKRQPVFRDMGSIAQSASEPQTR<br>LIIYMYKDSEVRGLAVTLSVKDSKMSTLSCKNKIISFEEMDPPENI<br>DDIQSDLIFFIKPVPGATKLEFESSLYEGHFLACQKEDGAFKLILK<br>KKDENGDNSVMFTLTNLHQS (SEQ ID NO: 150) |
| mD2D-E8 | YFGRLHCTTAVIRNINEQVLFVDKRQPVFTDMEAIGQSASEPQTR<br>LIIYFYKDSEVRGLAVTLSVKDSKMSTLSCKNKIISFEEMDPPENI<br>DDIQSDLIFFIKGVPGDRKMEFESSLYEGHFLACQKEDGAFKLIL<br>KKKDENGDKSVMFTLTNLHQS (SEQ ID NO: 151) |
| mD2D-E9 | FFGRLHCTTAVIRNINNQVLFVDKRQPVFEDMEYRLQSASEPQT<br>RLIIYMYKDSEVRGLAVTLSVKDSKMSTLSCKNKIISFEEMDPPE<br>NIDDIQSDLIFFLKPVPGASKLEFESSLYEGHFLACQKESDAFKLIL<br>KKKDENGDKSVMFTLTNLHQS (SEQ ID NO: 152) |

| | |
|---|---|
| mD2D-E10 | NFGRLHCTTAVIRNINNQVLFVDKRQPVFADMEDRLQSASEPQT<br>RLIIYMYKDSEVRGLAVTLSVKDSKMSTLSCKNKIISFEEMDPPE<br>NIDDIQSDLIFFLKGVPGDNKMEFESSLYEGHFLACQKEDHAFKL<br>ILKKKDENGDKSVMFTLTNLHQS (SEQ ID NO: 153) |
| mD2D-E11 | YFGRLHCTTAVIRNINAQVLFVDKRQPVFRDMGYILQSASEPQT<br>RLIIYLYKDSEVRGLAVTLSVKESKMSTLSCKNKIISFEEMDPPEN<br>IDDIQSDLIFFLKPVPGDTKIEFESSLYEGHFLACQKEDNAFKLILK<br>KKDENGDKSVMFTLTNLHQS (SEQ ID NO: 154) |
| mD2D-E12 | YFGRLHCTTAVIRNINDQVLFVDKRQPVFGDMADTAQSASEPQT<br>RLIIYFYKDSEVRGLAVTLSVKDSKMSTLSCKNKIISFEEMDPPEN<br>IDDIQSDLIFFIKPVPGDSKMEFESSLYEGHFLACQKEADAFKLIL<br>KKKDENGDKSVMFTLTNLHQS (SEQ ID NO: 155) |
| mD2D-F3 | DFGRLHCTTAVIRNINGQVLFVDKRQPVFEDMAYIAQSASEPQT<br>RLIIYFYKDSEVRGLAVTLSVKDSKMSTLSCKNKIISFEEMDPPEN<br>IDDIQSDLIFFIKPVPGDSKIEFESSLYEGHFLACQKEADAFKLILK<br>KKDENGDKSVMFTLTNLHQS (SEQ ID NO: 156) |
| mD2D-F4 | NFGRLHCTTAVIRNINEQVLSVDKRQPVFRDMKYILQSASEPQTR<br>LIIYFYKDSEVRGLAVTLSVKDSKMSTLSCKNKIISFEEMDPPENI<br>DDIQSDLIFFLKGVPGDNKMEFESSLYEGHFLACQKEYGAFKLIL<br>KKKDENGDKSVMFTLTNLHQS (SEQ ID NO: 157) |
| mD2D-F5 | DFGRLHCTTAVIRNINEQVLFVDKRQPVFTDMAYILQSASEPQTR<br>LIIYFYKDSEVRGLAVTLSVKESKMSTLSCKNKIISFEEMDPPENI<br>DDIQSDLIFFIKAVPGDSKLEFESSLYEGHFLACQKEDTAFKLILK<br>KKDENGDKSVMFTLTNLHQS (SEQ ID NO: 158) |
| mD2D-F7 | DFGRLHCTTAVIRNINNQVLFVDKRQPVFKDMESTAQSASEPQT<br>RLIIYMYKDSEVRGLAVTLSVKDSKMSTLSCKNKIISFEEMDPPE<br>NIDDIQSDLIFFLKGVPGASKLEFESSLYEGHFLACQKEAGAFKLI<br>LKKKDENGDKSVMFTLTNLHQS (SEQ ID NO: 159) |
| mD2D-F8 | HFGRLHCTTAVIRNINEQVLFVDKRQPVFADMEAIGQSASEPQTR<br>LIIYFYKDSEVRGLAVTLSVKESKMSTLSCKNKIISFEEMDPPENI<br>DDIQSDLIFFIKGVPGDTKLEFESSLYAGHFLACQKEDGAFKLILK<br>KKDENGDKSVMFTLTNLHQS (SEQ ID NO: 160) |
| mD2D-F9 | IFGRLHCTTAVIRNINEQVLFVDKRQPVFKDMRYIVQSASEPQTR<br>LIIYFYKDSEVRGLAVTLSVKDSKMSTLSCKNKIISFEEMDPPENI<br>DDIQSDLIFFIKEVPGASKLEFESSLYEGHFLACQKEDEAFKLILK<br>KKDENGDKSVMFTLTNLHQS (SEQ ID NO: 161) |
| mD2D-G1 | YFGRLHCTTAVIRNINAQVLFVDKRQPVFTDMGYTLQSASEPQT<br>RLIIYLYKDSEVRGLAVTLSVKDSKMSTLSCKNKIISFEEMDPPEN<br>IDDIQSDLIFFIKPVPGHNKIEFESSLYEGHFLACQKEDRAFKLILK<br>KKDENGDKSVMFTLTNLHQS (SEQ ID NO: 162) |
| mD2D-G7 | NFGRLHCTTAVIRNINNQVLFVDKRQPVFRDMASTAQSASEPQT<br>RLIIYMYKDSEVRGLAVTLSVKDSKMSTLSCKNKIISFEEMDPPE<br>NIDDIQSDLIFFIKGVPGANKIEFESSLYEGHFLACQKEDDAFKLIL<br>KKKDENGDKSVMFTLTNLHQS (SEQ ID NO: 163) |
| mD2D-G9 | DFGRLHCTTAVIRNINGQVLFVDKRQPVFEDMKDRAQSASEPQT<br>RLIIYFYKDSEVRGLAVTLSVKDSKMSTLSCKNKIISFEEMDPPEN<br>IDDIQSDLIFFLKAVPGHSKMEFESSLYEGHFLACQKEDEAFKLIL<br>KKKDENGDKSVMFTLTNLHQS (SEQ ID NO: 164) |
| mD2D-H7 | NFGRLHCTTAVIRNINEQVLFVDKRQPVFADMTDIAQSASEPQTR<br>LIIYMYKDSEVRGLAVTLSVKESKMSTLSCKNKIISFEEMDPPENI<br>DDIQSDLIFFLKPVPGDIKMEFESSLYEGHFLACQKEYGAFKLILK<br>KKDENGDNSVMFTLTNLHQS (SEQ ID NO: 165) |
| mD2D-E1 | YFGRLHCTTAVIRNINEQVLFVDKRQPVFADMTDTLQSASEPQT<br>RLIIYFYKDSEVRGLAVTLSVKDSKMSTLSCKNKIISFEEMDPPEN<br>IDDIQSDLIFFLKGVPGDNKMEFESSLYEGHFLACQKEDTAFKLIL<br>KKKDENGDKSVMFTLTNLHQS (SEQ ID NO: 166) |
| mD2D-G8 | YFGRLHCTTAVIRNINEQVLFVDKRQPVFADMTDTLQSASEPQT<br>RLIIYFYKDSEVRGLAVTLSVKDSKMSTLSCKNKIISFEEMDPPEN<br>IDDIQSDLIFFLKGVPGDNKMEFESSLYEGHFLACQKEDTAFKLIL<br>KKKDENGDKSVMFTLTNLHQS (SEQ ID NO: 167) |

-continued

| | |
|---|---|
| mD2D-H3 | YFGRLHCTTAVIRNINEQVLFVDKRQPVFADMTDTLQSASEPQT<br>RLIIYFYKDSEVRGLAVTLSVKDSKMSTLSCKNKIISFEEMDPPEN<br>IDDIQSDLIFFLKGVPGDNKMEFESSLYEGHFLACQKEDTAFKLIL<br>KKKDENGDKSVMFTLTNLHQS (SEQ ID NO: 168) |
| mD2D-A10 | HFGRLHCTTAVIRNINGQVLFVDKRQPVFKDMKYIVQSASEPQT<br>RLIIYMYKDSEVRGLAVTLSVKDSKMSTLSCKNKIISFEEMDPPE<br>NIDDIQSDLIFFLKAVPGHSKIEFESSLYEGHFLACQKEDSAFKLIL<br>KKKDENGDKSVMFTLTNLHQS (SEQ ID NO: 169) |
| mD2D-H1 | HFGRLHCTTAVIRNINGQVLFVDKRQPVFKDMKYIVQSASEPQT<br>RLIIYMYKDSEVRGLAVTLSVKDSKMSTLSCKNKIISFEEMDPPE<br>NIDDIQSDLIFFLKAVPGHSKIEFESSLYEGHFLACQKEDSAFKLIL<br>KKKDENGDKSVMFTLTNLHQS (SEQ ID NO: 170) |
| mD2D-F12 | YFGRLHCTTAVIRNINGQVLFVDKRQPVFEDMKAKAQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEDGAFKLIL<br>KKKDENGDKSVMFTLTNLHQS (SEQ ID NO: 171) |
| mD2D-G10 | YFGRLHCTTAVIRNINGQVLFVDKRQPVFEDMKAKAQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEDGAFKLIL<br>KKKDENGDKSVMFTLTNLHQS (SEQ ID NO: 172) |
| mD2D-G12 | YFGRLHCTTAVIRNINGQVLFVDKRQPVFEDMKAKAQSASEPQT<br>RLIIYFYKDSEVRGLAVTLSVKDSKMSTLSCKNKIISFEEMDPPEN<br>IDDIQSDLIFFIKPVPGASKMEFESSLYEGHFLACQKEDGAFKLIL<br>KKKDENGDKSVMFTLTNLHQS (SEQ ID NO: 173) |
| mD2D-E2 | LFGRLHCTTAVIRNINGQVLFVDKRQPVFGDMGSIPQSASEPQTR<br>LIIYFYKDSEVRGLAVTLSVKDSKMSTLSCKNKIISFEEMDPPENI<br>DDIQSDLIFFIKHVPGATKMEFESSLYEGHFLACQKEDNAFKLILK<br>KKDENGDKSVMFTLTNLHQS (SEQ ID NO: 174) |
| mD2D-G11 | LFGRLHCTTAVIRNINGQVLFVDKRQPVFGDMGSIPQSASEPQTR<br>LIIYFYKDSEVRGLAVTLSVKDSKMSTLSCKNKIISFEEMDPPENI<br>DDIQSDLIFFIKHVPGATKMEFESSLYEGHFLACQKEDNAFKLILK<br>KKDENGDKSVMFTLTNLHQS (SEQ ID NO: 175) |
| mD2D-C4 | YFGRLHCTTAVIRNINSQVLFVDKRQPVFTDMAYTVQSASEPQT<br>RLIIYFYKDSEVRGLAVTLSVKDSKMSTLSCKNKIISFEEMDPPEN<br>IDDIQSDLIFFIKAVPGDSKLEFESSLYEGHFLACQKEDNAFKLILK<br>KKDENGDKSVMFTLTNLHQS (SEQ ID NO: 176) |
| mD2D-F11 | YFGRLHCTTAVIRNINSQVLFVDKRQPVFTDMAYTVQSASEPQT<br>RLIIYFYKDSEVRGLAVTLSVKDSKMSTLSCKNKIISFEEMDPPEN<br>IDDIQSDLIFFIKAVPGDSKLEFESSLYEGHFLACQKEDNAFKLILK<br>KKDENGDKSVMFTLTNLHQS (SEQ ID NO: 177) |
| mD2D-C2 | YFGRLHCTTAVIRNINGQVLFVDKRQPVFTDMGARVQSASEPQT<br>RLIIYFYKDSEVRGLAVTLSVKDSKMYTLSCKNKIISFEEMDPPE<br>NIDDIQSDLIFFLKPVPGDNKLEFESSLYEGHFLACQKESGAFKLI<br>LKKKDENGDKSVMFTLTNLHQS (SEQ ID NO: 178) |
| mD2D-F10 | YFGRLHCTTAVIRNINGQVLFVDKRQPVFTDMGARVQSASEPQT<br>RLIIYFYKDSEVRGLAVTLSVKDSKMYTLSCKNKIISFEEMDPPE<br>NIDDIQSDLIFFLKPVPGDNKLEFESSLYEGHFLACQKESGAFKLI<br>LKKKDENGDKSVMFTLTNLHQS (SEQ ID NO: 179) |
| mD2D-A2 | DFGRLHCTTAVIRNINGQVLFVDKRQPVFGDMKATGQSASEPQT<br>RLIIYFYKDSEVRGLAVTLSVKDSKMSTLSCKNKIISFEEMDPPEN<br>IDDIQSDLIFFIKAVPGANKLEFESSLYEGHFLACQKEAGAFKLIL<br>KKKDENGDKSVMFTLTNLHQS (SEQ ID NO: 180) |
| mD2D-F6 | DFGRLHCTTAVIRNINGQVLFVDKRQPVFGDMKATGQSASEPQT<br>RLIIYFYKDSEVRGLAVTLSVKDSKMSTLSCKNKIISFEEMDPPEN<br>IDDIQSDLIFFIKAVPGANKLEFESSLYEGHFLACQKEAGAFKLIL<br>KKKDENGDKSVMFTLTNLHQS (SEQ ID NO: 181) |
| mD2D-A1 | DFGRLHCTTAVIRNINSQVLFVDKRQPVFRDMGSIHQSASEPQTR<br>LIIYFYKDSEVRGLAVTLSVKDSKMSTLSCKNKIISFEEMDPPENI<br>DDIQSDLIFFLKAVPGANKLEFESSLYEGHFLACQKEDGAFKLIL<br>KKKDENGDKSVMFTLTNLHQS (SEQ ID NO: 182) |
| mD2D-E6 | DFGRLHCTTAVIRNINSQVLFVDKRQPVFRDMGSIHQSASEPQTR<br>LIIYFYKDSEVRGLAVTLSVKDSKMSTLSCKNKIISFEEMDPPENI<br>DDIQSDLIFFLKAVPGANKLEFESSLYEGHFLACQKEDGAFKLIL<br>KKKDENGDKSVMFTLTNLHQS (SEQ ID NO: 183) |

```
mD2D-D4      YFGRLHCTTAVIRNINEQVLFVDKRQPVFKDMKDKLQSASEPQT
             RLIIYFYKDSEVRGLAVTLSVKDSKMSTLSCKNKIISFEEMDPPEN
             IDDIQSDLIFFLKGVPGDNKLEFESSLYEGHFLACQKEFGAFKLIL
             KKKDENGDKSVMFTLTNLHQS (SEQ ID NO: 184)

mD2D-D6      YFGRLHCTTAVIRNINEQVLFVDKRQPVFKDMKDKLQSASEPQT
             RLIIYFYKDSEVRGLAVTLSVKDSKMSTLSCKNKIISFEEMDPPEN
             IDDIQSDLIFFLKGVPGDNKLEFESSLYEGHFLACQKEFGAFKLIL
             KKKDENGDKSVMFTLTNLHQS (SEQ ID NO: 185)

mD2D-A3      YFGRLHCTTAVIRNINGQVLFVDKRQPVFADMASTHQSASEPQT
             RLIIYFYKDSEVRGLAVTLSVKDSKMSTLSCKNKIISFEEMDPPEN
             IDDIQSDLIFFLKGVPGANKIEFESSLYEGHFLACQKEDDAFKLIL
             KKKDENGDKSVMFTLTNLHQS (SEQ ID NO: 186)

mD2D-A4      YFGRLHCTTAVIRNINGQVLFVDKRQPVFADMASTHQSASEPQT
             RLIIYFYKDSEVRGLAVTLSVKDSKMSTLSCKNKIISFEEMDPPEN
             IDDIQSDLIFFLKGVPGANKIEFESSLYEGHFLACQKEDDAFKLIL
             KKKDENGDKSVMFTLTNLHQS (SEQ ID NO: 187)

mD2D-B10     YFGRLHCTTAVIRNINGQVLFVDKRQPVFADMASTHQSASEPQT
             RLIIYFYKDSEVRGLAVTLSVKDSKMSTLSCKNKIISFEEMDPPEN
             IDDIQSDLIFFLKGVPGANKIEFESSLYEGHFLACQKEDDAFKLIL
             KKKDENGDKSVMFTLTNLHQS (SEQ ID NO: 188)

mD2D-B8      YFGRLHCTTAVIRNINSQVLFVDKRQPVFGDMKYIVQSASEPQT
             RLIIYFYKDSEVRGLAVTLSVKDSKMSTLSCKNKIISFEEMDPPEN
             IDDIQSDLIFFLKGVPGDTKMEFESSLYEGHFLACQKESGAFKLIL
             KKKDENGDKSVMFTLTNLHQS (SEQ ID NO: 189)

mD2D-B9      YFGRLHCTTAVIRNINSQVLFVDKRQPVFGDMKYIVQSASEPQT
             RLIIYFYKDSEVRGLAVTLSVKDSKMSTLSCKNKIISFEEMDPPEN
             IDDIQSDLIFFLKGVPGDTKMEFESSLYEGHFLACQKESGAFKLIL
             KKKDENGDKSVMFTLTNLHQS (SEQ ID NO: 190)

SEQ ID NO: 89 (also referred to herein as "6-12")
                                                        (SEQ ID NO: 89)
YFGKLESKLSVIRNLNDQVLFIDQGNRPLFEDMTDSDCRDNAPRTIFIISKYSDSLARG

LAVTISVKCEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 6
variant of SEQ ID NO: 89 (C38S/C68S)
                                                        (SEQ ID NO: 6)
YFGKLESKLSVIRNLNDQVLFIDQGNRPLFEDMTDSDSRDNAPRTIFIISKYSDSLARG

LAVTISVKSEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 16
variant of SEQ ID NO: 89 (C38S/C68G)
                                                        (SEQ ID NO: 16)
YFGKLESKLSVIRNLNDQVLFIDQGNRPLFEDMTDSDSRDNAPRTIFIISKYSDSLARG

LAVTISVKGEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 17
variant of SEQ ID NO: 89 (C38S/C68A)
                                                        (SEQ ID NO: 17)
YFGKLESKLSVIRNLNDQVLFIDQGNRPLFEDMTDSDSRDNAPRTIFIISKYSDSLARG

LAVTISVKAEKISTLSCENKIISFKEMNPPDNIKDTKSDIIFFQRDVPGHSRKMQFESSS

YEGYFLACEKERDLFKLILKKEDELGDRSIMFTVQNED
```

SEQ ID NO: 18
variant of SEQ ID NO: 89 (C38S/C68V)
(SEQ ID NO: 18)
YFGKLESKLSVIRNLNDQVLFIDQGNRPLFEDMTDSDSRDNAPRTIFIISKYSDSLARG

LAVTISVKVEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 19
variant of SEQ ID NO: 89 (C38S/C68D)
(SEQ ID NO: 19)
YFGKLESKLSVIRNLNDQVLFIDQGNRPLFEDMTDSDSRDNAPRTIFIISKYSDSLARG

LAVTISVKDEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 20
variant of SEQ ID NO: 89 (C38S/C68E)
(SEQ ID NO: 20)
YFGKLESKLSVIRNLNDQVLFIDQGNRPLFEDMTDSDSRDNAPRTIFIISKYSDSLARG

LAVTISVKEEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 21
variant of SEQ ID NO: 89 (C38S/C68N)
(SEQ ID NO: 21)
YFGKLESKLSVIRNLNDQVLFIDQGNRPLFEDMTDSDSRDNAPRTIFIISKYSDSLARG

LAVTISVKNEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 1
(SEQ ID NO: 1)
YFGKLESKLSVIRNLNDQVLFIDQGNRPLFEDMTDSDSRDNAPRTIFIISKYSDSLARG

LAVTISVKSEKISTLSSENKIISFKEMNPPDNIKDTKSDIIFFQRDVPGHSRKMQFESSSY

EGYFLASEKERDLFKLILKKEDELGDRSIMFTVQNED

SEQ ID NO: 2
(SEQ ID NO: 2)
YFGKLESKLSVIRNLNDQVLFIDQGNRPLFEDMTDSDCRDNAPRTIFIISKYSDSLARG

LAVTISVKSEKISTLSSENKIISFKEMNPPDNIKDTKSDIIFFQRDVPGHSRKMQFESSSY

EGYFLASEKERDLFKLILKKEDELGDRSIMFTVQNED

SEQ ID NO: 3
(SEQ ID NO: 3)
YFGKLESKLSVIRNLNDQVLFIDQGNRPLFEDMTDSDSRDNAPRTIFIISKYSDSLARG

LAVTISVKCEKISTLSSENKIISFKEMNPPDNIKDTKSDIIFFQRDVPGHSRKMQFESSS

YEGYFLASEKERDLFKLILKKEDELGDRSIMFTVQNED

SEQ ID NO: 4
(SEQ ID NO: 4)
YFGKLESKLSVIRNLNDQVLFIDQGNRPLFEDMTDSDSRDNAPRTIFIISKYSDSLARG

LAVTISVKSEKISTLSCENKIISFKEMNPPDNIKDTKSDIIFFQRDVPGHSRKMQFESSS

YEGYFLASEKERDLFKLILKKEDELGDRSIMFTVQNED

SEQ ID NO: 5
(SEQ ID NO: 5)
YFGKLESKLSVIRNLNDQVLFIDQGNRPLFEDMTDSDSRDNAPRTIFIISKYSDSLARG

LAVTISVKSEKISTLSSENKIISFKEMNPPDNIKDTKSDIIFFQRDVPGHSRKMQFESSSY

EGYFLACEKERDLFKLILKKEDELGDRSIMFTVQNED

```
SEQ ID NO: 7
                                                 (SEQ ID NO: 7)
YFGKLESKLSVIRNLNDQVLFIDQGNRPLFEDMTDSDSRDNAPRTIFIISKYSDSLARG

LAVTISVKCEKISTLSSENKIISFKEMNPPDNIKDTKSDIIFFQRDVPGHSRKMQFESSS

YEGYFLACEKERDLFKLILKKEDELGDRSIMFTVQNED

SEQ ID NO: 8
                                                 (SEQ ID NO: 8)
YFGKLESKLSVIRNLNDQVLFIDQGNRPLFEDMTDSDSRDNAPRTIFIISKYSDSLARG

LAVTISVKCEKISTLSCENKIISFKEMNPPDNIKDTKSDIIFFQRDVPGHSRKMQFESSS

YEGYFLASEKERDLFKLILKKEDELGDRSIMFTVQNED

SEQ ID NO: 9
                                                 (SEQ ID NO: 9)
YFGKLESKLSVIRNLNDQVLFIDQGNRPLFEDMTDSDCRDNAPRTIFIISKYSDSLARG

LAVTISVKSEKISTLSSENKIISFKEMNPPDNIKDTKSDIIFFQRDVPGHSRKMQFESSSY

EGYFLACEKERDLFKLILKKEDELGDRSIMFTVQNED

SEQ ID NO: 10
                                                (SEQ ID NO: 10)
YFGKLESKLSVIRNLNDQVLFIDQGNRPLFEDMTDSDCRDNAPRTIFIISKYSDSLARG

LAVTISVKSEKISTLSCENKIISFKEMNPPDNIKDTKSDIIFFQRDVPGHSRKMQFESSS

YEGYFLASEKERDLFKLILKKEDELGDRSIMFTVQNED

SEQ ID NO: 11
                                                (SEQ ID NO: 11)
YFGKLESKLSVIRNLNDQVLFIDQGNRPLFEDMTDSDCRDNAPRTIFIISKYSDSLARG

LAVTISVKCEKISTLSSENKIISFKEMNPPDNIKDTKSDIIFFQRDVPGHSRKMQFESSS

YEGYFLASEKERDLFKLILKKEDELGDRSIMFTVQNED

SEQ ID NO: 12
                                                (SEQ ID NO: 12)
YFGKLESKLSVIRNLNDQVLFIDQGNRPLFEDMTDSDSRDNAPRTIFIISKYSDSLARG

LAVTISVKCEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 13
                                                (SEQ ID NO: 13)
YFGKLESKLSVIRNLNDQVLFIDQGNRPLFEDMTDSDCRDNAPRTIFIISKYSDSLARG

LAVTISVKSEKISTLSCENKIISFKEMNPPDNIKDTKSDIIFFQRDVPGHSRKMQFESSS

YEGYFLACEKERDLFKLILKKEDELGDRSIMFTVQNED

SEQ ID NO: 14
                                                (SEQ ID NO: 14)
YFGKLESKLSVIRNLNDQVLFIDQGNRPLFEDMTDSDCRDNAPRTIFIISKYSDSLARG

LAVTISVKCEKISTLSSENKIISFKEMNPPDNIKDTKSDIIFFQRDVPGHSRKMQFESSS

YEGYFLACEKERDLFKLILKKEDELGDRSIMFTVQNED

SEQ ID NO: 15
                                                (SEQ ID NO: 15)
YFGKLESKLSVIRNLNDQVLFIDQGNRPLFEDMTDSDCRDNAPRTIFIISKYSDSLARG

LAVTISVKCEKISTLSCENKIISFKEMNPPDNIKDTKSDIIFFQRDVPGHSRKMQFESSS

YEGYFLASEKERDLFKLILKKEDELGDRSIMFTVQNED

Example SUMO tag
                                                (SEQ ID NO: 26)
DSEVNQEAKPEVKPEVKPETHINLKVSDGSSEIFFKIKKTTPLRRLMEAFAKRQGKEM

DSLRFLYDGIRIQADQAPEDLDMEDNDIIEAHREQIGG
```

-continued

Example His tagged SUMO tag
(SEQ ID NO: 27)
MGHHHHHHGSLQDSEVNQEAKPEVKPEVKPETHINLKVSDGSSEIFFKIKKTTPLRR

LMEAFAKRQGKEMDSLRFLYDGIRIQADQAPEDLDMEDNDIIEAHREQIGG

Example SUMO protease
(SEQ ID NO: 28)
LVPELNEKDDDQVQKALASRENTQLMNRDNIEITVRDFKTLAPRRWLNDTIIEFFMK

YIEKSTPNTVAFNSFFYTNLSERGYQGVRRWMKRKKTQIDKLDKIFTPINLNQSHWA

LGIIDLKKKTIGYVDSLSNGPNAMSFAILTDLQKYVMEESKHTIGEDFDLIHLDCPQQ

PNGYDCGIYVCMNTLYGSADAPLDFDYKDAIRMRRFIAHLILTDALK

Example His tagged SUMO protease
(SEQ ID NO: 29)
MGSSHHHHHHSSGA LVPELNEKDDDQVQKALASRENTQLMNRDNIEITVRDFKTLA

PRRWLNDTHIEFFMKYIEKSTPNTVAFNSFFYTNLSERGYQGVRRWMKRKKTQIDKL

DKIFTPINLNQSHWALGIIDLKKKTIGYVDSLSNGPNAMSFAILTDLQKYVMEESKHT

IGEDFDLIHLDCPQQPNGYDCGIYVCMNTLYGSADAPLDFDYKDAIRMRRFIAHLILT

DALK

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below in SET A and SET B. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

What is claimed is:

1. A method of promoting interleukin-18 (IL-18) signaling activity in a human subject in need thereof, the method comprising administering an effective amount of a human decoy-resistant (DR) modified IL-18 polypeptide to the human subject in need thereof, the human DR modified IL-18 polypeptide comprising:

(i) one or more substitution mutations selected from the group consisting of: (1) Tyrosine-1 to histidine, or Tyrosine-1 to arginine, (2) Leucine-5 to histidine, Leucine-5 to isoleucine, or Leucine-5 to tyrosine, (3) Lysine-8 to glutamine, or Lysine-8 to arginine, (4) Methionine-51 to threonine, Methionine-51 to lysine, Methionine-51 to aspartic acid, Methionine-51 to asparagine, Methionine-51 to glutamic acid, or Methionine-51 to arginine, (5) Lysine-53 to arginine, Lysine 53-glycine, Lysine-53 to serine, or Lysine-53 to threonine, (6) Serine-55 to lysine, or Serine-55 to arginine, (7) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (8) Proline-57 to leucine, Proline-57 to glycine, Proline-57 to alanine, or Proline-57 to lysine, (9) Glycine-59 to threonine, or Glycine-59 to alanine, (10) Methionine-60 to lysine, Methionine-60 to glutamine, Methionine-60 to arginine, or Methionine-60 to leucine, (11) Glutamic acid-77 to aspartic acid, (12) Glutamine-103 to glutamic acid, Glutamine-103 to lysine, Glutamine-103 to proline, Glutamine-103 to alanine, or Glutamine-103 to arginine, (13) Serine-105 to arginine, Serine-105 to aspartic acid, Serine-105 to lysine, Serine-105 to asparagine, or Serine-105 to alanine, (14) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, or Aspartic acid-110 to glycine, (15) Asparagine-111 to histidine, Asparagine-111 to tyrosine, Asparagine-111 to aspartic acid, Asparagine-111 to arginine, Asparagine-111 to serine, or Asparagine-111 to glycine, (16) Methionine-113 to valine, Methionine-113 to arginine, Methionine-113 to threonine, or Methionine-113 to lysine, (17) Valine-153 to isoleucine, Valine-153 to threonine, or Valine-153 to alanine, and (18) Asparagine-155 to lysine, or Asparagine-155 to histidine, relative to wild-type (WT) IL-18 as set forth in SEQ ID NO: 30; and (ii) mutations at amino acid positions Cysteine-38 and Cysteine-68, relative to WT IL-18 as set forth in SEQ ID NO: 30, wherein the mutation at position Cysteine-38 is a substitution of Cysteine-38 to serine and the mutation at Cysteine-68 is a substitution selected from the group consisting of: Cysteine-68 to serine, Cysteine-68 to glycine, Cysteine-68 to alanine, Cysteine-68 to valine, Cysteine-68 to aspartic acid, Cysteine-68 to glutamic acid, and Cysteine-68 to asparagine, thereby promoting IL-18 signaling activity.

2. The method of claim 1, wherein the mutation at position Cysteine-68 is a substitution of Cysteine-68 to glycine.

3. The method of claim 1, wherein the mutation at position Cysteine-68 is a substitution of Cysteine-68 to alanine.

4. The method of claim 1, wherein the mutation at position Cysteine-68 is a substitution of Cysteine-68 to aspartic acid.

5. The method of claim 1, wherein the mutation at position Cysteine-68 is a substitution of Cysteine-68 to asparagine.

6. The method of claim 1, wherein the human DR modified IL-18 polypeptide comprises an amino acid sequence with no pegylated amino acids .

7. The method of claim 1, wherein the human DR modified IL-18 polypeptide comprises mutations in at least two of the following positions: Tyrosine-1, Leucine-5, Lysine-8, Methionine-51, Lysine-53, Serine-55, Glutamine-56, Proline-57, Glycine-59, Methionine-60, Glutamic acid-77, Glutamine-103, Serine-105, Aspartic acid-110, Asparagine-111, Methionine-113, Valine-153, and Asparagine-155, relative to SEQ ID NO: 30.

8. The method of claim 1, wherein the human DR modified IL-18 polypeptide comprises mutations in at least two of the following positions: Methionine-51, Lysine-53, Serine-55, Glutamine-56, Proline-57, Methionine-60, Glutamine-103, Serine-105, Aspartic acid-110, Asparagine-111, and Methionine-113, relative WT IL-18 as set forth in SEQ ID NO: 30.

9. The method of claim 1, wherein the human DR modified IL-18 polypeptide comprises mutations at positions Methionine-51, Lysine-53, Glutamine-56, Aspartic acid-110, and Asparagine-111, relative to WT IL-18 as set forth in SEQ ID NO: 30.

10. The method of claim 9, wherein the human DR modified IL-18 polypeptide further comprises mutations at positions Proline-57 and Methionine-60, relative to WT IL-18 as set forth in SEQ ID NO: 30.

11. The method of claim 10, wherein the human DR modified IL-18 polypeptide further comprises a mutation at position Serine-105, relative to WT IL-18 as set forth in SEQ ID NO: 30.

12. The method of claim 1, wherein the human DR modified IL-18 polypeptide has at least four substitutions selected from the group consisting of: (1) Methionine-51 to threonine, Methionine-51 to lysine, Methionine-51 to aspartic acid, Methionine-51 to asparagine, Methionine-51 to glutamic acid, or Methionine-51 to arginine, (2) Lysine-53 to arginine, Lysine-53 to glycine, Lysine-53 to serine, or Lysine-53 to threonine, (3) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (4) Proline-57 to leucine, Proline-57 to glycine, Proline-57 to alanine, or Proline-57 to lysine, (5) Methionine-60 to lysine, Methionine-60 glutamine, Methionine-60 to arginine, or Methionine-60 to leucine, (6) Glutamine-103 to glutamic acid, Glutamine-103 to lysine, Glutamine-103 to proline, Glutamine-103 to alanine, or Glutamine-103 to arginine, (7) Serine-105 to arginine, Serine-105 to aspartic acid, Serine-105 to lysine, Serine-105 to asparagine, or Serine-105 to alanine, (8) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, or Aspartic acid-110 to glycine, (9) Asparagine-111 to histidine, Asparagine-111 to tyrosine, Asparagine-111 to aspartic acid, Asparagine-111 to arginine, Asparagine-111 to serine, or Asparagine-111 to glycine, and (10) Methionine-113 to valine, Methionine-113 to arginine, Methionine-113 to threonine, or Methionine-113 to lysine, relative to SEQ ID NO: 30.

13. The method of claim 1, wherein the human DR modified IL-18 polypeptide has at least five substitutions selected from the group consisting of: (1) Methionine-51 to glutamic acid, Methionine-51 to arginine, Methionine-51 to lysine, Methionine-51 to threonine, Methionine-51 to aspartic acid, or Methionine-51 to asparagine; (2) Lysine-53 to glycine, Lysine-53 to serine, Lysine-53 to threonine, or Lysine-53 to arginine; (3) Glutamine-56 to glycine, Glutamine-56 to arginine, Glutamine-56 to leucine, Glutamine-56 to glutamic acid, Glutamine-56 to alanine, Glutamine-56 to valine, or Glutamine-56 to lysine; (4) Aspartic acid-110 to serine, Aspartic acid-110 to asparagine, Aspartic acid-110 to glycine, Aspartic acid-110 to lysine, Aspartic acid-110 to histidine, Aspartic acid-110 to glutamine, or Aspartic acid-110 to glutamic acid; (5) Asparagine-111 to glycine, Asparagine-111 to arginine, Asparagine-111 to serine, Asparagine-111 to aspartic acid, Asparagine-111 to histidine, or Asparagine-111 to tyrosine; (6) Proline-57 to alanine, Proline-57 to leucine, Proline-57 to glycine, or Proline-57 lysine; and (7) Methionine-60 to leucine, Methionine-60 to arginine, Methionine-60 to lysine, or Methionine-60 to glutamine, relative to SEQ ID NO: 30.

14. The method of claim 13, wherein the human DR modified IL-18 polypeptide further comprises the substitution Serine-105 to aspartic acid, Serine-105 to alanine, Serine-105 to asparagine, Serine-105 to arginine, or Serine-105 to lysine relative to SEQ ID NO: 30.

15. The method of claim 14, wherein the human DR modified IL-18 polypeptide comprises substitutions of Methionine-51 to lysine, Lysine-53 to serine, Glutamine-56 to leucine, Aspartic acid-110 to serine, and Asparagine-111 to arginine, relative to SEQ ID NO: 30.

16. The method of claim 15, wherein the human DR modified IL-18 polypeptide further comprises substitutions of Proline-57 to alanine, Methionine-60 to leucine, and Serine-105 to aspartic acid, relative to SEQ ID NO: 30.

17. The method of claim 16, wherein the mutations at amino acid position Cysteine-68, relative to WT IL-18 as set forth in SEQ ID NO: 30, is a Cysteine-68 to serine substitution.

18. The method of claim 16, wherein the mutation at amino acid position Cysteine-68, relative to WT IL-18 as set forth in SEQ ID NO: 30, is a Cysteine-68 to glycine substitution.

19. The method of claim 16, wherein the mutation at amino acid position Cysteine-68, relative to WT IL-18 as set forth in SEQ ID NO: 30, is a Cysteine-68 to alanine substitution.

20. The method of claim 16, wherein the mutation at amino acid position Cysteine-68, relative to WT IL-18 as set forth in SEQ ID NO: 30, is a Cysteine-68 to aspartic acid substitution.

21. The method of claim 16, wherein the mutation at amino acid position Cysteine-68, relative to WT IL-18 as set forth in SEQ ID NO: 30, is a Cysteine-68 to asparagine substitution.

22. A composition comprising a human decoy-resistant (DR) modified IL-18 polypeptide, wherein the human DR modified IL-18 specifically binds to IL-18 receptor (IL-18R) but exhibits reduced binding to IL-18 binding protein (IL-18BP) compared to the wildtype (WT) IL-18, wherein the human DR modified IL-18 polypeptide comprises:

(i) one or more mutations selected from the group consisting of: (1) Tyrosine-1 to histidine, or Tyrosine-1 to arginine, (2) Leucine-5 to histidine, Leucine-5 to isoleucine, or Leucine-5 to tyrosine, (3) Lysine-8 to glutamine, or Lysine-8 to arginine, (4) Methionine-51 to threonine, Methionine-51 to lysine, Methionine-51 to aspartic acid, Methionine-51 to asparagine, Methionine-51 to glutamic acid, or Methionine-51 to arginine, (5) Lysine-53 to arginine, Lysine 53-glycine, Lysine-53 to serine, or Lysine-53 to threonine, (6) Serine-55 to lysine, or Serine-55 to arginine, (7) Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, (8) Proline-57 to leucine, Proline-57 to glycine, Proline-57 to alanine, or Proline-57 to lysine, (9) Glycine-59 to threonine, or Glycine-59 to alanine, (10) Methionine-60 to lysine, Methionine-60 to glutamine, Methionine-60 to arginine, or Methionine-60 to leucine, (11) Glutamic acid-77 to aspartic acid, (12) Glutamine-103 to glutamic acid, Glutamine-103 to lysine, Glutamine-103 to proline, Glutamine-103 to alanine, or Glutamine-103 to arginine, (13) Serine-105 to arginine, Serine-105 to aspartic acid, Serine-105 to lysine, Serine-105 to asparagine, or Serine-105 to alanine, (14) Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, or Aspartic acid-110 to glycine, (15) Asparagine-111 to histidine, Asparagine-111 to tyrosine, Asparagine-111 to aspartic acid, Asparagine-111 to arginine, Asparagine-111 to serine, or Asparagine-111 to glycine, (16) Methionine-113 to valine, Methionine-113 to arginine, Methionine-113 to threonine, or Methionine-113 to lysine, (17) Valine-153 to isoleucine, Valine-153 to threonine, or Valine-153 to alanine, and (18) Asparagine-155 to lysine, or Asparaginegine-155 to histidine, relative to wild-type (WT) IL-18 as set forth in SEQ ID NO: 30; and (ii) mutations at amino acid positions Cysteine-38 and Cysteine-68, relative to wild-type (WT) IL-18 as set forth in SEQ ID NO: 30, wherein the mutation at position Cysteine-38 is a substitution of Cysteine-38 to serine and the mutation at Cysteine-68 is a substitution selected from the group consisting of: Cysteine-68 to serine, Cysteine-68 to glycine, Cysteine-68 to alanine, Cysteine-68 to valine, Cysteine-68 to aspartic acid, Cysteine-68 to glutamic acid, and Cysteine-68 to asparagine.

23. The composition of claim 22, wherein the one or more mutations comprise a substitution of Methionine-51 to threonine, Methionine-51 to lysine, Methionine-51 to aspartic acid, Methionine-51 to asparagine, Methionine-51 to glutamic acid, or Methionine-51 to arginine, relative to WT IL-18 as set forth in SEQ ID NO: 30.

24. The composition of claim 22, wherein the one or more mutations comprise a substitution of Lysine-53 to glycine, Lysine-53 to serine, Lysine-53 to threonine, or Lysine-53 to arginine, relative to WT IL-18 as set forth in SEQ ID NO: 30.

25. The composition of claim 22, wherein the one or more mutations comprise a substitution of Glutamine-56 to glutamic acid, Glutamine-56 to alanine, Glutamine-56 to arginine, Glutamine-56 to valine, Glutamine-56 to glycine, Glutamine-56 to lysine, or Glutamine-56 to leucine, relative to WT IL-18 as set forth in SEQ ID NO: 30.

26. The composition of claim 22, wherein the one or more mutations comprise a substitution of Proline-57 to leucine, Proline-57 to glycine, Proline-57 to alanine, or Proline-57 to lysine, relative to WT IL-18 as set forth in SEQ ID NO: 30.

27. The composition of claim 22, wherein the one or more mutations comprise a substitution of Aspartic acid-110 to histidine, Aspartic acid-110 to lysine, Aspartic acid-110 to asparagine, Aspartic acid-110 to glutamine, Aspartic acid-110 to glutamic acid, Aspartic acid-110 to serine, Aspartic acid-110 to glycine, relative to WT IL-18 as set forth in SEQ ID NO: 30.

28. The composition of claim 22, wherein the one or more mutations comprise a substitution of Asparagine-111 to histidine, Asparagine-111 to tyrosine Asparagine-111 to aspartic acid, Asparagine-111 to arginine, Asparagine-111 to serine, or Asparagine-111 to glycine, relative to WT IL-18 as set forth in SEQ ID NO: 30.

29. The composition of claim 22, wherein the one or more mutations comprise a substitution of Serine-105 to aspartic acid, Serine-105 to alanine, Serine-105 to asparagine, Serine-105 to arginine, Serine 105 to aspartic acid, or Serine-105 to lysine, relative to WT IL-18 as set forth in SEQ ID NO: 30.

30. The composition of claim 22, wherein the one or more mutations comprise a substitution of Methionine-60 to lysine, Methionine-60 to glutamine, Methionine-60 to arginine, or Methionine-60 to leucine, relative to WT IL-18 as set forth in SEQ ID NO: 30.

31. The composition of claim 22, wherein the mutations at amino acid positions Cysteine-38 and Cysteine-68 comprise substitutions of Cysteine-38 to serine and Cysteine-68 to aspartic acid, relative to WT IL-18 as set forth in SEQ ID NO: 30.

* * * * *